United States Patent
Yeager et al.

(10) Patent No.: US 11,840,521 B2
(45) Date of Patent: Dec. 12, 2023

(54) MODULATORS OF MAS-RELATED G-PROTEIN RECEPTOR X4 AND RELATED PRODUCTS AND METHODS

(71) Applicant: Escient Pharmaceuticals, Inc., San Diego, CA (US)

(72) Inventors: Adam Yeager, San Diego, CA (US); Brandon Selfridge, San Diego, CA (US); Marcos Sainz, San Diego, CA (US); Esther Martinborough, San Diego, CA (US); Marcus Boehm, San Diego, CA (US); Liming Huang, San Diego, CA (US)

(73) Assignee: Escient Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 17/858,840

(22) Filed: Jul. 6, 2022

(65) Prior Publication Data

US 2023/0159474 A1    May 25, 2023

Related U.S. Application Data

(60) Continuation of application No. 17/531,662, filed on Nov. 19, 2021, now abandoned, which is a division of application No. 16/831,638, filed on Mar. 26, 2020, now abandoned.

(60) Provisional application No. 62/959,799, filed on Jan. 10, 2020, provisional application No. 62/955,967, filed on Dec. 31, 2019, provisional application No. 62/938,277, filed on Nov. 20, 2019, provisional application No. 62/864,306, filed on Jun. 20, 2019, provisional application No. 62/849,095, filed on May 16, 2019, provisional application No. 62/825,741, filed on Mar. 28, 2019.

(51) Int. Cl.
| | | |
|---|---|---|
| C07D 265/30 | (2006.01) | |
| C07C 69/78 | (2006.01) | |
| C07C 255/41 | (2006.01) | |
| C07D 213/79 | (2006.01) | |
| C07D 241/24 | (2006.01) | |
| C07D 261/18 | (2006.01) | |
| C07D 277/64 | (2006.01) | |
| C07D 333/38 | (2006.01) | |
| A61K 45/06 | (2006.01) | |

(52) U.S. Cl.
CPC ............ *C07D 265/30* (2013.01); *C07C 69/78* (2013.01); *C07C 255/41* (2013.01); *C07D 213/79* (2013.01); *C07D 241/24* (2013.01); *C07D 261/18* (2013.01); *C07D 277/64* (2013.01); *C07D 333/38* (2013.01); *A61K 45/06* (2013.01)

(58) Field of Classification Search
None
See application file for complete search history.

(56) References Cited

FOREIGN PATENT DOCUMENTS

| | | |
|---|---|---|
| WO | 2008/109737 A1 | 9/2008 |
| WO | 2011/127388 A2 | 10/2011 |
| WO | 2013/025425 A1 | 2/2013 |
| WO | 2014/144545 A2 | 9/2014 |
| WO | 2018/232316 A1 | 12/2018 |
| WO | 2019/045035 A1 | 3/2019 |
| WO | 2019/213148 A1 | 11/2019 |

*Primary Examiner* — Samantha L Shterengarts
(74) *Attorney, Agent, or Firm* — Seed IP Law Group LLP

(57) ABSTRACT

Methods are provided for modulating MRGPR X4 generally, or for treating a MRGPR X4 dependent condition more specifically, by contacting the MRGPR X4 or administering to a subject in need thereof, respectively, an effective amount of a compound having the structure of Formula (I):

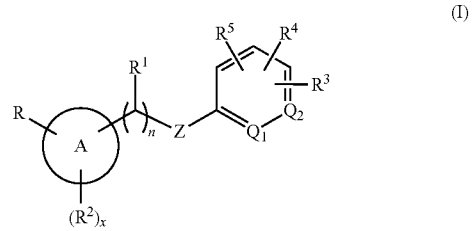

or a pharmaceutically acceptable isomer, racemate, hydrate, solvate, isotope, or salt thereof, wherein n, x, A, $Q_1$, $Q_2$, Z, R, $R^1$, $R^2$, $R^3$, $R^4$ and $R^5$ are as defined herein. Pharmaceutical compositions containing such compounds, as well as to compounds themselves, are also provided.

32 Claims, 6 Drawing Sheets

MODULATORS OF MAS-RELATED G-PROTEIN RECEPTOR X4 AND RELATED PRODUCTS AND METHODS

RELATED APPLICATIONS

This application is related to U.S. Provisional Application Nos. 62/825,741 filed Mar. 28, 2019; 62/849,095 filed May 16, 2019; 62/864,306 filed Jun. 20, 2019; 62/938,277 filed Nov. 20, 2019; 62/955,967 filed Dec. 31, 2019; and 62/959,799 filed Jan. 10, 2020; each of which are hereby incorporated by reference in their entirety.

BACKGROUND

Technical Field

The invention relates to modulators of the Mas-related G-protein coupled receptor X4, to products containing the same, as well as to methods of their use and preparation.

Description of the Related Art

Mas-related G protein receptors (MRGPRs) are a group of orphan receptors with limited expression in very specialized tissues. Very little is known about the function of most of these receptors. There are eight related receptors in this class expressed in humans, only four of which have readily identifiable orthologs in other species (i.e., MRGPR D, E, F and G). The other four receptors (MRGPR X1, X2, X3 and X4) have no counterpart, based on homology, in species other than human.

BRIEF SUMMARY

This invention is based, in part, on the identification that functionally in mice MRGPR A1 corresponds, at least in part, to the human MRGPR X4. These receptors mediate disorders including chronic itch (e.g., pruritus), inflammation disorders, autoimmunity, skin disorders, cardiovascular disease, lung inflammation/COPD, and adverse skin reactions to drugs. More specifically, both MRGPR A1 and MRGPR X4 are expressed in sensory neurons, skin melanocytes, dendritic cells, polymorphonuclear cells, macrophages, bronchial epithelial cells, lung smooth muscle and dorsal root ganglia. It has now been identified that both MRGPR A1 and MRGPR X4 are receptors for (or sensitive to activation by) circulating bilirubin and its metabolites, and thus are important for itch sensation in conditions of elevated bilirubin such as cholestatic pruritus. In addition, MRGPR X4 is activated by multiple additional components of bile including bile acids and metabolites thereof and heme metabolites including bilirubin and urobilin. Bile acids and bilirubin are highly elevated in cholestatic pruritus while urobilin, which is a potent mediator of itch induction in mouse model, and thus may be important for itch sensation in conditions of elevated urobilin such as uremic pruritus. Thus, modulating MRGPR X4 allows for treatment of autoimmune diseases such as psoriasis, multiple sclerosis, Steven Johnson's Syndrome, and other chronic itch conditions as explained in more detail below.

Accordingly, in an embodiment, methods are provided for modulating a MRGPR X4 by contacting the MRGPR X4 with an effective amount of a compound having the structure of Formula (I):

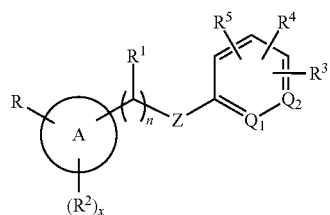

or a pharmaceutically acceptable isomer, racemate, hydrate, solvate, isotope, or salt thereof, wherein n, x, A, $Q_1$, $Q_2$, Z, R, $R^1$, $R^2$, $R^3$, $R^4$ and $R^5$ are as defined below.

In another embodiment, methods are provided for treating a MRGPR X4 dependent condition by administering to a subject in need thereof an effective amount of a compound having the structure of Formula (I), or a pharmaceutically acceptable isomer, racemate, hydrate, solvate, isotope, or salt thereof.

In more specific embodiments, the MRGPR X4 dependent condition is one or more of an itch associated condition, a pain associated condition, an inflammation-associated condition, or an autoimmune disorder.

In another embodiment, pharmaceutical compositions are provided comprising a compound having the structure of Formula (I), or a pharmaceutically acceptable isomer, racemate, hydrate, solvate, isotope, or salt thereof, in combination with a pharmaceutically acceptable excipient.

In another embodiment, compounds are provided having one or more of the structures disclosed herein, or a pharmaceutically acceptable isomer, racemate, hydrate, solvate, isotope, or salt thereof.

In further embodiments, prodrugs and/or metabolites of a compound having the structure of Formula (I) are also provided. In the case of prodrugs, a compound (i.e., prodrug) may be administered to a subject which is then converted in vivo to a compound having the structure of Formula (I). In the case of metabolites, following administration to a subject of a compound having the structure of Formula (I) such compound may be converted in vivo to an active metabolite.

DETAILED DESCRIPTION

Figure 1:
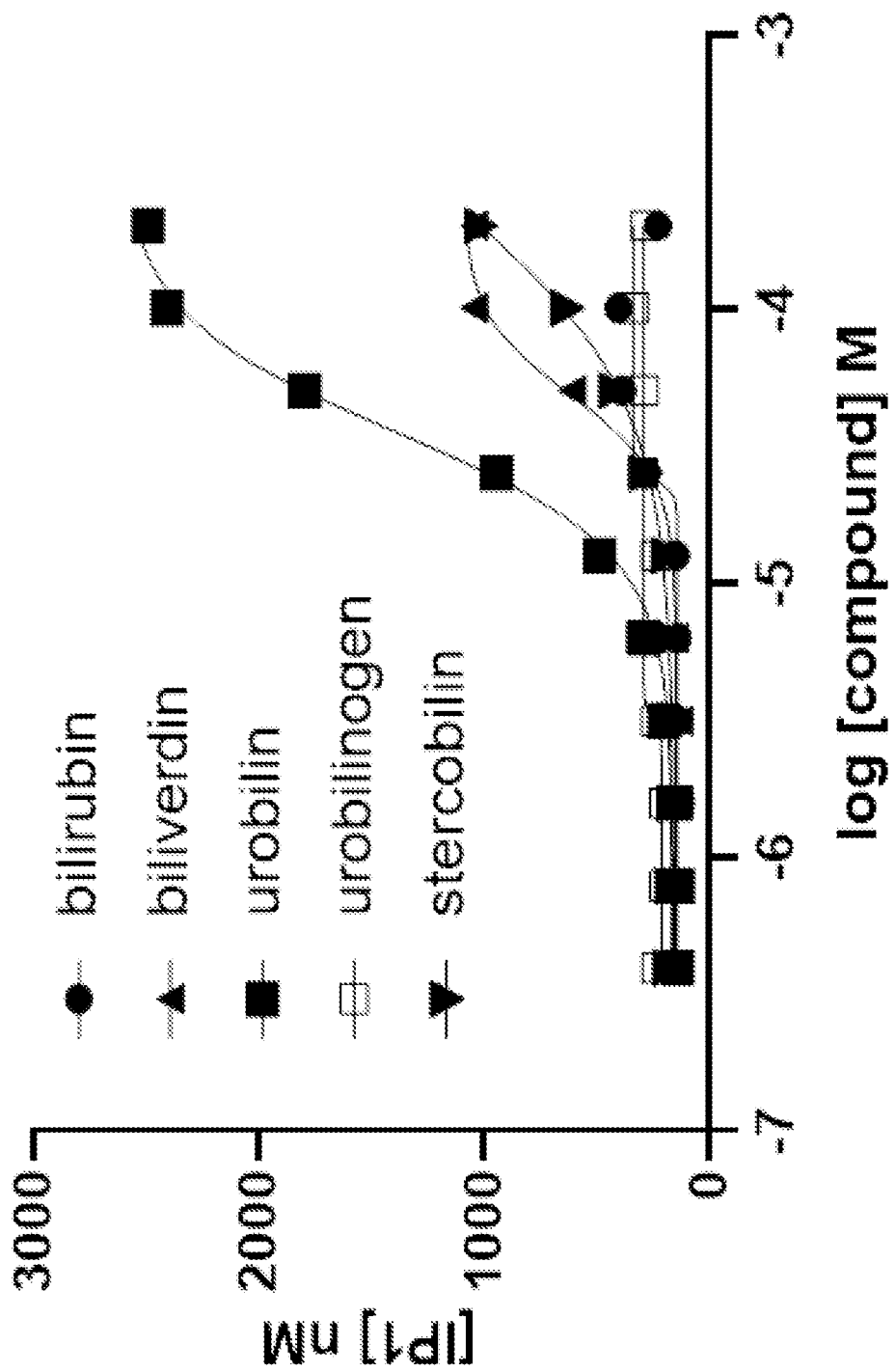
FIG. 1 shows in vitro activation of MRGPR X4 by heme metabolites bilirubin, biliverdin, urobilin, urobilinogen, and stercobilin.

As mentioned above, the invention relates to modulators of the MRGPR X4, to products containing the same, as well as to methods of their use and preparation. This invention is based, in part, on the identification that in mice MRGPR A1 functionally corresponds to the human MRGPR X4. These receptors mediate disorders including chronic and intermittent itch (e.g., pruritus), inflammation disorders, autoimmunity, skin disorders, and adverse skin reactions to drugs and infectious diseases. More specifically, both MRGPR A1 and MRGPR X4 are expressed in sensory neurons and dorsal root ganglia. It has now been identified that both MRGPR A1 and MRGPR X4 are receptors for (or sensitive to activation by) circulating bilirubin and its metabolites, and thus are important for itch sensation in conditions of elevated bilirubin such as cholestatic pruritus and end-stage renal failure. In addition, MRGPR X4 is also activated by bile acids and metabolites thereof, which are also elevated in cholestatic pruritus. Furthermore, urobilin, an oxidative product of the heme metabolite urobilinogen solely excreted by the kidney, is a potent agonist of MRGPRX4 and pruritogen, and thus may be important for itch sensation in conditions of elevated urobilin such as uremic pruritus, kidney disease and end-stage renal failure. Thus, modulating MRGPR X4 allows for treatment of autoimmune diseases such as psoriasis, multiple sclerosis, Steven Johnson's Syndrome, atopic disorders such as atopic dermatitis and other chronic itch conditions as explained in more detail below.

MRGPRs appear to be sensory receptors that recognize their external environment to exogenous or endogenous signals/chemicals. These receptors likely respond to multiple chemical ligands/agonists. For example MRGPR X4 recognizes bilirubin, bile acids, and urobilin as agonist signals. In certain embodiments, molecules of this invention modulate MRGPR X4 by functioning as inverse agonists that are capable of blocking multiple chemical entities, and/or as competitive antagonists that can specifically block individual ligands. In one embodiment, such modulations are selective against other MRGPRs, such as MRGPR X1, X2 and/or X3.

Accordingly, in one embodiment, methods for modulating a MRGPR X4 are provided comprising contacting the MRGPR X4 with an effective amount of compound having the structure of Formula (I):

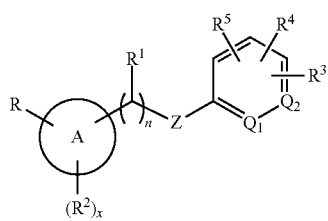

or a pharmaceutically acceptable isomer, racemate, hydrate, solvate, isotope, or salt thereof, wherein:
n is 0 or 1;
x is 0, 1 or 2;
A is aryl or heteroaryl;
$Q_1$ and $Q_2$ are both $CR^{10}$, or one of $Q_1$ or $Q_2$ is $CR^{10}$ and the other is N;
Z is —O—, —S—, —N($R^{11}$)—, —$CH_2$— or —C≡C—;
each $R^{10}$ is H or alkyl;
R is —$(CH_2)_m C(=O)OR^{12}$, —$(CH_2)_m NHR^{13}$, —(C=O)$NR^{14}R^{15}$, —$CH_2OH$, —CN, haloalkyl, carbocycle, heterocycle, or a carboxylic acid isostere;
m is 0 or 1;

$R^{11}$, $R^{12}$ and $R^{13}$ are the same or different and individually H or alkyl;
$R^{14}$ is H and $R^{15}$ is H, —$SO_2CH_3$, carbocycle, heterocyle, or alkyl substituted with 0, 1, 2 or 3 substituents selected from —OH, —CN, —NR'R", C(=O)OH, C(=O)NR'R", —$SO_2OH$, alkoxy, carbocycle, or heterocycle, wherein R' and R" are individually H or alkyl, or $R^{14}$ and $R^{15}$ are taken together with the nitrogen atom to which they are attached to form heterocycle;
$R^1$ is H or alkyl;
$R^2$ is halo, cyano, amino, alkyl, alkoxy, carbocycle or heterocycle;
$R^3$, $R^4$ and $R^5$ are the same or different and either absent or, when present, cyano, nitro, halogen, alkyl, haloalkyl, cyanoalkyl, alkoxy, haloalkoxy, —(C=O)alkyl, —(C=O)NHalkyl, carbocycle, heterocycle, —O-carbocycle or —O-heterocycle, or any two R and $R^2$ taken together with the atoms to which they are attached form heterocycle;
any two $R^3$, $R^4$, $R^5$ and $R^{10}$, taken together with the atoms to which they are attached form carbocycle or heterocycle;
and wherein each occurrence of carbocycle or heterocycle is substituted with 0, 1, 2 or 3 substituents individually selected from halogen, hydroxyl, oxo, halo, alkyl, haloalkyl, alkoxy, haloalkoxy, carbocycle, or heterocycle.

"Modulating" MRGPR X4 means that the compound interacts with the MRGPR X4 in a manner such that it functions as an inverse agonist to the receptor, and/or as a competitive antagonist to the receptor. In one embodiment, such modulation is partially or fully selective against other MRGPRs, such as MRGPR X1, X2 and/or X3.

"MRGPR" refers to one or more of the Mas-related G protein coupled receptors, which are a group of orphan receptors with limited expression in very specialized tissues (e.g., in sensory neurons and dorsal root ganglia) and barrier tissues. There are eight related receptors in this class expressed in humans, only 4 of which have readily identifiable orthologs in other species (i.e., MRGPR D, E, F and G). The other four receptors (MRGPR X1, X2, X3 and X4) have no counterpart, based on homology, in non-human species.

"Effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

"Alkyl" means a saturated or unsaturated straight chain or branched alkyl group having from 1 to 8 carbon atoms, in some embodiments from 1 to 6 carbon atoms, in some embodiments from 1 to 4 carbon atoms, and in some embodiments from 1 to 3 carbon atoms. Examples of saturated straight chain alkyl groups include, but are not limited to, methyl, ethyl, n-propyl, n-butyl, n-pentyl-, n-hexyl, n-heptyl, and n-octyl groups. Examples of branched alkyl groups include, but are not limited to, isopropyl, iso-butyl, sec-butyl, t-butyl, neopentyl, isopentyl, and 2,2- dimethylpropyl groups. An unsaturated alkyl includes alkenyl and alkynyl as defined below.

"Alkenyl" means a straight chain or branched alkenyl group having from 2 to 8 carbon atoms, in some embodiments from 2 to 6 carbon atoms, in some embodiments from 2 to 4 carbon atoms, and in some embodiments from 2 to 3 carbon atoms. Alkenyl groups are unsaturated hydrocarbons that contain at least one carbon-carbon double bond. Examples of lower alkenyl groups include, but are not limited to, vinyl, propenyl, butenyl, pentenyl, and hexenyl.

"Alkynyl" means a straight chain or branched alkynyl group having from 2 to 8 carbon atoms, in some embodiments from 2 to 6 carbon atoms, in some embodiments from 2 to 4 carbon atoms, and in some embodiments from 2 to 3 carbon atoms. Alkynyl groups are unsaturated hydrocarbons that contain at least one carbon-carbon triple bond. Examples of alkynyl groups include, but are not limited to, ethynyl, propynyl, butynyl, pentynyl, and hexynyl.

"Halo" or "halogen" refers to fluorine, chlorine, bromine, and iodine.

"Hydroxy" refers to —OH.

"Cyano" refers to —CN.

Amino refers to —NH$_2$, —NHalkyl or N(alkyl)$_2$, wherein alkyl is as defined above. Examples of amino include, but are not limited to —NH$_2$, —NHCH$_3$, —N(CH$_3$)$_2$, and the like.

"Haloalkyl" refers to alkyl as defined above with one or more hydrogen atoms replaced with halogen. Examples of lower haloalkyl groups include, but are not limited to, —CF$_3$, —CHF$_2$, and the like.

"Alkoxy" refers to alkyl as defined above joined by way of an oxygen atom (i.e., —O-alkyl). Examples of alkoxy groups include, but are not limited to, methoxy, ethoxy, n-propoxy, n-butoxy, isopropoxy, sec-butoxy, tert-butoxy, and the like.

"Haloalkoxy" refers to haloalkyl as defined above joined by way of an oxygen atom (i.e., —O-haloalkyl). Examples of lower haloalkoxy groups include, but are not limited to, —OCF$_3$, and the like.

"Cycloalkyl" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"Aryl" groups are cyclic aromatic hydrocarbons that do not contain heteroatoms. Representative aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The terms "aryl" and "aryl groups" include fused rings wherein at least one ring, but not necessarily all rings, are aromatic, such as fused aromatic-aliphatic ring systems (e.g., indanyl, tetrahydronaphthyl, and the like). In one embodiment, aryl is phenyl or naphthyl, and in another embodiment aryl is phenyl.

"Carbocycle" refers to alkyl groups forming a ring structure, which can be substituted or unsubstituted, wherein the ring is either completely saturated, partially unsaturated, or fully unsaturated, wherein if there is unsaturation, the conjugation of the pi-electrons in the ring may give rise to aromaticity. In one embodiment, carbocycle includes cycloalkyl as defined above. In another embodiment, carbocycle includes aryl as defined above.

"Heterocycle" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heteroaryl" refers to aromatic ring moieties containing 5 or more ring members, of which, one or more is a heteroatom such as, but not limited to, N, O, and S. Heteroaryl groups include, but are not limited to, groups such as pyrrolyl, pyrazolyl, pyridinyl, pyridazinyl, pyrimidyl, pyrazyl, pyrazinyl, pyrimidinyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl, and 2,3-dihydro indolyl.

"Carboxylic acid isostere" refers to a group that serves as a surrogate to a carboxylic acid group (i.e., —COOH). Use of a carboxylic acid isostore may be preferable to a carboxylic acid group for a number or reasons, including greater selectivity, reduced side effects, decreased toxicity, improved pharmacokinetics, increased stability, and/or simplified synthesis. Carboxylic acid isosteres include hydroxamic acids, acylcyanamides, sulfonamides, phosphonic acids, phosphinc acids, cyanoacetamides, sulfonates, sulfonamides, acylsulfonamides, arylsulfonamides, sulfonylureas, tetrazoles, thiazolidinediones, oxazolidinediones, isoxazoles, isothiazoles, squaric acids, 3-hydroxyquinolin-2-ones, 4-hydroxyquinolin-2-ones, 5-oxo-1,2,4-oxadiazoles, 5-oxo-1,2,4-thiadiazoles, 5-thioxo-1,2,4-oxadiazoles, hydroxyisoxazoles, phenols, tetramic acids, tetronic acids, cyclopentane-1,3-diones, 6-hydroxy-1,3-dioxin-4ones, 3-hydroxypyridin-4(1H)-ones, and oxadiazolones.

In an embodiment, a carboxylic acid isostere may be acyclic and have one of the following structures (wherein $R^a$ is alkyl, carbocycle, or heterocycle, wherein each of carbocycle and heterocycle may be singly or multiply substituted with $R^2$):

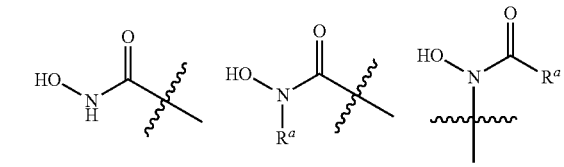

Hydroxamic acids

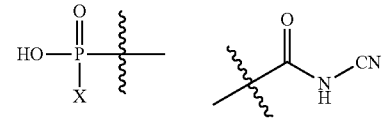

Phosphonic acids, X = O
Phosphinic acids, X = H     N-cyanoacetamide

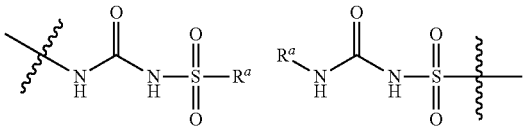

Acylsulfonamides

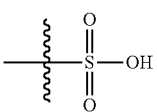

Sulfonylureas

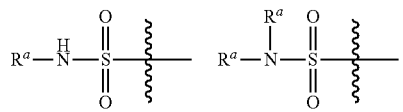

Sulfonic acid

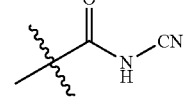

Sulfonamides

In another embodiment, a carboxylic acid isostere may be cyclic and have one of the following structures:

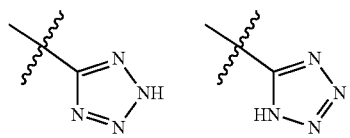

Tetrazoles

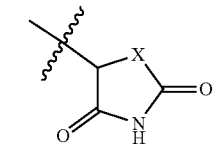

Thiazolidinediones, X = S
Oxazolidinediones, X = O

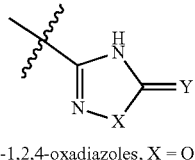

5-Oxo-1,2,4-oxadiazoles, X = O, Y = O
5-Oxo-1,2,4-thiadiazoles, X = S, Y = O
5-Thioxo-1,2,4-oxadiazoles, X = O, Y = S

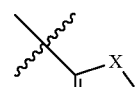

Isoxazoles, X = O
Isothiazoles, X = S

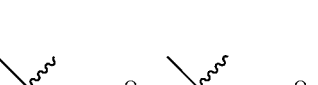

Squaric acids

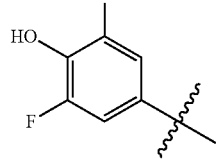

Phenols

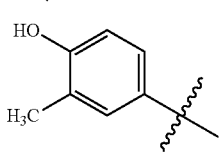

Tetramic acids, X = NH
Tetronic acids, X = O
Cyclopentane-1,3-diones, X = $CH_2$

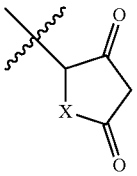

3-hydroxypyridin-4(1H)-ones

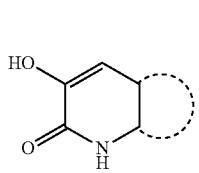

3- and 4-hydroxyquinolin-2-ones

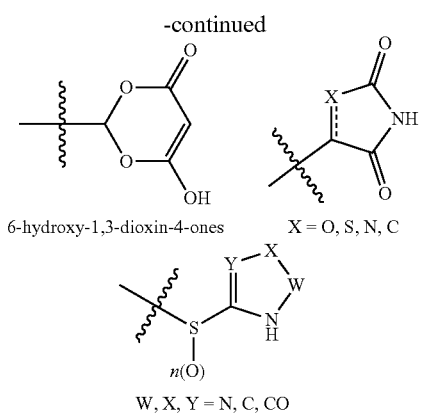

6-hydroxy-1,3-dioxin-4-ones       X = O, S, N, C

W, X, Y = N, C, CO

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of nonsuperimposable-isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure by weight. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out). All compounds with an asterisk (*) adjacent to a tertiary or quaternary carbon are optically active isomers, which may be purified from the respective racemate and/or synthesized by appropriate chiral synthesis.

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of Formula (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine-19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, *Int. J. Pharm.*, 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, Phydroxybutyric, salicylic, -galactaric, and galacturonic acid.

Although pharmaceutically unacceptable salts are not generally useful as medicaments, such salts may be useful, for example as intermediates in the synthesis of compounds having the structure of Formula I, for example in their purification by recrystallization.

In another embodiment, a method of treating a subject having a MRGPR X4 dependent condition is provided, the method comprising administering to the subject a pharmaceutically effective amount of a compound having the structure of Formula (I):

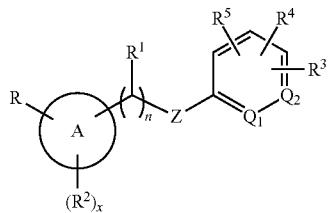

or a pharmaceutically acceptable isomer, racemate, hydrate, solvate, isotope, or salt thereof, wherein:
- n is 0 or 1;
- x is 0 or 1;
- A is aryl or heteroaryl;
- $Q_1$ and $Q_2$ are both $CR^{10}$, or one of $Q_1$ or $Q_2$ is $CR^{10}$ and the other is N;
- Z is —O—, —S—, —N($R^{11}$)—, —$CH_2$— or —C≡C—;
- each $R^{10}$ is H or alkyl;
- R is —$(CH_2)_m$C(=O)$OR^{12}$, —$(CH_2)_m$$NHR^{13}$, —(C=O)$NR^{14}R^{15}$, —$CH_2OH$, —CN, haloalkyl, carbocycle, heterocycle, or a carboxylic acid isostere;
- m is 0 or 1;
- $R^{11}$, $R^{12}$ and $R^{13}$ are the same or different and individually H or alkyl;
- $R^{14}$ is H and $R^{15}$ is H, —$SO_2CH_3$, carbocycle, heterocyle, or alkyl substituted with 0, 1, 2 or 3 substituents selected from —OH, —CN, —NR'R", C(=O)OH, C(=O)NR'R", —$SO_2OH$, alkoxy, carbocycle, or heterocycyle, wherein R' and R" are individually H or alkyl, or
- $R^{14}$ and $R^{15}$ are taken together with the nitrogen atom to which they are attached to form heterocycle;
- $R^1$ is H or alkyl;
- $R^2$ is halo, cyano, alkyl, alkoxy, carbocycle or heterocycle;
- $R^3$, $R^4$ and $R^5$ are the same or different and either absent or, when present, cyano, nitro, halogen, alkyl, haloalkyl, alkoxy, haloalkoxy, carbocycle, heterocycle, —O-carbocycle or —O-heterocycle, or
- any two R and $R^2$ taken together with the atoms to which they are attached form heterocycle;
- any two $R^3$, $R^4$, $R^5$ and $R^{10}$, taken together with the atoms to which they are attached form carbocycle or heterocycle;
- and wherein each occurrence of carbocycle or heterocycle is substituted with 0, 1, 2 or 3 substituents individually selected from halogen, oxo, halo, alkyl, haloalkyl, alkoxy, haloalkoxy, carbocycle, or heterocycle.

As used herein, the phrase "MRGPR X4 dependent condition" means a condition where the activation, over sensitization, or desensitization of MRGPR X4 by a natural or synthetic ligand initiates, mediates, sustains, or augments a pathological condition. For example, it is known that some itch or pain sensations are caused by elevated bilirubin and its metabolites or bile acids in patients suffering from pruritus, atopic or other autoimmune or inflammatory diseases. It has been found that MRGPR X4 is sensitive to (or activated by) bilirubin and its metabolites, including urobilin, or bile acids. Without limited by theory, it is to be understood that by modulating MRGPR X4, the itch or pain sensations can be eased.

In some embodiments, the MRGPR X4 dependent condition is a condition that is caused by the activation of MRGPR X4 by a bile acid. As used herein, the term "bile acid" includes primary bile acids (e.g., cholic acid, chenodeoxycholic acid), conjugated bile acids, also referred to as bile salts (e.g., taurocholic acid, glycocholic acid, taurochenodeoxycholic acid, glycochenodeoxycholic acid), secondary bile acids (e.g., deoxycholic acid, lithocholic acid), and bile acid analogs. In some embodiments, a bile acid analog is a farnesoid X-receptor (FXR) agonist. Thus, the compounds of the present disclosure may be used for treating an MRGPR X4 dependent condition caused by activation of MRGPR X4 by a bile acid and that would benefit from modulating MRGPR X4.

In some embodiments, the MRGPR X4 dependent condition is an itch associated condition, a pain associated condition, an autoimmune condition, or an autoimmune or inflammatory disorder.

As used herein, the phrase "itch associated condition" means pruritus (including acute and chronic pruritus) associated with any condition. The itch sensation can originate, e.g., from the peripheral nervous system (e.g., dermal or neuropathic itch) or from the central nervous system (e.g., neuropathic, neurogenic or psychogenic itch). Thus, in one embodiment, the method of present invention is provided to treat an itch associated condition, such as chronic itch; cholestatic pruritus; contact dermatitis; Allergic blepharitis; Anemia; Atopic dermatitis; Bullous pemphigoid; Candidiasis; Chicken pox; Cholestasis; end-stage renal failure; hemodialysis; Contact dermatitis, Atopic Dermatitis; Dermatitis herpetiformis; Diabetes; Drug allergy, Dry skin; Dyshidrotic dermatitis; Ectopic eczema; Erythrasma; Folliculitis; Fungal skin infection; Hemorrhoids; Herpes; HIV infection; Hodgkin's disease; Hyperthyroidism; Iron deficiency anemia; Kidney disease; Leukemia, porphyrias; Liver disease, including primary biliary cholangitis, primary sclerosing cholangitis, Alagille syndrome, Progressive familial intrahepatic cholestasis, Intrahepatic cholestasis of pregnancy, nonalcoholic steatohepatitis (NASH), nonalcoholic fatty liver disease (NAFLD), biliary atresia, chronic B hepatitis, drug-chronic viral hepatitis, induced liver injury (DILI), liver fibrosis, cholestatic liver disease, and alcoholic liver disease; Lymphoma; Malignancy; Multiple myeloma; Neurodermatitis; Onchocerciasis; Paget's disease; Pediculosis; Polycythemia *rubra* vera; Lichen Planus; Lichen Sclerosis; Pruritus ani; Pseudorabies; Psoriasis; Rectal prolapse; Scabies; Schistosomiasis; Scleroderma, Severe stress, Stasia dermatitis; Swimmer's itch; Thyroid disease; Tinea cruris; Uremic Pruritus; Rosacea; Cutaneous amyloidosis; Scleroderma; Acne; wound healing; ocular itch; and Urticaria.

As used herein, the phrase "pain associated condition" means any pain due to a medical condition. Thus, in one embodiment, the method of present invention is provided to treat a pain associated condition, such as Acute Pain, Advanced Prostate Cancer, AIDS-Related Pain, Ankylosing Spondylitis, Arachnoiditis, Arthritis, Arthrofibrosis, Ataxic Cerebral Palsy, Autoimmune Atrophic Gastritis, Avascular Necrosis, Back Pain, Behcet's Disease (Syndrome), Burning Mouth Syndrome, Bursitis, Cancer Pain, Carpal Tunnel, Cauda Equina Syndrome, Central Pain Syndrome, Cerebral Palsy, Cervical Stenosis, Charcot-Marie-Tooth (CMT) Disease, Chronic Fatigue Syndrome (CFS), Chronic Functional Abdominal Pain (CFAP), Chronic Pain, Chronic Pancreatitis, Collapsed Lung (Pneumothorax), Complex Regional Pain Syndrome (RSD), Corneal Neuropathic Pain, Crohn's Disease, Degenerative Disc Disease, Dercum's Disease, Dermatomyositis, Diabetic Peripheral Neuropathy (DPN), Dystonia, Ehlers-Danlos Syndrome (EDS), Endometriosis, Eosinophilia-Myalgia Syndrome (EMS), Erythromelalgia, Fibromyalgia, Gout, Headaches, Herniated disc, Hydrocephalus, Intercostal Neuraligia, Interstitial Cystitis, Irritable Bowel syndrome (IBS), Juvenile Dermatositis (Dermatomyositis), Knee Injury, Leg Pain, Loin Pain-Haematuria Syndrome, Lupus, Lyme Disease, Medullary Sponge Kidney (MSK), Meralgia Paresthetica, Mesothelioma, Migraine, Musculoskeletal pain, Myofascial Pain, Myositis, Neck Pain, Neuropathic Pain, Occipital Neuralgia, Osteoarthritis, Paget's Disease, Parsonage Turner Syndrome, Pelvic Pain, Peripheral Neuropathy, Phantom Limb Pain, Pinched Nerve, Polycystic Kidney Disease, Polymyalgia Rhuematica, Polymyositis, *Porphyria*, Post Herniorraphy Pain Syndrome, Post Mastectomy, Pain Syndrome, Post Stroke Pain, Post Thorocotomy Pain Syndrome, Postherpetic Neuralgia (Shingles), Post-Polio Syndrome, Primary Lateral Sclerosis, Psoriatic Arthritis, Pudendal Neuralgia, Radiculopathy, Raynaud's Disease, Rheumatoid Arthritis (RA), Sacroiliac Joint Dysfunction, Sarcoidosi, Scheuemann's Kyphosis Disease, Sciatica, Scoliosis, Shingles (Herpes Zoster), Sjogren's Syndrome, Spasmodic Torticollis, Sphincter of Oddi Dysfunction, Spinal Cerebellum Ataxia (SCA Ataxia), Spinal Cord Injury, Spinal Stenosis, Syringomyelia, Tarlov Cysts, Transverse Myelitis, Trigeminal Neuralgia, Neuropathic Pain, Ulcerative Colitis, Vascular Pain and Vulvodynia.

As used herein, the term "autoimmune disorder", or "inflammatory disorder" means a disease or disorder arising from and/or directed against an individual's own tissues or organs, or a co-segregate or manifestation thereof, or resulting condition therefrom. Typically, various clinical and laboratory markers of autoimmune diseases may exist including, but not limited to, hypergammaglobulinemia, high levels of autoantibodies, antigen-antibody complex deposits in tissues, clinical benefit from corticosteroid or immunosuppressive treatments, and lymphoid cell aggregates in affected tissues. Thus, in one embodiment, the method of present invention is provided to treat an autoimmune disorder, such as chronic inflammation, Multiple Sclerosis, Steven Johnson's Syndrome, appendicitis, bursitis, colitis, cystitis, dermatitis, phlebitis, reflex sympathetic dystrophy/complex regional pain syndrome (rsd/crps), rhinitis, tendonitis, tonsillitis, acne vulgaris, reactive airway disorder, asthma, airway infection, autoinflammatory disease, celiac disease, chronic prostatitis, diverticulitis, glomerulonephritis, hidradenitis suppurativa, hypersensitivities, intestinal disorder, epithelial intestinal disorder, inflammatory bowel disease, irritable bowel syndrome, colitis, interstitial cystitis, otitis, pelvic inflammatory disease, endometrial pain, reperfusion injury, rheumatic fever, rheumatoid arthritis, sarcoidosis, transplant rejection, psoriasis, lung inflammation, chronic obstructive pulmonary disease, cardiovascular disease, and vasculitis.

As used herein, the term "administration" refers to providing a compound, or a pharmaceutical composition comprising the compound as described herein. The compound or composition can be administered by another person to the subject or it can be self-administered by the subject. Non-limiting examples of routes of administration are oral, parenteral (e.g., intravenous), or topical.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a MRGPR X4 dependent condition, such as an itch associated condition, a pain associated condition, or an autoimmune disorder. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

In another embodiment, the method of treating a subject having a MRGPR X4 dependent condition (e.g., an itch associated condition, a pain associated condition, an autoimmune condition, or an autoimmune disorder) described herein further comprises administering to the subject a pharmaceutically effective amount of a second therapeutic agent. In one embodiment, the itch associated condition is a liver disease. In one embodiment, the second therapeutic agent is a liver disease therapeutic agent. In one embodiment, the liver disease therapeutic agent is ursodeoxycholic acid (UDCA), norUrsodeoxycholic acid, cholestyramine, stanozolol, naltrexone, rifampicin, Alisol B 23-acetate (AB23A), curcumin, dihydroartemisinin, fenofibrate, bezafibrate, metronidazole, methotrexate, colchicine, metformin, betaine, glucagon, naltrexone, a farnesoid X-receptor (FXR) agonist, a peroxisome proliferator-activated receptor (PPAR) agonist, a thyroid hormone receptor beta (TRO) agonist, or any combination thereof.

Examples of FXR agonists that may be used in the methods described herein include obeticholic acid, Turofexorate isopropyl (WAY-362450), 3-(2,6-dichlorophenyl)-4-(3'-carboxy-2-chlorostilben-4-yl)oxymethyl-5-isopropylisoxazole (GW4064), PX20606 (PX-102), PX-101, INT-767, INT-787, TERN-101, altenusin, tropifexor (LJN452), nidufexor, turofexorate isopropyl, fexaramine, silymarin, silybin, hedragonic acid, cafestol, Cilofexor (GS-9674 or Px-104), EDP-305, BAR704, BAR502, EYP-001, RDX-023, AGN-242266, HPG-1860, MET-409, AGN-242256, EP-024297, IOT-022, M-480, INV-33, RDX023-02, or any combination thereof. In one embodiment, a FXR agonist is a bile acid or analog thereof (e.g., obeticholic acid, INT-767, INT-787, BAR502, hedragonic acid or BAR704) or a non-bile acid agonist (e.g., EDP-305, tropifexor, nidufexor, cilofexor, GW4064, Turofexorate isopropyl, fexaramine, PX20606 (PX-102), TERN-101, altenusin, silymarin, silybin, EYP-001, RDX023-2, AGN-242266, HPG-1860, MET-409, EP-024297, M-480, or cafestol).

In one embodiment, a PPAR agonist is a PPAR-alpha agonist, a PPAR-gamma agonist, a PPAR-delta agonist, a PPAR-alpha/gamma dual agonist, a PPAR alpha/delta dual agonist, a PPAR gamma/delta dual agonist, or PPAR alpha/gamma/delta pan agonist.

Examples of PPAR alpha agonists that may be used in the methods described herein include fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, and SRI 0171.

Examples of PPAR gamma agonists that may be used in the methods described herein include rosiglitazone, pioglitazone, deuterium-stabilized R-pioglitazone, efatutazone, ATx08-001, OMS-405, CHS-131, THR-0921, SER-150-DN, KDT-501, GED-0507-34-Levo, CLC-3001, and ALL-4.

Examples of PPAR delta agonists that may be used in the methods described herein include GW501516 (endurabol or ({4-[({4-methyl-2-[4-(trifluoromethyl)phenyl]-1,3-thiazol-5-yl}methyl)sulfanyl]-2-methylphenoxy} acetic acid)), MBX8025 (seladelpar or {2-methyl-4-[5-methyl-2-(4-trifluoromethyl-phenyl)-2H-[1,2,3]triazol-4-ylmethylsylfanyl]-phenoxy}-acetic acid), GW0742 ([4-[[[2-[3-fluoro-4-(trifluoromethyl)phenyl]-4-methyl-5-thiazolyl]methyl]thio]-2-methyl phenoxy] acetic acid), L165041, HPP-593, and NCP-1046.

Examples of PPAR alpha/gamma agonists that may be used in the methods described herein include saroglitazar, aleglitazar, muraglitazar, tesaglitazar, and DSP-8658.

Examples of PPAR alpha/delta agonists that may be used in the methods described herein include elafibranor and T913659.

Examples of PPAR gamma/delta agonists that may be used in the methods described herein include a conjugated linoleic acid (CLA) and T3D-959.

Examples of PPAR alpha/gamma/delta agonists that may be used in the methods described herein include IVA337 (lanifibranor), TTA (tetradecylthioacetic acid), bavachinin, GW4148, GW9135, bezafibrate, lobeglitazone, 2-(4-(5,6-methylenedioxybenzo[d]thiazol-2-yl)-2-methylphenoxy)-2-methylpropanoic acid (MHY2013), and CS038.

Examples of thyroid hormone receptor beta agonists that may be used in the methods described herein include sobetirome, eprotirome, GC-24, MGL-3196, MGL-3745, VK-2809, KB141 [3,5-dichloro-4-(4-hydroxy-3-isopropylphenoxy) phenylacetic acid], and MB07811 (2R,4S)-4-(3-chlorophenyl)-2-[(3,5-dimethyl-4-(4'-hydroxy-3'-isopropylbenzyl)phenoxy)methyl]-2-oxido-[1,3,2]-dioxaphosphonane).

The second therapeutic agent may be administered simultaneously, separately, or sequentially with the compounds of the present disclosure. If administered simultaneously, the second therapeutic agent and compound of the present disclosure may be administered in separate dosage forms or in the same dosage form.

In another embodiment, a method of treating a subject having an itch associated condition is provided, the method comprising administering to the subject a pharmaceutically effective amount of a compound having the structure of Formula (I) or pharmaceutically acceptable isomer, racemate, hydrate, solvate, isotope or salt thereof, or a pharmaceutical composition thereof. In one embodiment, the itch associated condition is cholestatic pruritus, uremic pruritus, atopic dermatitis, dry skin, psoriasis, contact dermatitis, or eczema.

In one embodiment of Formula (I), n is 1, $R^1$ is H, Z is O, R is —C(=O)O$R^{12}$, and the compound has the structure of Formula (II):

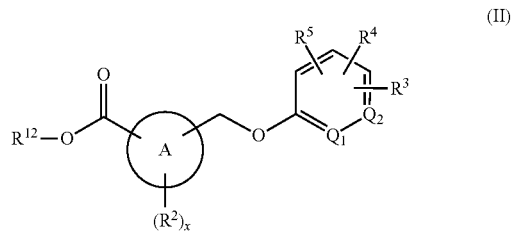

or a pharmaceutically acceptable isomer, racemate, hydrate, solvate, isotope, or salt thereof, wherein x, A, $Q_1$, $Q_2$, $R^2$, $R^3$, $R^4$, $R^5$ and $R^{12}$ are as defined above.

In one embodiment of Formula (I), n is 0, Z is O and the compound has the structure of Formula (III):

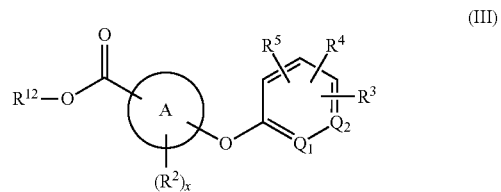

or a pharmaceutically acceptable isomer, racemate, hydrate, solvate, isotope, or salt thereof, wherein x, A, $Q_1$, $Q_2$, $R^2$, $R^3$, $R^4$, $R^5$ and $R^{12}$ are as defined above.

In one embodiment of Formula (II), x is 0 and the compound has the structure of Formula (IV):

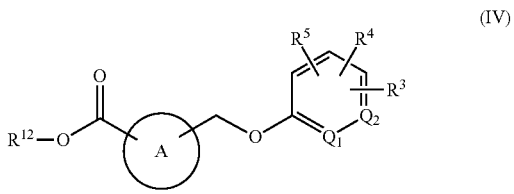

or a pharmaceutically acceptable isomer, racemate, hydrate, solvate, isotope, or salt thereof, wherein A, $Q_1$, $Q_2$, $R^3$, $R^4$, $R^5$ and $R^{12}$ are as defined above.

In one embodiment of Formula (II), x is 1 and the compound has the structure of Formula (V):

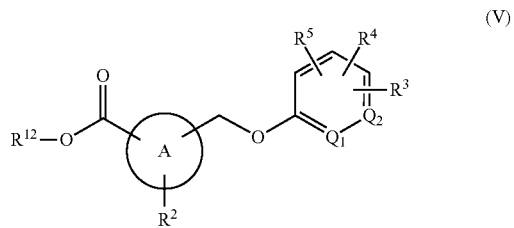

or a pharmaceutically acceptable isomer, racemate, hydrate, solvate, isotope, or salt thereof, wherein A, $Q_1$, $Q_2$, $R^2$, $R^3$, $R^4$, $R^5$ and $R^{12}$ are as defined above.

In one embodiment of Formula (III), x is 0 and the compound has the structure of Formula (VI):

(VI)

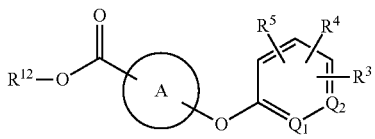

or a pharmaceutically acceptable isomer, racemate, hydrate, solvate, isotope, or salt thereof, wherein x, A, $Q_1$, $Q_2$, $R^3$, $R^4$, $R^5$ and $R^{12}$ are as defined above.

In one embodiment of Formula (III), x is 1 and the compound has the structure of Formula (VII):

(VII)

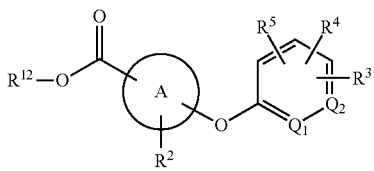

or a pharmaceutically acceptable isomer, racemate, hydrate, solvate, isotope, or salt thereof, wherein x, A, $Q_1$, $Q_2$, $R^2$, $R^3$, $R^4$, $R^5$ and $R^{12}$ are as defined above.

In another embodiment, when $R^{12}$ is hydrogen in each of Formulas (II) through (VII) the resulting carboxylic acid group (—COOH) is replaced with a carboxylic acid isostere as defined herein.

In one embodiment of Formula (I), n is 1, $R^1$ is H, Z is O, R is —(C=O)NHR$^{15}$, —CH$_2$OH, —CH$_2$NH$_2$ or —CN, and the compound has the structure of Formula (VIII), (IX), (X) or (XI), respectively:

(VIII)

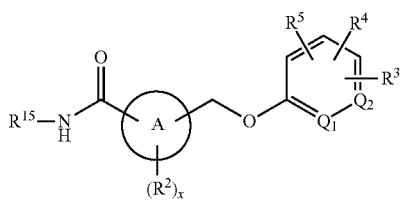

(IX)

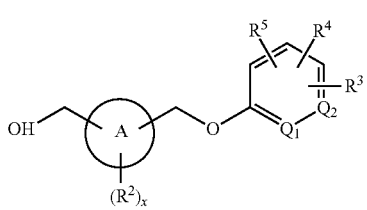

(X)

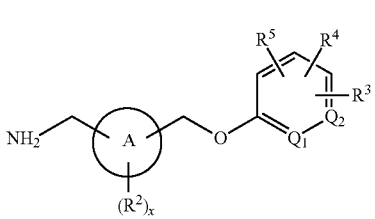

(XI)

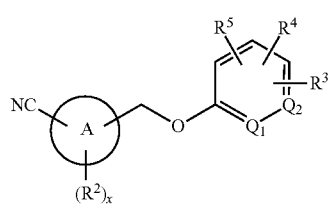

or a pharmaceutically acceptable isomer, racemate, hydrate, solvate, isotope, or salt thereof, wherein x, A, $Q_1$, $Q_2$, $R^2$, $R^3$, $R^4$, $R^5$ and R" are as defined above.

In one embodiment of Formula (I), n is 0, Z is O, R is —(C=O)NHR$^{15}$, —CH$_2$OH, —CH$_2$NH$_2$ or —CN, and the compound has the structure of Formula (XII), (XIII), (XIV) or (XV), respectively:

(XII)

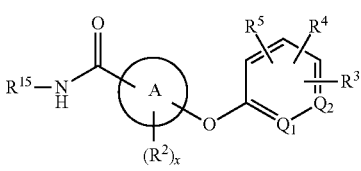

(XIII)

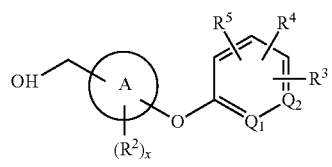

(XIV)

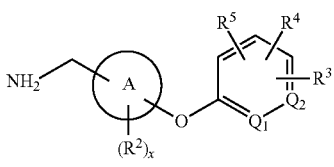

(XV)

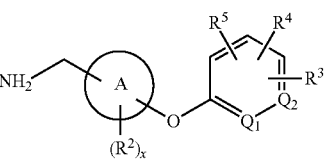

or a pharmaceutically acceptable isomer, racemate, hydrate, solvate, isotope, or salt thereof, wherein x, A, $Q_1$, $Q_2$, $R^2$, $R^3$, $R^4$, $R^5$ and $R^{15}$ are as defined above.

In one embodiment of Formula (I), Z is —S—, —N(R$^{11}$)—, —CH$_2$— or —C≡C— and the compound has the structure of Formula (XVI), (XVII), (XVIII) or (IX), respectively:

(XVI)

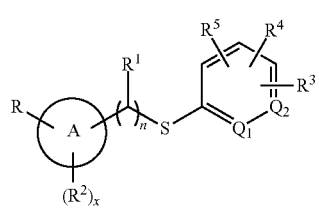

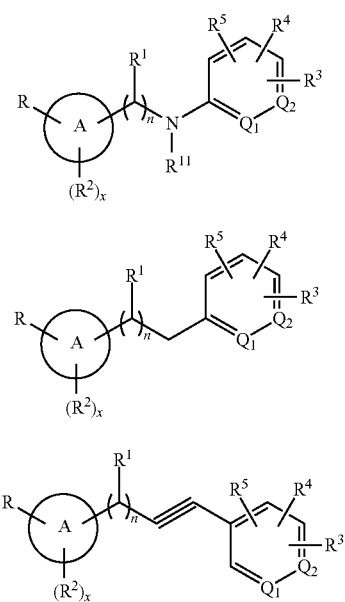

(XVII)

(XVIII)

(XIX)

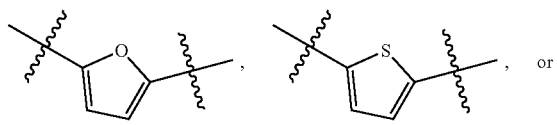, or

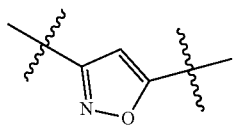

or a pharmaceutically acceptable isomer, racemate, hydrate, solvate, isotope, or salt thereof, wherein n, x, A, $Q_1$, $Q_2$, R, $R^1$, $R^2$, $R^3$, $R^4$, $R^5$ and $R^{11}$ are as defined above.

In one embodiment of any one of Formulas (I) through (XIX), A is aryl.

In one embodiment of any one of Formulas (I) through (XIX), A is phenyl.

In one embodiment of any one of Formulas (I) through (XIX), A is phenyl with the following points of attachment:

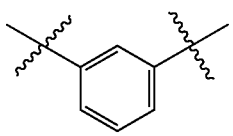 [SMILES: *c1cccc(*)c1]

In one embodiment of any one of Formulas (I) through (XIX), A is heteroaryl.

In one embodiment of any one of Formulas (I) through (XIX), A is pyridine or pyrazine.

In one embodiment of any one of Formulas (I) through (XIX), A is pyridine or pyrazine with the following points of attachment, respectively:

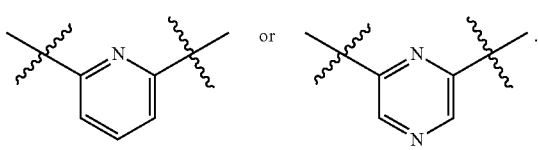 [SMILES: *c1cccc(*)n1 ; *c1cncc(*)n1]

In one embodiment of any one of Formulas (I) through (XIX), A is furan, thiophene or isoxazole.

In one embodiment of any one of Formulas (I) through (XIX), A is furan, thiophene or isoxazole with the following points of attachment, respectively:

In one embodiment of any one of Formulas (I) through (XIX), $Q_1$ and $Q_2$ are both CH.

In one embodiment of any one of Formulas (I) through (XIX), $Q_1$ is CH and $Q_2$ is N.

In one embodiment of any one of Formulas (I) through (XIX), $Q_1$ is N and $Q_2$ is CH.

In one embodiment of any one of Formulas (I) through (XIX), $R^1$ is hydrogen.

In one embodiment of any one of Formulas (I) through (XIX), $R^1$ is alkyl.

In one embodiment of any one of Formulas (I) through (XIX), $R^1$ is methyl.

In one embodiment of Formula (I), the compound has the structure of Formula (XX):

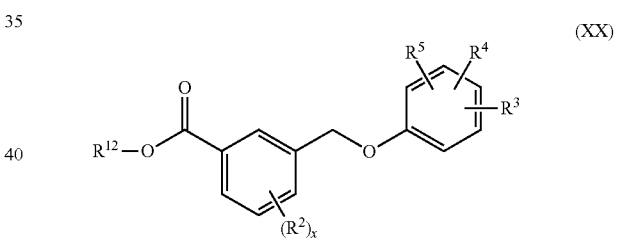

(XX)

or a pharmaceutically acceptable isomer, racemate, hydrate, solvate, isotope, or salt thereof, wherein x, $R^2$, $R^3$, $R^4$, $R^5$ and $R^{12}$ are as defined above.

In one embodiment of Formula (I), the compound has the structure of Formula (XXI):

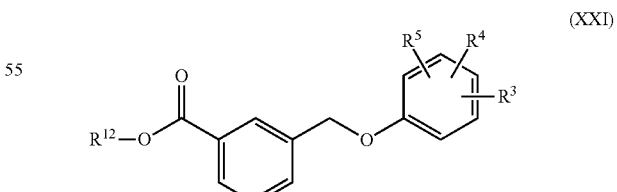

(XXI)

or a pharmaceutically acceptable isomer, racemate, hydrate, solvate, isotope, or salt thereof, wherein $R^3$, $R^4$, $R^5$ and $R^{12}$ are as defined above.

In one embodiment of Formula (I), the compound has the structure of Formula (XXII):

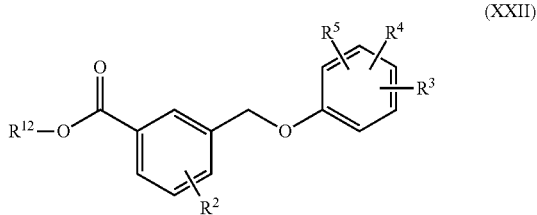

(XXII)

or a pharmaceutically acceptable isomer, racemate, hydrate, solvate, isotope, or salt thereof, wherein $R^2$, $R^3$, $R^4$, $R^5$ and $R^{12}$ are as defined above.

In another embodiment, when $R^{12}$ in hydrogen in each of Formulas (XX) through (XXII) above the resulting carboxylic acid group (—COOH) is replaced with a carboxylic acid isostere as defined herein.

In one embodiment of Formula (I), the compound has the structure of Formula (XXIII):

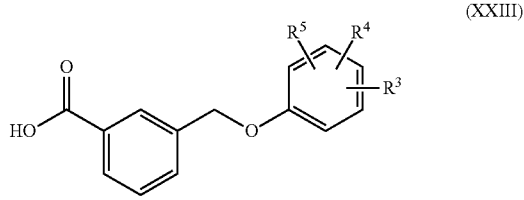

(XXIII)

or a pharmaceutically acceptable isomer, racemate, hydrate, solvate, isotope, or salt thereof, wherein $R^3$, $R^4$ and $R^5$ are as defined above.

In one embodiment of Formula (I), the compound has the structure of Formula (XXIV):

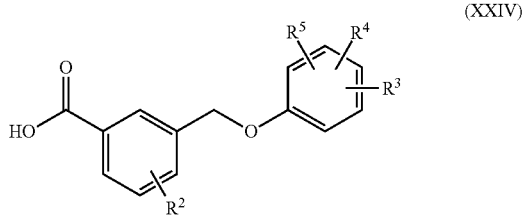

(XXIV)

or a pharmaceutically acceptable isomer, racemate, hydrate, solvate, isotope, or salt thereof, wherein $R^2$, $R^3$, $R^4$ and $R^5$ are as defined above.

In another embodiment, the carboxylic acid group (—COOH) of each of Formulas (XXIII) and (XXIV) above is replaced with a carboxylic acid isostere as defined herein.

In one embodiment of any one of Formulas (I) through (XXIV), n is 0.

In one embodiment of any one of Formulas (I) through (XXIV), n is 1.

In one embodiment of any one of Formulas (I) through (XXIV), x is 0.

In one embodiment of any one of Formulas (I) through (XXIV), x is 1.

In one embodiment of any one of Formulas (I) through (XXIV), x is 2.

In one embodiment of any one of Formulas (I) through (XXIV), A is aryl.

In one embodiment of any one of Formulas (I) through (XXIV), A is heteroaryl.

In one embodiment of any one of Formulas (I) through (XXIV), Z is —O—.

In one embodiment of any one of Formulas (I) through (XXIV), Z is —S—.

In one embodiment of any one of Formulas (I) through (XXIV), Z is —N($R^{11}$)—.

In one embodiment of any one of Formulas (I) through (XXIV), Z is —$CH_2$—.

In one embodiment of any one of Formulas (I) through (XXIV), Z is or —C≡C—.

In one embodiment of any one of Formulas (I) through (XXIV), R is —$(CH_2)_m$C(=O)$OR^{12}$.

In one embodiment of any one of Formulas (I) through (XXIV), R is —$(CH_2)_m$$NHR^{13}$.

In one embodiment of any one of Formulas (I) through (XXIV), R is —(C=O)$NR^{14}R^{15}$.

In one embodiment of any one of Formulas (I) through (XXIV), R is —$CH_2$OH.

In one embodiment of any one of Formulas (I) through (XXIV), R is —CN.

In one embodiment of any one of Formulas (I) through (XXIV), R is haloalkyl.

In one embodiment of any one of Formulas (I) through (XXIV), R is carbocycle.

In one embodiment of any one of Formulas (I) through (XXIV), R is heterocycle.

In one embodiment of any one of Formulas (I) through (XXIV), m is 0.

In one embodiment of any one of Formulas (I) through (XXIV), m is 1.

In one embodiment of any one of Formulas (I) through (XXIV), $R^{14}$ is H and $R^{15}$ is H, —$SO_2CH_3$, carbocycle, heterocyle, or alkyl substituted with 0, 1, 2 or 3 substituents selected from —OH, —CN, —NR'R", C(=O)OH, C(=O)NR'R", —$SO_2$OH, alkoxy, carbocycle, or heterocycle, wherein R' and R" are individually H or alkyl.

In one embodiment of any one of Formulas (I) through (XXIV), $R^{14}$ and $R^{15}$ are taken together with the nitrogen atom to which they are attached to form heterocycle.

In one embodiment of any one of Formulas (I) through (XXIV), $R^1$ is H.

In one embodiment of any one of Formulas (I) through (XXIV), $R^1$ is alkyl.

In one embodiment of any one of Formulas (I) through (XXIV), $R^2$ is halo.

In one embodiment of any one of Formulas (I) through (XXIV), $R^2$ is cyano.

In one embodiment of any one of Formulas (I) through (XXIV), $R^2$ is amino.

In one embodiment of any one of Formulas (I) through (XXIV), $R^2$ is alkyl.

In one embodiment of any one of Formulas (I) through (XXIV), $R^2$ is alkoxy.

In one embodiment of any one of Formulas (I) through (XXIV), $R^2$ is carbocycle.

In one embodiment of any one of Formulas (I) through (XXIV), $R^2$ is heterocycle.

In one embodiment of any one of Formulas (I) through (XXIV), $R^3$, $R^4$ and $R^5$ are the same or different and either absent or, when present, cyano, cyanoalkyl, nitro, halogen, alkyl, haloalkyl, alkoxy, haloalkoxy, —(C=O)alkyl, —(C=O)NHalkyl, carbocycle, heterocycle, —O-carbocycle or —O-heterocycle.

In one embodiment of any one of Formulas (I) through (XXIV), $R^3$, $R^4$ and $R^5$ are the same or different and either absent or, when present, cyano, nitro, halogen, alkyl, haloalkyl, alkoxy, or haloalkoxy.

In one embodiment of any one of Formulas (I) through (XXIV), $R^3$, $R^4$ and $R^5$ are the same or different and either absent or, when present, —CN, —NO$_2$, —F, —Cl, —Br, —CH$_3$, —CF$_3$, —CHF$_2$, —C(CH$_3$)$_3$, —OCH$_3$, or —OCF$_3$.

In one embodiment of any one of Formulas (I) through (XXIV), any two of $R^3$, $R^4$ and $R^5$ taken together with the atoms to which they are attached form carbocycle or heterocycle which is unsubstituted or substituted with 1, 2 or 3 substituents independently selected from halogen, hydroxyl, oxo, halo, alkyl, haloalkyl, alkoxy, haloalkoxy, carbocycle, or heterocycle.

In one embodiment of any one of Formulas (I) through (XXIV), $R^3$ and $R^4$ taken together with the atoms to which they are attached form heterocycle as depicted below which is unsubstituted or substituted with 1, 2 or 3 substituents independently selected from halogen, hydroxyl, oxo, halo, alkyl, haloalkyl, alkoxy, haloalkoxy, carbocycle, or heterocycle:

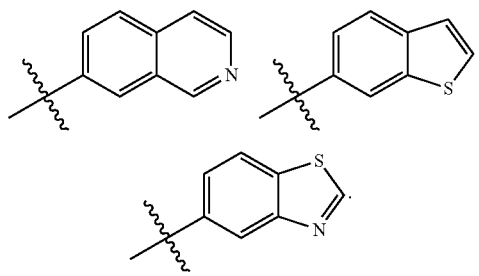 [SMILES: *c1ccc2ccncc2c1 ; *c1ccc2ccsc2c1 ; *c1ccc2scnc2c1]

In one embodiment of any one of Formulas (I) through (XXIV), $R^3$ and $R^4$ taken together with the atoms to which they are attached form carbocycle as depicted below which is unsubstituted or substituted with 1, 2 or 3 substituents independently selected from halogen, oxo, halo, alkyl, haloalkyl, alkoxy, haloalkoxy, carbocycle, or heterocycle:

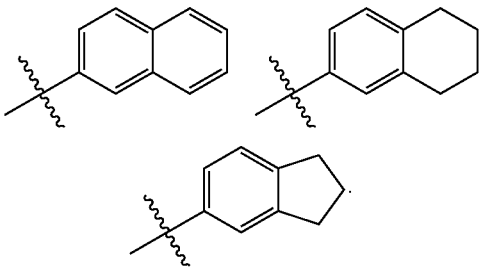 [SMILES: *c1ccc2ccccc2c1 ; *c1ccc2c(c1)CCCC2 ; *c1ccc2c(c1)CCC2]

Representative compounds of Formula (I), as well as Formulas (II) through (XXIV) as applicable, include any one of the compounds listed in Table A below, as well as a pharmaceutically acceptable isomer, racemate, hydrate, solvate, isotope, or salt thereof. To this end, representative compounds are identified herein by their respective "Compound Number", which is sometimes abbreviated as "Compound No." or "Cpd. No."

TABLE A

Representative Compounds

| Cpd. No. | Structure |
|---|---|
| 1-1 | 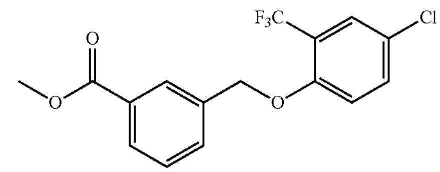 [SMILES: COC(=O)c1cccc(COc2ccc(Cl)cc2C(F)(F)F)c1] |
| 1-2 | 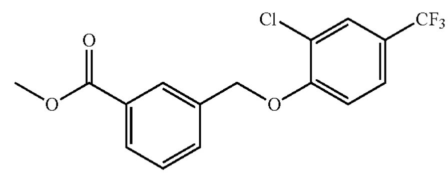 |
| 1-3 | 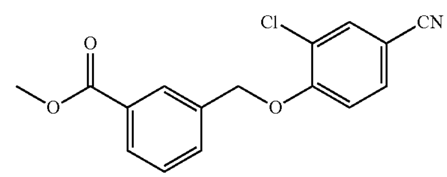 [SMILES: COC(=O)c1cccc(COc2ccc(C#N)cc2Cl)c1] |
| 1-4 | 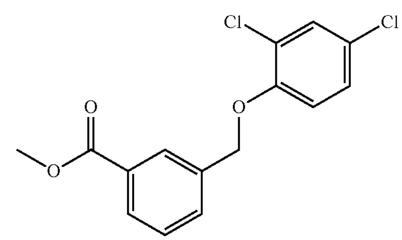 [SMILES: COC(=O)c1cccc(COc2ccc(Cl)cc2Cl)c1] |
| 1-5 | 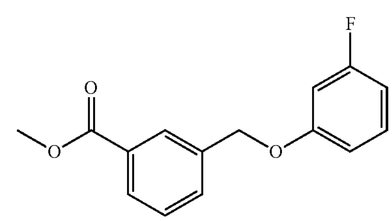 [SMILES: COC(=O)c1cccc(COc2cccc(F)c2)c1] |
| 1-6 | 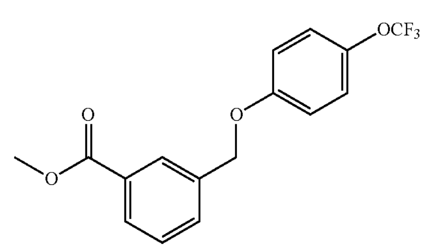 [SMILES: COC(=O)c1cccc(COc2ccc(OC(F)(F)F)cc2)c1] |
| 1-7 | 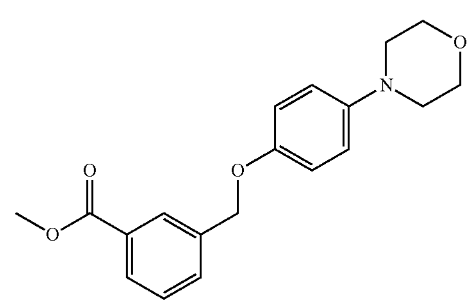 [SMILES: COC(=O)c1cccc(COc2ccc(N3CCOCC3)cc2)c1] |

TABLE A-continued

Representative Compounds

| Cpd. No. | Structure |
|---|---|
| 1-8 | (methyl 3-((benzo[d]thiazol-6-yloxy)methyl)benzoate) |
| 1-9 | (methyl 6-((2,4-dichlorophenoxy)methyl)pyrazine-2-carboxylate) |
| 1-10 | (methyl 6-((4-chloro-2-(trifluoromethyl)phenoxy)methyl)picolinate) |
| 1-11 | (methyl 6-((2-chloro-4-(trifluoromethyl)phenoxy)methyl)picolinate) |
| 1-12 | (methyl 6-((naphthalen-2-yloxy)methyl)picolinate) |
| 1-13 | (methyl 6-((4-chloro-2-methylphenoxy)methyl)picolinate) |
| 1-14 | (methyl 5-((2,4-dichlorophenoxy)methyl)thiophene-2-carboxylate) |
| 1-15 | (methyl 5-((2,4-dichlorophenoxy)methyl)isoxazole-3-carboxylate) |
| 1-16 | (3-((2-methyl-4-(trifluoromethyl)phenoxy)methyl)benzoic acid) |
| 1-17 | (3-((naphthalen-2-yloxy)methyl)benzoic acid) |
| 1-18 | (3-((2,4-dichlorophenoxy)methyl)benzoic acid) |
| 1-19 | (3-((2,5-dichlorophenoxy)methyl)benzoic acid) |

TABLE A-continued

Representative Compounds

| Cpd. No. | Structure |
|---|---|
| 1-20 | 3-methoxy-4-((4-chlorobenzyl)oxy)benzoic acid |
| 1-21 | 3-((4-chlorophenoxy)methyl)benzoic acid (with additional Cl) |
| 1-22 | 3-((2-chlorophenoxy)methyl)benzoic acid |
| 1-23 | 3-((4-chloro-2-fluorophenoxy)methyl)benzoic acid |
| 1-24 | 3-((2-chloro-4-fluorophenoxy)methyl)benzoic acid |
| 1-25 | 3-((2,6-dichlorophenoxy)methyl)benzoic acid |
| 1-26 | 5-((2,4-dichlorophenoxy)methyl)furan-2-carboxylic acid |
| 1-27 | 3-((2,4-dichlorophenoxy)methyl)-4-methoxybenzoic acid |
| 1-28 | 3-((4-chloro-2-(trifluoromethyl)phenoxy)methyl)benzoic acid |
| 1-29 | 3-((2-chloro-4-(trifluoromethyl)phenoxy)methyl)benzoic acid |
| 1-30 | 6-((naphthalen-2-yloxy)methyl)picolinic acid |
| 1-31 | 6-((4-chloro-2-(trifluoromethyl)phenoxy)methyl)picolinic acid |

TABLE A-continued

Representative Compounds

| Cpd. No. | Structure |
|---|---|
| 1-32 | 2-methoxy-5-[(2,4-dichlorophenoxy)methyl]benzoic acid |
| 1-33 | 3-[(2,3-dihydro-1H-inden-4-yloxy)methyl]benzoic acid |
| 1-34 | 3-[(4-cyanophenoxy)methyl]benzoic acid |
| 1-35 | 3-[(2-chloro-4-cyanophenoxy)methyl]benzoic acid |
| 1-36 | 6-[(4-chlorophenoxy)methyl]pyridine-2-carboxylic acid |
| 1-37 | 3-[(2-methoxyphenoxy)methyl]benzoic acid |
| 1-38 | 3-[(4-methoxyphenoxy)methyl]benzoic acid |
| 1-39 | 3-[(3-methoxyphenoxy)methyl]benzoic acid |
| 1-40 | 3-[(2-fluorophenoxy)methyl]benzoic acid |
| 1-41 | 3-[(4-trifluoromethylphenoxy)methyl]benzoic acid |
| 1-42 | 3-[(2,3-dihydro-1H-inden-5-yloxy)methyl]benzoic acid |
| 1-43 | 5-[(2,4-dichlorophenoxy)methyl]thiophene-2-carboxylic acid |

TABLE A-continued

Representative Compounds

| Cpd. No. | Structure |
|---|---|
| 1-44 | |
| 1-45 | |
| 1-46 | |
| 1-47 | |
| 1-48 | |
| 1-49 | |
| 1-50 | 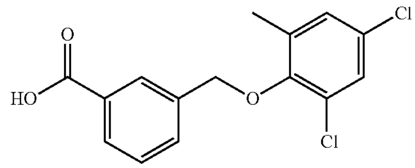 [SMILES: Cc1cc(Cl)cc(Cl)c1OCc1cccc(C(=O)O)c1] |
| 1-51 | 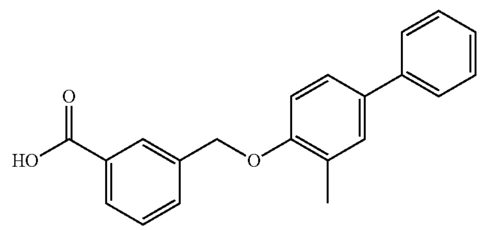 [SMILES: Cc1cc(-c2ccccc2)ccc1OCc1cccc(C(=O)O)c1] |
| 1-52 | 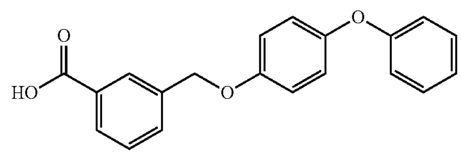 [SMILES: O=C(O)c1cccc(COc2ccc(Oc3ccccc3)cc2)c1] |
| 1-53 | 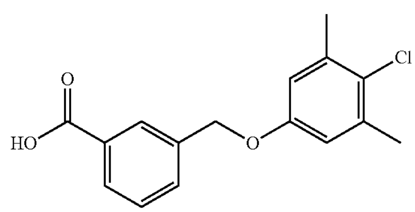 [SMILES: Cc1cc(OCc2cccc(C(=O)O)c2)cc(C)c1Cl] |
| 1-54 | 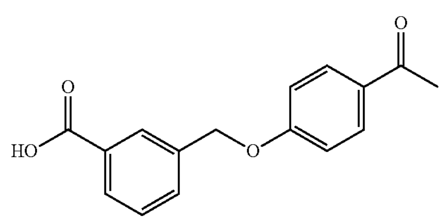 [SMILES: CC(=O)c1ccc(OCc2cccc(C(=O)O)c2)cc1] |
| 1-55 | 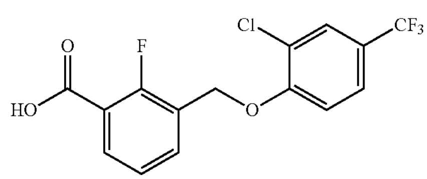 [SMILES: O=C(O)c1cccc(COc2ccc(C(F)(F)F)cc2Cl)c1F] |
| 1-56 | 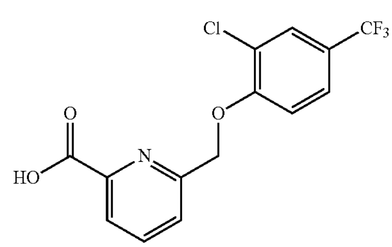 [SMILES: O=C(O)c1cccc(COc2ccc(C(F)(F)F)cc2Cl)n1] |

TABLE A-continued

Representative Compounds

| Cpd. No. | Structure |
|---|---|
| 1-57 | 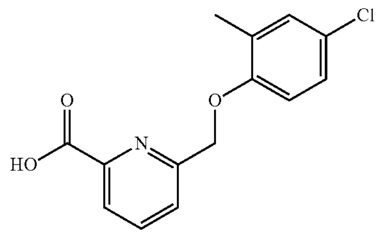 [SMILES: Cc1cc(Cl)ccc1OCc1cccc(C(=O)O)n1] |
| 1-58 | 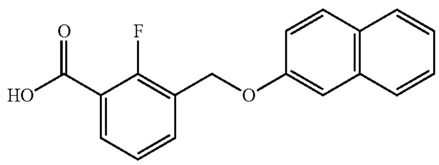 [SMILES: O=C(O)c1cccc(COc2ccc3ccccc3c2)c1F] |
| 1-59 | 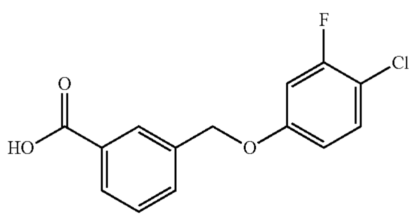 [SMILES: O=C(O)c1cccc(COc2ccc(Cl)c(F)c2)c1] |
| 1-60 | 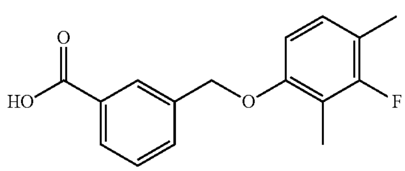 [SMILES: Cc1ccc(OCc2cccc(C(=O)O)c2)c(C)c1F] |
| 1-61 | 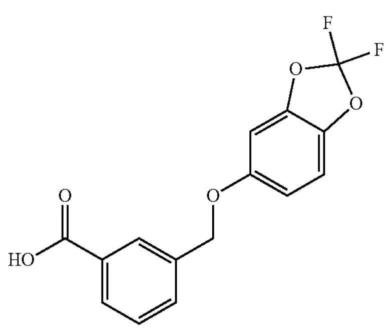 [SMILES: O=C(O)c1cccc(COc2ccc3c(c2)OC(F)(F)O3)c1] |
| 1-62 | 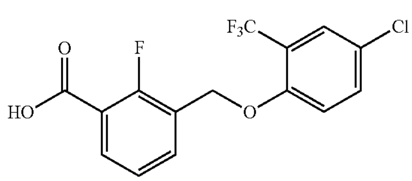 [SMILES: O=C(O)c1cccc(COc2ccc(Cl)cc2C(F)(F)F)c1F] |
| 1-63 | 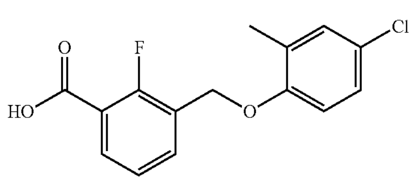 [SMILES: Cc1cc(Cl)ccc1OCc1cccc(C(=O)O)c1F] |
| 1-64 | |
| 1-65 | |
| 1-66 | |
| 1-67 | |
| 1-68 | |
| 1-69 | |
| 1-70 | |

TABLE A-continued
Representative Compounds
| Cpd. No. | Structure |
|---|---|
| 1-71 | 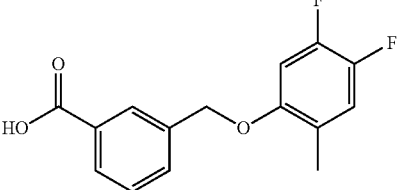 |
| 1-72 | 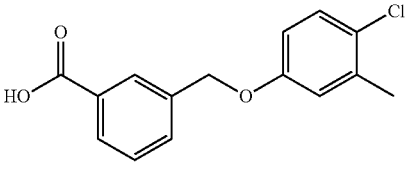 [SMILES: Cc1cc(OCc2cccc(C(=O)O)c2)ccc1Cl] |
| 1-73 | 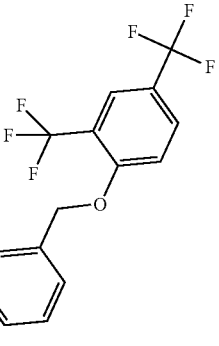 |
| 1-74 | 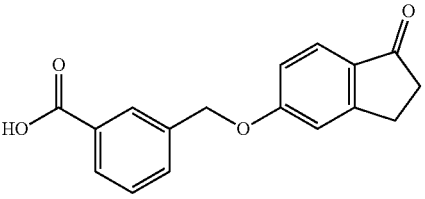 [SMILES: O=C(O)c1cccc(COc2ccc3c(c2)CCC3=O)c1] |
| 1-75 | 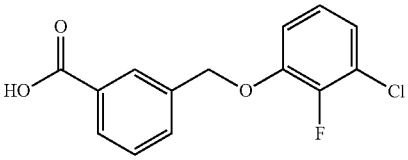 [SMILES: O=C(O)c1cccc(COc2cccc(Cl)c2F)c1] |
| 1-76 | 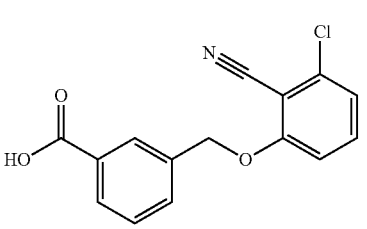 [SMILES: N#Cc1c(Cl)cccc1OCc1cccc(C(=O)O)c1] |
| 1-77 | 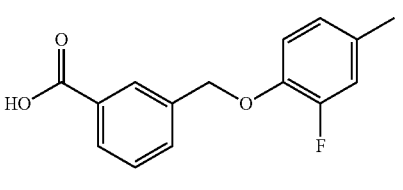 [SMILES: Cc1ccc(OCc2cccc(C(=O)O)c2)c(F)c1] |
| 1-78 | 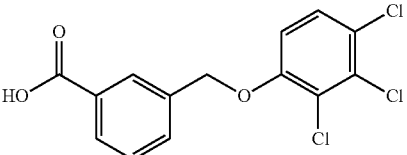 |
| 1-79 | 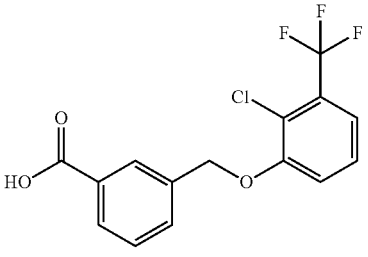 [SMILES: O=C(O)c1cccc(COc2cccc(C(F)(F)F)c2Cl)c1] |
| 1-80 | 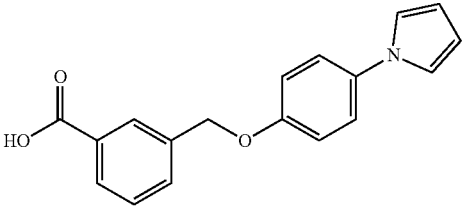 [SMILES: O=C(O)c1cccc(COc2ccc(-n3cccc3)cc2)c1] |
| 1-81 | 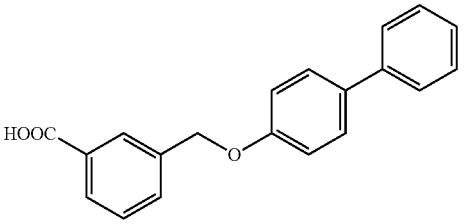 [SMILES: O=C(O)c1cccc(COc2ccc(-c3ccccc3)cc2)c1] |
| 1-82 | 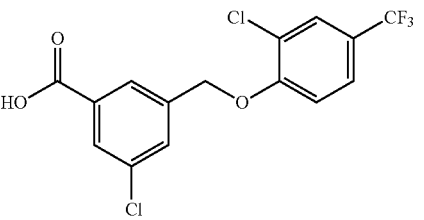 |
| 1-83 | 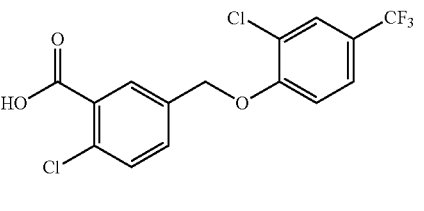 |
| 1-84 | 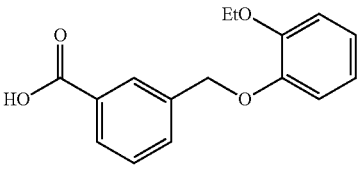 [SMILES: CCOc1ccccc1OCc1cccc(C(=O)O)c1] |

TABLE A-continued

Representative Compounds

| Cpd. No. | Structure |
|---|---|
| 1-85 | (2-chloro-4-trifluoromethylphenoxymethyl)-2-fluorobenzoic acid |
| 1-86 | 3-((4-isopropylphenoxy)methyl)benzoic acid |
| 1-87 | 3-((4-oxo-5,6,7,8-tetrahydronaphthalen-1-yloxy)methyl)benzoic acid |
| 1-88 | 3-((2-tert-butyl-5-methylphenoxy)methyl)benzoic acid |
| 1-89 | 3-((3-fluoro-4-methylphenoxy)methyl)benzoic acid |
| 1-90 | 3-((3-chloro-4-cyanophenoxy)methyl)benzoic acid |
| 1-91 | 3-((4-fluoro-2-(trifluoromethyl)phenoxy)methyl)benzoic acid |
| 1-92 | 3-((2-chloro-4-methoxyphenoxy)methyl)benzoic acid |
| 1-94 | 3-((4-fluoro-2-methylphenoxy)methyl)benzoic acid |
| 1-95 | 3-((3-chloro-2-methylphenoxy)methyl)benzoic acid |
| 1-96 | 3-((2,3-difluoro-4-methoxyphenoxy)methyl)benzoic acid |
| 1-97 | 3-((benzo[b]thiophen-6-yloxy)methyl)benzoic acid |
| 1-98 | 3-((isoquinolin-7-yloxy)methyl)benzoic acid |
| 1-99 | 3-((4-cyano-2-methylphenoxy)methyl)benzoic acid |
| 1-100 | 3-((3-(difluoromethyl)phenoxy)methyl)benzoic acid |

TABLE A-continued

Representative Compounds

| Cpd. No. | Structure |
|---|---|
| 1-101 | 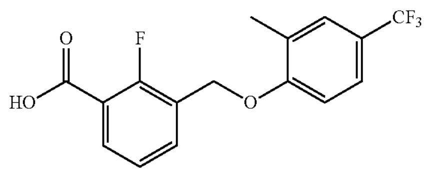 [SMILES: Cc1cc(C(F)(F)F)ccc1OCc1cccc(C(=O)O)c1F] |
| 1-102 | 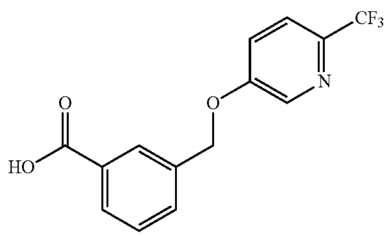 [SMILES: O=C(O)c1cccc(COc2ccc(C(F)(F)F)nc2)c1] |
| 1-103 | 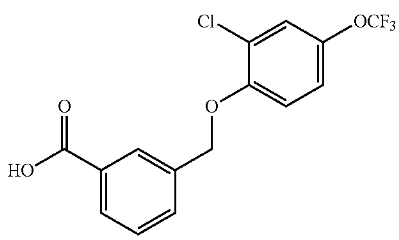 [SMILES: O=C(O)c1cccc(COc2ccc(OC(F)(F)F)cc2Cl)c1] |
| 1-108 | 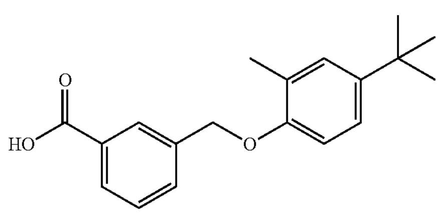 [SMILES: Cc1cc(C(C)(C)C)ccc1OCc1cccc(C(=O)O)c1] |
| 1-109 | 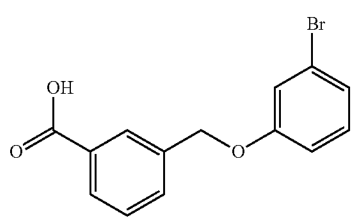 [SMILES: O=C(O)c1cccc(COc2cccc(Br)c2)c1] |
| 1-110 | 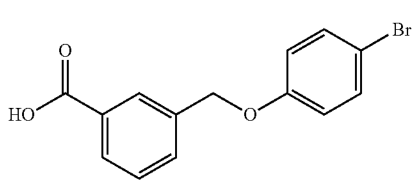 [SMILES: O=C(O)c1cccc(COc2ccc(Br)cc2)c1] |
| 1-112 | 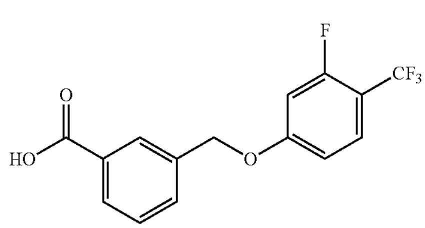 |
| 1-113 | |
| 1-114 | |
| 1-115 | |
| 1-116 | |
| 1-117 | |
| 1-118 | |

TABLE A-continued
Representative Compounds
| Cpd. No. | Structure |
|---|---|
| 1-119 | 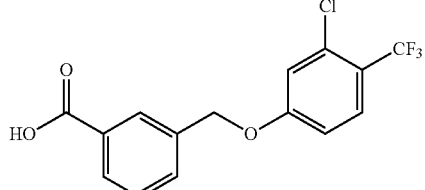 |
| 1-120 | 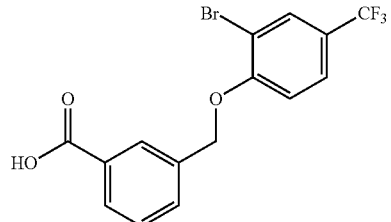 |
| 1-121 | 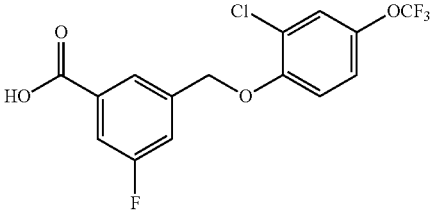 [SMILES: O=C(O)c1cc(F)cc(COc2ccc(OC(F)(F)F)cc2Cl)c1] |
| 1-122 | 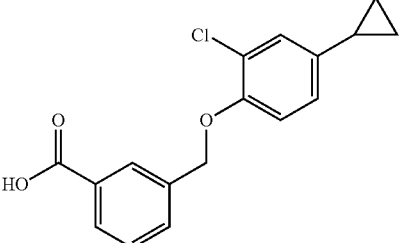 |
| 1-123 | 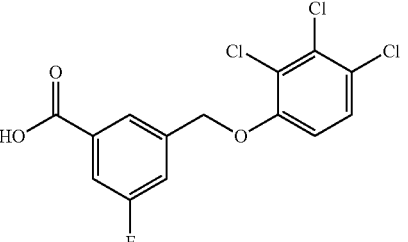 |
| 1-124 | 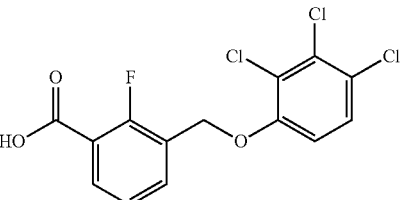 |
| 1-125 | 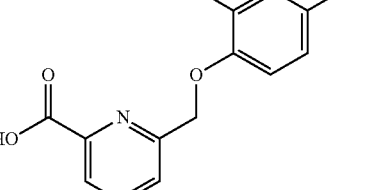 |
| 1-126 | 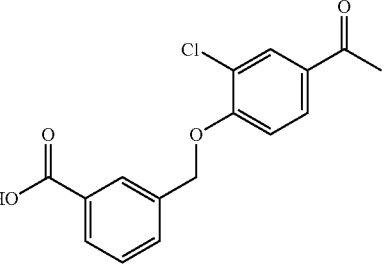 |
| 1-127 | 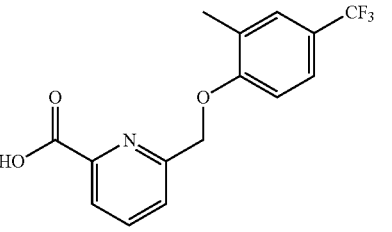 |
| 1-128 | 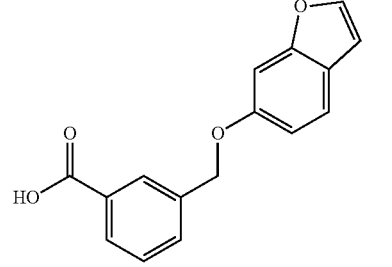 |
| 1-129 | 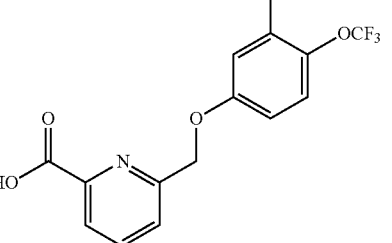 |
| 1-130 | 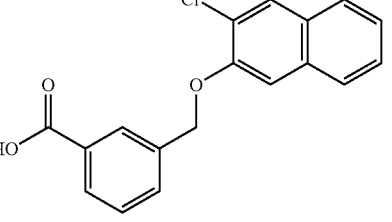 |

TABLE A-continued

Representative Compounds

| Cpd. No. | Structure |
|---|---|
| 1-131 | |
| 1-132 | |
| 1-133 | |
| 1-134 | |
| 1-135 | |
| 1-136 | 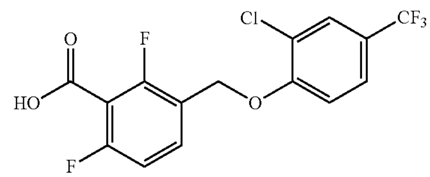 [SMILES: O=C(O)c1c(F)ccc(COc2ccc(C(F)(F)F)cc2Cl)c1F] |
| 1-137 | 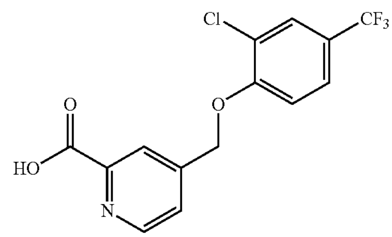 [SMILES: O=C(O)c1cc(COc2ccc(C(F)(F)F)cc2Cl)ccn1] |
| 1-138 | 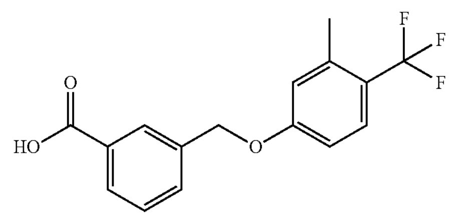 [SMILES: Cc1cc(OCc2cccc(C(=O)O)c2)ccc1C(F)(F)F] |
| 1-139 | 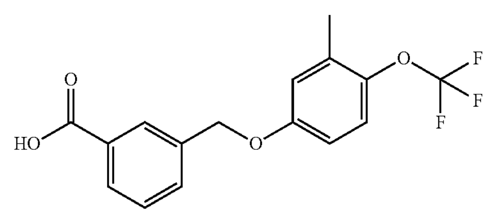 [SMILES: Cc1cc(OCc2cccc(C(=O)O)c2)ccc1OC(F)(F)F] |
| 1-140 | 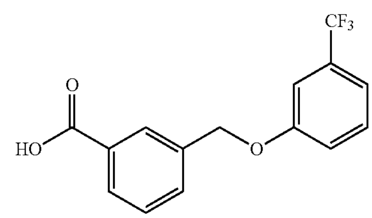 [SMILES: O=C(O)c1cccc(COc2cccc(C(F)(F)F)c2)c1] |
| 1-141 | 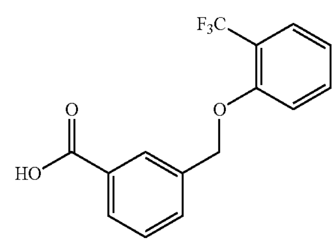 [SMILES: O=C(O)c1cccc(COc2ccccc2C(F)(F)F)c1] |
| 1-142 | 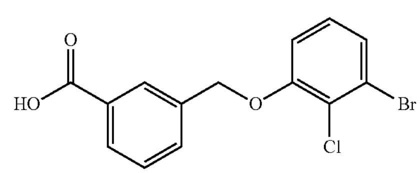 [SMILES: O=C(O)c1cccc(COc2cccc(Br)c2Cl)c1] |

TABLE A-continued
Representative Compounds
| Cpd. No. | Structure |
|---|---|
| 1-143 | 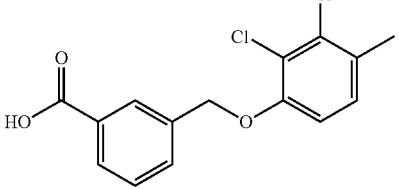 |
| 1-144 | 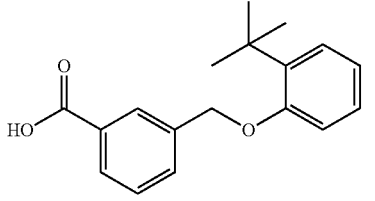 [SMILES: CC(C)(C)c1ccccc1OCc1cccc(C(=O)O)c1] |
| 1-145 | 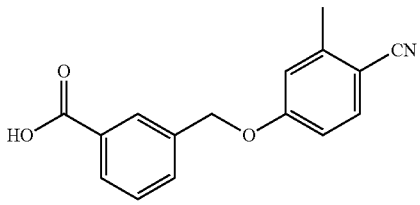 [SMILES: Cc1cc(OCc2cccc(C(=O)O)c2)ccc1C#N] |
| 1-146 | 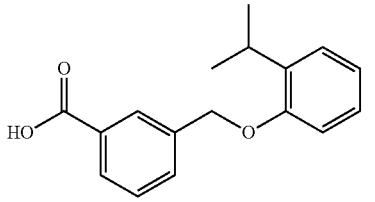 [SMILES: CC(C)c1ccccc1OCc1cccc(C(=O)O)c1] |
| 1-147 | 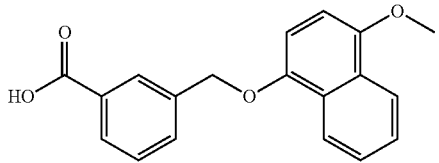 [SMILES: COc1ccc(OCc2cccc(C(=O)O)c2)c2ccccc12] |
| 1-148 | 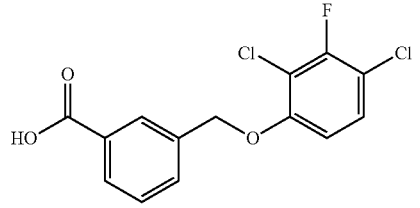 [SMILES: O=C(O)c1cccc(COc2ccc(Cl)c(F)c2Cl)c1] |
| 1-149 | 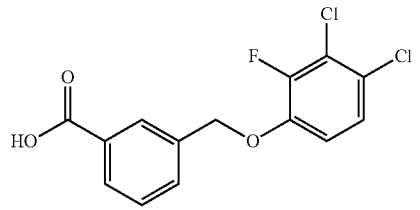 [SMILES: O=C(O)c1cccc(COc2ccc(Cl)c(Cl)c2F)c1] |
| 1-150 | 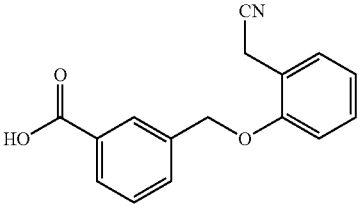 [SMILES: N#CCc1ccccc1OCc1cccc(C(=O)O)c1] |
| 1-151 | |
| 1-152 | |
| 1-153 | |
| 1-154 | |
| 2-1 | |

TABLE A-continued

Representative Compounds

| Cpd. No. | Structure |
|---|---|
| 2-2 | 3-methoxy-5-((2-chloro-4-(trifluoromethyl)phenoxy)methyl)benzoic acid |
| 2-3 | 3-bromo-5-((2-chloro-4-(trifluoromethyl)phenoxy)methyl)benzoic acid |
| 2-4 | 4-methyl-6-((2,3,4-trichlorophenoxy)methyl)picolinic acid |
| 3-1 | 3-((2,4-dichlorophenoxy)methyl)benzonitrile |
| 3-2 | 3-((2-chloro-4-methylphenoxy)methyl)benzoic acid |
| 3-3 | 3-(([1,1'-biphenyl]-3-yloxy)methyl)benzoic acid |
| 3-4 | 3-((2,3-dichlorophenoxy)methyl)benzoic acid |
| 3-5 | 3-((4-chloro-2-methylphenoxy)methyl)benzoic acid |
| 3-6 | 3-((3,4-dichlorophenoxy)methyl)benzoic acid |
| 3-7 | 3-((2,4-dimethylphenoxy)methyl)benzoic acid |
| 3-8 | 3-((2,4-dichlorobenzyloxy)methyl)benzoic acid |
| 3-9 | 3-((3,5-dichlorophenoxy)methyl)benzoic acid |
| 4-1 | 3-((2,4-dichlorophenoxy)methyl)-2-fluorobenzoic acid |
| 4-2 | 3-((2,4-dichlorophenoxy)methyl)-4-fluorobenzoic acid |

TABLE A-continued

Representative Compounds

| Cpd. No. | Structure |
|---|---|
| 4-3 | 2-fluoro-5-[(2,4-dichlorophenoxy)methyl]benzoic acid |
| 4-4 | 3-fluoro-5-[(2,4-dichlorophenoxy)methyl]benzoic acid |
| 4-5 | 3-methoxy-5-[(2,4-dichlorophenoxy)methyl]benzoic acid |
| 4-6 | 2-cyano-3-[(2,4-dichlorophenoxy)methyl]benzoic acid |
| 4-7 | 3-methyl-5-[(2,4-dichlorophenoxy)methyl]benzoic acid |
| 4-8 | 2-methyl-3-[(2,4-dichlorophenoxy)methyl]benzoic acid |
| 4-9 | 2-chloro-3-[(2,4-dichlorophenoxy)methyl]benzoic acid |
| 4-10 | 3-methyl-5-[(2-chloro-4-trifluoromethylphenoxy)methyl]benzoic acid |
| 4-11 | 3-methyl-5-[(2-methyl-4-trifluoromethylphenoxy)methyl]benzoic acid |
| 4-12 | 3-methyl-5-[(naphthalen-2-yloxy)methyl]benzoic acid |
| 4-13 | 2-fluoro-3-[(2-chloro-4-trifluoromethoxyphenoxy)methyl]benzoic acid |
| 4-14 | 3-methyl-5-[(2-chloro-4-trifluoromethoxyphenoxy)methyl]benzoic acid |

TABLE A-continued

Representative Compounds

| Cpd. No. | Structure |
|---|---|
| 4-15 | (structure) |
| 4-16 | (structure) |
| 4-17 | (structure) |
| 4-18 | (structure) |
| 4-19 | (structure) |
| 4-20 | (structure) |
| 4-21 | (structure) |
| 4-22 | (structure) |
| 4-23 | (structure) |
| 4-24 | (structure) |
| 4-25 | (structure) |
| 4-26 | (structure) |
| 4-27 | (structure) |

TABLE A-continued

Representative Compounds

| Cpd. No. | Structure |
|---|---|
| 4-28 | |
| 4-29 | |
| 5-1 | 3-((2,4-dichlorophenoxy)methyl)-5-cyanobenzoic acid |
| 5-2 | 5-((2,4-dichlorophenoxy)methyl)-2-cyanobenzoic acid |
| 6-1 | 3-((2,4-dichlorophenoxy)methyl)-2-methoxybenzoic acid |
| 7-1 | (3-((2,4-dichlorophenoxy)methyl)phenyl)methanamine |
| 8-1 | 5-((2,4-dichlorophenoxy)methyl)-2-methylbenzoic acid |
| 8-2 | 3-((2,4-dichlorophenoxy)methyl)-4-methylbenzoic acid |
| 8-3 | 6-((2-chloro-4-(trifluoromethyl)phenoxy)methyl)-4-cyclopropylpicolinic acid |
| 8-4 | 5-((2-chloro-4-(trifluoromethyl)phenoxy)methyl)-[1,1'-biphenyl]-3-carboxylic acid |
| 9-1 | 4-bromo-6-((2-chloro-4-(trifluoromethyl)phenoxy)methyl)picolinic acid |
| 9-2 | 3-fluoro-5-((2-methyl-4-(trifluoromethyl)phenoxy)methyl)benzoic acid |
| 9-3 | 3-fluoro-5-((naphthalen-2-yloxy)methyl)benzoic acid |
| 10-1 | 3-(((5-(trifluoromethyl)pyridin-2-yl)oxy)methyl)benzoic acid |

TABLE A-continued

Representative Compounds

| Cpd. No. | Structure |
|---|---|
| 11-1 | 3-(cyclopropyl)-5-((2-chloro-4-(trifluoromethyl)phenoxy)methyl)benzoic acid |
| 12-1 | 3-(((2,4-dichlorophenyl)amino)methyl)benzoic acid |
| 12-2 | 3-((naphthalen-2-ylamino)methyl)benzoic acid |
| 12-3 | 6-(((2-chloro-4-(trifluoromethyl)phenyl)amino)methyl)picolinic acid |
| 12-4 | 3-(((2-chloro-4-(trifluoromethyl)phenyl)amino)methyl)benzoic acid |
| 13-1 | 3-((2,3-dichlorophenoxy)methyl)benzamide |
| 14-1 | (3-((2,4-dichlorophenoxy)methyl)phenyl)methanol |
| 15-1 | 3-(((2,4-dichlorophenyl)thio)methyl)benzoic acid |
| 16-1 | 3-(2,4-dichlorophenoxy)benzoic acid |
| 16-2 | 3-(2-chloro-4-nitrophenoxy)benzoic acid |
| 17-1 | 3-((2-chloro-4-(trifluoromethyl)phenoxy)methyl)benzonitrile |
| 17-2 | 5-(3-((3-chloro-4-(trifluoromethyl)phenoxy)methyl)phenyl)-1H-tetrazole |
| 17-3 | 5-(3-((4-chloro-2-(trifluoromethyl)phenoxy)methyl)phenyl)-1H-tetrazole |
| 17-4 | 5-(3-((2,3,4-trichlorophenoxy)methyl)phenyl)-1H-tetrazole |

TABLE A-continued

Representative Compounds

| Cpd. No. | Structure |
|---|---|
| 17-5 | 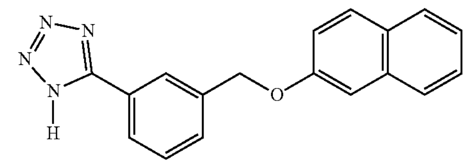 [SMILES: c1cc(COc2ccc3ccccc3c2)cc(-c2nnn[nH]2)c1] |
| 17-6 | 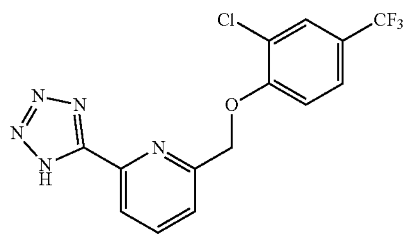 [SMILES: FC(F)(F)c1ccc(OCc2cccc(-c3nnn[nH]3)n2)c(Cl)c1] |
| 17-7 | 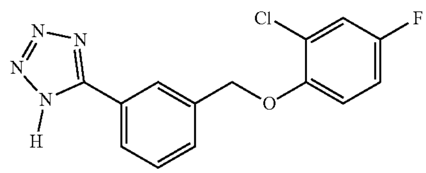 [SMILES: Fc1ccc(OCc2cccc(-c3nnn[nH]3)c2)c(Cl)c1] |
| 17-8 | 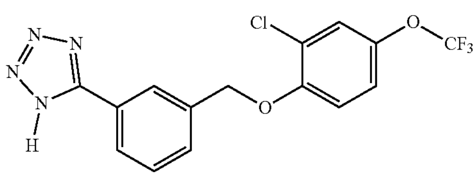 [SMILES: FC(F)(F)Oc1ccc(OCc2cccc(-c3nnn[nH]3)c2)c(Cl)c1] |
| 17-9 | 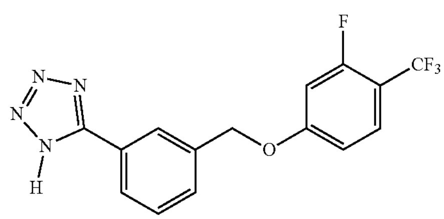 [SMILES: Fc1cc(OCc2cccc(-c3nnn[nH]3)c2)ccc1C(F)(F)F] |
| 17-10 | 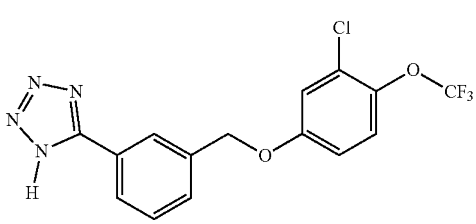 [SMILES: FC(F)(F)Oc1ccc(OCc2cccc(-c3nnn[nH]3)c2)cc1Cl] |
| 17-11 | 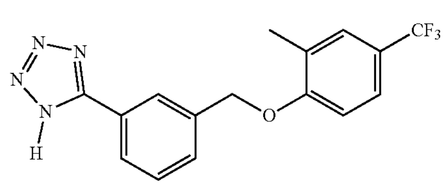 [SMILES: Cc1cc(C(F)(F)F)ccc1OCc1cccc(-c2nnn[nH]2)c1] |
| 17-12 | |
| 17-13 | |
| 17-14 | |
| 17-15 | |
| 17-16 | |
| 31-2 | |

TABLE A-continued

Representative Compounds

| Cpd. No. | Structure |
|---|---|
| 32-1 | 3-cyano-5-((2-chloro-4-(trifluoromethyl)phenoxy)methyl)benzoic acid |
| 32-2 | 3-cyano-5-((2-methyl-4-(trifluoromethyl)phenoxy)methyl)benzoic acid |
| 32-3 | 3-cyano-5-((2,3,4-trichlorophenoxy)methyl)benzoic acid |
| 32-4 | 3-cyano-5-((2-chloro-4-(trifluoromethoxy)phenoxy)methyl)benzoic acid |
| 32-5 | 3-cyano-5-((3-chloro-4-(trifluoromethyl)phenoxy)methyl)benzoic acid |
| 33-1 | 3-((2-(difluoromethyl)phenoxy)methyl)benzoic acid |
| 33-2 | 3-((4-(difluoromethyl)phenoxy)methyl)benzoic acid |
| 33-3 | 3-((2-chloro-4-(difluoromethyl)phenoxy)methyl)benzoic acid |
| 33-4 | 3-((2-fluoro-4-(difluoromethyl)phenoxy)methyl)benzoic acid |
| 34-1 | 3-((2-cyclopropyl-4-(trifluoromethyl)phenoxy)methyl)benzoic acid |
| 35-1 | 3-(((3-chloro-5-(trifluoromethyl)pyridin-2-yl)oxy)methyl)benzoic acid |

TABLE A-continued

Representative Compounds

| Cpd. No. | Structure |
|---|---|
| 36-1 | (structure) |
| 37-1 | (structure) |
| 38-1 | (structure) |
| 39-1 | (structure) |
| 40-1 | (structure) |
| 41-1 | (structure) |
| 41-2 | (structure) |
| 42-1 | (structure) |
| 42-2 | (structure) |
| 42-3 | (structure) |
| 43-1 | (structure) |
| 44-1 | (structure) |

TABLE A-continued
Representative Compounds
| Cpd. No. | Structure |
|---|---|
| 45-1 | 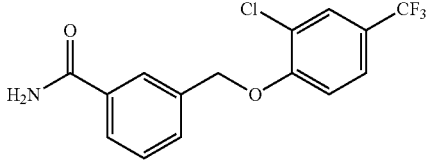 [SMILES: NC(=O)c1cccc(COc2ccc(C(F)(F)F)cc2Cl)c1] |
| 45-2 | 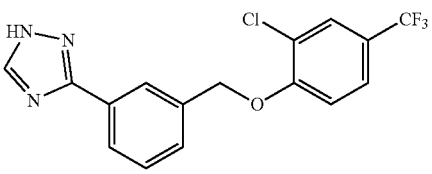 [SMILES: FC(F)(F)c1ccc(OCc2cccc(-c3nc[nH]n3)c2)c(Cl)c1] |
| 46-1 | 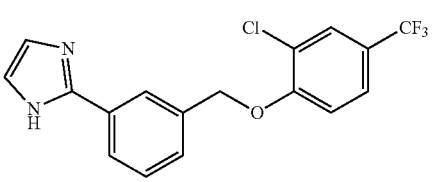 [SMILES: FC(F)(F)c1ccc(OCc2cccc(-c3ncc[nH]3)c2)c(Cl)c1] |
| 47-1 | 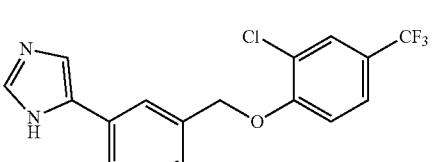 |
| 48-1 | 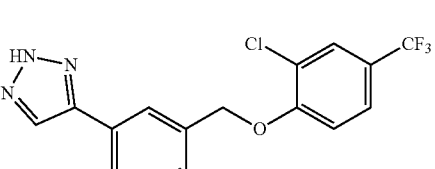 |
| 49-1 | 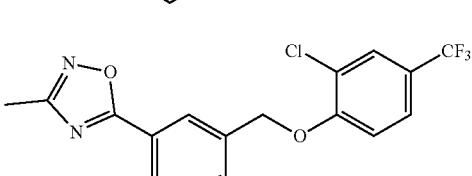 |
| 50-1 | 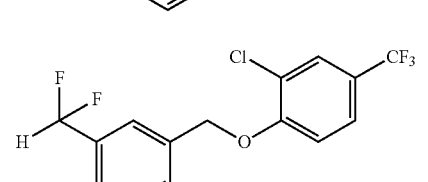 |
| 52-1 | 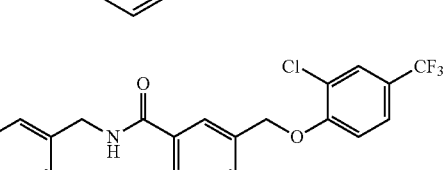 |
| 52-2 | 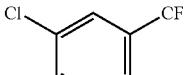 |
| 52-3 | 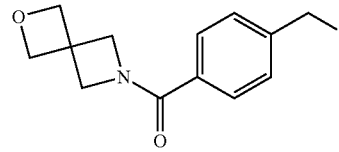 |
| 52-4 | 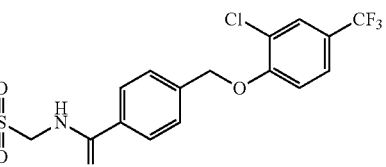 |
| 52-5 | 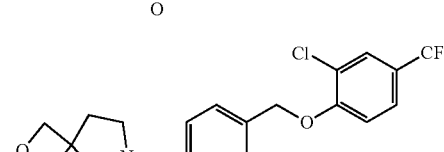 |
| 52-6 | 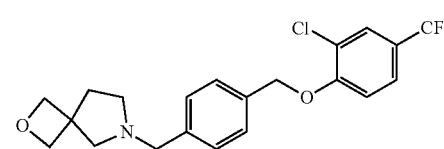 |
| 52-7 | 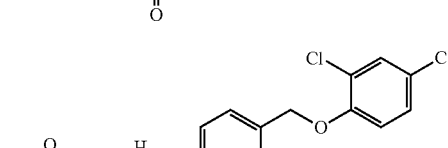 |
| 52-8 | 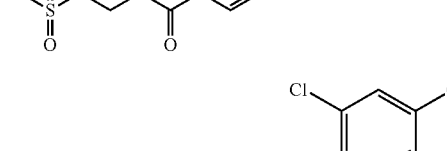 |
| 52-9 | 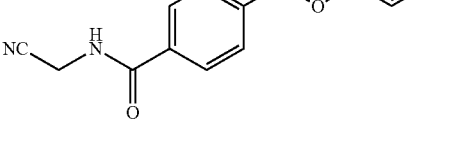 |

TABLE A-continued

Representative Compounds

| Cpd. No. | Structure |
|---|---|
| 52-10 | 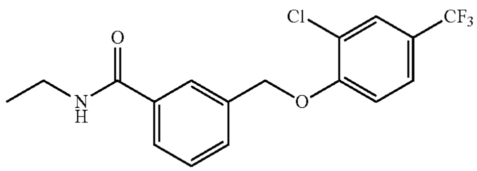 [SMILES: CCNC(=O)c1cccc(COc2ccc(C(F)(F)F)cc2Cl)c1] |
| 52-11 | 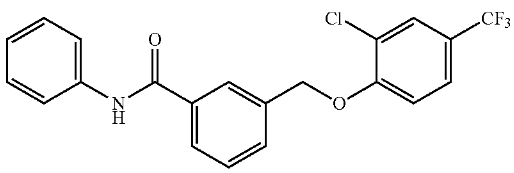 [SMILES: O=C(Nc1ccccc1)c1cccc(COc2ccc(C(F)(F)F)cc2Cl)c1] |
| 52-12 | 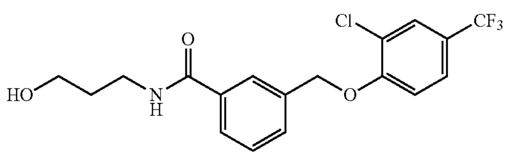 [SMILES: O=C(NCCCO)c1cccc(COc2ccc(C(F)(F)F)cc2Cl)c1] |
| 52-13 | 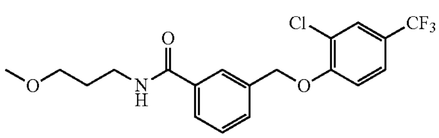 [SMILES: COCCCNC(=O)c1cccc(COc2ccc(C(F)(F)F)cc2Cl)c1] |
| 52-14 | 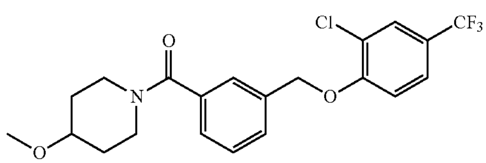 [SMILES: COC1CCN(C(=O)c2cccc(COc3ccc(C(F)(F)F)cc3Cl)c2)CC1] |
| 52-15 | 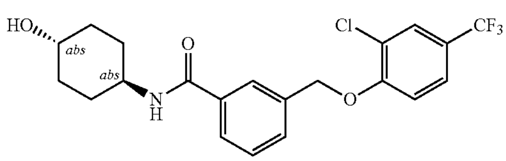 [SMILES: O=C(N[C@H]1CC[C@H](O)CC1)c1cccc(COc2ccc(C(F)(F)F)cc2Cl)c1] |
| 52-16 | 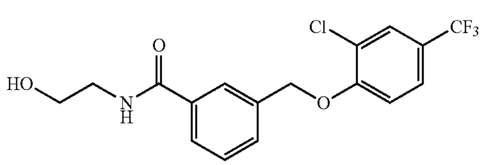 [SMILES: O=C(NCCO)c1cccc(COc2ccc(C(F)(F)F)cc2Cl)c1] |
| 52-17 | 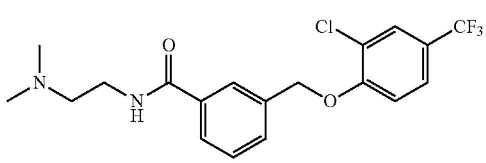 [SMILES: CN(C)CCNC(=O)c1cccc(COc2ccc(C(F)(F)F)cc2Cl)c1] |
| 52-18 | 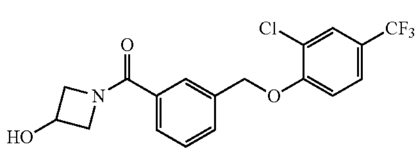 [SMILES: O=C(c1cccc(COc2ccc(C(F)(F)F)cc2Cl)c1)N1CC(O)C1] |
| 52-19 | |
| 52-20 | |
| 52-21 | |
| 52-22 | |
| 52-23 | |
| 52-24 | |
| 52-25 | |
| 52-26 | |

TABLE A-continued

Representative Compounds

| Cpd. No. | Structure |
|---|---|
| 52-27 | 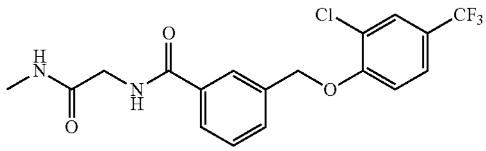 [SMILES: CNC(=O)CNC(=O)c1cccc(COc2ccc(C(F)(F)F)cc2Cl)c1] |
| 52-28 | 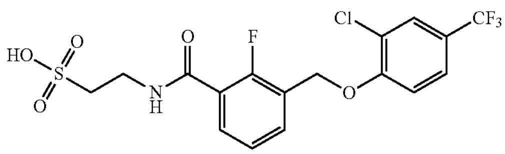 [SMILES: O=C(NCCS(=O)(=O)O)c1cccc(COc2ccc(C(F)(F)F)cc2Cl)c1F] |
| 53-1 | 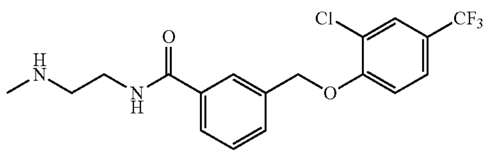 [SMILES: CNCCNC(=O)c1cccc(COc2ccc(C(F)(F)F)cc2Cl)c1] |
| 53-2 | 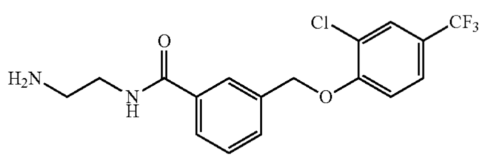 [SMILES: NCCNC(=O)c1cccc(COc2ccc(C(F)(F)F)cc2Cl)c1] |
| 54-1 | 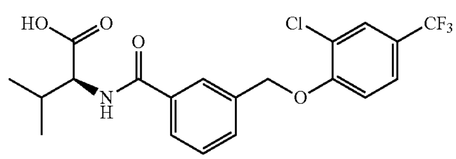 [SMILES: CC(C)[C@H](NC(=O)c1cccc(COc2ccc(C(F)(F)F)cc2Cl)c1)C(=O)O] |
| 54-2 | 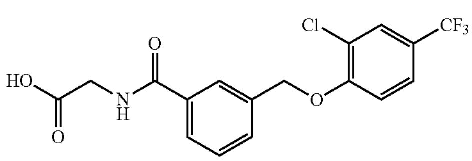 [SMILES: O=C(O)CNC(=O)c1cccc(COc2ccc(C(F)(F)F)cc2Cl)c1] |
| 54-3 | 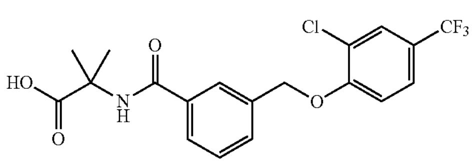 [SMILES: CC(C)(NC(=O)c1cccc(COc2ccc(C(F)(F)F)cc2Cl)c1)C(=O)O] |
| 54-4 | 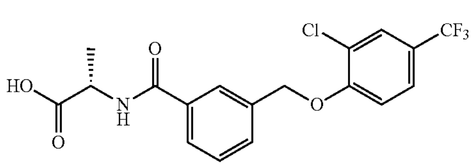 [SMILES: C[C@H](NC(=O)c1cccc(COc2ccc(C(F)(F)F)cc2Cl)c1)C(=O)O] |
| 54-5 | 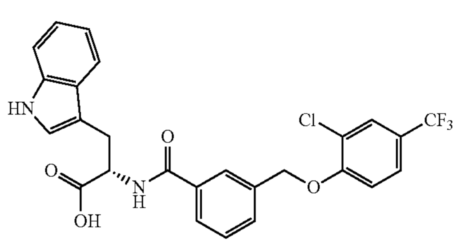 [SMILES: O=C(N[C@@H](Cc1c[nH]c2ccccc12)C(=O)O)c1cccc(COc2ccc(C(F)(F)F)cc2Cl)c1] |
| 54-6 | |
| 54-7 | |
| 54-8 | |
| 54-9 | |
| 54-10 | |
| 54-11 | |
| 54-12 | |
| 55-1 | |
| 55-2 | |

TABLE A-continued

Representative Compounds

| Cpd. No. | Structure |
|---|---|
| 55-3 | 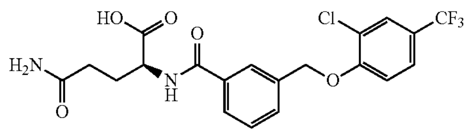 [SMILES: NC(=O)CC[C@H](NC(=O)c1cccc(COc2ccc(C(F)(F)F)cc2Cl)c1)C(=O)O] |
| 56-1 | 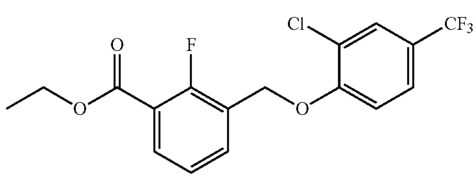 [SMILES: CCOC(=O)c1cccc(COc2ccc(C(F)(F)F)cc2Cl)c1F] |
| 56-2 | 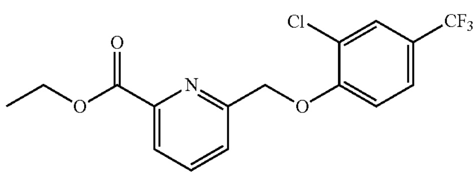 [SMILES: CCOC(=O)c1cccc(COc2ccc(C(F)(F)F)cc2Cl)n1] |
| 57-1 | 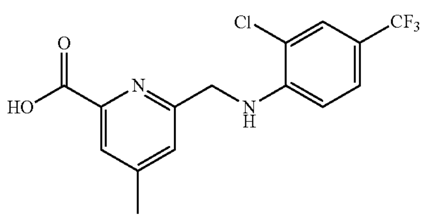 |
| 58-1 | 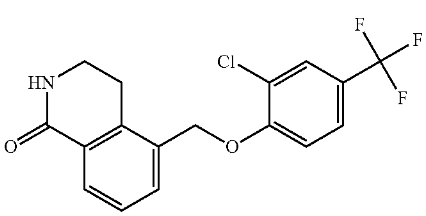 [SMILES: O=C1NCCc2c(COc3ccc(C(F)(F)F)cc3Cl)cccc21] |
| 58-2 | 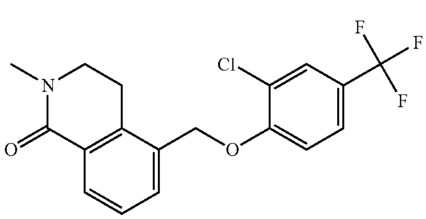 [SMILES: CN1CCc2c(COc3ccc(C(F)(F)F)cc3Cl)cccc2C1=O] |
| 59-1 | 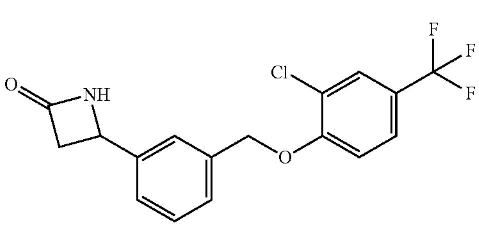 [SMILES: O=C1CC(c2cccc(COc3ccc(C(F)(F)F)cc3Cl)c2)N1] |
| 60-1 | |
| 61-1 | |
| 62-1 | |
| 63-1 | |
| 64-1 | |
| 65-1 | |

In a more specific embodiment, the compound has the following structure, or a pharmaceutically acceptable isomer, racemate, hydrate, solvate, isotope, or salt thereof:

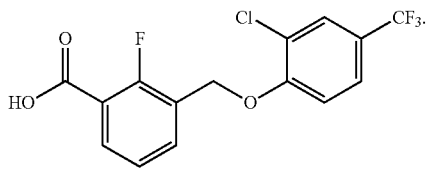 [SMILES: O=C(O)c1cccc(COc2ccc(C(F)(F)F)cc2Cl)c1F]

In a more specific embodiment, the compound has the following structure, or a pharmaceutically acceptable isomer, racemate, hydrate, solvate, isotope, or salt thereof:

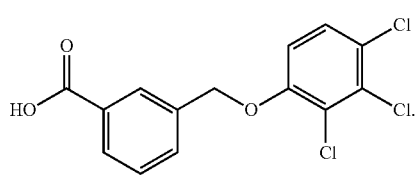 [SMILES: O=C(O)c1cccc(COc2ccc(Cl)c(Cl)c2Cl)c1]

In a more specific embodiment, the compound has the following structure, or a pharmaceutically acceptable isomer, racemate, hydrate, solvate, isotope, or salt thereof:

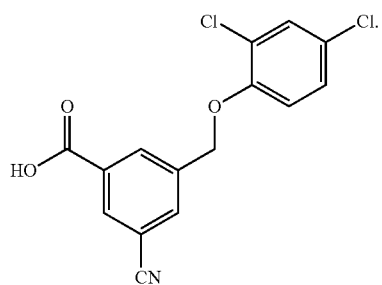 [SMILES: N#Cc1cc(COc2ccc(Cl)cc2Cl)cc(C(=O)O)c1]

In a more specific embodiment, the compound has the following structure, or a pharmaceutically acceptable isomer, racemate, hydrate, solvate, isotope, or salt thereof:

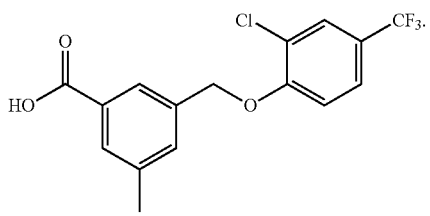 [SMILES: Cc1cc(COc2ccc(C(F)(F)F)cc2Cl)cc(C(=O)O)c1]

In a more specific embodiment, the compound has the following structure, or a pharmaceutically acceptable isomer, racemate, hydrate, solvate, isotope, or salt thereof:

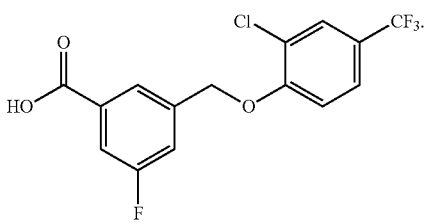 [SMILES: O=C(O)c1cc(F)cc(COc2ccc(C(F)(F)F)cc2Cl)c1]

In a more specific embodiment, the compound has the following structure, or a pharmaceutically acceptable isomer, racemate, hydrate, solvate, isotope, or salt thereof:

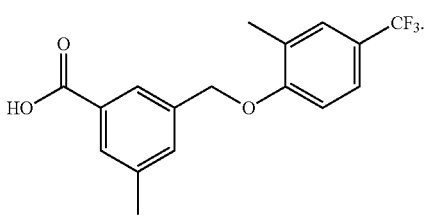 [SMILES: Cc1cc(COc2ccc(C(F)(F)F)cc2C)cc(C(=O)O)c1]

In a more specific embodiment, the compound has the following structure, or a pharmaceutically acceptable isomer, racemate, hydrate, solvate, isotope, or salt thereof:

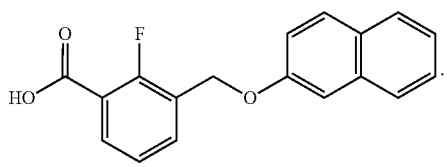 [SMILES: O=C(O)c1cccc(COc2ccc3ccccc3c2)c1F]

In a more specific embodiment, the compound has the following structure, or a pharmaceutically acceptable isomer, racemate, hydrate, solvate, isotope, or salt thereof:

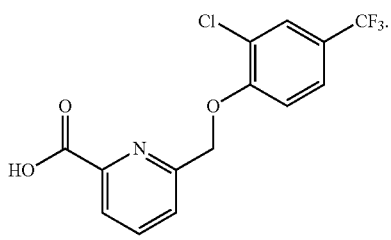

In a more specific embodiment, the compound has the following structure, or a pharmaceutically acceptable isomer, racemate, hydrate, solvate, isotope, or salt thereof:

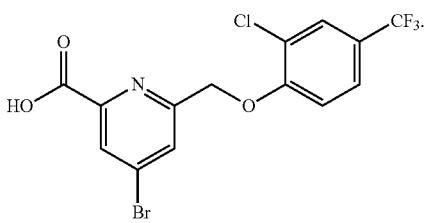 [SMILES: O=C(O)c1cc(Br)cc(COc2ccc(C(F)(F)F)cc2Cl)n1]

In a more specific embodiment, the compound has the following structure, or a pharmaceutically acceptable isomer, racemate, hydrate, solvate, isotope, or salt thereof:

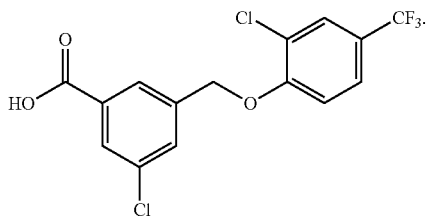

In a more specific embodiment, the compound has the following structure, or a pharmaceutically acceptable isomer, racemate, hydrate, solvate, isotope, or salt thereof:

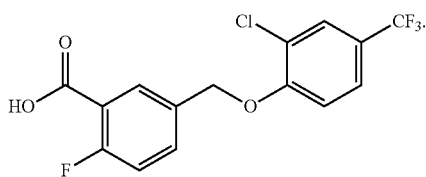 [SMILES: O=C(O)c1cc(COc2ccc(C(F)(F)F)cc2Cl)ccc1F]

In a more specific embodiment, the compound has the following structure, or a pharmaceutically acceptable isomer, racemate, hydrate, solvate, isotope, or salt thereof:

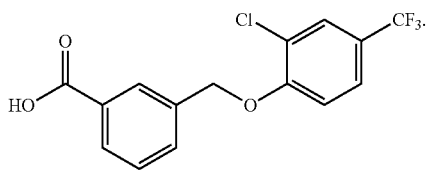 [SMILES: O=C(O)c1cccc(COc2ccc(C(F)(F)F)cc2Cl)c1]

In a more specific embodiment, the compound has the following structure, or a pharmaceutically acceptable isomer, racemate, hydrate, solvate, isotope, or salt thereof:

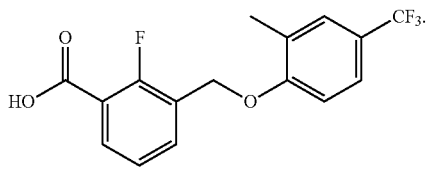 [SMILES: Cc1cc(C(F)(F)F)ccc1OCc1cccc(C(=O)O)c1F]

In a more specific embodiment, the compound has the following structure, or a pharmaceutically acceptable isomer, racemate, hydrate, solvate, isotope, or salt thereof:

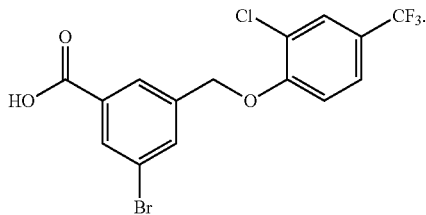

In a more specific embodiment, the compound has the following structure, or a pharmaceutically acceptable isomer, racemate, hydrate, solvate, isotope, or salt thereof:

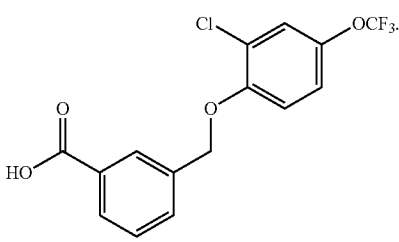 [SMILES: O=C(O)c1cccc(COc2ccc(OC(F)(F)F)cc2Cl)c1]

In a more specific embodiment, the compound has the following structure, or a pharmaceutically acceptable isomer, racemate, hydrate, solvate, isotope, or salt thereof:

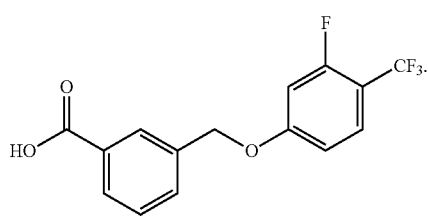 [SMILES: O=C(O)c1cccc(COc2ccc(C(F)(F)F)c(F)c2)c1]

In a more specific embodiment, the compound has the following structure, or a pharmaceutically acceptable isomer, racemate, hydrate, solvate, isotope, or salt thereof:

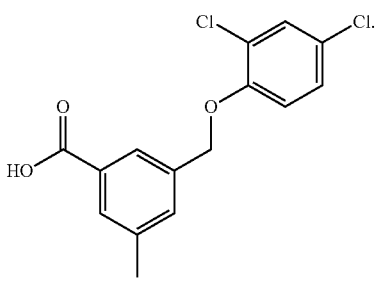 [SMILES: Cc1cc(COc2ccc(Cl)cc2Cl)cc(C(=O)O)c1]

In a more specific embodiment, the compound has the following structure, or a pharmaceutically acceptable isomer, racemate, hydrate, solvate, isotope, or salt thereof:

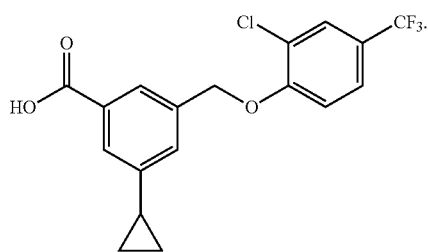 [SMILES: O=C(O)c1cc(COc2ccc(C(F)(F)F)cc2Cl)cc(C2CC2)c1]

In another embodiment, certain compounds of Formula (I), as well as Formulas (II) through (XXIV), as applicable, can have their carboxylic acid moiety substituted for a carboxylic acid isostere group, as described herein. Representative carboxylic acid isostere compounds derived from the representative compounds listed below are presented in Table B.
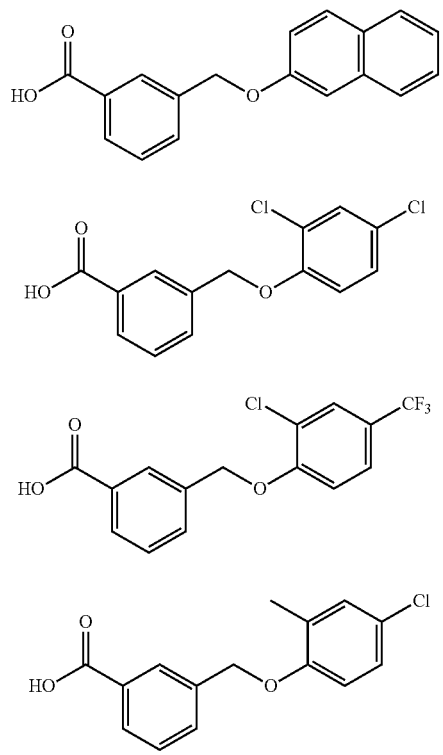
To this end, the carboxylic acid isostere groups used for compounds of Table B are as follows:
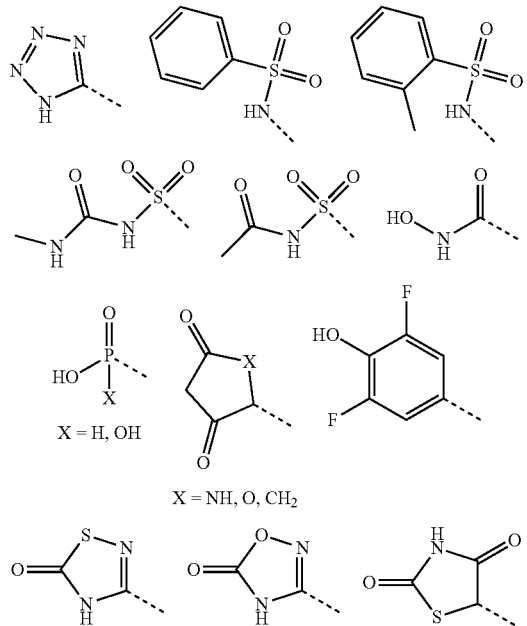
TABLE B
Representative Carboxylic Acid Isostere Compounds
| Cpd. No. | Structure |
|---|---|
| I-1 | 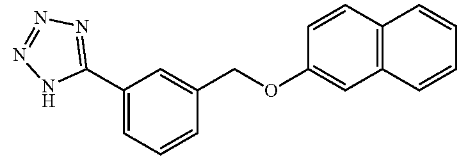 [SMILES: c1cc(COc2ccc3ccccc3c2)cc(-c2nnn[nH]2)c1] |
| I-2 | 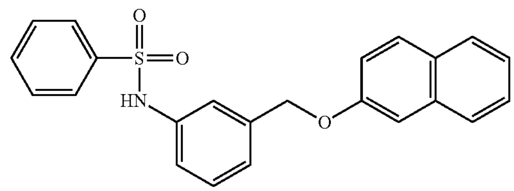 [SMILES: O=S(=O)(Nc1cccc(COc2ccc3ccccc3c2)c1)c1ccccc1] |
| I-3 | 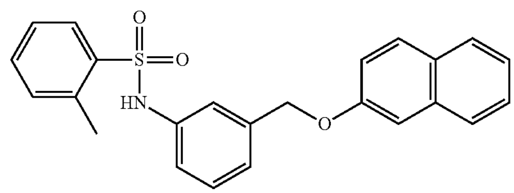 [SMILES: Cc1ccccc1S(=O)(=O)Nc1cccc(COc2ccc3ccccc3c2)c1] |
| I-4 | 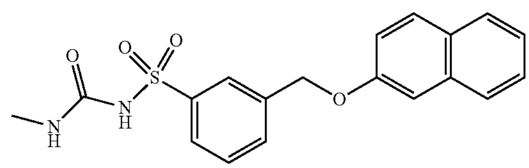 [SMILES: CNC(=O)NS(=O)(=O)c1cccc(COc2ccc3ccccc3c2)c1] |
| I-5 | 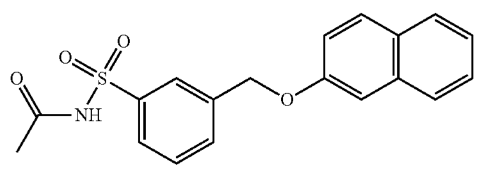 [SMILES: CC(=O)NS(=O)(=O)c1cccc(COc2ccc3ccccc3c2)c1] |
| I-6 | 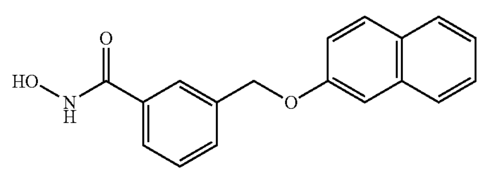 [SMILES: O=C(NO)c1cccc(COc2ccc3ccccc3c2)c1] |
| I-7 | 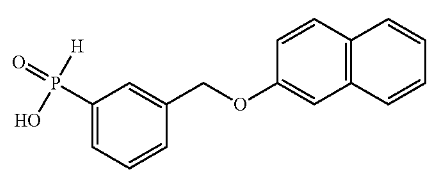 [SMILES: O=[PH](O)c1cccc(COc2ccc3ccccc3c2)c1] |
| I-8 | 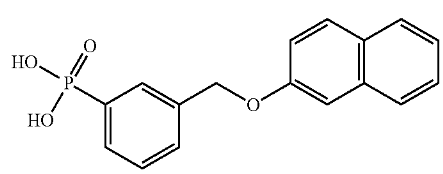 [SMILES: O=P(O)(O)c1cccc(COc2ccc3ccccc3c2)c1] |

TABLE B-continued

Representative Carboxylic Acid Isostere Compounds

| Cpd. No. | Structure |
|---|---|
| I-9 | 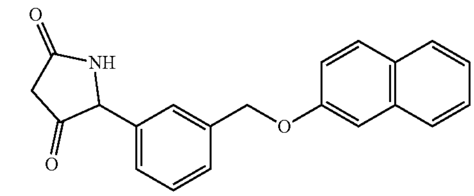 [SMILES: O=C1CC(=O)C(c2cccc(COc3ccc4ccccc4c3)c2)N1] |
| I-10 | 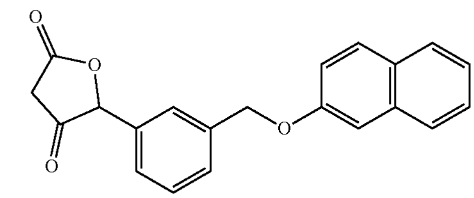 [SMILES: O=C1CC(=O)C(c2cccc(COc3ccc4ccccc4c3)c2)O1] |
| I-11 | 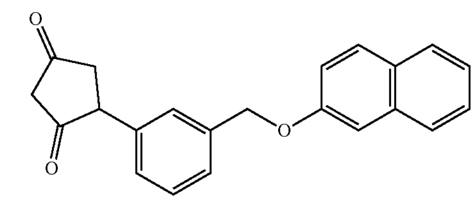 [SMILES: O=C1CC(=O)C(c2cccc(COc3ccc4ccccc4c3)c2)C1] |
| I-12 | 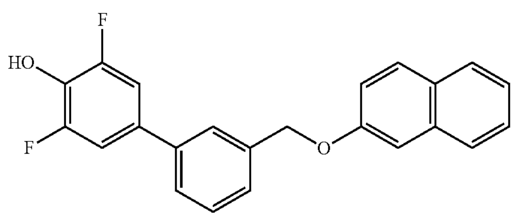 [SMILES: Oc1c(F)cc(-c2cccc(COc3ccc4ccccc4c3)c2)cc1F] |
| I-13 | 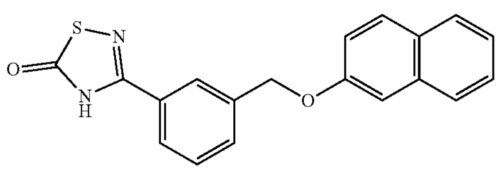 [SMILES: O=c1[nH]c(-c2cccc(COc3ccc4ccccc4c3)c2)ns1] |
| I-14 | 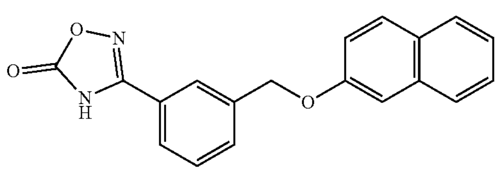 [SMILES: O=c1[nH]c(-c2cccc(COc3ccc4ccccc4c3)c2)no1] |
| I-15 | 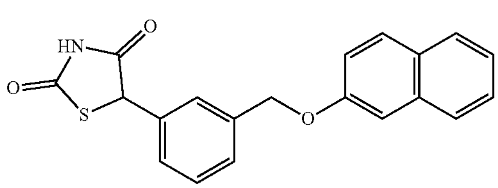 [SMILES: O=C1NC(=O)C(c2cccc(COc3ccc4ccccc4c3)c2)S1] |
| I-16 | 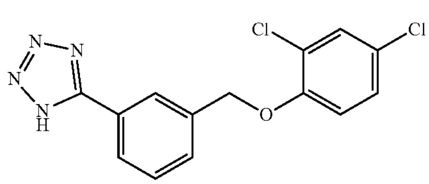 [SMILES: Clc1ccc(OCc2cccc(-c3nnn[nH]3)c2)c(Cl)c1] |
| I-17 | |
| I-18 | |
| I-19 | |
| I-20 | |
| I-21 | |
| I-22 | |
| I-23 | |
| I-24 | |

TABLE B-continued

Representative Carboxylic Acid Isostere Compounds

| Cpd. No. | Structure |
|---|---|
| I-25 | (2,4-dichlorophenoxymethyl-phenyl)-furan-2,4-dione |
| I-26 | (2,4-dichlorophenoxymethyl-phenyl)-cyclopentane-1,3-dione |
| I-27 | 3,5-difluoro-4-hydroxy-3'-(2,4-dichlorophenoxymethyl)biphenyl |
| I-28 | 3-[3-(2,4-dichlorophenoxymethyl)phenyl]-1,2,4-thiadiazol-5(4H)-one |
| I-29 | 3-[3-(2,4-dichlorophenoxymethyl)phenyl]-1,2,4-oxadiazol-5(4H)-one |
| I-30 | 5-[3-(2,4-dichlorophenoxymethyl)phenyl]thiazolidine-2,4-dione |
| I-31 | 5-[3-(2-chloro-4-trifluoromethylphenoxymethyl)phenyl]-1H-tetrazole |
| I-32 | N-[3-(2-chloro-4-trifluoromethylphenoxymethyl)phenyl]benzenesulfonamide |
| I-33 | N-[3-(2-chloro-4-trifluoromethylphenoxymethyl)phenyl]-2-methylbenzenesulfonamide |
| I-34 | N-methyl-N'-{[3-(2-chloro-4-trifluoromethylphenoxymethyl)phenyl]sulfonyl}urea |
| I-35 | N-acetyl-3-(2-chloro-4-trifluoromethylphenoxymethyl)benzenesulfonamide |
| I-36 | N-hydroxy-3-(2-chloro-4-trifluoromethylphenoxymethyl)benzamide |
| I-37 | [3-(2-chloro-4-trifluoromethylphenoxymethyl)phenyl]phosphinic acid |
| I-38 | [3-(2-chloro-4-trifluoromethylphenoxymethyl)phenyl]phosphonic acid |
| I-39 | 3-[3-(2-chloro-4-trifluoromethylphenoxymethyl)phenyl]pyrrolidine-2,5-dione |
| I-40 | 5-[3-(2-chloro-4-trifluoromethylphenoxymethyl)phenyl]furan-2,4-dione |

TABLE B-continued

Representative Carboxylic Acid Isostere Compounds

| Cpd. No. | Structure |
|---|---|
| I-41 | 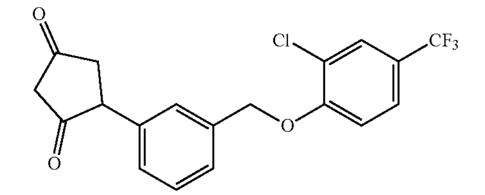 [SMILES: O=C1CC(=O)C(c2cccc(COc3ccc(C(F)(F)F)cc3Cl)c2)C1] |
| I-42 | 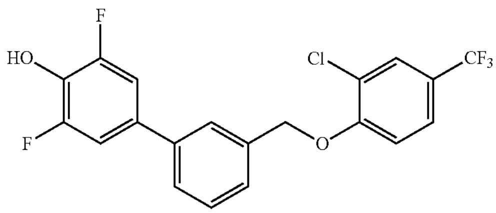 [SMILES: Oc1c(F)cc(-c2cccc(COc3ccc(C(F)(F)F)cc3Cl)c2)cc1F] |
| I-43 | 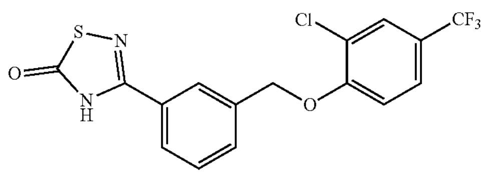 [SMILES: O=c1[nH]c(-c2cccc(COc3ccc(C(F)(F)F)cc3Cl)c2)ns1] |
| I-44 | 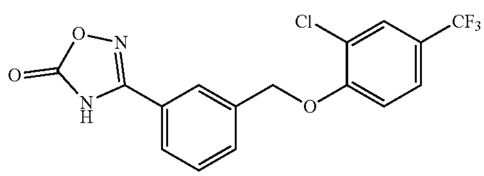 [SMILES: O=c1[nH]c(-c2cccc(COc3ccc(C(F)(F)F)cc3Cl)c2)no1] |
| I-45 | 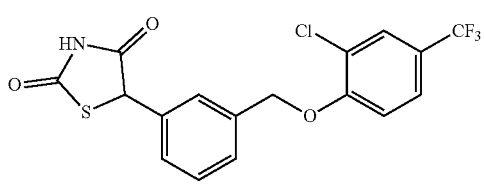 [SMILES: O=C1NC(=O)C(c2cccc(COc3ccc(C(F)(F)F)cc3Cl)c2)S1] |
| I-46 | 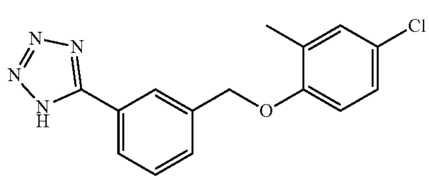 [SMILES: Cc1cc(Cl)ccc1OCc1cccc(-c2nnn[nH]2)c1] |
| I-47 | 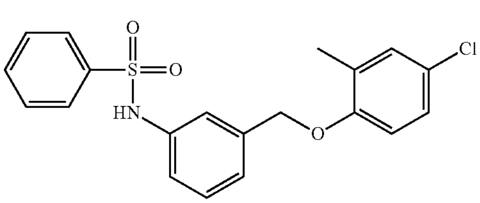 [SMILES: Cc1cc(Cl)ccc1OCc1cccc(NS(=O)(=O)c2ccccc2)c1] |
| I-48 | 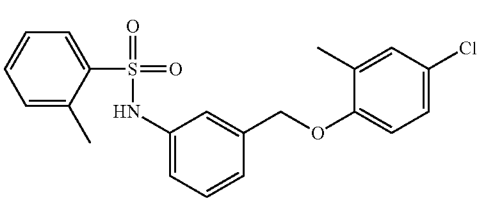 [SMILES: Cc1cc(Cl)ccc1OCc1cccc(NS(=O)(=O)c2ccccc2C)c1] |
| I-49 | |
| I-50 | |
| I-51 | |
| I-52 | |
| I-53 | |
| I-54 | |
| I-55 | |
| I-56 | |

TABLE B-continued

Representative Carboxylic Acid Isostere Compounds

| Cpd. No. | Structure |
|---|---|
| I-57 | ![structure] |
| I-58 | ![structure] |
| I-59 | ![structure] |
| I-60 | ![structure] |

In other embodiments, prodrugs and/or metabolites of compounds of Formula (I), as well as Formulas (II) through (XXIV), are provided.

Thus, in one embodiment, prodrugs of a compound of the invention are provided, which upon administration to a subject, undergo chemical conversion by metabolic or other physiological processes to become active pharmacological substances. Conversion by metabolic or other physiological processes includes, without limitation, enzymatic (e.g., specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

Accordingly, a "prodrug" is a substance that, upon administration to a subject, is converted in vivo by the action of biochemicals within the subject's body, such as enzymes, to an active pharmaceutical ingredient. Examples of prodrugs include esters of carboxylic acid groups, which can be hydrolyzed by endogenous esterases as are found in the bloodstream of humans and other mammals. In one embodiment, substances are provided that can be administered to a subject which are then converted within the subject's body to provide a compound having the structure of Formula (I), or any of Formulas (II) through (XXIV).

In this regard, prodrugs of carboxylic acids are typically esters and amides, which can readily be made from the corresponding carboxylic acid by known techniques. For example, in one embodiment, prodrugs may be generated by converting the carboxylic acid moiety of the compounds of Formula (I) through (VII) and (XVI) through (XXIV) to an ester functional group: including, alkyl esters such as methyl, ethyl, isopropyl and n-butyl esters; aryl esters such as phenyl and indanyl esters; double esters such as (acyloxy)alkyl or [(alkoxycarbonyl)oxy]methyl esters; and cyclic carbonates such as (oxodioxolyl)methyl esters. In another embodiment, the carboxylic acid moiety may incorporate a carbamoylmethyl, aminoalkyl, or amidoalkyl moiety to provide carbamoylmethyl, aminoalkyl and amidoalkyl esters, respectively. In yet another embodiment, the carboxylic acid moiety can incorporate esters of acylglycerols and bis(acylamino)propan-2-ols. In a further embodiment, the carboxylic acid moiety can incorporate amide groups, including N-hydroxyamide, N-acylsulfonamides and N-acylsulfonylureas.

As used herein, a "metabolite" is a compound that, following administration to a subject, is converted within the body of the subject to yield an active substance. Such conversion often involves hydrolysis, phosphorylation and/or oxidation/reduction processes, and may be mediated by any number of enzymes (e.g., esterases, phosphatases, cytochrome P450, and the like), as well by different environments within the body (e.g., changes in pH).

In one embodiment, compounds of Formula (I), as well as Formulas (II) through (XXII), as applicable, are modified to encompass metabolites of the parent compound. In another embodiment, compounds of Formula (I), as well as Formulas (II) through (XXII), are modified to have the "A-ring" carboxylic acid of Formula (I) derivatized with carbohydrate or amino acid compounds. In a further embodiment, the A-ring carboxylic acid moiety is derivatized with glucuronic acid or the amino acid glycine to give compounds of Formulas (XXV) and (XXVI), respectively:

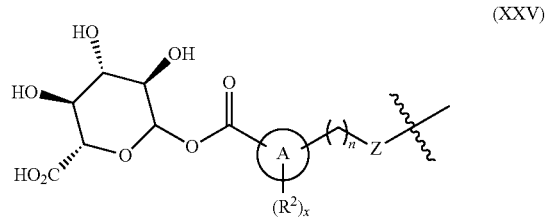
(XXV)

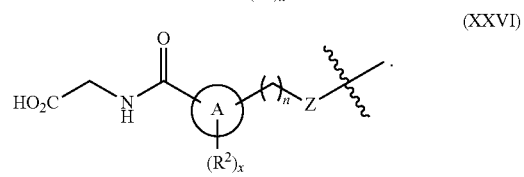
(XXVI)

In certain embodiments, the invention provides a pharmaceutical composition comprising a compound of any one of Formulas (I) through (XIV) together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in *Remington: The Science and Practice of Pharmacy*, 21$^{st}$ Ed., Gennaro, Ed., Lippencott Williams & Wilkins (2005) and in The United States Pharmacopeia: The National Formulary (USP 36 NF31), published in 2013.

In some embodiments, the pharmaceutical composition comprising a compound of any one of Formulas (I) through (XIV) with at least one pharmaceutically acceptable carrier, diluent, or excipient further comprises a second therapeutic agent. In one embodiment, the second therapeutic agent is a liver disease therapeutic agent. In one embodiment, the liver disease therapeutic agent is ursodeoxycholic acid (UDCA), norUrsodeoxycholic acid, cholestyramine, stanozolol, naltrexone, rifampicin, Alisol B 23-acetate (AB23A), curcumin, dihydroartemisinin, fenofibrate, bezafibrate, metronidazole, methotrexate, colchicine, metformin, betaine, glucagon, naltrexone, a farnesoid X-receptor (FXR) agonist, a peroxisome proliferator-activated receptor (PPAR) agonist, a thyroid hormone receptor beta (TRO) agonist, or any combination thereof.

Examples of FXR agonists that may be used in the pharmaceutical compositions described herein include obeticholic acid, Turofexorate isopropyl (WAY-362450), 3-(2,6-dichlorophenyl)-4-(3'-carboxy-2-chlorostilben-4-yl)oxymethyl-5-isopropylisoxazole (GW4064), PX20606 (PX-102), PX-101, INT-767, INT-787, TERN-101, altenusin, tropifexor (LJN452), nidufexor, turofexorate isopropyl, fexaramine, silymarin, silybin, hedragonic acid, cafestol, Cilofexor (GS-9674 or Px-104), EDP-305, BAR704, BAR502, EYP-001, RDX-023, AGN-242266, HPG-1860, MET-409, AGN-242256, EP-024297, IOT-022, M-480, INV-33, RDX023-02, or any combination thereof. In one embodiment, a FXR agonist is a bile acid or analog thereof (e.g., obeticholic acid, INT-767, INT-787, turofexorate isopropyl (WAY-362450), or BAR704) or a non-bile acid agonist (e.g., EDP-305, tropifexor, nidufexor, cilofexor, GW4064, Turofexorate isopropyl, fexaramine, PX20606 (PX-102), TERN-101, altenusin, silymarin, silybin, hedragonic acid, BAR502, EYP-001, RDX023-2, AGN-242266, HPG-1860, MET-409, EP-024297, M-480, or cafestol).

In one embodiment, a PPAR agonist is a PPAR-alpha agonist, a PPAR-gamma agonist, a PPAR-delta agonist, a PPAR-alpha/gamma dual agonist, a PPAR alpha/delta dual agonist, a PPAR gamma/delta dual agonist, a PPAR alpha/gamma/delta pan agonist, or any combination thereof.

Examples of PPAR alpha agonists that may be used in the pharmaceutical compositions described herein include fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, and SRI 0171.

Examples of PPAR gamma agonists that may be used in the pharmaceutical compositions described herein include rosiglitazone, pioglitazone, deuterium-stabilized R-pioglitazone, efatutazone, ATx08-001, OMS-405, CHS-131, THR-0921, SER-150-DN, KDT-501, GED-0507-34-Levo, CLC-3001, and ALL-4.

Examples of PPAR delta agonists that may be used in the pharmaceutical compositions described herein include GW501516 (endurabol or ({4-[({4-methyl-2-[4-(trifluoromethyl)phenyl]-1,3-thiazol-5-yl}methyl)sulfanyl]-2-methylphenoxy} acetic acid)), MBX8025 (seladelpar or {2-methyl-4-[5-methyl-2-(4-trifluoromethyl-phenyl)-2H-[1,2,3]triazol-4-ylmethylsylfanyl]-phenoxy}-acetic acid), GW0742 ([4-[[[2-[3-fluoro-4-(trifluoromethyl)phenyl]-4-methyl-5-thiazolyl]methyl]thio]-2-methyl phenoxy] acetic acid), L165041, HPP-593, and NCP-1046.

Examples of PPAR alpha/gamma agonists that may be used in the pharmaceutical compositions described herein include saroglitazar, aleglitazar, muraglitazar, tesaglitazar, and DSP-8658.

Examples of PPAR alpha/delta agonists that may be used in the pharmaceutical compositions described herein include elafibranor and T913659.

Examples of PPAR gamma/delta agonists that may be used in the pharmaceutical compositions described herein include a conjugated linoleic acid (CLA) and T3D-959.

Examples of PPAR alpha/gamma/delta agonists that may be used in the pharmaceutical compositions described herein include IVA337 (lanifibranor), TTA (tetradecylthioacetic acid), bavachinin, GW4148, GW9135, bezafibrate, lobeglitazone, 2-(4-(5,6-methylenedioxybenzo[d]thiazol-2-yl)-2-methylphenoxy)-2-methylpropanoic acid (MHY2013), and CS038.

Examples of thyroid hormone receptor beta agonists that may be used in the pharmaceutical compositions described herein include sobetirome, eprotirome, GC-24, MGL-3196, MGL-3745, VK-2809, KB141 [3,5-dichloro-4-(4-hydroxy-3-isopropylphenoxy) phenylacetic acid], and MB07811 (2R, 4S)-4-(3-chlorophenyl)-2-[(3,5-dimethyl-4-(4'-hydroxy-3'-isopropylbenzyl)phenoxy)methyl]-2-oxido-[1,3,2]-dioxaphosphonane).

As used herein, the term "pharmaceutically acceptable carrier" refers to any ingredient other than the disclosed compounds, or a pharmaceutically acceptable isomer, racemate, hydrate, solvate, isotope or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, including intravenous, subcutaneous and/or intramuscular. In one embodiment, the route of administration is oral. In another embodiment, the route of administration is topical.

Dosage forms can be administered once a day, or more than once a day, such as twice or thrice daily. Alternatively, dosage forms can be administered less frequently than daily, such as every other day, or weekly, if found to be advisable by a prescribing physician or drug's prescribing information. Dosing regimens include, for example, dose titration to the extent necessary or useful for the indication to be treated, thus allowing the patient's body to adapt to the treatment, to minimize or avoid unwanted side effects associated with the treatment, and/or to maximize the therapeutic effect of the present compounds. Other dosage forms include delayed or controlled-release forms. Suitable dosage regimens and/or forms include those set out, for example, in the latest edition of the Physicians' Desk Reference, incorporated herein by reference.

In one embodiment, the invention provides an oral pharmaceutical composition comprising a compound of any one of Formulas (I) through (XXIV) together with at least one pharmaceutically acceptable oral carrier, diluent, or excipient. In another embodiment, the invention provide a topical pharmaceutical composition comprising a compound of any one of Formulas (I) through (XXIV) together with at least one pharmaceutically acceptable topical carrier, diluent, or excipient. For example, the oral pharmaceutical composition is provided to treat cholestatic pruritus, wherein the dosage regimen is, for example, once a day. In one embodiment, the topical pharmaceutical composition is provided to treat atopic dermatitis.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

In certain embodiments, the invention provides a compound having the structure of any one of Formulas (I) through (XXIV). Such compounds can be synthesized using standard synthetic techniques known to those skilled in the art. For example, compounds of the present invention can be synthesized using appropriately modified synthetic procedures set forth in the following Examples and Reaction Schemes. To this end, carboxylic acid isosteres, and their substitution in place of the carboxylic acids disclosed herein, may also be accomplished using standard synthetic techniques known to those skilled in the art.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation(s) necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

All reagents, for which the synthesis is not described in the experimental part, are either commercially available, or are known compounds or may be formed from known compounds by known methods by a person skilled in the art. The compounds and intermediates produced according to the methods of the invention may require purification. Purification of organic compounds is well known to a person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using purpose-made or prepacked silica gel cartridges and eluents such as gradients of solvents such as heptane, ether, ethyl acetate, acetonitrile, ethanol and the like. In some cases, the compounds may be purified by preparative HPLC using methods as described.

Purification methods as described herein may provide compounds of the present invention which possess a sufficiently basic or acidic functionality in the form of a salt, such as, in the case of a compound of the present invention which is sufficiently basic, a trifluoroacetate or formate salt, or, in the case of a compound of the present invention which is sufficiently acidic, an ammonium salt. A salt of this type can either be transformed into its free base or free acid form, respectively, by various methods known to a person skilled in the art, or be used as salts in subsequent biological assays. It is to be understood that the specific form of a compound of the present invention as isolated and as described herein is not necessarily the only form in which said compound can be applied to a biological assay in order to quantify the specific biological activity.

Chemical names were generated using the ChemDraw naming software (Version 17.0.0.206) by PerkinElmer Informatics, Inc. In some cases, generally accepted names of commercially available reagents were used in place of names generated by the naming software.

EXAMPLES

General Methods $^1$H NMR (400 MHz) spectra were obtained in solution of deuteriochloroform (CDCl$_3$), deuteriomethanol (CD$_3$OD) or dimethyl sulfoxide—D6 (DMSO). HPLC retention times, purities and mass spectra (LCMS) were obtained using one of the following methods:

Method 1: Agilent 1260 Infinity II System equipped with an Agilent Poroshell 120 EC-18, 2.7 μm, 4.6×100 mm column, using H$_2$O with 0.1% formic acid as the mobile phase A, and MeCN with 0.1% formic acid as the mobile phase B. An ESI detector in positive mode was used. The gradient was 20-95% mobile phase B over 5 min then held at 95% for 3.8 mins, then return to 20% mobile phase B over 0.2 min. The flow rate was 1 mL/min.

Method 2: Agilent 1260 Infinity II System equipped with an Agilent Poroshell 120 EC-18, 2.7 μm, 4.6×100 mm column, using H$_2$O with 0.1% formic acid as the mobile phase A, and MeCN with 0.1% formic acid as the mobile phase B. An ESI detector in negative mode was used. The gradient was 20-95% mobile phase B over 5 min then held at 95% for 3.8 mins, then return to 20% mobile phase B over 0.2 min. The flow rate was 1 mL/min.

Method 3: Agilent 1260 Infinity II System equipped with an Agilent Poroshell 120 EC-18, 2.7 μm, 4.6×100 mm column, using H$_2$O with 0.1% formic acid as the mobile phase A, and MeCN with 0.1% formic acid as the mobile phase B. An ESI detector in positive mode was used. The gradient was 20-95% mobile phase B over 5 min then held at 95% for 3.8 mins, then return to 20% mobile phase B over 0.2 min. The flow rate was 1 mL/min.

Method 4: Agilent 1260 Infinity II System equipped with an Agilent Poroshell 120 EC-18, 2.7 μm, 4.6×100 mm column, using H$_2$O with 0.1% formic acid as the mobile phase A, and MeCN with 0.1% formic acid as the mobile phase B. An ESI detector in negative mode was used. The gradient was 10-95% mobile phase B over 12 min then held at 95% for 2 min, return to 10% mobile phase B over 1 min. The flow rate was 1 mL/min.

Method 5: Shimadzu LCMS-2020 system equipped with a KinetiX EVO C18 2.1×30 mm, 5 μm column, using H$_2$O with 0.025% NH$_3$—H$_2$O as the mobile phase A, and MeCN as mobile phase B. The flow rate was 1.5 mL/min. An ESI mass detector in negative mode was used. The gradient was 0-60% B over 0.8 min, then hold at 60% B for 0.4 min, then return to 0% B over 0.01 min, and hold at 0% B for 0.34 min.

Method 6: Agilent 1200/G6110A System equipped with a Chromolith Flash RP-18e 25×2.0 mm column, using H$_2$O with 0.0375% TFA as mobile phase A, and MeCN with 0.01875% TFA as mobile phase B. An ESI mass detector set in positive mode was used. The gradient was 5-95% B over 0.8 min, hold at 95% B for 0.4 min, then return to 5% B over 0.01 min, and hold at 5% B for 0.29 min.

Method 7: Shimadzu LCMS-2020 system equipped with a KinetiX EVO C18 2.1×30 mm, 5 μm column, using H$_2$O with 0.025% NH$_3$ as the mobile phase A, and MeCN as mobile phase B. The flow rate was 1.5 mL/min. An ESI mass detector in negative mode was used. The gradient was 5-95% B over 0.8 min, hold at 95% B for 0.4 min, then return to 5% B over 0.01 min, and hold at 5% B for 0.34 min.

Method 8: Agilent 1200/G6110A System equipped with an ACE Excel C18, 2.1×30 mm, 5 μm column, using H$_2$O with 0.025% NH$_3$ as mobile phase A, and MeCN as mobile phase B. An ESI mass detector set in negative mode was used. The gradient was 10-80% B over 1.2 min, hold at 80% B for 0.4 min, then return to 5% B over 0.01 min, and hold at 5% B for 0.39 min.

Method 9: Agilent 1100 System equipped with an Agilent Eclipse XDB-C18, 3.5 μm, 4.6×150 mm column, using H$_2$O with 0.1% trifluoroacetic acid as the mobile phase A, and methanol with 0.1% trifluoroacetic acid as the mobile phase B. The gradient was 5-95% mobile phase B over 12 min then held at 95% mobile phase B for 3 min, then return to 5% mobile phase B for 1 min. The flow rate was 1 mL/min.

Method 10: Shimadzu SCL-10A system equipped with Agilent Eclipse XDB-C18, 3.5 μm, 4.6×150 mm column and PE Sciex API 150 EX, using H$_2$O with 0.1% trifluoroacetic acid as the mobile phase A, and methanol with 0.1% trifluoroacetic acid as the mobile phase B. The gradient was 5-95% mobile phase B over 12 min then held at 95% mobile phase B for 3 min, then return to 5% mobile phase B for 1 min. The flow rate was 1 mL/min.

Method 11: Shimadzu SCL-10A system equipped with Agilent Eclipse XDB-C18, 3.5 μm, 4.6×150 mm column and PE Sciex API 150 EX, using H$_2$O with 0.1% trifluoroacetic acid as the mobile phase A, and methanol with 0.1% trifluoroacetic acid as the mobile phase B. The gradient was 50-95% mobile phase B over 4 min then held at 95% mobile phase B for 4 min, then return to 50% mobile phase B for 0.1 min. The flow rate was 1 mL/min.

Method 12: Waters Acquity system equipped with an Acquity UPLC BEH C18 1.7 μm, 2.1×50 mm column, using H$_2$O with 0.1% ammonium formate adjusted to pH 3.8 with formic acid as the mobile phase A, and acetonitrile as the mobile phase B. The gradient was 5-100% over 9 minutes then held at 100% mobile phase B for 1 minute. The flow rate was 0.7 mL/min.

Method 13: Waters Acquity system equipped with an EVO C18 (5 μm, 3.0×50 mm) using a low pH buffer gradient of 5% to 100% of MeCN in H$_2$O (0.1% HCOOH) over 2.5 min at 2.2 mL/min, and holding at 100% for a total time of 3.5 min.

The pyridine, dichloromethane (DCM), tetrahydrofuran (THF), and toluene used in the procedures were from Aldrich Sure-Seal bottles kept under nitrogen (N$_2$). All reactions were stirred magnetically, and temperatures are external reaction temperatures. Chromatographies were typically carried out using a Combiflash Rf flash purification system (Teledyne Isco) equipped with Redisep (Teledyne Isco) Rf Gold Normal-Phase silica gel (SiO$_2$) columns or by using a similar system.

Preparative HPLC purifications were typically performed using one of the following systems: 1) Waters System equipped with a Waters 2489 uv/vis detector, an Aquity QDA detector, a Waters xBridge Prep C18 5 μm OBD, 30×1560 mm column, and eluting with various gradients of H$_2$O/MeCN (0.1% formic acid) at a 30 mL/min flow rate, or 2) column: Phenomenex Synergi C18 150×30 mm-4 μm; mobile phase: [H$_2$O (0.225% formic acid)-MeCN]; B %: 55%-85%, 12 min) and were typically concentrated using a Genevac EZ-2.

The following additional abbreviations are used: ethyl acetate (EA), triethylamine (TEA), dimethyl sulfoxide (DMSO), silica gel (SiO$_2$), azobisisobutyronitrile (AIBN), diisobutylaluminium hydride (DIBAL), trifluoroacetic acid (TFA), 4-dimethylaminopyridine (DMAP), diphenylphosphoryl azide (DPPA), benzoyl peroxide (BPO), 1,1'-bis (diphenylphosphino)ferrocene (dppf or DPPF), tetrahydrofuran (THF), 1,4-diazabicyclo[2.2.2]octane bis(sulfur dioxide) adduct (DABSO), hexafluorophosphate azabenzotriazole tetramethyl uronium (HATU), hydroxybenzotriazole (HOBt), N-methyl morpholine (NMM), N-Bromosuccinimide (NBS), diisopropylethyl amine (DIPEA), diethyl azodicarboxylate (DEAD), 2-[2-(dicyclohexylphosphino)phenyl]-N-methylindole (CM-Phos), 1-ethyl-3-(3-dimethylaminopropyl) carbodiimide hydrochloride (EDC), isopropanol (IPA), dimethylformamide (DMF), dimethyl acetamide (DMA), acetonitrile (MeCN or ACN), 1,1'-thiocarbonyldiimidazole (TCDI), petroleum ether (PE), not determined (ND), retention time (RT), molecular weight (MW), room temperature (rt), hour (h), and not applicable (N/A).

Example 1

Synthesis of Compound 1-0, Compound 1-16 and Other Representative Compounds

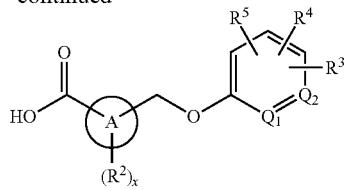

Reagents: (i) Base (Na$_2$CO$_3$, K$_2$CO$_3$, KO$^t$Bu), solvent (THF of DMF); ii. NaOH, solvent (THF, MeOH or DMF)

Step 1-1. Synthesis of methyl 3-((4-chloro-2-(trifluoromethyl)phenoxy)methyl)benzoate (Compound 1-0)

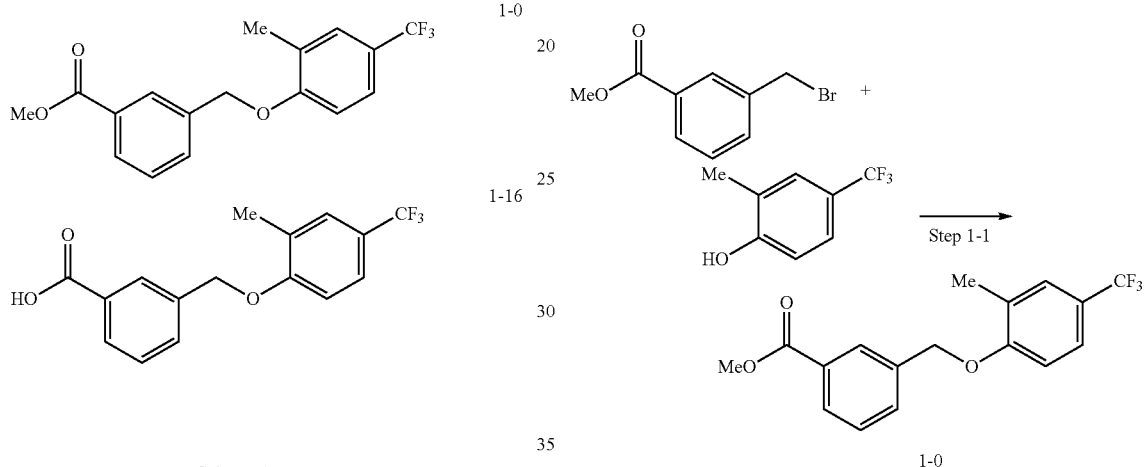

To a stirring solution of methyl 3-(bromomethyl)benzoate (150 mg, 655 μmol) in MeCN (3 mL) were added 2-methyl-4-(trifluoromethyl)phenol (115 mg, 655 μmol) and K$_2$CO$_3$ (118 mg, 0.85 mmol). The reaction mixture was heated at 60° C. for 3 h then cooled to room temperature and diluted with H$_2$O (3 mL). The aqueous layer was extracted with Et$_2$O (2×6 mL) and EA (1×6 mL) and the combined organic layers were dried (Na$_2$SO$_4$), filtered, concentrated and purified by SiO$_2$ chromatography (EA/hexanes) to afford 203 mg (77.4%) of methyl 3-((2-methyl-4-(trifluoromethyl)phenoxy)methyl)benzoate (Compound 1-0) as a white solid. LCMS-ESI (m/z) calculated for C$_{17}$H$_{15}$F$_3$O$_3$: 324.3. found 346.1 [M+Na]$^+$, t$_R$=6.68 min (Method 1).

The compounds listed in Table 1A were made using the procedures of Scheme 1.

TABLE 1A

| Structure | Cpd No. | Purity RT (min) | MW | Observed m/z | Ion | Purity Method |
|---|---|---|---|---|---|---|
| 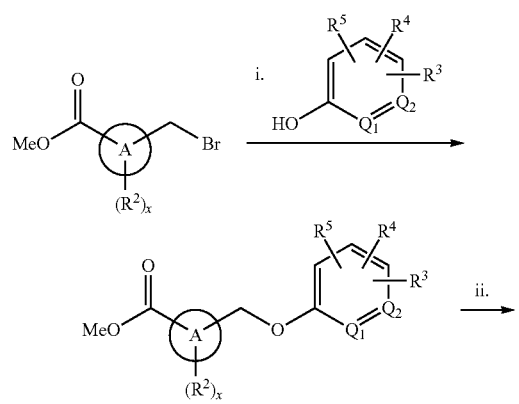 | 1-1 | 12.02 | 344.71 | 367.0 | [M + Na]$^+$ | 3 |

TABLE 1A-continued
| Structure | Cpd No. | Purity RT (min) | MW | Observed m/z | Ion | Purity Method |
|---|---|---|---|---|---|---|
| 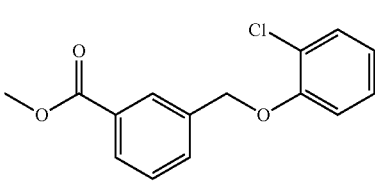 | 1-2 | 12.03 | 344.71 | 345.1 | [M + H]+ | 3 |
| 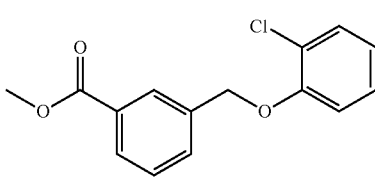 | 1-3 | 10.34 | 301.73 | 302.1 | [M + H]+ | 3 |
| 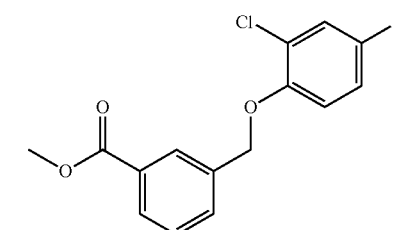 | 1-4 | 12.02 | 311.16 | 313.1 | [M + H]+ | 3 |
| 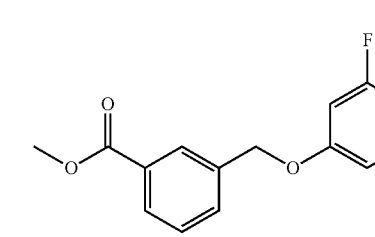 | 1-5 | 10.65 | 260.26 | 261.2 | [M + H]+ | 3 |
| 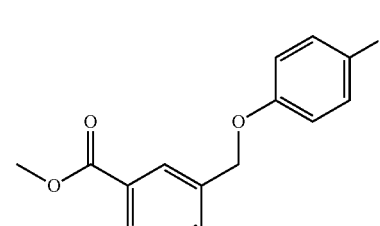 | 1-6 | 11.63 | 326.27 | 327.1 | [M + H]+ | 3 |
| 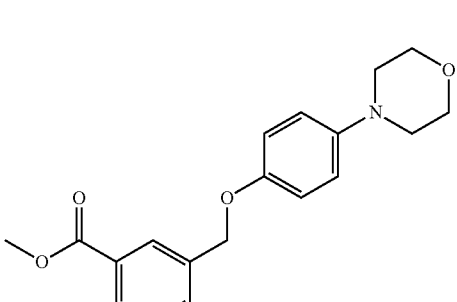 | 1-7 | 8.56 | 327.38 | 328.2 | [M + H]+ | 3 |

TABLE 1A-continued

| Structure | Cpd No. | Purity RT (min) | MW | Observed m/z | Ion | Purity Method |
|---|---|---|---|---|---|---|
| 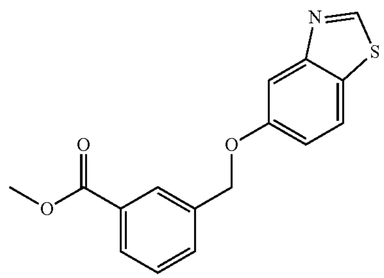 [SMILES: COC(=O)c1cccc(COc2ccc3scnc3c2)c1] | 1-8 | 9.48 | 299.34 | 300.1 | [M + H]⁺ | 3 |
| 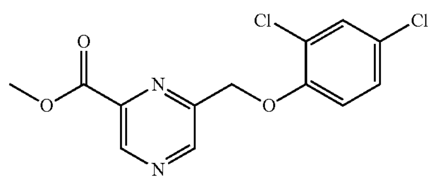 [SMILES: COC(=O)c1cncc(COc2ccc(Cl)cc2Cl)n1] | 1-9 | 9.98 | 313.13 | 313.1 | [M − H]⁺ | 4 |
| 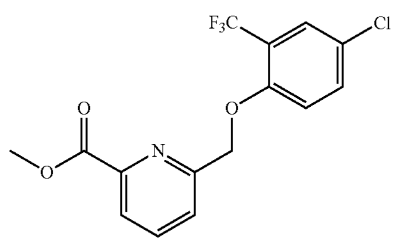 | 1-10 | 10.75 | 345.70 | 346.1 | [M + H]⁺ | 3 |
| 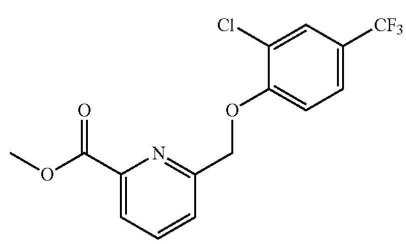 [SMILES: COC(=O)c1cccc(COc2ccc(C(F)(F)F)cc2Cl)n1] | 1-11 | 10.68 | 345.70 | 346.1 | [M + H]⁺ | 3 |
| 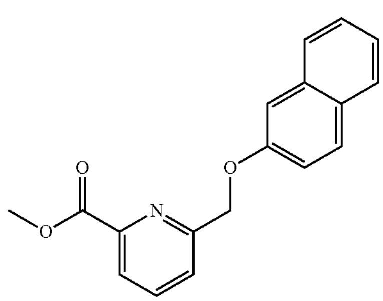 [SMILES: COC(=O)c1cccc(COc2ccc3ccccc3c2)n1] | 1-12 | 9.97 | 293.32 | 294.2 | [M + H]⁺ | 3 |
| 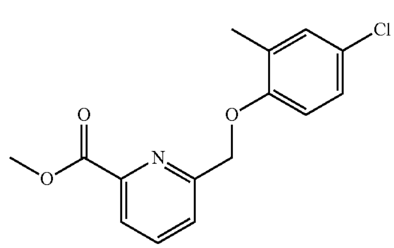 [SMILES: COC(=O)c1cccc(COc2ccc(Cl)cc2C)n1] | 1-13 | 10.39 | 291.73 | 292.1 | [M + H]⁺ | 3 |

TABLE 1A-continued

| Structure | Cpd No. | Purity RT (min) | MW | Observed m/z | Ion | Purity Method |
|---|---|---|---|---|---|---|
| 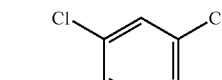 | 1-14 | 11.64 | 315.97 | 317.0 | [M + H]⁺ | 3 |
| 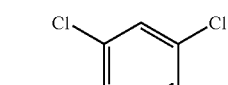 | 1-15 | 10.32 | 300.99 | 302.1 | [M + H]⁺ | 3 |
| 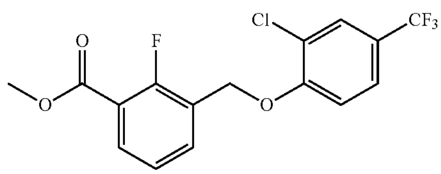 [SMILES: COC(=O)c1cccc(COc2ccc(C(F)(F)F)cc2Cl)c1F] | 1-117 | 10.36 | 362.7 | 361 | [M − H]⁺ | 4 |

Step 1-2. Synthesis of 3-((2-methyl-4-(trifluoromethyl)phenoxy)methyl)benzoic acid (Compound 1-16)

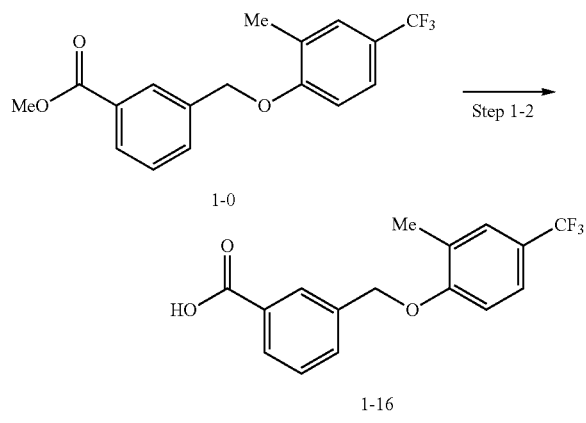

To a stirring solution of methyl 3-((2-methyl-4-(trifluoromethyl)-phenoxy)methyl)benzoate (Compound 1-0) (206 mg, 0.635 mmol) in THF (3 mL) was added 1M NaOH (3 mL, 3.18 mmol). The reaction mixture was heated at 60° C. overnight, the volatiles were removed in vacuo, and the resulting aqueous layer was acidified with 3M HCL. The resulting solution was extracted with EA and Et$_2$O, dried (Na$_2$SO$_4$), filtered and concentrated to give a crude solid that was purified by reversed phase SiO$_2$ chromatography to afford 155 mg (790%) of 3-((2-methyl-4-(trifluoromethyl)phenoxy)methyl)benzoic acid (Compound 1-16) as a white solid. LCMS-ESI (m/z) calculated for C$_{16}$H$_{13}$F$_3$O$_3$: 310.2. found 333.1 [M+Na]⁺, t$_R$=10.4 min. (Method 3).

The compounds listed in Table 1B were made using the procedures of Scheme 1.

TABLE 1B

| Structure | Cpd No. | Purity RT (min) | MW | Observed m/z | Ion | Purity Method |
|---|---|---|---|---|---|---|
| 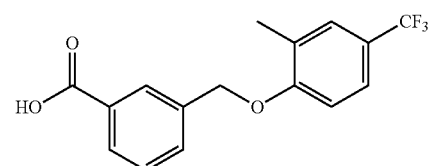 | 1-16 | 10.39 | 310.27 | 333.1, | [M + Na]⁺ | 3 |

TABLE 1B-continued

| Structure | Cpd No. | Purity RT (min) | MW | Oserved m/z | Ion | Purity Method |
|---|---|---|---|---|---|---|
| 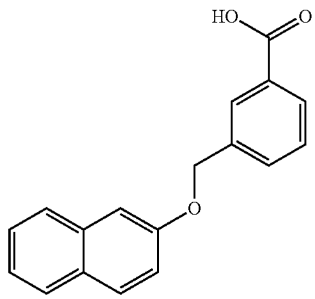 [SMILES: O=C(O)c1cccc(COc2ccc3ccccc3c2)c1] | 1-17 | 0.827 | 278.31 | 277 | [M − H]+ | 5 |
| 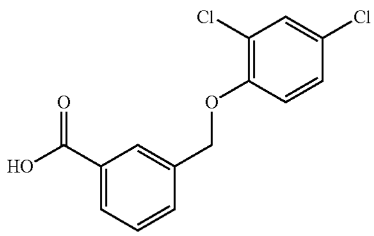 [SMILES: O=C(O)c1cccc(COc2ccc(Cl)cc2Cl)c1] | 1-18 | 10.15 | 297.13 | 299.1 | [M + H]+ | 3 |
| 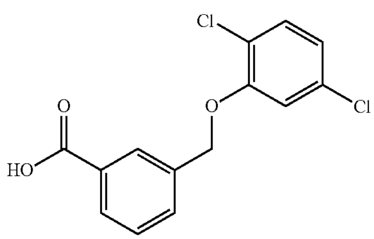 [SMILES: O=C(O)c1cccc(COc2cc(Cl)ccc2Cl)c1] | 1-19 | 9.90 | 297.13 | 296.0 | [M − H]+ | 4 |
| 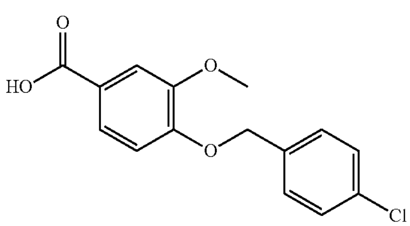 [SMILES: COc1cc(C(=O)O)ccc1OCc1ccc(Cl)cc1] | 1-20 | ND | 292.72 | ND | N/A | N/A |
| 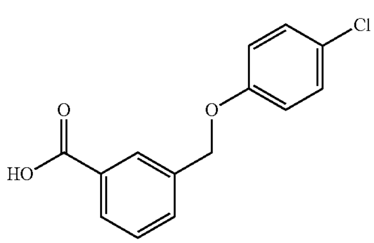 [SMILES: O=C(O)c1cccc(COc2ccc(Cl)cc2)c1] | 1-21 | 9.38 | 262.69 | 263.1 | [M + H]+ | 3 |
| 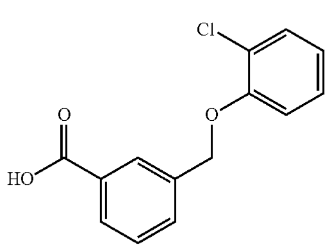 [SMILES: O=C(O)c1cccc(COc2ccccc2Cl)c1] | 1-22 | 9.04 | 262.69 | 263.1 | [M + H]+ | 3 |

TABLE 1B-continued

| Structure | Cpd No. | Purity RT (min) | MW | Oserved m/z | Ion | Purity Method |
|---|---|---|---|---|---|---|
| (2-F, 4-Cl phenoxy)methyl-3-benzoic acid | 1-23 | 9.43 | 280.68 | 281.1 | [M + H]⁺ | 3 |
| (2-Cl, 4-F phenoxy)methyl-3-benzoic acid | 1-24 | 9.29 | 280.68 | 281.0 | [M + H]⁺ | 3 |
| (2,6-diCl phenoxy)methyl-3-benzoic acid | 1-25 | 9.70 | 297.13 | 296.0 | [M − H]⁺ | 4 |
| 5-((2,4-diCl phenoxy)methyl)furan-2-carboxylic acid | 1-26 | 8.98 | 287.09 | 311.0 | [M + Na]⁺ | 3 |
| 3-((2,4-diCl phenoxy)methyl)-4-methoxybenzoic acid | 1-27 | 0.95 | 327.16 | 329.1 | [M + H]⁺ | 6 |
| 3-((2-CF₃, 4-Cl phenoxy)methyl)benzoic acid | 1-28 | 10.32 | 330.69 | 353.1 | [M + Na]⁺ | 3 |
| 3-((2-Cl, 4-CF₃ phenoxy)methyl)benzoic acid | 1-29 | 10.29 | 330.69 | 353.1 | [M + Na]⁺ | 3 |

TABLE 1B-continued
| Structure | Cpd No. | Purity RT (min) | MW | Observed m/z | Ion | Purity Method |
|---|---|---|---|---|---|---|
| 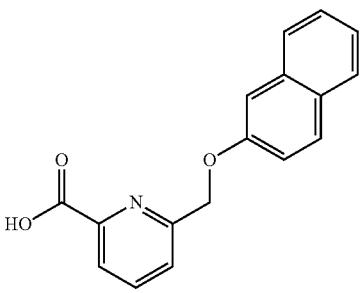 [SMILES: O=C(O)c1cccc(COc2ccc3ccccc3c2)n1] | 1-30 | 8.61 | 279.30 | 280.2 | [M + H]+ | 3 |
| 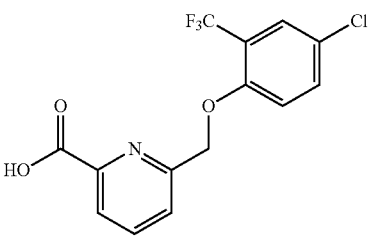 [SMILES: O=C(O)c1cccc(COc2ccc(Cl)cc2C(F)(F)F)n1] | 1-31 | 9.51 | 331.68 | 332.1 | [M + H]+ | 3 |
| 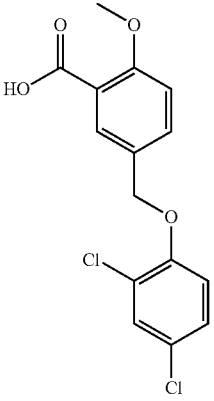 [SMILES: COc1ccc(COc2ccc(Cl)cc2Cl)cc1C(=O)O] | 1-32 | 0.932 | 327.16 | 327.1 | [M + H]+ | 6 |
| 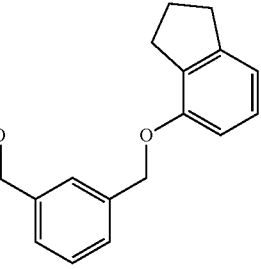 | 1-33 | 10.14 | 268.31 | 269.2 | [M + H]+ | 3 |
| 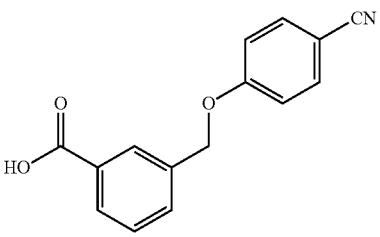 [SMILES: N#Cc1ccc(OCc2cccc(C(=O)O)c2)cc1] | 1-34 | 7.86 | 253.26 | 254.2 | [M + H]+ | 3 |

TABLE 1B-continued

| Structure | Cpd No. | Purity RT (min) | MW | Observed m/z | Ion | Purity Method |
|---|---|---|---|---|---|---|
| (3-carboxybenzyl 2-chloro-4-cyanophenyl ether) | 1-35 | 8.59 | 287.70 | 288.1 | [M + H]+ | 3 |
| (6-((4-chlorophenoxy)methyl)picolinic acid) | 1-36 | 8.04 | 263.68 | 264.1 | [M + H]+ | 3 |
| (3-((2-methoxyphenoxy)methyl)benzoic acid) | 1-37 | 7.97 | 258.27 | 259.2 | [M + H]+ | 3 |
| (3-((4-methoxyphenoxy)methyl)benzoic acid) | 1-38 | 8.28 | 258.27 | 259.1 | [M + H]+ | 3 |
| (3-((3-methoxyphenoxy)methyl)benzoic acid) | 1-39 | 8.51 | 258.27 | 259.2 | [M + H]+ | 3 |
| (3-((2-fluorophenoxy)methyl)benzoic acid) | 1-40 | 8.47 | 246.24 | 247.2 | [M + H]+ | 3 |
| (3-((4-(trifluoromethyl)phenoxy)methyl)benzoic acid) | 1-41 | 9.70 | 296.25 | 319.1 | [M + Na]+ | 3 |

TABLE 1B-continued

| Structure | Cpd No. | Purity RT (min) | MW | Observed m/z | Ion | Purity Method |
|---|---|---|---|---|---|---|
| (indane-substituted benzyloxy benzoic acid) | 1-42 | 10.14 | 268.31 | 269.2 | [M + H]⁺ | 3 |
| (2,4-dichlorophenoxy thiophene carboxylic acid) | 1-43 | 9.66 | 303.15 | 305.0 | [M + H]⁺ | 3 |
| (2,4-dichlorophenoxymethyl chlorobenzoic acid) | 1-44 | 0.702 | 331.57 | 328.8 | [M − H]⁺ | 7 |
| (4-ethoxyphenoxymethyl benzoic acid) | 1-45 | 0.629 | 272.30 | 271.0 | [M − H]⁺ | 7 |
| (4-cyclopropylphenoxymethyl benzoic acid) | 1-46 | 9.84 | 268.31 | 269.2 | [M + H]⁺ | 3 |
| (4-trifluoromethoxyphenoxymethyl benzoic acid) | 1-47 | 9.89 | 312.24 | 313.2 | [M + H]⁺ | 3 |

TABLE 1B-continued

| Structure | Cpd No. | Purity RT (min) | MW | Observed m/z | Ion | Purity Method |
|---|---|---|---|---|---|---|
| (structure) | 1-48 | 9.53 | 308.24 | 307.0 | [M − H]$^+$ | 3 |
| (structure) | 1-49 | 0.707 | 278.31 | 277.0 | [M − H]$^+$ | 7 |
| (structure) | 1-50 | 0.720 | 311.16 | 308.9 | [M − H]$^+$ | 7 |
| (structure) | 1-51 | 0.938 | 318.37 | 341.0 | [M + Na]$^+$ | 6 |
| (structure) | 1-52 | 0.904 | 320.34 | 321.1 | [M + H]$^+$ | 6 |
| (structure) | 1-53 | 0.915 | 290.74 | 291.1 | [M + H]$^+$ | 6 |
| (structure) | 1-54 | 7.50 | 270.28 | 271.2 | [M + H]$^+$ | 3 |

TABLE 1B-continued

| Structure | Cpd No. | Purity RT (min) | MW | Observed m/z | Ion | Purity Method |
|---|---|---|---|---|---|---|
| (3-((2-chloro-4-(trifluoromethyl)phenoxy)methyl)-2-fluorobenzoic acid) | 1-55 | 10.29 | 348.68 | 349.1 | [M + H]⁺ | 3 |
| (6-((2-chloro-4-(trifluoromethyl)phenoxy)methyl)picolinic acid) | 1-56 | 9.40 | 331.68 | 332.1 | [M + H]⁺ | 3 |
| (6-((4-chloro-2-methylphenoxy)methyl)picolinic acid) | 1-57 | 8.97 | 277.70 | 278.2 | [M + H]⁺ | 3 |
| (2-fluoro-3-((naphthalen-2-yloxy)methyl)benzoic acid) | 1-58 | 9.84 | 296.30 | 297.2 | [M + H]⁺ | 3 |
| (3-((4-chloro-3-fluorophenoxy)methyl)benzoic acid) | 1-59 | 0.813 | 280.68 | 278.9 | [M − H]⁺ | 5 |
| (3-((3-fluoro-2,4-dimethylphenoxy)methyl)benzoic acid) | 1-60 | 0.823 | 274.29 | 272.9 | [M − H]⁺ | 5 |
| (3-(((2,2-difluorobenzo[d][1,3]dioxol-5-yl)oxy)methyl)benzoic acid) | 1-61 | 9.73 | 308.24 | 307.0 | [M − H]⁺ | 4 |

TABLE 1B-continued

| Structure | Cpd No. | Purity RT (min) | MW | Oserved m/z | Ion | Purity Method |
|---|---|---|---|---|---|---|
| 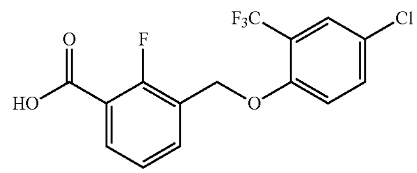 [SMILES: O=C(O)c1cccc(COc2ccc(Cl)cc2C(F)(F)F)c1F] | 1-62 | 10.35 | 348.68 | 348.1 | [M + H]+ | 3 |
| 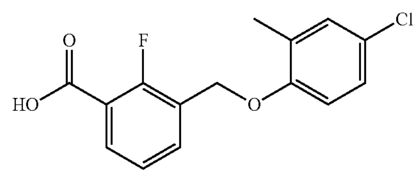 [SMILES: Cc1cc(Cl)ccc1OCc1cccc(C(=O)O)c1F] | 1-63 | 10.18 | 294.71 | 295.2 | [M + H]+ | 3 |
| 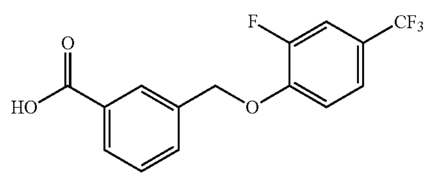 [SMILES: O=C(O)c1cccc(COc2ccc(C(F)(F)F)cc2F)c1] | 1-64 | 9.71 | 314.24 | 337.1 | [M + Na]+ | 3 |
| 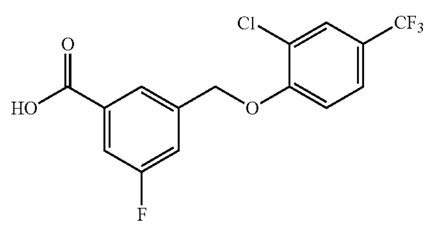 [SMILES: O=C(O)c1cc(F)cc(COc2ccc(C(F)(F)F)cc2Cl)c1] | 1-65 | 10.67 | 348.68 | 346.1 | [M − H]+ | 4 |
| 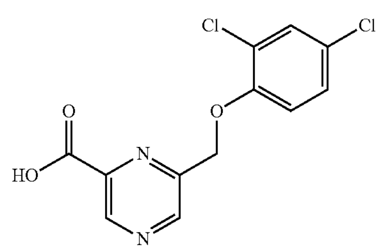 [SMILES: O=C(O)c1cncc(COc2ccc(Cl)cc2Cl)n1] | 1-66 | 8.268 | 299.10 | 299.1 | [M + H]+ | 3 |
| 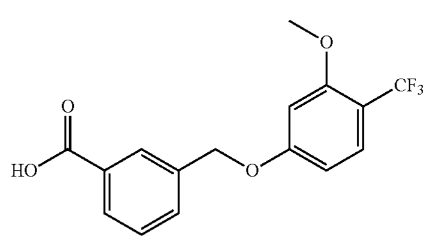 [SMILES: COc1cc(OCc2cccc(C(=O)O)c2)ccc1C(F)(F)F] | 1-67 | 9.68 | 326.27 | 327.1 | [M + H]+ | 3 |
| 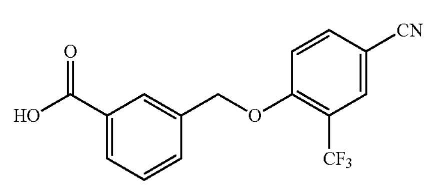 [SMILES: N#Cc1ccc(OCc2cccc(C(=O)O)c2)c(C(F)(F)F)c1] | 1-68 | 0.796 | 321.26 | 319.9 | [M − H]+ | 5 |

TABLE 1B-continued

| Structure | Cpd No. | Purity RT (min) | MW | Observed m/z | Ion | Purity Method |
|---|---|---|---|---|---|---|
| 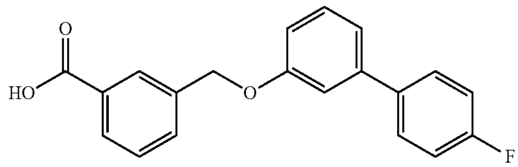 [SMILES: O=C(O)c1cccc(COc2cccc(-c3ccc(F)cc3)c2)c1] | 1-69 | 0.899 | 322.34 | 321.0 | [M − H]⁺ | 5 |
| 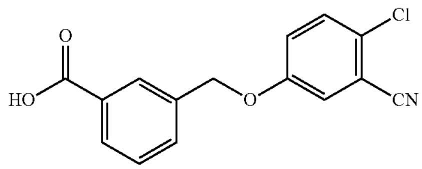 [SMILES: N#Cc1cc(OCc2cccc(C(=O)O)c2)ccc1Cl] | 1-70 | 0.757 | 287.70 | 285.9 | [M − H]⁺ | 5 |
| 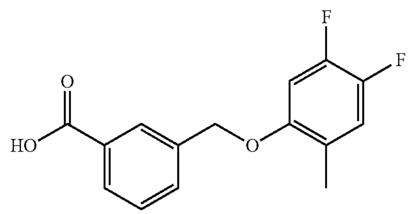 [SMILES: Cc1cc(F)c(F)cc1OCc1cccc(C(=O)O)c1] | 1-71 | 0.8 | 278.25 | 276.9 | [M − H]⁺ | 5 |
| 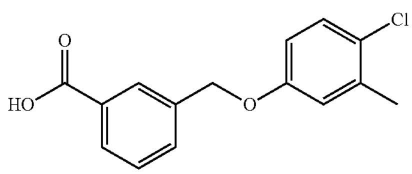 [SMILES: Cc1cc(OCc2cccc(C(=O)O)c2)ccc1Cl] | 1-72 | 0.683 | 276.72 | 274.9 | [M − H]⁺ | 5 |
| 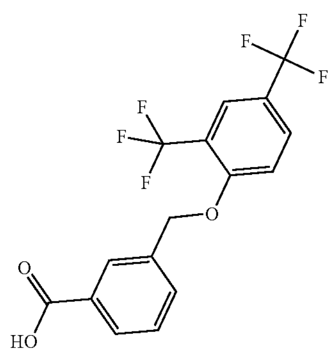 [SMILES: O=C(O)c1cccc(COc2ccc(C(F)(F)F)cc2C(F)(F)F)c1] | 1-73 | 10.14 | 364.2 | 363.0 | [M − H]⁺ | 4 |
| 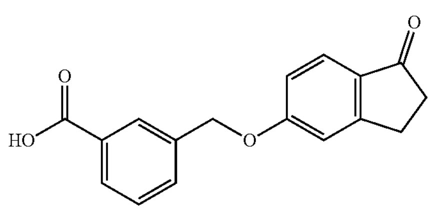 [SMILES: O=C(O)c1cccc(COc2ccc3c(c2)CCC3=O)c1] | 1-74 | 0.703 | 282.3 | 280.9 | [M − H]⁺ | 5 |
| 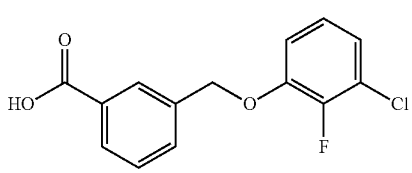 [SMILES: O=C(O)c1cccc(COc2cccc(Cl)c2F)c1] | 1-75 | 0.766 | 280.7 | 278.9 | [M − H]⁺ | 5 |

TABLE 1B-continued

| Structure | Cpd No. | Purity RT (min) | MW | Observed m/z | Ion | Purity Method |
|---|---|---|---|---|---|---|
| 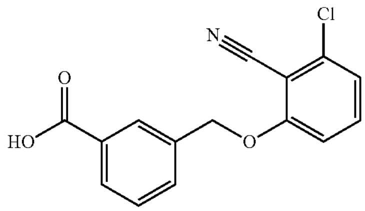 [SMILES: N#Cc1c(Cl)cccc1OCc1cccc(C(=O)O)c1] | 1-76 | 0.739 | 287.7 | 285.9 | [M − H]+ | 5 |
| 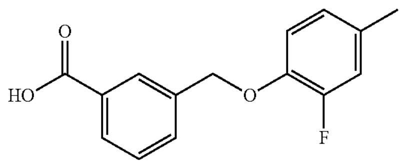 [SMILES: Cc1ccc(OCc2cccc(C(=O)O)c2)c(F)c1] | 1-77 | 0.84 | 260.3 | 261.1 | [M − H]+ | 6 |
| 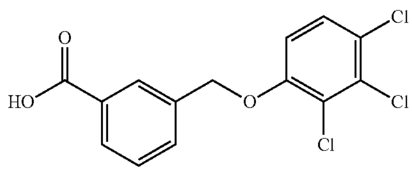 [SMILES: O=C(O)c1cccc(COc2ccc(Cl)c(Cl)c2Cl)c1] | 1-78 | 0.727 | 331.57 | 328.8 | [M − H]+ | 7 |
| 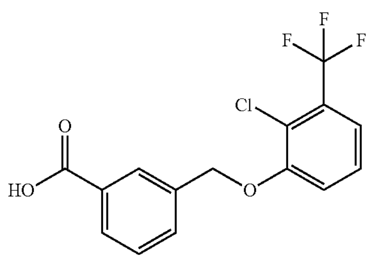 [SMILES: O=C(O)c1cccc(COc2cccc(C(F)(F)F)c2Cl)c1] | 1-79 | 0.717 | 330.7 | 328.9 | [M − H]+ | 7 |
| 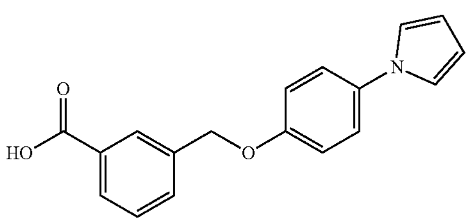 [SMILES: O=C(O)c1cccc(COc2ccc(-n3cccc3)cc2)c1] | 1-80 | 0.68 | 293.3 | 292 | [M − H]+ | 7 |
| 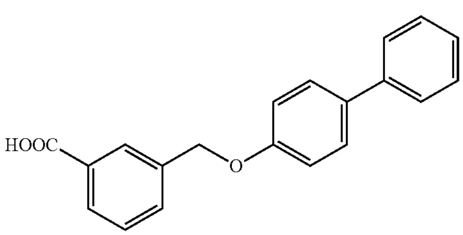 [SMILES: O=C(O)c1cccc(COc2ccc(-c3ccccc3)cc2)c1] | 1-81 | 14.24 | 304.4 | 327.1 | [M + Na]+ | 10 |
| 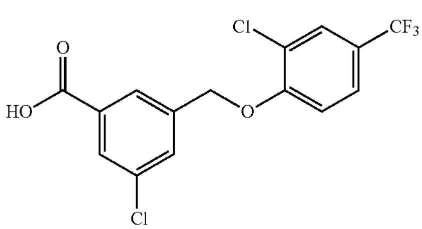 [SMILES: O=C(O)c1cc(Cl)cc(COc2ccc(C(F)(F)F)cc2Cl)c1] | 1-82 | 11.26 | 365.13 | 363.0 | [M − H]+ | 4 |

TABLE 1B-continued

| Structure | Cpd No. | Purity RT (min) | MW | Oserved m/z | Ion | Purity Method |
|---|---|---|---|---|---|---|
| 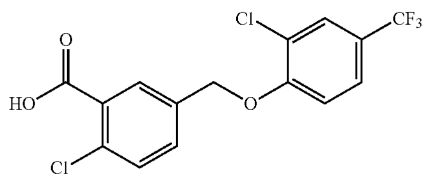 [SMILES: O=C(O)c1cc(COc2ccc(C(F)(F)F)cc2Cl)ccc1Cl] | 1-83 | 10.61 | 365.13 | 365.0 | [M − H]+ | 4 |
| 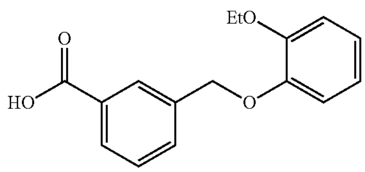 [SMILES: CCOc1ccccc1OCc1cccc(C(=O)O)c1] | 1-84 | 8.67 | 272.30 | 273.2 | [M + H]+ | 3 |
| 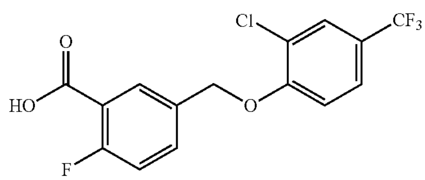 [SMILES: O=C(O)c1cc(COc2ccc(C(F)(F)F)cc2Cl)ccc1F] | 1-85 | 10.16 | 348.68 | 349.1 | [M + H]+ | 3 |
| 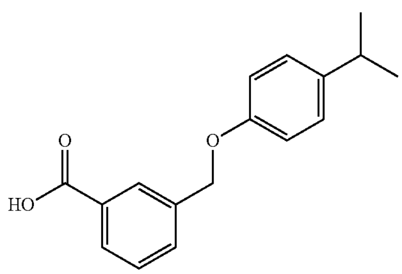 [SMILES: CC(C)c1ccc(OCc2cccc(C(=O)O)c2)cc1] | 1-86 | 10.47 | 270.33 | 271.2 | [M + H]+ | 3 |
| 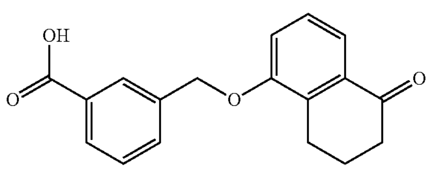 [SMILES: O=C(O)c1cccc(COc2cccc3c2CCCC3=O)c1] | 1-87 | 0.754 | 296.32 | 294.5 | [M − H]+ | 5 |
| 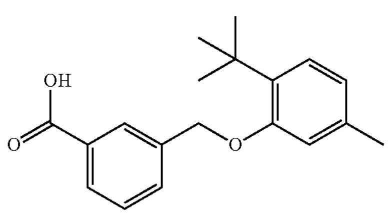 [SMILES: Cc1ccc(C(C)(C)C)c(OCc2cccc(C(=O)O)c2)c1] | 1-88 | 0.915 | 298.4 | 297 | [M − H]+ | 5 |
| 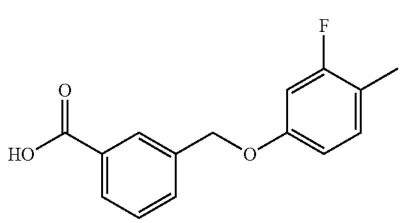 [SMILES: Cc1ccc(OCc2cccc(C(=O)O)c2)cc1F] | 1-89 | 0.78 | 260.3 | 259 | [M − H]+ | 5 |

TABLE 1B-continued

| Structure | Cpd No. | Purity RT (min) | MW | Observed m/z | Ion | Purity Method |
|---|---|---|---|---|---|---|
| (3-chloro-4-cyanophenoxymethyl)benzoic acid | 1-90 | 0.751 | 287.70 | 285.9 | [M − H]+ | 5 |
| (4-fluoro-2-trifluoromethylphenoxymethyl)benzoic acid | 1-91 | 0.817 | 314.24 | 312.9 | [M − H]+ | 5 |
| (2-chloro-4-methoxyphenoxymethyl)benzoic acid | 1-92 | 0.773 | 292.72 | 290.9 | [M − H]+ | 5 |
| (4-fluoro-2-methylphenoxymethyl)benzoic acid | 1-94 | 0.774 | 260.26 | 259 | [M − H]+ | 5 |
| (3-chloro-2-methylphenoxymethyl)benzoic acid | 1-95 | 0.824 | 276.72 | 274.9 | [M − H]+ | 5 |
| (2,3-difluoro-4-methoxyphenoxymethyl)benzoic acid | 1-96 | 0.752 | 294.25 | 292.9 | [M − H]+ | 5 |
| (benzo[b]thiophen-6-yloxymethyl)benzoic acid | 1-97 | 0.785 | 284.33 | 282.9 | [M − H]+ | 5 |
| (isoquinolin-7-yloxymethyl)benzoic acid | 1-98 | 0.607 | 279.30 | 280.1 | [M + H]+ | 6 |

TABLE 1B-continued

| Structure | Cpd No. | Purity RT (min) | MW | Observed m/z | Ion | Purity Method |
|---|---|---|---|---|---|---|
| 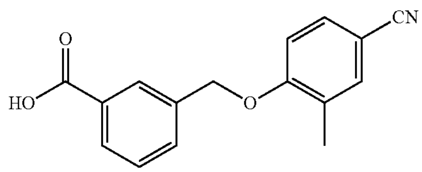 [SMILES: Cc1cc(C#N)ccc1OCc1cccc(C(=O)O)c1] | 1-99 | 1.13 | 267.28 | 266.1 | [M − H]+ | 5 |
| 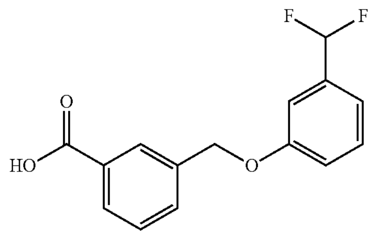 [SMILES: O=C(O)c1cccc(COc2cccc(C(F)F)c2)c1] | 1-100 | 8.80 | 278.25 | 301.1 | [M + Na]+ | 3 |
| 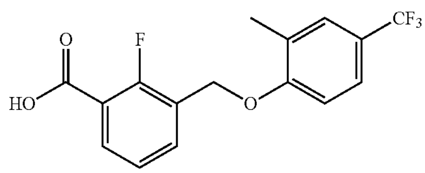 [SMILES: Cc1cc(C(F)(F)F)ccc1OCc1cccc(C(=O)O)c1F] | 1-101 | 10.33 | 328.26 | 351.1 | [M + Na]+ | 3 |
| 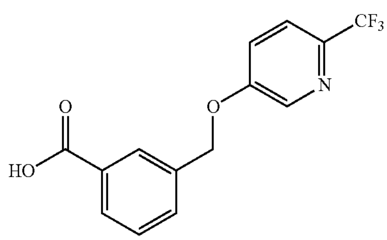 [SMILES: O=C(O)c1cccc(COc2ccc(C(F)(F)F)nc2)c1] | 1-102 | 8.28 | 297.23 | 298.2 | [M + H]+ | 3 |
| 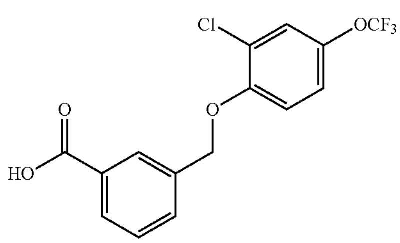 [SMILES: O=C(O)c1cccc(COc2ccc(OC(F)(F)F)cc2Cl)c1] | 1-103 | 10.46 | 346.69 | 369.1 | [M + Na]+ | 3 |
| 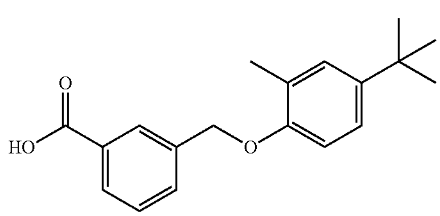 [SMILES: Cc1cc(C(C)(C)C)ccc1OCc1cccc(C(=O)O)c1] | 1-108 | 0.762 | 298.38 | 297.0 | [M − H]+ | 7 |
| 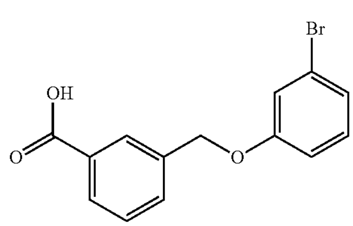 [SMILES: O=C(O)c1cccc(COc2cccc(Br)c2)c1] | 1-109 | 0.749 | 307.14 | 305.0 | [M − H]+ | 8 |

TABLE 1B-continued

| Structure | Cpd No. | Purity RT (min) | MW | Oserved m/z | Ion | Purity Method |
|---|---|---|---|---|---|---|
| (3-carboxybenzyl 4-bromophenyl ether) | 1-110 | 0.574 | 307.14 | 306.8 | [M − H]+ | 7 |
| (3-carboxybenzyl 3-fluoro-4-trifluoromethylphenyl ether) | 1-112 | 9.88 | 314.24 | 337.1 | [M + Na]+ | 3 |
| (4-carboxybenzyl 2,4-dichlorophenyl ether) | 1-113 | ND | 296.00 | ND | N/A | N/A |
| (2-carboxybenzyl 2,4-dichlorophenyl ether) | 1-114 | 10.72 | 296.00 | 297.1 | [M + H]+ | 3 |
| (6-((2,4-dichlorophenoxy)methyl)picolinic acid) | 1-115 | 9.12 | 298.12 | 300.1 | [M + H]+ | 3 |
| (pyrazine carboxylic acid with 2,4-dichlorophenoxymethyl) | 1-116 | 8.27 | 299.11 | 299.1 | [M + H]+ | 3 |

TABLE 1B-continued

| Structure | Cpd No. | Purity RT (min) | MW | Oserved m/z | Ion | Purity Method |
|---|---|---|---|---|---|---|
| (3-chloro-4-(trifluoromethyl)phenoxymethyl benzoic acid) | 1-118 | 10.362 | 330.69 | 329 | [M − H]⁺ | 4 |
| (3-chloro-4-(trifluoromethyl)phenoxymethyl benzoic acid) | 1-119 | 10.362 | 330.69 | 329 | [M − H]⁺ | 4 |
| (2-bromo-4-(trifluoromethyl)phenoxymethyl benzoic acid) | 1-120 | 10.43 | 375.14 | 399.0 | [M + Na]⁺ | 3 |
| (2-chloro-4-(trifluoromethoxy)phenoxymethyl-3-fluoro benzoic acid) | 1-121 | 10.872 | 364.68 | 363.0 | [M − H]⁺ | 4 |
| (2-chloro-4-cyclopropylphenoxymethyl benzoic acid) | 1-122 | 10.385 | 302.75 | 301.2 | [M − H]⁺ | 4 |
| (2,3,4-trichlorophenoxymethyl-3-fluoro benzoic acid) | 1-123 | 11.165 | 349.56 | 348.0 | [M − H]⁺ | 4 |

TABLE 1B-continued

| Structure | Cpd No. | Purity RT (min) | MW | Observed m/z | Ion | Purity Method |
|---|---|---|---|---|---|---|
| 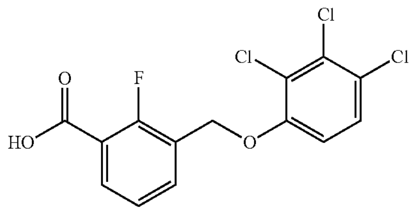 [SMILES: O=C(O)c1cccc(COc2ccc(Cl)c(Cl)c2Cl)c1F] | 1-124 | 10.773 | 349.56 | 347.0 | [M − H]+ | 4 |
| 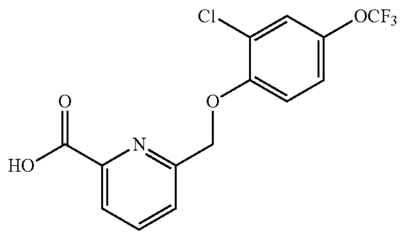 [SMILES: O=C(O)c1cccc(COc2ccc(OC(F)(F)F)cc2Cl)n1] | 1-125 | 9.637 | 347.67 | 348.1 | [M + H]+ | 3 |
| 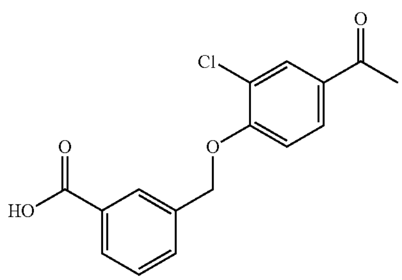 [SMILES: CC(=O)c1ccc(OCc2cccc(C(=O)O)c2)c(Cl)c1] | 1-126 | 8.279 | 304.73 | 303 | [M − H]+ | 4 |
| 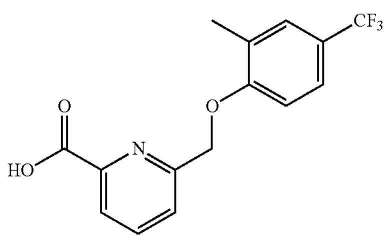 [SMILES: Cc1cc(C(F)(F)F)ccc1OCc1cccc(C(=O)O)n1] | 1-127 | 9.325 | 311.26 | 312.2 | [M + H]+ | 4 |
| 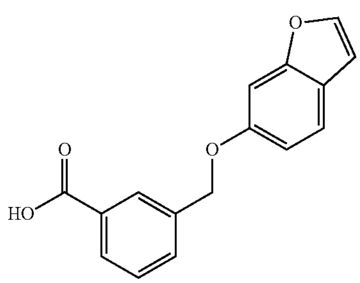 [SMILES: O=C(O)c1cccc(COc2ccc3ccoc3c2)c1] | 1-128 | 8.906 | 268.27 | 267.2 | [M − H]+ | 4 |
| 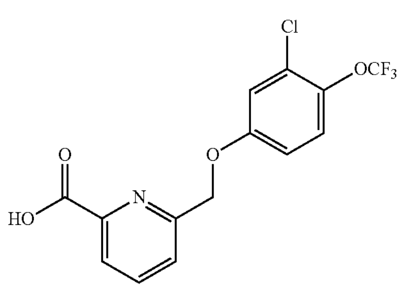 [SMILES: O=C(O)c1cccc(COc2ccc(OC(F)(F)F)c(Cl)c2)n1] | 1-129 | 9.54 | 347.67 | 348.1 | [M + H]+ | 3 |

TABLE 1B-continued

| Structure | Cpd No. | Purity RT (min) | MW | Oserved m/z | Ion | Purity Method |
|---|---|---|---|---|---|---|
| 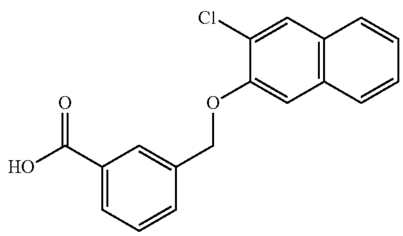 [SMILES: O=C(O)c1cccc(COc2cc3ccccc3cc2Cl)c1] | 1-130 | 10.488 | 312.75 | 311 | [M − H]⁺ | 4 |
| 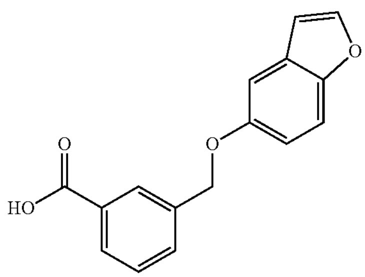 [SMILES: O=C(O)c1cccc(COc2ccc3occc3c2)c1] | 1-131 | 8.828 | 268.27 | 267.2 | [M − H]⁺ | 4 |
| 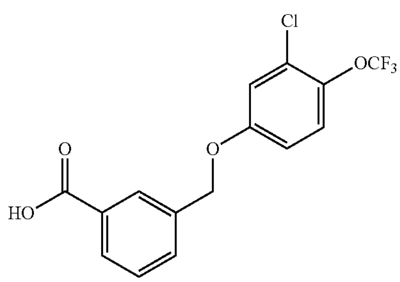 [SMILES: O=C(O)c1cccc(COc2ccc(OC(F)(F)F)c(Cl)c2)c1] | 1-132 | 10.581 | 346.69 | 345 | [M − H]⁺ | 4 |
| 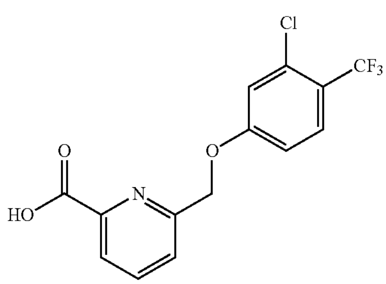 [SMILES: O=C(O)c1cccc(COc2ccc(C(F)(F)F)c(Cl)c2)n1] | 1-133 | 9.625 | 331.68 | 332.1 | [M − H]⁺ | 3 |
| 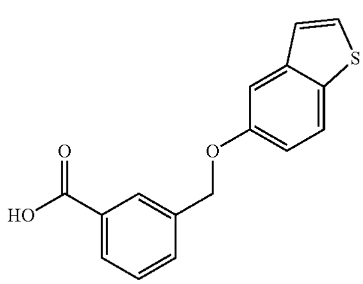 [SMILES: O=C(O)c1cccc(COc2ccc3sccc3c2)c1] | 1-134 | 9.469 | 284.33 | 283 | [M − H]⁺ | 4 |

TABLE 1B-continued

| Structure | Cpd No. | Purity RT (min) | MW | Oserved m/z | Ion | Purity Method |
|---|---|---|---|---|---|---|
| (structure) | 1-135 | 8.881 | 294.25 | 293.2 | [M − H]+ | 4 |
| (structure) | 1-136 | 10.155 | 366.67 | 366 | [M + H]+ | 3 |
| (structure) | 1-137 | 7.673 | 331.68 | 332.1 | [M + H]+ | 3 |
| (structure) | 1-138 | 4.97 | 310.27 | 309.07 | [M − H]+ | 12 |
| (structure) | 1-139 | 5.09 | 326.27 | 325.07 | [M − H]+ | 12 |
| (structure) | 1-140 | 13.65 | 296.25 | 297.4 | [M + H]+ | 10 |
| (structure) | 1-141 | 13.09 | 296.25 | 295 | [M − H]+ | 10 |

TABLE 1B-continued

| Structure | Cpd No. | Purity RT (min) | MW | Oserved m/z | Ion | Purity Method |
|---|---|---|---|---|---|---|
| 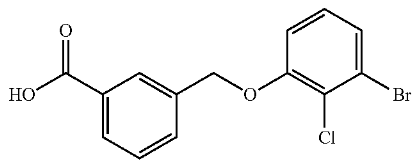 [SMILES: O=C(O)c1cccc(COc2cccc(Br)c2Cl)c1] | 1-142 | 0.704 | 341.59 | 340.8 | [M − H]+ | 7 |
| 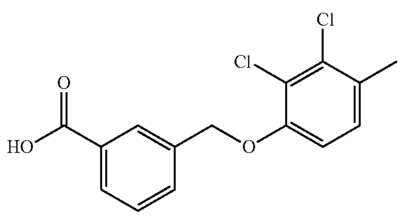 [SMILES: Cc1ccc(OCc2cccc(C(=O)O)c2)c(Cl)c1Cl] | 1-143 | 0.719 | 311.16 | 308.9 | [M − H]+ | 7 |
| 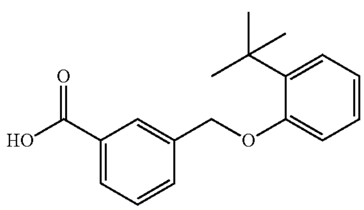 [SMILES: CC(C)(C)c1ccccc1OCc1cccc(C(=O)O)c1] | 1-144 | 0.733 | 284.36 | 283 | [M − H]+ | 7 |
| 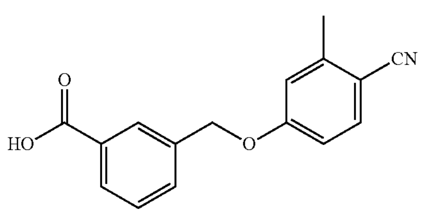 [SMILES: Cc1cc(OCc2cccc(C(=O)O)c2)ccc1C#N] | 1-145 | 0.387 | 267.28 | 265.9 | [M − H]+ | 7 |
| 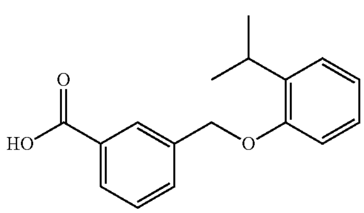 [SMILES: CC(C)c1ccccc1OCc1cccc(C(=O)O)c1] | 1-146 | 1.244 | 270.33 | 269.1 | [M − H]+ | 5 |
| 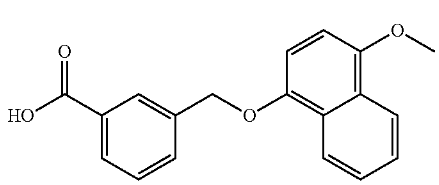 [SMILES: COc1ccc(OCc2cccc(C(=O)O)c2)c2ccccc12] | 1-147 | 0.722 | 308.33 | — | — | 7 |
| 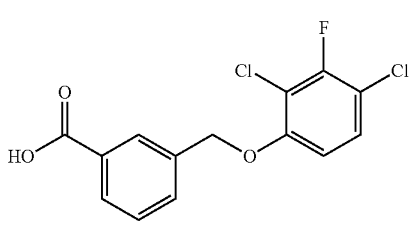 [SMILES: O=C(O)c1cccc(COc2ccc(Cl)c(F)c2Cl)c1] | 1-148 | 1.234 | 315.12 | 313 | [M − H]+ | 5 |

TABLE 1B-continued

| Structure | Cpd No. | Purity RT (min) | MW | Observed m/z | Ion | Purity Method |
|---|---|---|---|---|---|---|
| 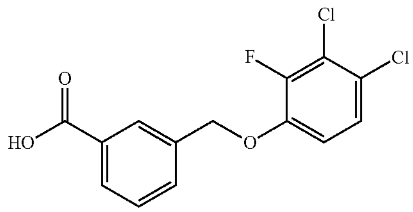 [SMILES: O=C(O)c1cccc(COc2ccc(Cl)c(Cl)c2F)c1] | 1-149 | 1.238 | 315.12 | 313 | [M − H]+ | 5 |
| 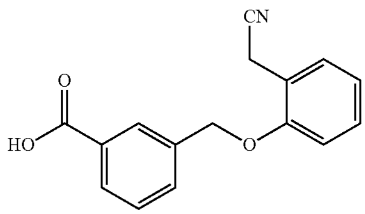 [SMILES: N#CCc1ccccc1OCc1cccc(C(=O)O)c1] | 1-150 | 0.688 | 267.28 | 265.9 | [M − H]+ | 5 |
| 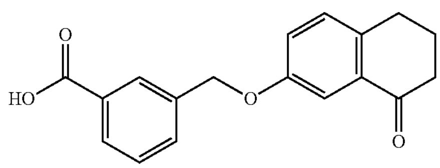 [SMILES: O=C(O)c1cccc(COc2ccc3c(c2)C(=O)CCC3)c1] | 1-151 | 1.117 | 296.32 | 295.1 | [M − H]+ | 5 |
| 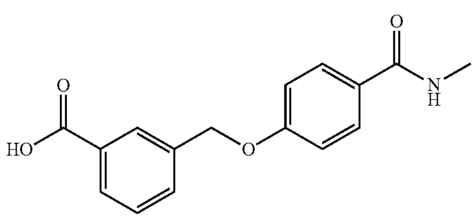 [SMILES: CNC(=O)c1ccc(OCc2cccc(C(=O)O)c2)cc1] | 1-152 | 0.615 | 285.30 | 285.9 | [M − H]+ | 7 |
| 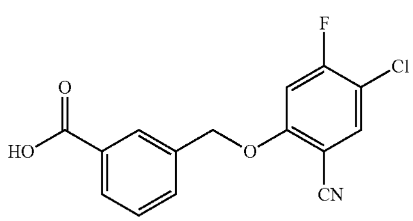 [SMILES: N#Cc1cc(Cl)c(F)cc1OCc1cccc(C(=O)O)c1] | 1-153 | 0.748 | 305.69 | 303.9 | [M − H]+ | 5 |
| 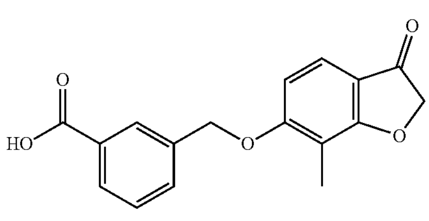 [SMILES: Cc1c(OCc2cccc(C(=O)O)c2)ccc2c1OCC2=O] | 1-154 | 0.719 | 298.29 | 296.9 | [M − H]+ | 5 |

Example 2

Synthesis of Compound 2-1 and Other Representative Compounds

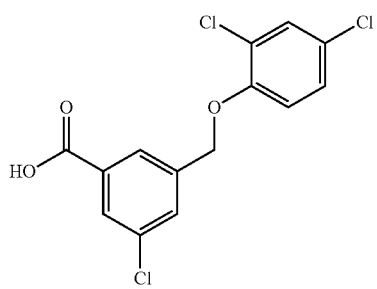

2-1

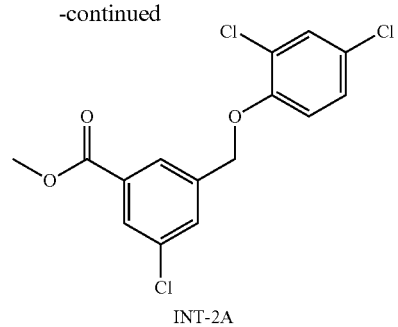

INT-2A

To a stirring solution of methyl 3-chloro-5-hydroxybenzoate (100 mg, 0.50 mmol) in DCM (5 mL) were added triphenylphosphine (131 mg, 0.50 mmol) and DEAD (108.7 µL, 0.60 mmol). The reaction mixture was purged with $N_2$ (3×) and stirred at 10° C. for 16 h (under an atmosphere of $N_2$) then concentrated and purified by flash $SiO_2$ chromatography (EA/petroleum ether) to afford 150 mg (87.0%) of methyl 3-chloro-5-((2,4-dichlorophenoxy)methyl)benzoate (INT 2-A) as a pink solid. TLC (10% EA/petroleum ether): $R_f$=0.50. $^1$H NMR (400 MHz, $CDCl_3$-d) δ 7.99 (d, J=1.8 Hz, 2H), 7.70-7.66 (m, 1H), 7.42 (d, J=2.6 Hz, 1H), 7.34 (d, J=2.4 Hz, 1H), 6.87 (d, J=8.8 Hz, 1H), 5.14 (s, 2H), 3.95 (s, 3H).

Step 2-2. Synthesis of 3-chloro-5-((2,4-dichlorophenoxy)methyl)benzoic acid (Compound 2-1

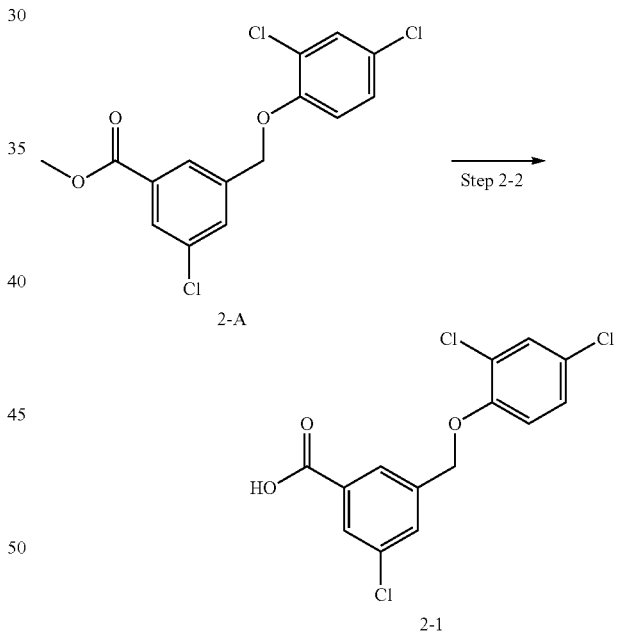

Scheme 2

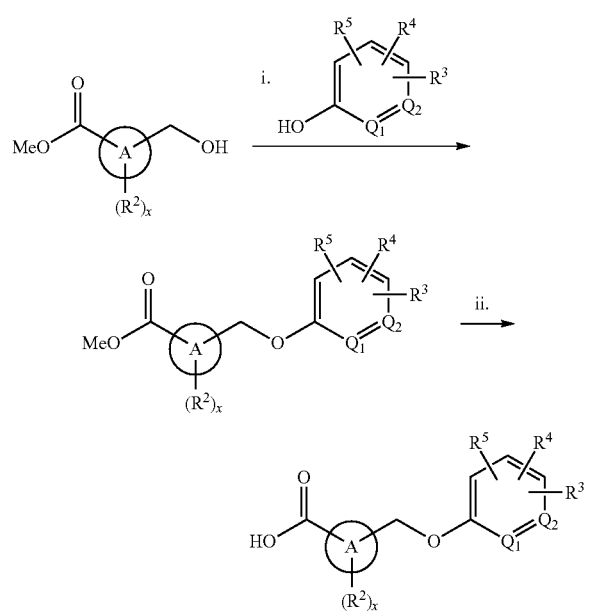

Reagents: (i) PPh₃, DIAD, THF; (ii) NaOH, solvent (THF, MeOH, or DMF)

Step 2-1. Synthesis of methyl 3-chloro-5-((2,4-dichlorophenoxy)methyl)benzoate (INT 2-A)

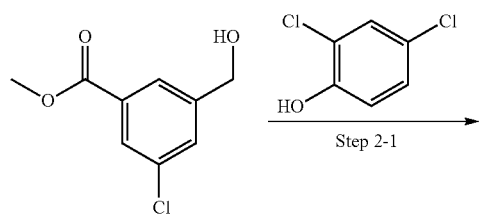

To a stirring solution of methyl 3-chloro-5-((2,4-dichlorophenoxy)methyl)benzoate (INT 2-A) (100 mg, 0.29 mmol) in MeOH (1 mL) and THF (1 mL) was added 2M NaOH (0.43 mL, 0.87 mmol). The reaction mixture was heated at 30° C. for 1 h and then concentrated in vacuo. The resulting residue was purified by reversed phase HPLC to afford 12.6 mg (13%) of 3-chloro-5-((2,4-dichlorophenoxy)methyl)benzoic acid (Compound 2-1) as a white solid. LCMS-ESI (m/z) calculated for $C_{14}H_9Cl_3O_3$: 331.5. found 328.8 [M−H]⁺, $t_R$=0.72 min. $^1$H NMR (400 MHz, DMSO-$d_6$) δ 7.99 (s, 1H), 7.86 (s, 1H), 7.77 (s, 1H), 7.62 (d, J=2.6 Hz, 1H), 7.40 (dd, J=2.6, 8.8 Hz, 1H), 7.25 (d, J=8.9 Hz, 1H), 5.31 (s, 2H).

The compounds listed in Table 2 were made using the procedures of Scheme 2.

TABLE 2
| Structure | Cpd No. | Purity RT (min) | MW | Observed m/z | Ion | Purity Method |
|---|---|---|---|---|---|---|
| ![structure] | 2-1 | 0.724 | 331.57 | 328.8 | [M − H]+ | 4 |
| ![structure] | 2-2 | 10.43 | 360.71 | 383.1 | [M + Na]+ | 3 |
| ![structure] | 2-3 | 11.38 | 409.58 | 433.0 | [M + Na]+ | 3 |
| ![structure] | 2-4 | 0.73 | 346.5 | 346 | [M − H]+ | 7 |
Example 3
Synthesis of Compound 3-1, Compound 3-2 and Other Representative Compounds
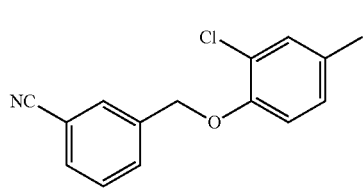
3-1
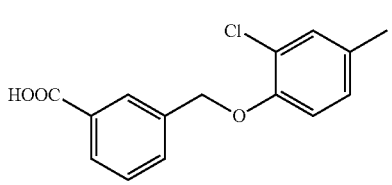 [SMILES: Cc1ccc(OCc2cccc(C(=O)O)c2)c(Cl)c1]
3-2
-continued

Scheme 3

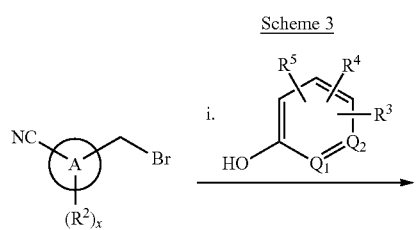

To a stirring solution of 3-(bromomethyl)benzonitrile (500 mg, 2.55 mmol) in DMF (8 mL) were added 2-chloro-4-methylphenol (360 mg, 2.5 mmol) and $Na_2CO_3$ (0.81 g, 7.65 mmol). The reaction mixture was stirred at rt overnight then quenched with 150 mL of $H_2O$. The resulting precipitate was collected, washed with $H_2O$ (2×20 mL) and dried to afford 600 mg (91.3%) of 3-((2-chloro-4-methylphenoxy)methyl)benzonitrile (INT 3-A). LCMS-ESI (m/z) calculated for $C_{15}H_{12}ClNO$: 257.7. found 258.0 $[M+H]^+$, $t_R$=5.43 min. (Method 11).

The compound listed in Table 3A was made using the procedures of Scheme 3, Step 3-1 using 3-(bromomethyl)benzonitrile and 2,4-dichlorophenol.

TABLE 3A

| Structure | Cpd No. | Purity RT (min) | MW | Observed m/z | Ion | Purity Method |
|---|---|---|---|---|---|---|
| (structure) | 3-1 | 11.49 | 278.13 | 277 | $[M - H]^+$ | 4 |

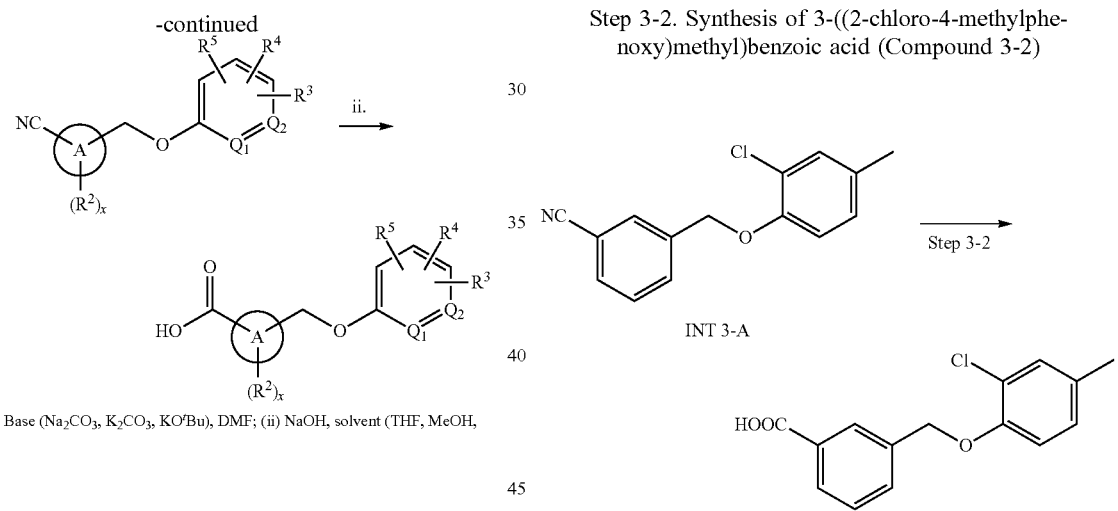

Reagents: (i) Base ($Na_2CO_3$, $K_2CO_3$, $KO^tBu$), DMF; (ii) NaOH, solvent (THF, MeOH, or DMF).

Step 3-1. Synthesis of 3-((2-chloro-4-methylphenoxy)methyl)benzonitrile (INT 3-A)

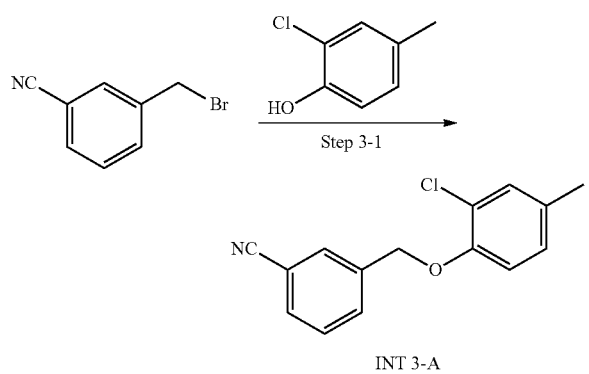

Step 3-2. Synthesis of 3-((2-chloro-4-methylphenoxy)methyl)benzoic acid (Compound 3-2)

To a stirring solution of 3-((2-chloro-4-methylphenoxy)methyl)benzonitrile (INT 3-A) (300 mg, 0.12 mmol) in MeOH (5 mL) was added a solution of NaOH (375 mg, 9.4 mmol) in $H_2O$ (8 mL). The reaction vessel was sealed and stirred at 90° C. overnight then cooled to room temperature and concentrated to remove the MeOH. The aqueous layer was washed with EA and acidified with 4N HCl. The resulting precipitate was collected to provide 210 mg (65%) of 3-((2-chloro-4-methylphenoxy)methyl)benzoic acid (Compound 3-2). LCMS-ESI (m/z) calculated for $C_{15}H_{13}Cl_1O_3$: 276.7. found 277.3 $[M+H]^+$, $t_R$=14.01 min. $^1H$ NMR (400 MHz, $CDCl_3$): 8.19 (s, 1H), 8.06 (d, J=8 Hz, 1H), 7.77 (d, J=8 Hz, 1H), 7.53 (t, J=8 Hz, 1H), 7.22 (s, 1H), 6.99 (d, J=8 Hz, 1H), 6.86 (d, J=8 Hz, 1H), 5.18 (s, 2H), 2.27 (s, 3H).

The compounds listed in Table 3B were made using the procedures of Scheme 3, Step 3-2.

TABLE 3B
| Structure | Cpd No. | Purity RT (min) | MW | Observed m/z | Ion | Purity Method |
|---|---|---|---|---|---|---|
| 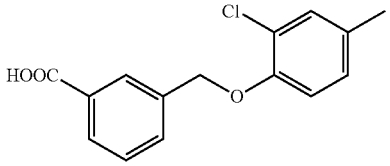 | 3-2 | 14.01 | 276.72 | 277.3 | [M + H]⁺ | 3 |
| 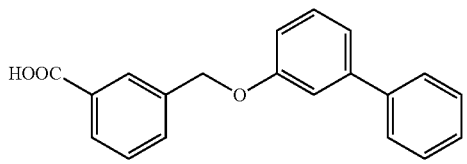 [SMILES: O=C(O)c1cccc(COc2cccc(-c3ccccc3)c2)c1] | 3-3 | 11.49 | 278.13 | 305.1 | [M + H]⁺ | 3 |
| 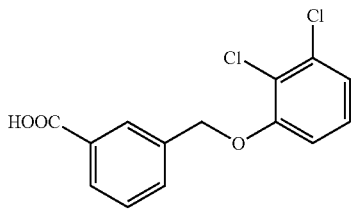 [SMILES: O=C(O)c1cccc(COc2cccc(Cl)c2Cl)c1] | 3-4 | 11.49 | 278.13 | 297.5 | [M + H]⁺ | 3 |
| 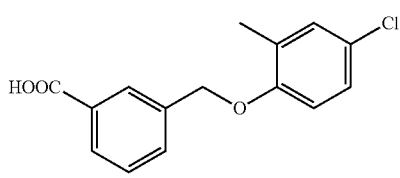 [SMILES: Cc1cc(Cl)ccc1OCc1cccc(C(=O)O)c1] | 3-5 | 11.49 | 278.13 | 275 | [M − H]⁺ | 4 |
| 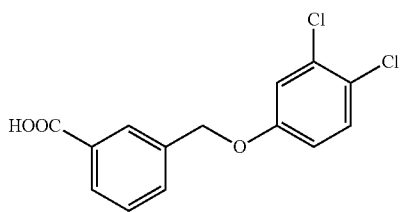 [SMILES: O=C(O)c1cccc(COc2ccc(Cl)c(Cl)c2)c1] | 3-6 | 11.49 | 278.13 | 297 | [M − H]⁺ | 4 |
| 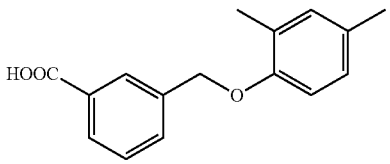 [SMILES: Cc1ccc(OCc2cccc(C(=O)O)c2)c(C)c1] | 3-7 | 11.49 | 278.13 | 257.5 | [M + H]⁺ | 10 |
| 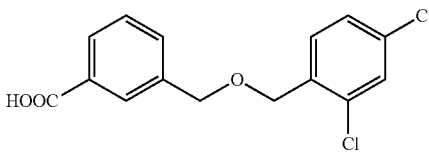 | 3-8 | 11.49 | 278.13 | 311.3 | [M + H]⁺ | 10 |
| 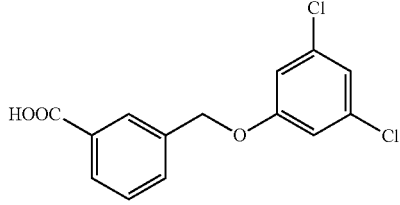 [SMILES: O=C(O)c1cccc(COc2cc(Cl)cc(Cl)c2)c1] | 3-9 | 11.49 | 278.13 | 297.6 | [M + H]⁺ | 10 |

Example 4

Synthesis of Compound 4-1 and Other Representative Compounds

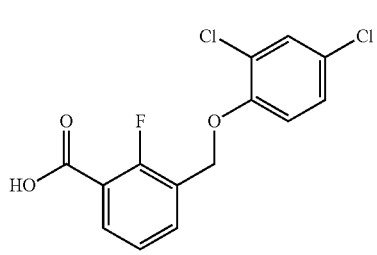

4-1

Scheme 4

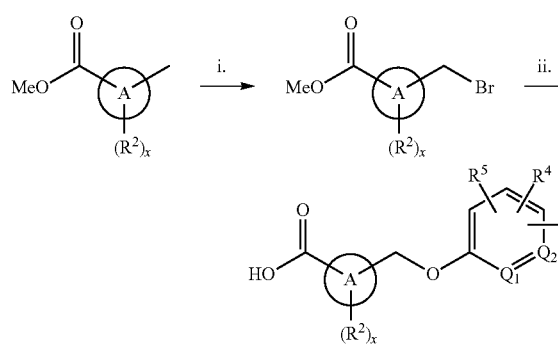

Reagents: (i) NBS, AIBN, CCl₄, 100° C. (ii) See Scheme 1.

Step 4-1. Synthesis of methyl 3-(bromomethyl)-2-fluorobenzoate (INT-4A)

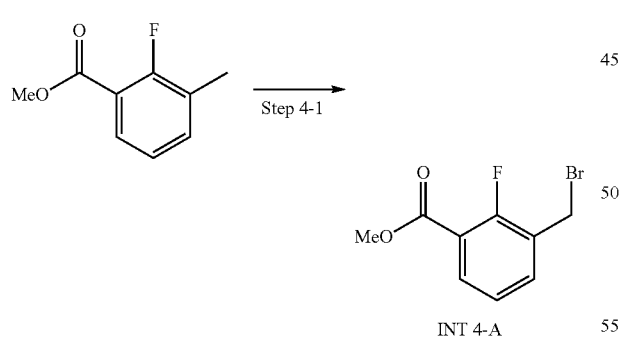

To a stirring solution of methyl 2-fluoro-3-methylbenzoate (1.0 g, 5.95 mmol) in CCl₄ (5 mL) were added NBS (1.06 g, 5.95 mmol) and AIBN (19.6 mg, 119 mmol). After stirring at 100° C. for 2 h, the reaction mixture was concentrated, and the resulting residue was purified by SiO₂ chromatography to provide 858 mg (58%) of methyl 3-(bromomethyl)-2-fluorobenzoate (INT-4A) as a white solid. TLC (10% EA/petroleum ether): $R_f$=0.50. LCMS-ESI (m/z) calculated for $C_9H_8BrFO_2$: 245.97. found 247.0 $[M+H]^+$, $t_R$=0.86 min (Method 6).

Step 4-2. Synthesis of methyl 3-((2,4-dichlorophenoxy)methyl)-2-fluorobenzoate (INT 4-B)

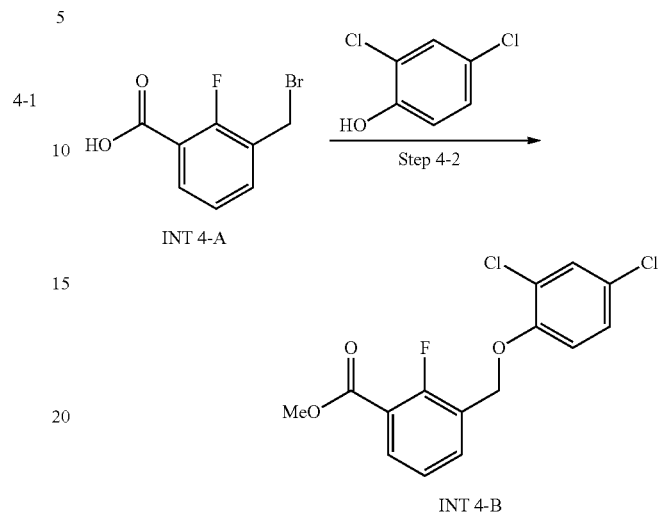

To a stirring solution of methyl 3-(bromomethyl)-2-fluorobenzoate (INT-4A) (500 mg, 2.02 mmol) in MeCN (2 mL) were added K₂CO₃ (559.4 mg, 4.05 mmol) and 2,4-dichlorophenol (329.9 mg, 2.02 mmol). After stirring at 50° C. for 16 h, the reaction mixture was concentrated and the resulting residue was purified by flash SiO₂ chromatography to provide 537 mg (81%) of methyl 3-((2,4-dichlorophenoxy)methyl)-2-fluorobenzoate (INT 4-B) as a white solid. TLC (10% EA/petroleum ether): $R_f$=0.45. LCMS-ESI (m/z) calculated for $C_{15}H_{11}Cl_2BrFO_3$: 328.01. found 329.1 $[M+H]^+$, $t_R$=1.03 min (Method 6).

Step 4-3. Synthesis of 3-((2,4-dichlorophenoxy)methyl)-2-fluorobenzoic acid (Compound 4-1)

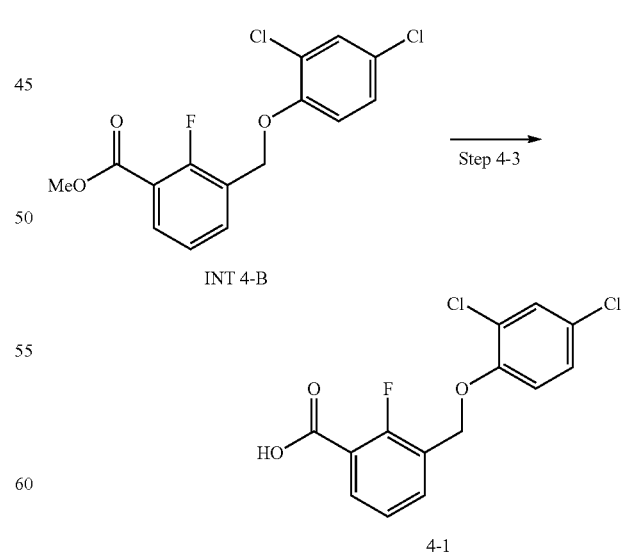

To a stirring solution of methyl 3-((2,4-dichlorophenoxy)methyl)-2-fluorobenzoate (INT 4-B) (100 mg, 0.303 mmol) in MeOH (1 mL) and THF (1 mL) was added a solution of 2 M NaOH (455.7 μL, 0.9 mmol). After stirring at 10° C. for 16 h, the reaction mixture was concentrated and the resulting residue was purified by prep HPLC to provide 6.4 mg (7%) of 3-((2,4-dichlorophenoxy)methyl)-2-fluorobenzoic acid (Compound 4-1) as a white solid. LCMS-ESI (m/z) calculated for $C_{14}H_9Cl_2FO_3$: 313.99. found 312.9 [M–H]$^+$, $t_R$=0.663 min (Method 7). $^1$H NMR (400 MHz, DMSO-d6) δ 7.84 (t, J=6.7 Hz, 1H), 7.75 (br t, J=7.0 Hz, 1H), 7.60 (d, J=2.4 Hz, 1H), 7.42-7.30 (m, 3H), 5.28 (s, 2H).

Synthesis of Compound 1-55

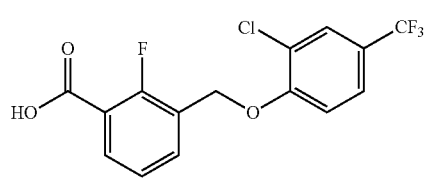

Step 4-4. Synthesis of methyl 3-(bromomethyl)-2-fluorobenzoate (INT 4-C)

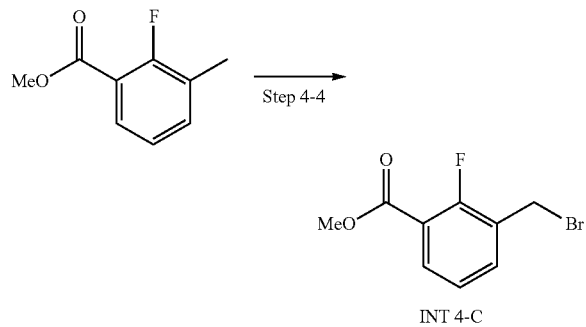

To a stirring solution of methyl 2-fluoro-3-methylbenzoate (1.0 g, 5.9 mmol) in CCl$_4$ (20 mL) were added NBS (1.2 g, 6.5 mmol) and AIBN (98 mg, 0.59 mmol). The reaction mixture was heated to reflux for 3 h, then cooled to rt and concentrated in vacuo to afford crude product. The crude product was purified by SiO$_2$ chromatography (EA/hexanes) to afford 399 mg (27%) of methyl 3-(bromomethyl)-2-fluorobenzoate (INT 4-C) as a white solid. LCMS-ESI (m/z) not observed, $t_R$=5.05 min. (Method 7 minute).

Step 4-5. Synthesis of methyl 3-((2-chloro-4-(trifluoromethyl)phenoxy)methyl)-2-fluorobenzoate (INT 4-D)

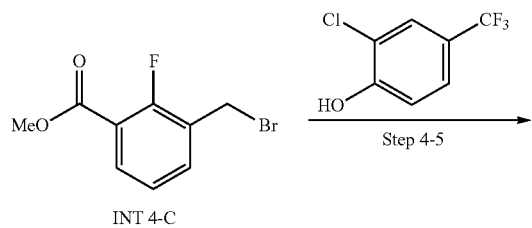

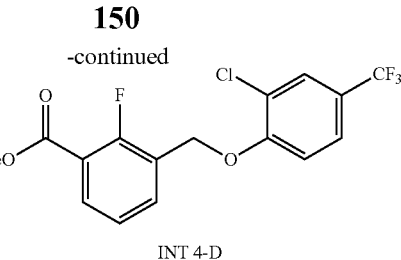

To a stirring solution of INT 4-C (449 mg, 1.82 mmol) in MeCN (4 mL) were added 2-chloro-4-(trifluoromethyl)phenol (357 mg, 1.82 mmol) and K$_2$CO$_3$ (327 mg, 2.36 mmol). After heating for 18 h at 60° C., the reaction mixture was cooled to rt and diluted with H$_2$O (3 mL). The aqueous layer was extracted with Et$_2$O (2×6 mL) and by EA (6 mL). The combined organic layers were dried (Na$_2$SO$_4$), filtered, and concentrated in vacuo to afford a crude white solid that was purified by SiO$_2$ chromatography (EA/hexanes) to afford 551.6 mg (83.7%) of methyl 3-((2-chloro-4-(trifluoromethyl)phenoxy)methyl)-2-fluorobenzoate (INT 4-D) as a white solid. LCMS-ESI (m/z) calculated for $C_{16}H_{11}ClF_4O_3$: 362.7. found 363.1 [M+H]$^+$, (Method 7 minute).

Step 4-6. Synthesis of 3-((2-chloro-4-(trifluoromethyl)phenoxy)methyl)-2-fluorobenzoic acid (1-55)

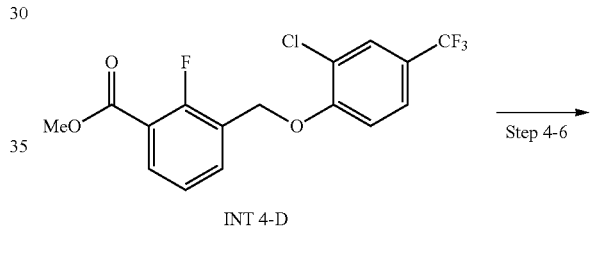

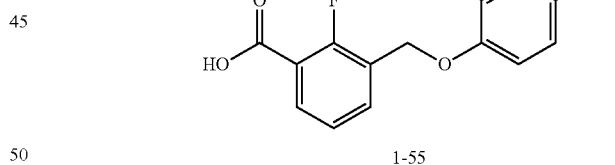

To a stirring solution of INT 4-D (551 mg, 1.52 mmol) in THF (8 mL) was added 1M NaOH (7.6 mL, 7.60 mmol). The reaction mixture was heated at 60° C. overnight then concentrated in vacuo, diluted with 3M HCl, extracted with EA and Et$_2$O, dried (Na$_2$SO$_4$), filtered and concentrated in vacuo. The resulting white solid was dissolved in MeCN (5 mL) and H$_2$O (5 mL) and lyophilized to afford 460.5 mg (86.9%) of 3-((2-chloro-4-(trifluoromethyl)phenoxy)methyl)-2-fluorobenzoic acid (Compound 1-55) as a white solid. LCMS-ESI (m/z) calculated for $C_{15}H_9ClF_4O_3$: 348.68. found 349.1 [M+H]$^+$, $t_R$=10.28 min. (15 min purity). $^1$H NMR (500 MHz, DMSO-d6) δ 13.36 (br s, 1H), 7.92-7.87 (m, 2H), 7.83-7.80 (m, 1H), 7.73 (dd, J=8.5, 2.0 Hz, 1H), 7.51 (d, J=8.5 Hz, 1H), 7.36 (app t, J=7.5 Hz, 1H), 5.40 (s, 2H).

Synthesis of Compound 1-65

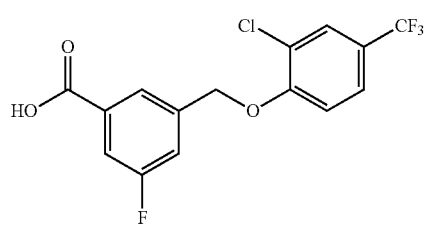

Step 4-7. Synthesis of methyl 3-fluoro-5-methylbenzoate (INT 4-E)

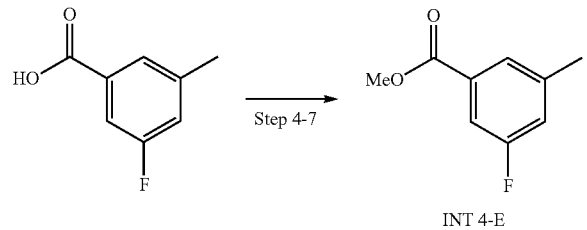

A solution of 3-fluoro-5-methyl-benzoic acid (5 g, 32.4 mmol) and $H_2SO_4$ (15.91 g, 162.2 mmol, 8.65 mL) in MeOH (30 mL) was stirred at 70° C. for 12 h. The reaction mixture was poured into $H_2O$ (100 mL) and extracted into EA. The combined organic phases were dried and concentrated to give a residue that was purified by SI02 chromatography (PE/EA) to provide 4.5 g (82.5%) of methyl 3-fluoro-5-methyl-benzoate (INT 4-E) as a yellow oil. $^1$H NMR (400 MHz, CDCl$_3$) δ ppm 2.40 (s, 3H) 3.92 (s, 3H) 7.08 (br d, J=9.26 Hz, 1H) 7.51 (br d, J=9.13 Hz, 1H) 7.65 (s, 1H).

Step 4-8. Synthesis of methyl 3-(bromomethyl)-5-fluorobenzoate (INT 4-F)

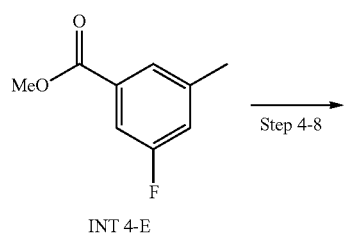

A solution of methyl INT 4-E (4.5 g, 26.76 mmol), NBS (5.24 g, 29.44 mmol) and AIBN (219.71 mg, 1.34 mmol) in CCl$_4$ (50 mL) was stirred at 70° C. for 12 hr. The reaction was concentrated and purified by SiO$_2$ chromatography (PE/EA) to provide 4.9 g (74%) of crude methyl 3-(bromomethyl)-5-fluoro-benzoate (INT 4-F) as a yellow oil. TLC (10:1 petroleum ether: EA): R$_f$=0.70. 1H NMR (400 MHz, CDCl$_3$) δ ppm 7.86 (t, J=1.41 Hz, 1H) 7.64-7.67 (m, 1H) 7.31 (dt, J=8.71, 2.06 Hz, 1H), 4.48 (s, 2H) 3.94 (s, 3H).

Step 4-9. Synthesis of methyl 3-((2-chloro-4-(trifluoromethyl)phenoxy)methyl)-5-fluorobenzoate (INT 4-G)

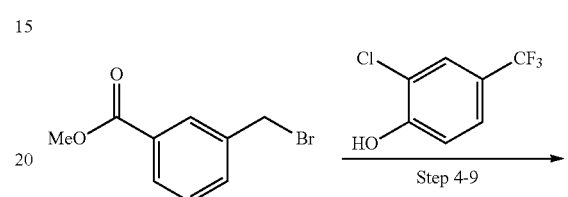

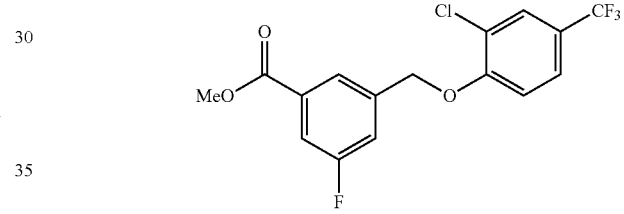

A mixture of INT 4-F (3 g, 12.1 mmol), 2-chloro-4-(trifluoromethyl)phenol (3.58 g, 18.2 mmol) and K$_2$CO$_3$ (5.03 g, 36.4 mmol) in MeCN (50 mL) was stirred at 30° C. for 12 hr. The reaction mixture was filtered and concentrated to give a residue that was purified by SiO$_2$ chromatography (PE/EA) to provide 2.4 g (55%) of methyl 3-((2-chloro-4-(trifluoromethyl)phenoxy)methyl)-5-fluorobenzoate (INT 4-G) as a white solid. TLC (5:1 petroleum ether: EA): R$_f$=0.60.

Step 4-10. Synthesis of 3-((2-chloro-4-(trifluoromethyl)phenoxy)methyl)-5-fluorobenzoic acid (1-65)

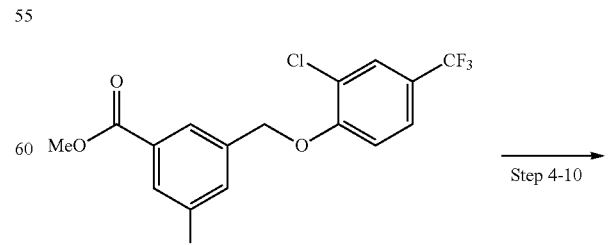

153

-continued

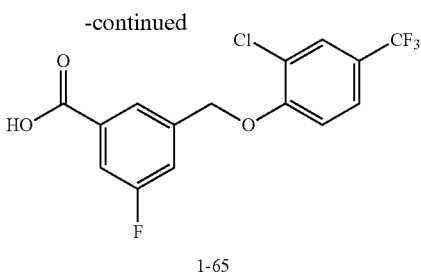

1-65

A mixture of INT 4-G (2.4 g, 6.6 mmol) and NaOH (794 mg, 19.9 mmol) in THF (1 mL) and H$_2$O (0.5 mL) was stirred at 30° C. for 2 hr. The reaction mixture was acidified with 1N HCl and extracted with EA. The combined organic layers were dried (Na$_2$SO$_4$) and concentrated to provide a residue that was dissolved in PE/EA and filtered. The filter cake was diluted with MeCN/H$_2$O and lyophilized to provide 1.91 g (82%) of 3-((2-chloro-4-(trifluoromethyl)phenoxy)methyl)-5-fluorobenzoic acid (Compound 1-56) as a white solid. LCMS-ESI (m/z) calculated for C$_{15}$H$_9$ClF$_4$O$_3$: 348.6. found 347.0 [M−H]$^+$, t$_R$=0.958 min. (Method 8). $^1$H NMR (400 MHz, CDCl$_3$-d) δ ppm 7.99 (s, 1H) 7.77 (br d, J=8.19 Hz, 1H) 7.70 (d, J=1.96 Hz, 1H) 7.51 (br d, J=8.68 Hz, 2H) 7.03 (d, J=8.56 Hz, 1H) 5.26 (s, 2H).

Synthesis of Compound 1-85

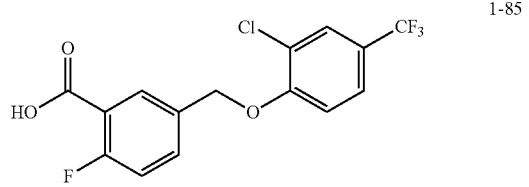 [SMILES: O=C(O)c1cc(COc2ccc(C(F)(F)F)cc2Cl)ccc1F]

1-85

Step 4-11. Synthesis of methyl 2-fluoro-5-methylbenzoate (INT 4-H)

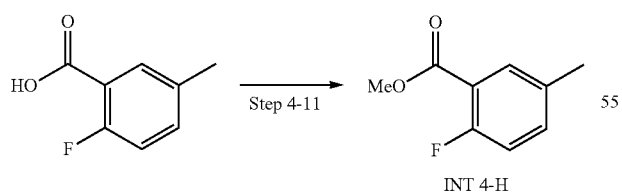

To a solution of 2-fluoro-5-methyl-benzoic acid (10 g, 64.9 mmol) in MeOH (200 mL) was added thionyl chloride (23.53 mL, 324.4 mmol) dropwise at 25° C. After 0.5 h at 25° C., the mixture was concentrated and purified by SiO$_2$ chromatography (PE/EA) to provide 10.6 g (97%) of methyl 2-fluoro-5-methylbenzoate (INT 4-H) as a colorless oil. TLC (1:1 petroleum ether: EA): R$_f$=0.90.

154

Step 4-12. Synthesis of methyl 5-(bromomethyl)-2-fluorobenzoate (INT 4-I)

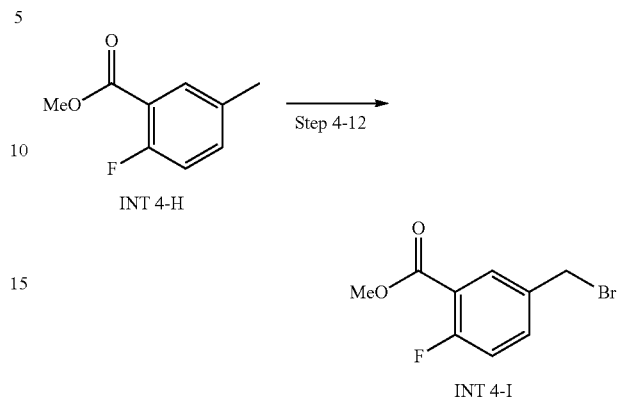

Into a solution of INT 4-H (8 g, 47.6 mmol), in CHCl$_3$ (200 mL) were added NBS (10.16 g, 57.1 mmol) and AIBN (781.2 mg, 4.76 mmol). After 12 h at 70° C., the reaction was diluted with H$_2$O (200 mL) and extracted into EA (3×100 mL). The combined organic layers were dried (Na$_2$SO$_4$), concentrated and purified by SiO$_2$ chromatography (PE/EA) to provide 10.6 g (97%) of methyl 5-(bromomethyl)-2-fluorobenzoate (INT 4-I) as a white solid that was contaminated with a second, unidentified product. TLC (10:1 petroleum ether: EA): R$_f$=0.4, 0.35. LCMS-ESI (m/z) calculated for C$_9$H$_8$BrFO$_2$: 247.06. found 248.8 [M−H]$^+$, t$_R$=0.702 min. $^1$H NMR (400 MHz, CDCl$_3$-d) δ 8.01-7.94 (m, 1H), 7.62-7.52 (m, 1H), 7.17-7.10 (m, 1H), 4.49 (s, 2H), 3.95 (s, 3H).

Step 4-13. Synthesis of methyl 5-((2-chloro-4-(trifluoromethyl)phenoxy)methyl)-2-fluorobenzoate (INT 4-J)

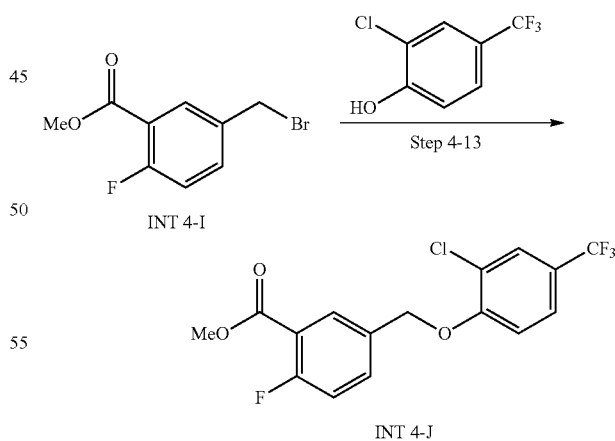

To a solution of INT 4-I (4 g, 16.19 mmol) and 2-chloro-4-(trifluoromethyl)phenol (3.18 g, 16.19 mmol) in MeCN (30 mL) was added K$_2$CO$_3$ (6.71 g, 48.57 mmol). After 2 h at 50° C., the reaction mixture was filtered, concentrated, and purified by SiO$_2$ chromatography (PE) to provide 1.7 g (29%) of methyl 5-((2-chloro-4-(trifluoromethyl)phenoxy) methyl)-2-fluorobenzoate (INT 4-J) as a white solid. TLC (10:1 petroleum ether: EA): R$_f$=0.40. LCMS-ESI (m/z) calculated for C$_{16}$H$_{11}$ClF$_4$O$_3$: 362.7. found 363.0 [M–H]$^+$, t$_R$=1.07 min (Method 6). $^1$H NMR (400 MHz, CDCl$_3$-d) δ 8.05 (dd, J=2.3, 6.7 Hz, 1H), 7.72-7.63 (m, 2H), 7.55-7.45 (m, 1H), 7.26-7.15 (m, 1H), 7.04 (d, J=8.6 Hz, 1H), 5.20 (s, 2H), 3.97 (s, 3H).

Step 4-14. Synthesis of 5-((2-chloro-4-(trifluoromethyl)phenoxy)methyl)-2-fluorobenzoic acid (1-85)

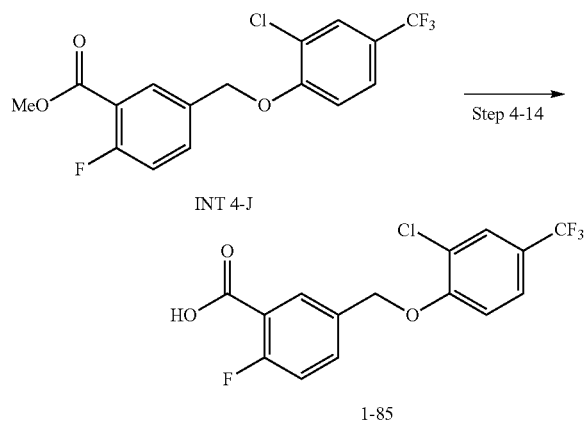

To a solution of INT 4-J (1.7 g, 4.63 mmol) in H$_2$O (10 mL), THF (10 mL) and MeOH (5 mL) was added LiOH·H$_2$O (582.33 mg, 13.88 mmol). After 2 h at 25° C., H$_2$O (30 μL) was added into the reaction mixture and the organic solvent was removed by reduced pressure to provide 1.57 g (97%) of 5-((2-chloro-4-(trifluoromethyl)phenoxy)methyl)-2-fluorobenzoic acid (Compound 1-85) as a white solid. LCMS-ESI (m/z) calculated for C$_{15}$H$_9$ClF$_4$O$_3$: 348.68. found 349.0 [M–H]$^+$, t$_R$=0.925 min. (Method 6). $^1$H NMR (400 MHz, DMSO-d6) δ 7.96-7.90 (m, 1H), 7.87 (d, J=2.0 Hz, 1H), 7.72 (dd, J=1.7, 8.7 Hz, 1H), 7.66 (dt, J=2.3, 5.3 Hz, 1H), 7.44 (d, J=8.6 Hz, 1H), 7.36-7.28 (m, 1H), 5.34 (s, 2H).

Synthesis of Compound 1-101

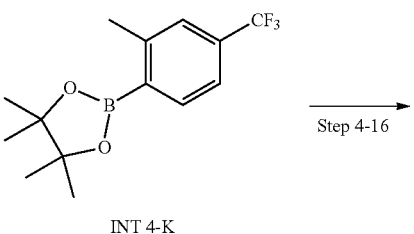

1-101

Step 4-15. Synthesis of 4,4,5,5-tetramethyl-2-(2-methyl-4-(trifluoromethyl)phenyl)-1,3,2-dioxaborolane (INT 4-K)

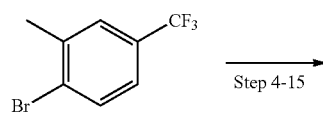

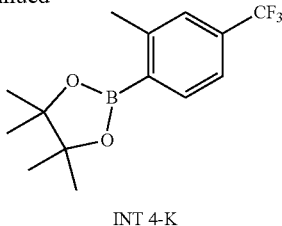

Into a solution of 1-bromo-2-methyl-4-(trifluoromethyl)benzene (7.3 g, 30.5 mmol) in dioxane (100 mL) were added AcOK (11.99 g, 122.16 mmol, 4 eq), 4,4,4',4',5,5,5',5'-octamethyl-2,2'-bi(1,3,2-dioxaborolane) (15.51 g, 61.1 mmol) and Pd(dppf)Cl$_2$·CH$_2$Cl$_2$ (2.49 g, 3.05 mmol). After stirring for 12 h at 100° C. under N$_2$, The mixture was filtered and the filtrate was concentrated to give a crude product that was purified by SiO$_2$ chromatography (PE) to provide 6.3 g (72%) of 4,4,5,5-tetramethyl-2-(2-methyl-4-(trifluoromethyl)phenyl)-1,3,2-dioxaborolane (INT 4-K) as a yellow oil. TLC (PE): Rt=0.90. $^1$H NMR (400 MHz, CDCl$_3$-d) δ 7.93-7.84 (m, 1H), 7.46-7.39 (m, 2H), 2.61 (s, 3H), 1.38 (s, 13H).

Step 4-16. Synthesis of 2-methyl-4-(trifluoromethyl)phenol (INT 4-L)

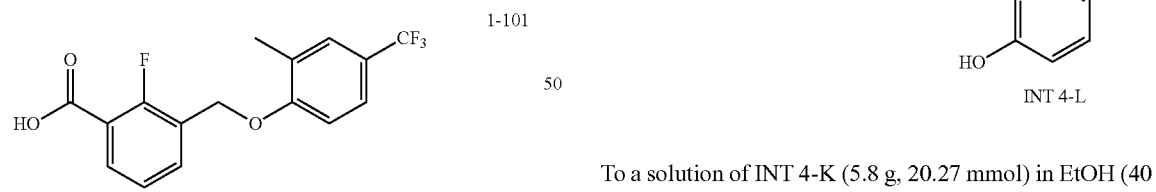

To a solution of INT 4-K (5.8 g, 20.27 mmol) in EtOH (40 mL) and H$_2$O (20 mL) was added m-CPBA (6.17 g, 30.41 mmol, 85% purity). After stirring for 12 h at 25° C. the mixture was poured into saturated Na$_2$SO$_3$ (100 mL) and concentrated to remove volatiles. The resulting solution was diluted with H$_2$O (50 mL) and extracted with EA (3×80 mL). The combined organic layers were washed with saturated NaHCO$_3$ solution (2×50 mL) and brine (100 mL×2), then dried (Na$_2$SO$_4$), concentrated and purified by SiO$_2$ chromatography to provide 2.5 g (70%) of 2-methyl-4-(trifluoromethyl)phenol (INT 4-L) as a colorless oil. TLC (5:1 PE:EA): R$_f$=0.50. $^1$H NMR (400 MHz, CDCl$_3$-d) δ 7.45-7.39 (m, 1H), 7.38-7.32 (m, 1H), 6.90-6.79 (m, 1H), 5.87-5.77 (m, 1H), 2.31 (s, 3H).

Step 4-17. Synthesis of methyl 2-fluoro-3-((2-methyl-4-(trifluoromethyl)phenoxy)-methyl)benzoate (INT 4-M)

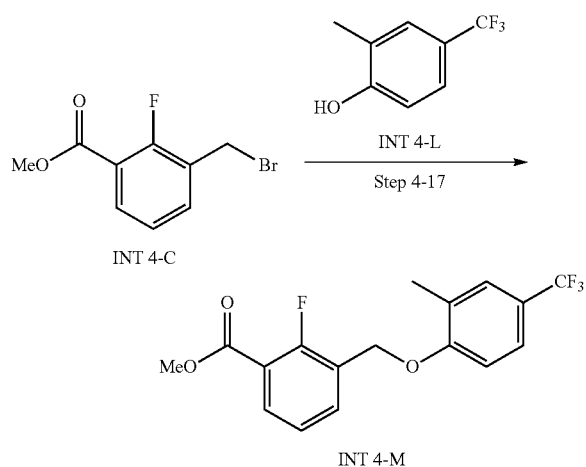

INT 4-C

INT 4-M

To a solution of INT 4-C (2.8 g, 11.33 mmol) and INT 4-L (2.4 g, 13.6 mmol) in MeCN (30 mL) was added K$_2$CO$_3$ (2.04 g, 14.7 mmol). After 12 h at 60° C., the reaction mixture was filtered, concentrated, and purified by SiO$_2$ chromatography (EA/PE) to provide 3.0 g (77%) of methyl 2-fluoro-3-((2-methyl-4-(trifluoromethyl)phenoxy)methyl)benzoate (INT 4-M) as a colorless oil. LCMS-ESI (m/z) calculated for C$_{17}$H$_{14}$F$_4$O$_3$: 342.29. found 343.0 [M+H]$^+$, t$_R$=1.04 min (Method 6). $^1$H NMR (400 MHz, CDCl$_3$-d) δ 7.98-7.91 (m, 1H), 7.77-7.69 (m, 1H), 7.49-7.41 (m, 2H), 7.31-7.22 (m, 1H), 7.03-6.92 (m, 1H), 5.40-5.15 (m, 2H), 3.98 (s, 3H), 2.34 (s, 3H).

Step 4-18. Synthesis of 5-((2-methyl-4-(trifluoromethyl)phenoxy)methyl)-2-fluorobenzoic acid (1-101)

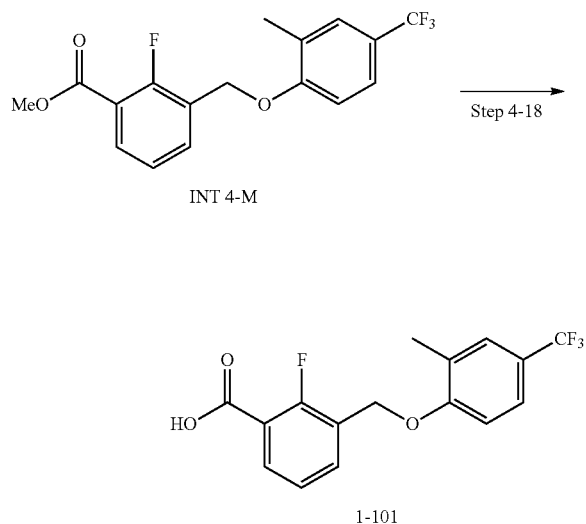

INT 4-M 1-101

To a solution of INT 4-M (3.0 g, 8.76 mmol) in THF (30 mL) and MeOH (30 mL) was added 2 M NaOH (30 mL, 60 mmol). After 12 h at 40° C., the pH was adjusted to pH 5 with HCl (1M) to produce a solid precipitate that was filtered and collected. The resulting product was dissolved in EA (500 mL), dried (Na$_2$SO$_4$), filtered and concentrated to provide 2.35 g (81%) of 5-((2-methyl-4-(trifluoromethyl)phenoxy)methyl)-2-fluorobenzoic acid (1-101) as a light yellow solid. LCMS-ESI (m/z) calculated for C$_{16}$H$_{12}$F$_4$O$_3$: 328.2. found 326.9 [M−H]$^+$, t$_R$=0.73 min. (Method 7). $^1$H NMR (400 MHz, CD$_4$OD) δ 7.90-7.82 (m, 1H), 7.74-7.66 (m, 1H), 7.52-7.42 (m, 2H), 7.32-7.24 (m, 1H), 7.20-7.13 (m, 1H), 5.44-5.15 (m, 2H), 2.30 (s, 3H).

Synthesis of Compound 4-10

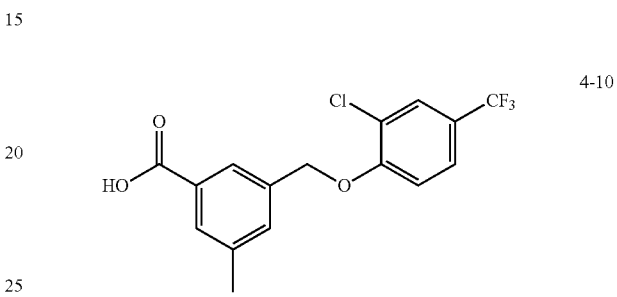

4-10

Step 4-19. Synthesis of methyl 3-(bromomethyl)-5-methylbenzoate (INT 4-N)

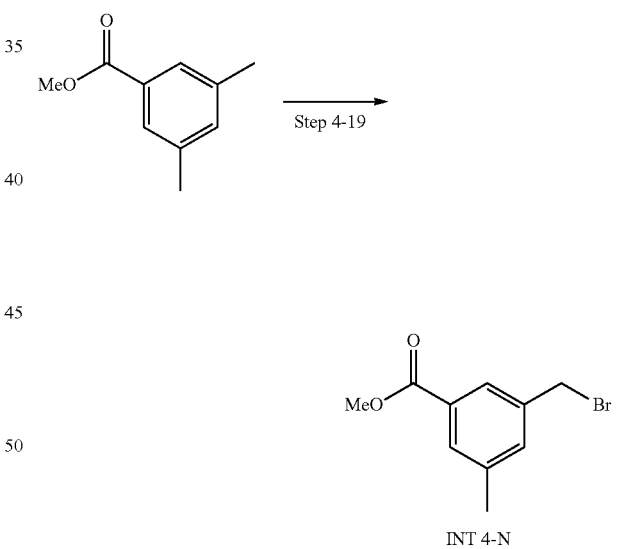

INT 4-N

To a solution of methyl 3,5-dimethylbenzoate (5 g, 30.5 mmol) in CCl$_4$ (200 mL) were added NBS (5.96 g, 33.5 mmol) and AIBN (1.00 g, 6.1 mmol). After stirring for 12 h at 80° C., the reaction mixture was concentrated and purified by SiO$_2$ chromatography (PE/EA) to provide 8.4 g (79%) of crude methyl 3-(bromomethyl)-5-methylbenzoate (INT 4-N) as a colorless oil with 70% purity LCMS-ESI (m/z) calculated for C$_{10}$H$_{11}$BrO$_2$: 243.1. found 245 [M+H]$^+$, t$_R$=0.873 min. $^1$H NMR (400 MHz, CDCl$_3$-d) δ 7.87 (s, 1H), 7.80 (s, 1H), 7.48-7.37 (m, 1H), 4.49 (s, 2H), 3.96-3.89 (m, 4H), 2.41 (s, 5H).

Step 4-20. Synthesis of methyl 3-((2-chloro-4-(trifluoromethyl)phenoxy)methyl)-5-methylbenzoate (INT 4-O)

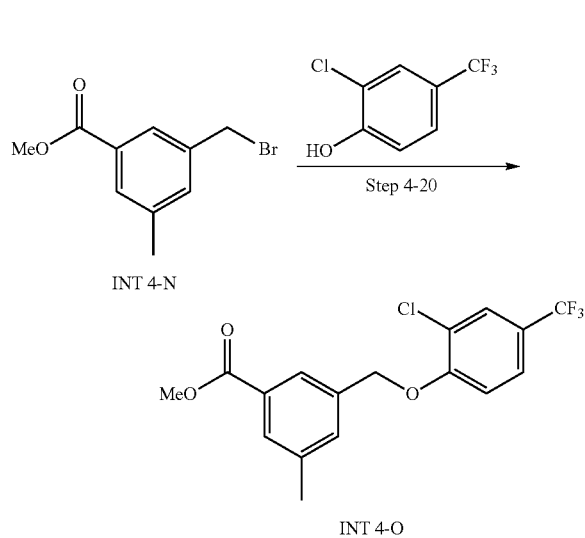

A mixture of INT 4-N (3 g, 8.64 mmol), 2-chloro-4-(trifluoromethyl)phenol (1.7 g, 8.64 mmol) and $K_2CO_3$ (5.03 g, 36.4 mmol) in MeCN (30 mL) was stirred at 60° C. for 12 hr. The reaction mixture was filtered and concentrated to give a residue that was purified by SiO2 chromatography (PE/EA) to provide 2.8 g (90%) of methyl 3-((2-chloro-4-(trifluoromethyl)phenoxy)methyl)-5-methylbenzoate (INT 4-O) as a white solid. TLC (5:1 petroleum ether: EA): $R_f$=0.60. LCMS-ESI (m/z) calculated for $C_{17}H_{14}ClF_3O_3$: 358.7. found 359 [M+H]$^+$, $t_R$=1.06 min.

Step 4-21. Synthesis of 3-((2-chloro-4-(trifluoromethyl)phenoxy)methyl)-5-methylbenzoic acid (4-10)

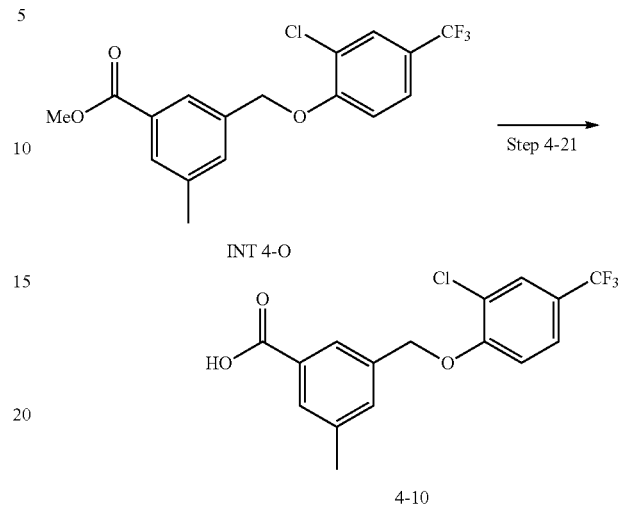

A mixture of INT 4-0 (2.8 g, 7.81 mmol) and 2M NaOH (30 mL, 30 mmol) in THF (30 mL) and MeOH (30 mL) was stirred at 30° C. for 12 hr. The volatile solvents were removed in vacuo and the resulting solution was acidified with 1N HCl to pH 5. The resulting precipitate was collected by filtration and the crude product was triturated with 10:1 PE:EA to provide 2.1 g (72%) of 3-((2-chloro-4-(trifluoromethyl)phenoxy)methyl)-5-methylbenzoic acid (Compound 4-10) as a white solid. LCMS-ESI (m/z) calculated for $C_{16}H_{12}ClF_3O_3$: 344.71. found 342.9 [M+H]$^+$, $t_R$=0.761 min. (Method 7). $^1$H NMR (400 MHz, CD$_4$OD) δ 8.02-7.95 (m, 1H), 7.86-7.81 (m, 1H), 7.75-7.68 (m, 1H), 7.62-7.52 (m, 2H), 7.36-7.27 (m, 1H), 5.29 (s, 2H), 2.44 (s, 3H).

The compounds listed in Table 4 were made using the procedures of Scheme 4:

TABLE 4

| Structure | Cpd No. | Purity RT (min) | MW | Observed m/z | Ion | Purity Method |
|---|---|---|---|---|---|---|
| 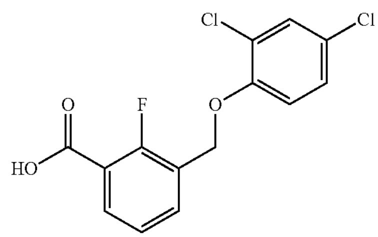 | 4-1 | 0.67 | 315.12 | 312.9 | [M − H]$^+$ | 7 |
| 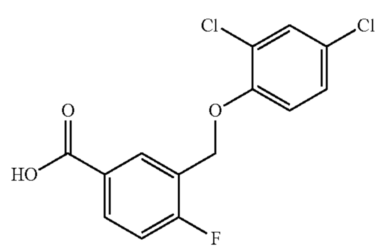 [SMILES: O=C(O)c1ccc(F)c(COc2ccc(Cl)cc2Cl)c1] | 4-2 | 0.68 | 315.12 | 312.9 | [M − H]$^+$ | 7 |

TABLE 4-continued
| Structure | Cpd No. | Purity RT (min) | MW | Observed m/z | Ion | Purity Method |
|---|---|---|---|---|---|---|
| 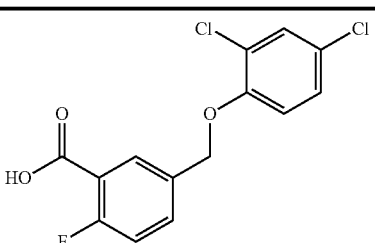 | 4-3 | 0.683 | 315.12 | 312.9 | [M − H]+ | 7 |
| 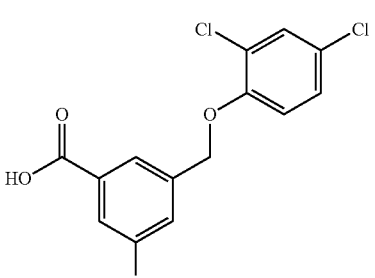 | 4-4 | 0.74 | 315.12 | 313.0 | [M − H]+ | 7 |
| 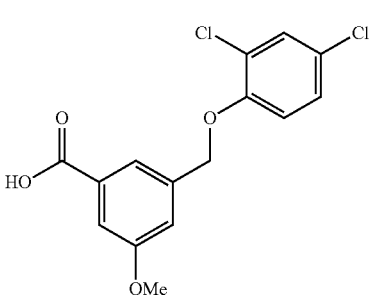 [SMILES: COc1cc(COc2ccc(Cl)cc2Cl)cc(C(=O)O)c1] | 4-5 | 0.72 | 327.16 | 324.9 | [M − H]+ | 7 |
| 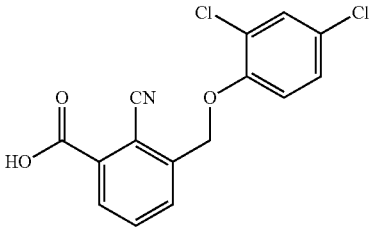 [SMILES: N#Cc1c(COc2ccc(Cl)cc2Cl)cccc1C(=O)O] | 4-6 | 0.72 | 322.14 | 319.9 | [M − H]+ | 7 |
| 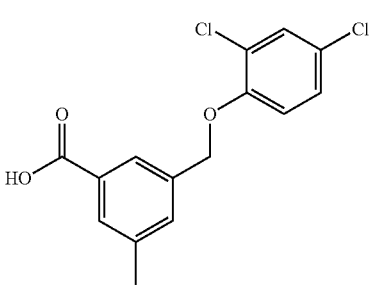 [SMILES: Cc1cc(COc2ccc(Cl)cc2Cl)cc(C(=O)O)c1] | 4-7 | 0.92 | 311.16 | 313.0 | [M + H]+ | 6 |
| 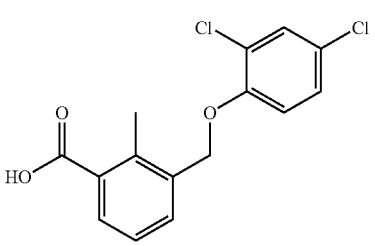 | 4-8 | 0.70 | 326.01 | 324.9 | [M − H]+ | 7 |

TABLE 4-continued

| Structure | Cpd No. | Purity RT (min) | MW | Observed m/z | Ion | Purity Method |
|---|---|---|---|---|---|---|
| 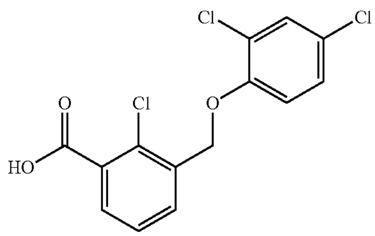 [SMILES: O=C(O)c1cccc(COc2ccc(Cl)cc2Cl)c1Cl] | 4-9 | 0.70 | 331.57 | 328.8 | [M − H]⁺ | 7 |
| 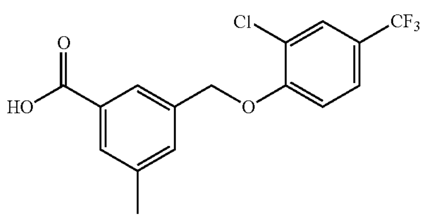 | 4-10 | 10.80 | 344.71 | 367.1 | [M + Na]⁺ | 3 |
| 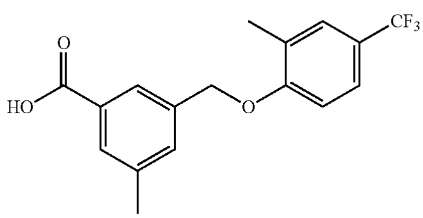 [SMILES: Cc1cc(COc2ccc(C(F)(F)F)cc2C)cc(C(=O)O)c1] | 4-11 | 10.91 | 324.30 | 347.2 | [M + Na]⁺ | 3 |
| 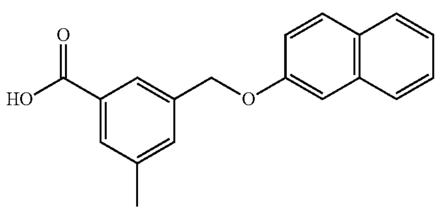 [SMILES: Cc1cc(COc2ccc3ccccc3c2)cc(C(=O)O)c1] | 4-12 | 10.44 | 292.33 | 293.2 | [M − H]⁺ | 4 |
| 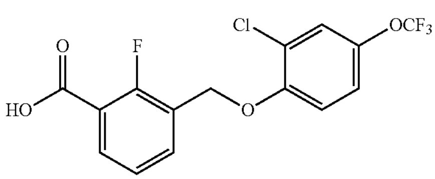 [SMILES: O=C(O)c1cccc(COc2ccc(OC(F)(F)F)cc2Cl)c1F] | 4-13 | 10.506 | 364.68 | 363.0 | [M − H]⁺ | 4 |
| 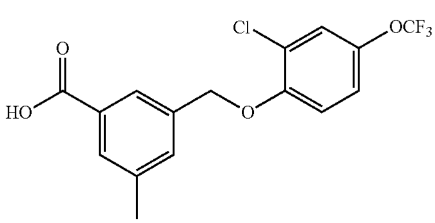 [SMILES: Cc1cc(COc2ccc(OC(F)(F)F)cc2Cl)cc(C(=O)O)c1] | 4-14 | 11.007 | 360.71 | 359 | [M − H]⁺ | 4 |
| 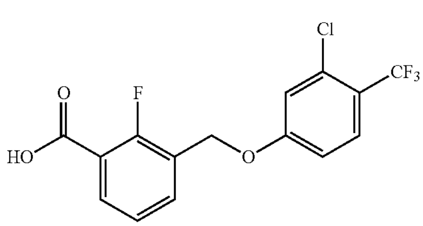 [SMILES: O=C(O)c1cccc(COc2ccc(C(F)(F)F)c(Cl)c2)c1F] | 4-15 | 10.278 | 348.68 | 347.0 | [M − H]⁺ | 4 |

TABLE 4-continued

| Structure | Cpd No. | Purity RT (min) | MW | Observed m/z | Ion | Purity Method |
|---|---|---|---|---|---|---|
| (3-carboxy-5-trifluoromethylbenzyl 3-chloro-4-trifluoromethylphenyl ether) | 4-16 | 11.354 | 398.69 | 397 | [M − H]+ | 4 |
| (3-carboxy-5-methylbenzyl 3-chloro-4-trifluoromethylphenyl ether) | 4-17 | 10.918 | 344.71 | 343 | [M − H]+ | 4 |
| (pyridine carboxylic acid derivative with 2-chloro-4-trifluoromethylphenoxymethyl) | 4-18 | 9.388 | 349.67 | 348 | [M − H]+ | 4 |
| (pyridine carboxylic acid derivative with 3-chloro-4-trifluoromethylphenoxymethyl) | 4-19 | 9.223 | 349.67 | 348 | [M − H]+ | 4 |
| (3-carboxy-5-trifluoromethylbenzyl 2-chloro-4-trifluoromethylphenyl ether) | 4-20 | 11.319 | 398.69 | 397 | [M − H]+ | 4 |
| (3-carboxy-2-fluorobenzyl 1-chloronaphthalen-2-yl ether) | 4-21 | 0.7 | 330.74 | 328.9 | [M − H]+ | 7 |

TABLE 4-continued

| Structure | Cpd No. | Purity RT (min) | MW | Observed m/z | Ion | Purity Method |
|---|---|---|---|---|---|---|
| 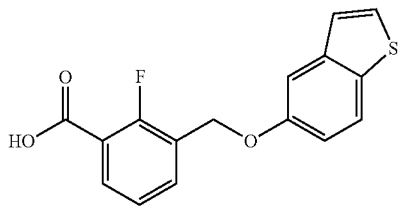 [SMILES: O=C(O)c1cccc(COc2ccc3sccc3c2)c1F] | 4-22 | 0.655 | 302.32 | 300.9 | [M + H]⁺ | 7 |
| 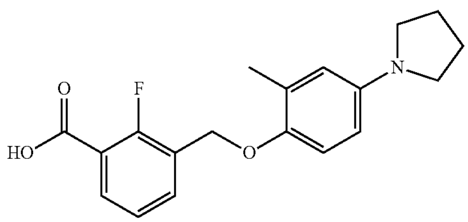 [SMILES: Cc1cc(N2CCCC2)ccc1OCc1cccc(C(=O)O)c1F] | 4-23 | 0.663 | 329.37 | 330.1 | [M − H]⁺ | 6 |
| 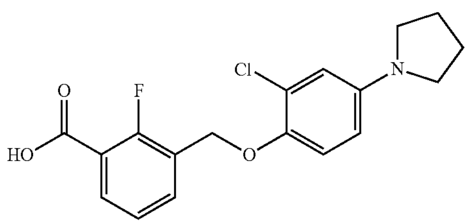 [SMILES: O=C(O)c1cccc(COc2ccc(N3CCCC3)cc2Cl)c1F] | 4-24 | 0.825 | 349.79 | 350.1 | [M + H]⁺ | 6 |
| 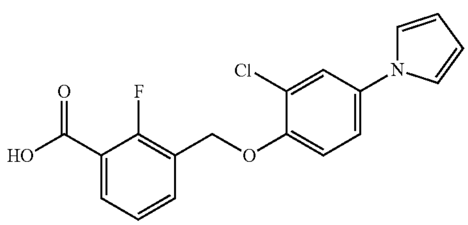 [SMILES: O=C(O)c1cccc(COc2ccc(-n3cccc3)cc2Cl)c1F] | 4-25 | 0.954 | 345.75 | 346 | [M + H]⁺ | 6 |
| 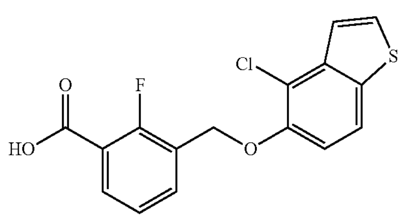 [SMILES: O=C(O)c1cccc(COc2ccc3sccc3c2Cl)c1F] | 4-26 | 0.858 | 336.76 | 335 | [M − H]⁺ | 8 |
| 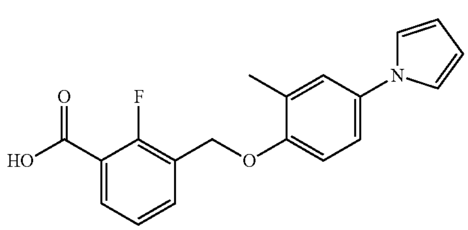 [SMILES: Cc1cc(-n2cccc2)ccc1OCc1cccc(C(=O)O)c1F] | 4-27 | 0.873 | 325.34 | 324.1 | [M − H]⁺ | 6 |
| 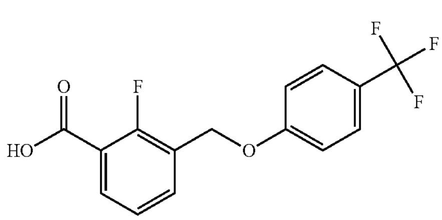 [SMILES: O=C(O)c1cccc(COc2ccc(C(F)(F)F)cc2)c1F] | 4-28 | 13.32 | 314.2 | 315.2 | [M + H]⁺ | 9 |

TABLE 4-continued

| Structure | Cpd No. | Purity RT (min) | MW | Observed m/z | Ion | Purity Method |
|---|---|---|---|---|---|---|
| (structure shown) | 4-29 | 3.12 | 280.7 | 281.3 | [M + H]+ | 9 |

Example 5

Synthesis of Compound 5-1 and Other Representative Compounds 5-1

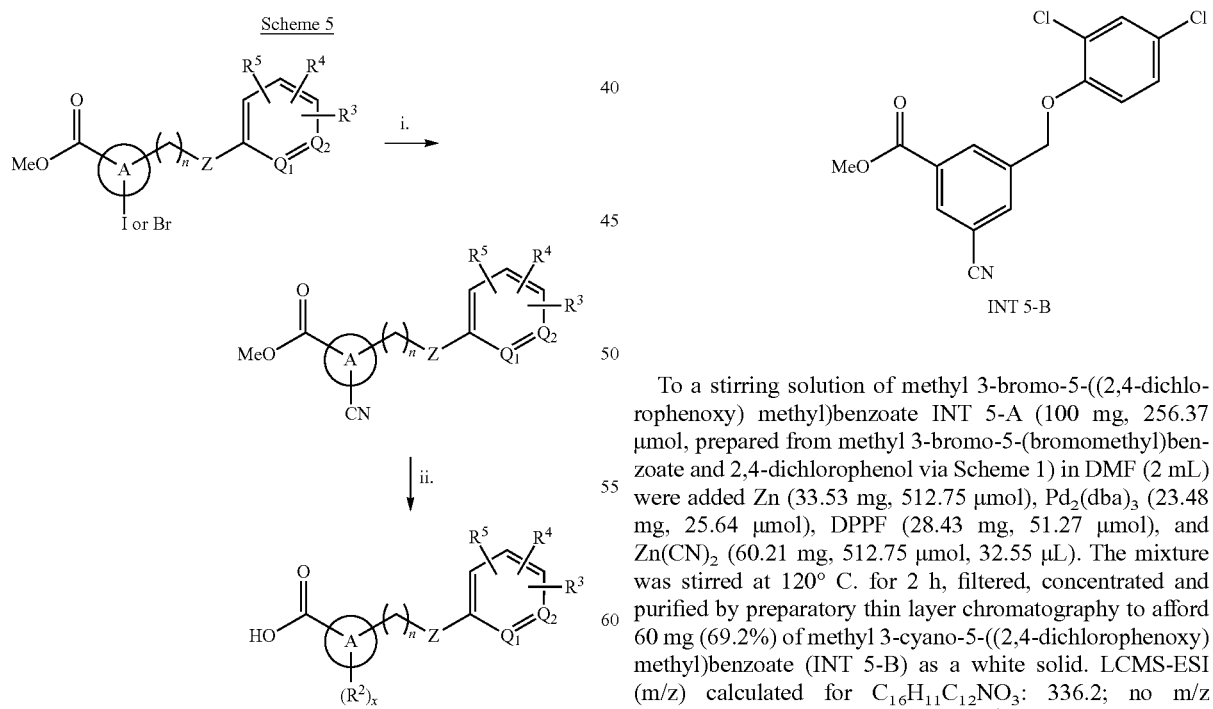

Reagents: (i) Zn(CN)₂, Pd₂(dba)₃, dppf, DMF, 120° C.; (ii) NaOH, solvent (THF, MeOH, or DMF).

Step 5-1. Synthesis of methyl 3-cyano-5-((2,4-dichlorophenoxy)methyl)benzoate (INT 5-B)

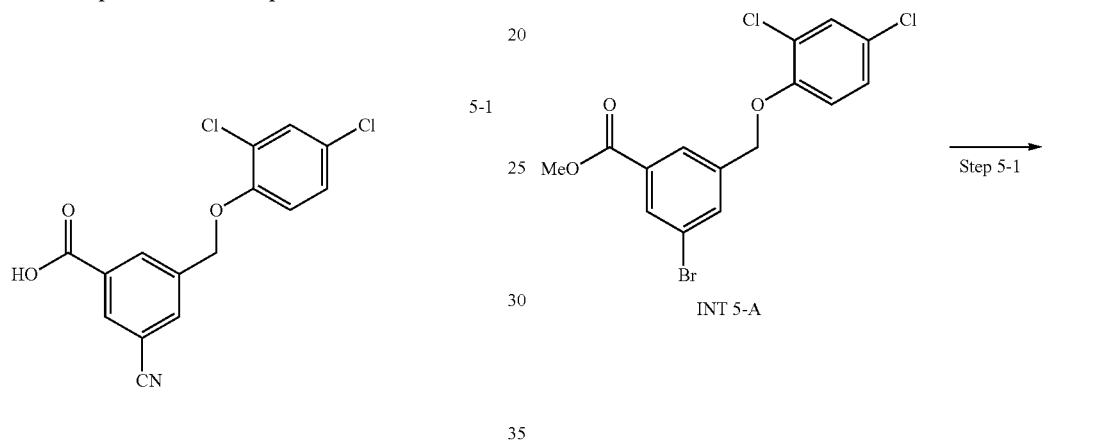

To a stirring solution of methyl 3-bromo-5-((2,4-dichlorophenoxy) methyl)benzoate INT 5-A (100 mg, 256.37 µmol, prepared from methyl 3-bromo-5-(bromomethyl)benzoate and 2,4-dichlorophenol via Scheme 1) in DMF (2 mL) were added Zn (33.53 mg, 512.75 µmol), Pd₂(dba)₃ (23.48 mg, 25.64 µmol), DPPF (28.43 mg, 51.27 µmol), and Zn(CN)₂ (60.21 mg, 512.75 µmol, 32.55 µL). The mixture was stirred at 120° C. for 2 h, filtered, concentrated and purified by preparatory thin layer chromatography to afford 60 mg (69.2%) of methyl 3-cyano-5-((2,4-dichlorophenoxy) methyl)benzoate (INT 5-B) as a white solid. LCMS-ESI (m/z) calculated for $C_{16}H_{11}C_{12}NO_3$: 336.2; no m/z observed, $t_R$=1.1 min (Method 6). ¹H NMR (400 MHz, CDCl₃) δ 8.34 (s, 1H), 8.31 (s, 1H), 7.99 (s, 1H), 7.44 (d, J=2.4 Hz, 1H), 7.24-7.17 (m, 1H), 6.89 (d, J=8.8 Hz, 1H), 5.19 (s, 2H), 3.99 (s, 3H).

Step 5-2. Synthesis of 3-cyano-5-((2,4-dichlorophenoxy)methyl)benzoic acid (Compound 5-1)

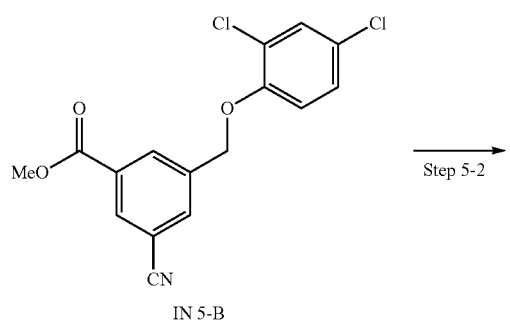

IN 5-B → Step 5-2

To a stirring solution of methyl 3-cyano-5-[(2,4-dichlorophenoxy) methyl]-benzoate (INT 5-B) (60 mg, 178.48 µmol) in MeOH (1 mL) and THF (1 mL) was added NaOH (2 M, 267.72 µL). The mixture was stirred at 10° C. for 16 h then concentrated. The resulting residue was dissolved in H$_2$O (20 mL) and acidified (1M HCl) to pH 5 and the resulting precipitate was collected and purified by prep-HPLC to afford 3.2 mg (5.6%) of 3-cyano-5-((2,4-dichlorophenoxy)methyl)benzoic acid (Compound 5-1) as a white solid. LCMS-ESI (m/z) calculated for C$_{15}$H$_9$Cl$_2$NO$_3$: 322.14. found 319.9 [M–H]$^+$, t$_R$=0.727 min. (Method 6) $^1$H NMR (400 MHz, DMSO-d$_6$) δ 8.32 (s, 1H), 8.25 (s, 1H), 8.11 (s, 1H), 7.62 (s, 1H), 7.41 (br d, J=8.8 Hz, 1H), 7.27 (d, J=8.9 Hz, 1H), 5.34-5.32 (m, 1H), 5.35 (s, 1H).

The compounds listed in Table 5 were made using the procedures of Scheme 5.

TABLE 5

| Structure | Cpd No. | Purity RT (min) | MW | Observed m/z | Ion | Purity Method |
|---|---|---|---|---|---|---|
| (structure) | 5-1 | 0.724 | 322.14 | 319.9 | [M – H]$^+$ | 7 |
| (structure) | 5-2 | 0.71 | 322.14 | 319.9 | [M – H]$^+$ | 7 |

-continued

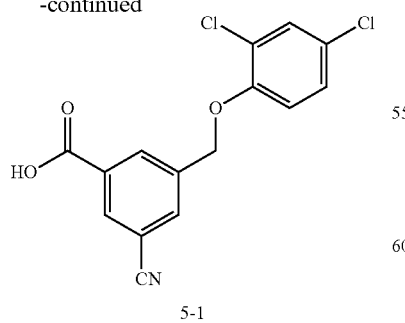

5-1

Example 6

Synthesis of Compound 6-1

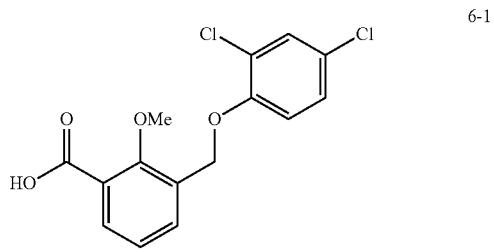 [SMILES: COc1c(COc2ccc(Cl)cc2Cl)cccc1C(=O)O]

6-1

Scheme 6

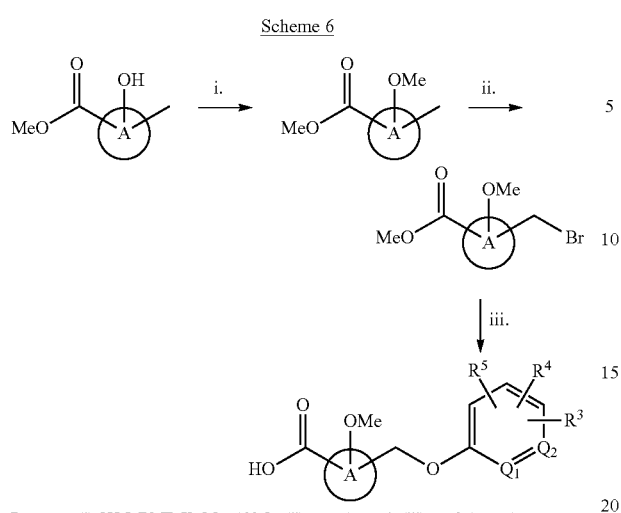

Reagents: (i) CH₃I, DMF, K₂CO₃, 10° C.; (ii) see scheme 4; (iii) see Scheme 1.

Step 6-1. Synthesis of methyl 2-methoxy-3-methylbenzoate (INT 6-A)

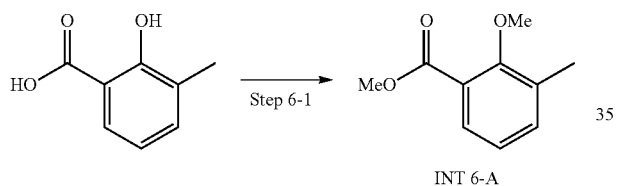

To a solution of 2-hydroxy-3-methyl-benzoic acid (1 g, 6.6 mmol) in DMF (15 mL) was added $K_2CO_3$ (2.73 g, 19.7 mmol) and $CH_3I$ (4.66 g, 32.86 mmol, 2.1 mL). The mixture was stirred at 10° C. for 2 h. Additional $CH_3I$ (2.33 g, 16.43 mmol, 1.0 mL) was added and the mixture stirred for an additional 16 h. The reaction mixture was quenched by the addition of $H_2O$ (50 mL), and then extracted with EA (100 mL×3). The combined organic layers were dried ($Na_2SO_4$), filtered and concentrated in vacuo pressure to give a residue that was purified by $SiO_2$ chromatography to provide 1.0 g (85%) of methyl 2-methoxy-3-methylbenzoate (INT 6-A) as a colorless oil. TLC (33% EA/petroleum ether), $R_f$=0.45. ¹H NMR (400 MHz, CDCl₃) δ ppm 2.33 (s, 3H) 3.84 (s, 3H) 3.92 (s, 3H) 7.06 (t, J=7.64 Hz, 1H) 7.35 (d, J=7.46 Hz, 1H) 7.64 (d, J=7.70 Hz, 1H).

Step 6-2. Synthesis of 3-((2,4-dichlorophenoxy)methyl)-2-methoxybenzoic acid (Compound 6-1)

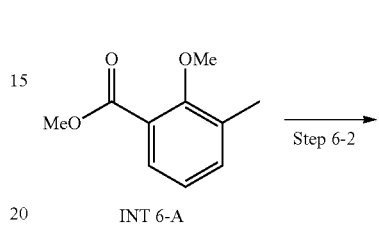

Compound 6-1 was prepared from INT 6-A according to the procedures of Schemes 4 and then Scheme 1 to provide 1.0 g (85%) of 3-((2,4-dichlorophenoxy)methyl)-2-methoxybenzoic acid (6-1) as a colorless oil. LCMS-ESI (m/z) calculated for $C_{10}H_{12}O_3$: 180.2; m/z not observed, $t_R$=0.70 min (Method 7). ¹H NMR (400 MHz, DMSO-d₆) δ ppm 3.82 (s, 3H) 5.22 (s, 2H) 7.25 (t, J=7.64 Hz, 1H) 7.30-7.35 (m, 1H) 7.37-7.43 (m, 1H) 7.60 (d, J=2.57 Hz, 1H) 7.68 (dd, J=7.52, 1.65 Hz, 1H) 7.73 (dd, J=7.76, 1.77 Hz, 1H) 13.03 (br s, 1H).

The compound listed in Table 6 was made using the procedures of Scheme 6.

TABLE 6

| Structure | Cpd No. | RT (min) | Purity MW | Observed m/z | Ion | Purity Method |
|---|---|---|---|---|---|---|
| ![structure] | 6-1 | 0.701 | 327.16 | 324.9 | [M − H]⁺ | 7 |

Example 7

Synthesis of Compound 7-1

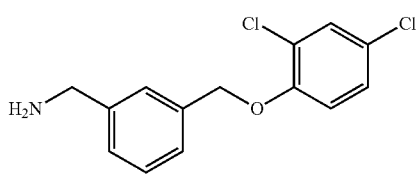 [SMILES: NCc1cccc(COc2ccc(Cl)cc2Cl)c1]

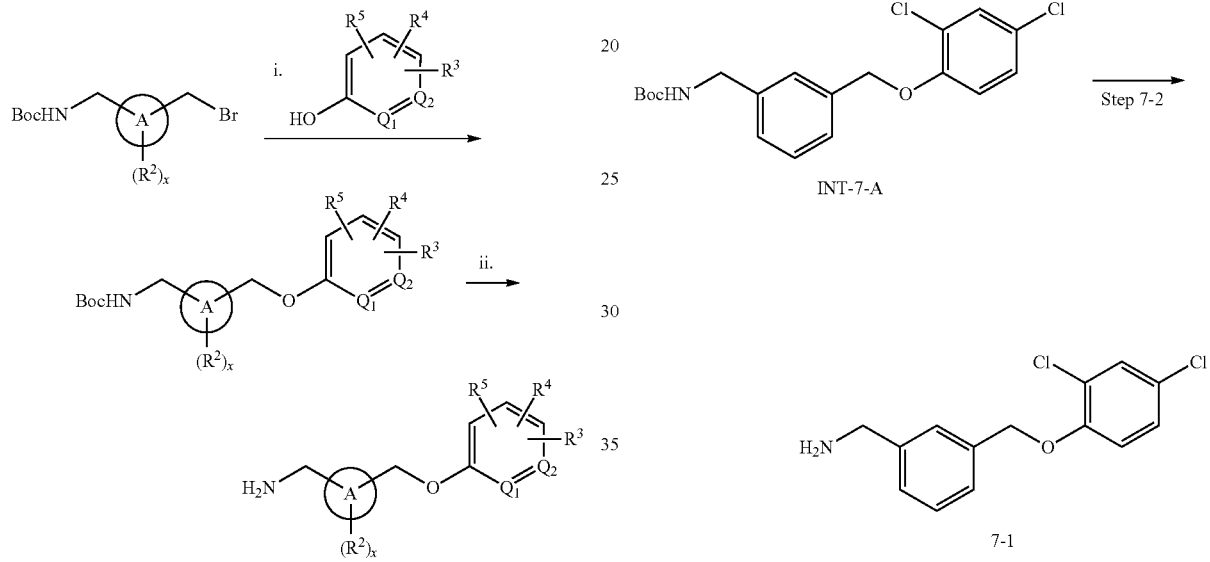

Reagents: (i) Base (Na₂CO₃ K₂CO₃, KO'Bu), MeCN, 60° C.; (ii) 4M HCl/dioxanes.

Step 7-1. Synthesis of tert-butyl (3-((2,4-dichlorophenoxy)methyl)benzyl)carbamate (INT 7-A)

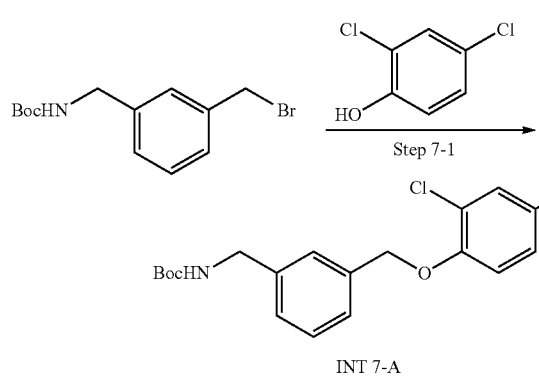

To a stirring solution of 2,4-dichlorophenol (271 mg, 1.67 mmol) in MeCN (7 mL) were added tert-butyl (3-(bromomethyl)benzyl)carbamate (500 mg, 1.67 mmol) and K₂CO₃ (299 mg, 2.17 mmol). The flask was sealed, and the resulting white suspension was heated at 60° C. for 3 h. The reaction mixture was cooled to room temperature, diluted with H₂O (10 mL), extracted with Et₂O (2×10 mL), dried (Na₂SO₄), filtered through Celite, and concentrated in vacuo to afford 627 mg (96%) of tert-butyl (3-((2,4-dichlorophenoxy)methyl)benzyl)carbamate (INT 7-A). LCMS-ESI (m/z) calculated for $C_{19}H_{21}Cl_2NO_3$: 381. found 404.1 [M+Na]⁺, $t_R$=12.2 min. (Method 3). ¹H NMR (500 Hz, CDCl₃) 7.37 (d, J=2.5, 1H), 7.34-7.33 (m, 3H), 7.25-7.22 (m, 1H), 7.134 (dd, J=9.0, 2.5, 1H), 6.858 (d, J=9.0, 1H), 5.10 (s, 2H), 4.33 (d, J=5.5, 2H), 1.45 (s, 9H).

Step 7-2. Synthesis of (3-((2,4-dichlorophenoxy)methyl)phenyl)methanamine (Compound 7-1)

To a stirring solution of tert-butyl (3-((2,4-dichlorophenoxy) methyl)-benzyl) carbamate (INT 7-A) (200 mg, 523 µmol) in dioxane (5 mL) was added 4M Hydrogen chloride in dioxanes (5 mL, 20.9 mmol). After 3 h, the reaction mixture became a suspension and was filtered. The filtrate was concentrated to afford 101 mg of crude white solid that was recrystallized from EtOH (0.7 mL) to afford 15.5 mg (10.5%) of (3-((2,4-dichlorophenoxy)methyl)phenyl)methanamine (Compound 7-1) as a white solid. LCMS-ESI (m/z) calculated for $C_{14}H_{13}Cl_2NO$: 281. found 282.1 [M+H]⁺, $t_R$=6.345 min. (Method 3). ¹H NMR (500 Hz, DMSO-d6) 8.26 (br s, 3H), 7.61 (d, J=3.0, 1H), 7.55 (s, 1H), 7.49-7.47 (m, 3H), 7.39 (dd, J=9.0, 2.5, 1H), 7.28 (d, J=9.0, 1H), 5.22 (s, 2H), 4.05 (s, 2H).

The compound listed in the Table 7 was made using the procedures of Scheme 7.

TABLE 7
| Structure | Cpd No. | Purity RT (min) | MW | Observed m/z | Ion | Purity Method |
|---|---|---|---|---|---|---|
| 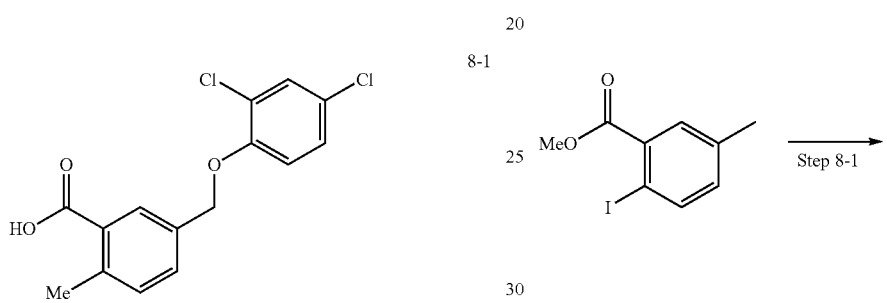 | 7-1 | 6.35 | 282.16 | 282.1 | [M − H]⁺ | 4 |
Example 8
Synthesis of Compound 8-1 and Other Representative Compounds
Step 8-1. Synthesis of methyl 5-(bromomethyl)-2-iodobenzoate (INT 8-A)
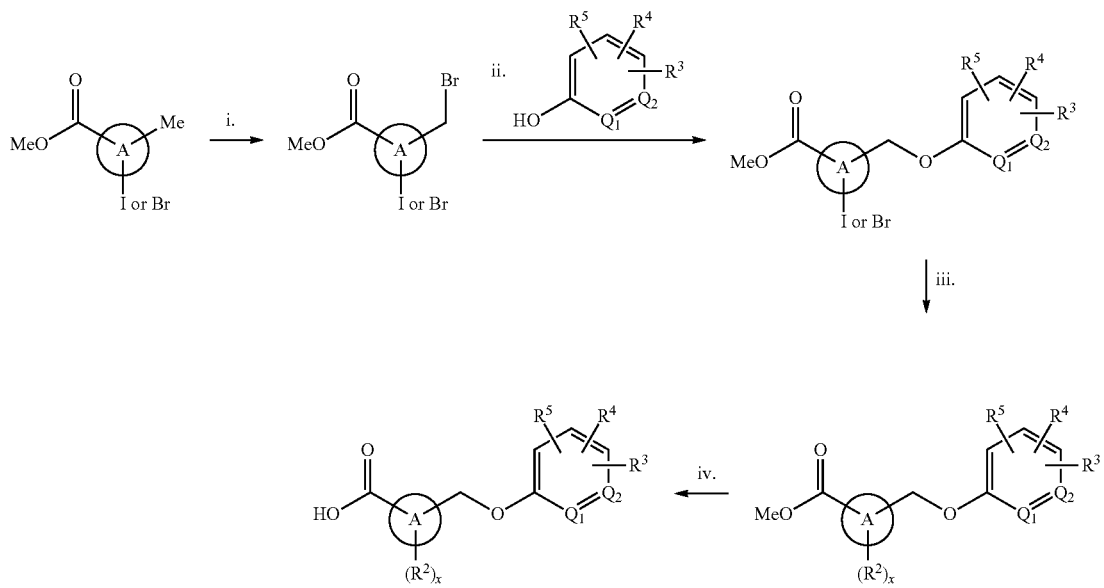
Reagents: (i) NBS, AIBN, CCl$_4$, 100° C.; (ii) Base (K$_2$CO$_3$, KO$^t$Bu), solvent (MeCN, DMF, DCM); (iii) Pd(dppf)Cl$_2$, Boronic Acid, K$_2$CO$_3$, dioxane; (iv) NaOH, solvent (THF, MeOH, or DMF).

-continued

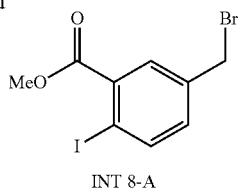

INT 8-A

To a solution of methyl 2-iodo-5-methyl-benzoate (1 g, 3.62 mmol) in CCl$_4$ (10 mL) were added NBS (644.7 mg, 3.62 mmol) and AIBN (11.9 mg, 72.5 μmol). The mixture was stirred at 100° C. for 2 h and was concentrated under reduced pressure to give a residue that was purified by flash SiO$_2$ chromatography (EA/petroleum ether) to afford 733 mg (57.0%) of methyl 5-(bromomethyl)-2-iodobenzoate (INT 8-A) as a brown solid. TLC: (10% EA/Petroleum ether) R$_f$: 0.5. $^1$H NMR (400 MHz, CDCl$_3$) δ 7.98 (d, J=8.1 Hz, 1H), 7.84 (d, J=2.3 Hz, 1H), 7.20 (dd, J=2.3, 8.1 Hz, 1H), 4.46-4.43 (m, 2H), 3.95 (s, 3H).

Step 8-2. Synthesis of methyl 5-((2,4-dichlorophenoxy)methyl)-2-iodo-benzoate (INT 8-B)

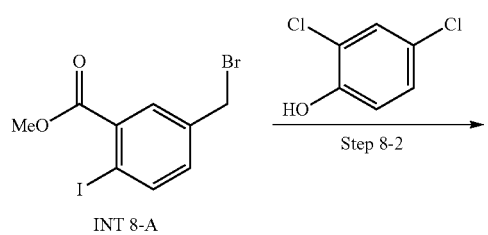

To a solution of methyl 5-(bromomethyl)-2-iodo-benzoate (INT 8-A) (733 mg, 2.06 mmol) in MeCN (5 mL) were added K$_2$CO$_3$ (571 mg, 4.13 mmol) and 2,4-dichlorophenol (337 mg, 2.06 mmol). After stirring at 50° C. for 16 h the reaction mixture was concentrated in vacuo and was purified by flash SiO$_2$ chromatography to provide 780 mg, (86.4%) yield methyl 5-((2,4-dichlorophenoxy)methyl)-2-iodo-benzoate (INT 8-B) as a white solid. TLC: (10% EA/Petroleum ether) R: 0.3. $^1$H NMR (400 MHz, CDCl$_3$) δ 8.02 (d, J=8.2 Hz, 1H), 7.88 (d, J=2.1 Hz, 1H), 7.41 (d, J=2.4 Hz, 1H), 7.30-7.28 (m, 1H), 7.17 (dd, J=2.4, 8.8 Hz, 1H), 6.86 (d, J=8.8 Hz, 1H), 5.10 (s, 2H), 3.96 (s, 3H).

Step 8-3. Synthesis of methyl 5-((2,4-dichlorophenoxy)methyl)-2-methylbenzoate (INT 8-C)

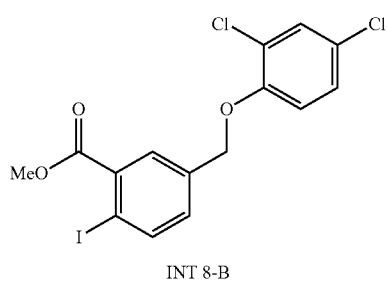

To a solution of methyl 5-((2,4-dichlorophenoxy)methyl)-2-iodo-benzoate (INT 8-B) (200 mg, 457.6 μmol) in dioxane (1 mL) and H$_2$O (1 mL) were added Pd(dppf)Cl$_2$ (16.7 mg, 22.9 μmol), K$_2$CO$_3$ (189.7 mg, 1.4 mmol), and MeB(OH)$_2$ (54.8 mg, 915 μmol). The mixture was stirred at 100° C. for 2 hr, concentrated and purified by flash SiO$_2$ chromatography (EA/petroleum ether) to provide 100 mg (67.2%) of methyl 5-((2,4-dichlorophenoxy)methyl)-2-methyl-benzoate (INT 8-C) as a white solid. TLC: (10% EA/Petroleum ether) R$_f$=0.4. $^1$H NMR (400 MHz, CDCl$_3$) δ 7.98 (d, J=1.6 Hz, 1H), 7.51 (dd, J=1.7, 7.8 Hz, 1H), 7.40 (d, J=2.6 Hz, 1H), 7.31-7.28 (m, 1H), 7.16 (dd, J=2.4, 8.8 Hz, 1H), 6.88 (d, J=8.8 Hz, 1H), 5.12 (s, 2H), 3.96-3.90 (m, 3H), 2.61 (s, 3H).

Step 8-4. Synthesis of 5-((2,4-dichlorophenoxy)methyl)-2-methylbenzoic acid (Compound 8-1)

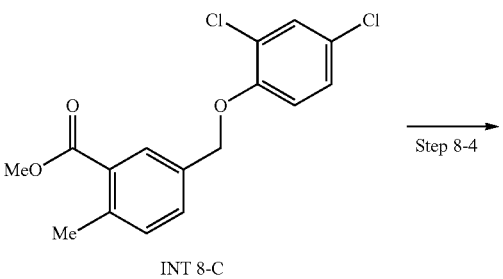

-continued

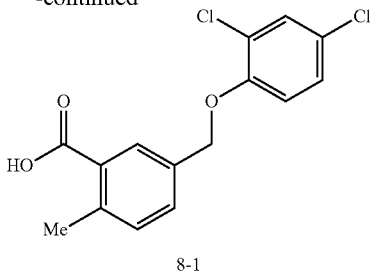

8-1

To a solution of methyl 5-[(2,4-dichlorophenoxy)methyl]-2-methyl-benzoate (INT 8-C) (100 mg, 307.52 μmol) in MeOH (1 mL) and THF (1 mL) was added NaOH (2 M, 461.27 μL). After stirring at 10° C. for 16 h the mixture was concentrated in vacuo and purified by prep-HPLC to provide 29 mg (30.3%) of 5-((2,4-dichlorophenoxy)methyl)-2-methylbenzoic acid (Compound 8-1) as a white solid. LCMS-ESI (m/z) calculated for $C_{15}H_{12}Cl_2O_3$: 310.02. found 308.9 $[M-H]^+$, $t_R$=0.718 min. (Method 7). $^1$H NMR (400 MHz, CDCl$_3$) δ 8.12 (s, 1H), 7.57 (br d, J=7.9 Hz, 1H), 7.40 (d, J=2.4 Hz, 1H), 7.32 (d, J=7.5 Hz, 1H), 7.17 (dd, J=2.4, 8.8 Hz, 1H), 6.89 (d, J=8.8 Hz, 1H), 5.14 (s, 2H), 2.67 (s, 3H).

The compounds listed in Table 8 were made using the procedures of Scheme 8.

TABLE 8

| Structure | Cpd No. | Purity RT (min) | MW | Observed m/z | Ion | Purity Method |
|---|---|---|---|---|---|---|
| 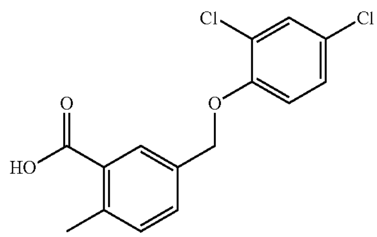 [SMILES: Cc1ccc(COc2ccc(Cl)cc2Cl)cc1C(=O)O] | 8-1 | 0.72 | 311.16 | 308.9 | $[M - H]^+$ | 7 |
| 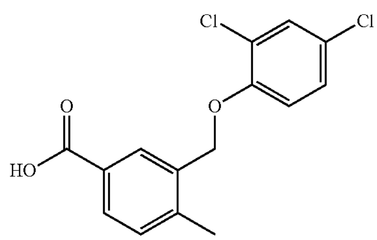 [SMILES: Cc1ccc(C(=O)O)cc1COc1ccc(Cl)cc1Cl] | 8-2 | 0.724 | 311.16 | 308.9 | $[M - H]^+$ | 7 |
| 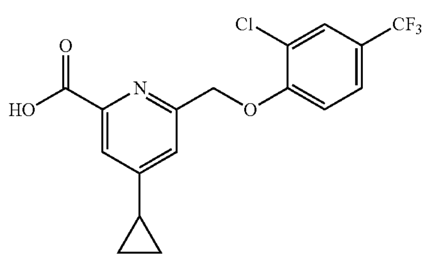 [SMILES: O=C(O)c1cc(C2CC2)cc(COc2ccc(C(F)(F)F)cc2Cl)n1] | 8-3 | 10.326 | 371.74 | 370 | $[M - H]^+$ | 4 |
| 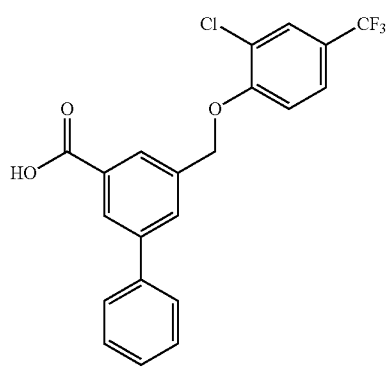 [SMILES: O=C(O)c1cc(COc2ccc(C(F)(F)F)cc2Cl)cc(-c2ccccc2)c1] | 8-4 | 11.819 | 406.79 | 405 | $[M - H]^+$ | 4 |

Example 9

Synthesis of Compound 9-1

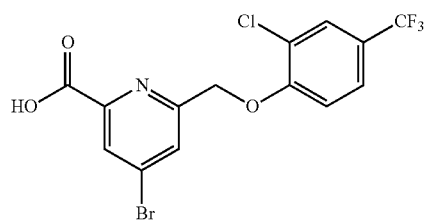

9-1

To a stirring solution of dimethyl 4-bromopyridine-2,6-dicarboxylate (1.0 g, 3.6 mmol) in MeOH (12 mL) and DCM (6 mL) at 0° C. was added sodium borohydride (0.17 g, 4.4 mmol) in 3 portions. The reaction mixture was warmed to room temperature and stirred overnight. Additional sodium borohydride (0.17 g, 4.4 mmol) was added. After 2 h, the reaction mixture was diluted with $NH_4Cl$ (aq) (10 mL) and DCM (10 mL). The aqueous layer was extracted with DCM (2×10 mL) and EA (10 mL), dried ($Na_2SO_4$), filtered through Celite, and concentrated in vacuo to afford a crude white solid that was purified by $SiO_2$ chromatography (10% MeOH in EA/hexanes) to afford 514 mg, (57%) of methyl 4-bromo-6-(hydroxymethyl)picolinate (INT 9-A) as a white solid. LCMS-ESI (m/z) calculated for $C_9H_{10}BrNO_3$: 258.98; m/z not observed, $t_R$=3.21 min. (Method 1).

Scheme 9

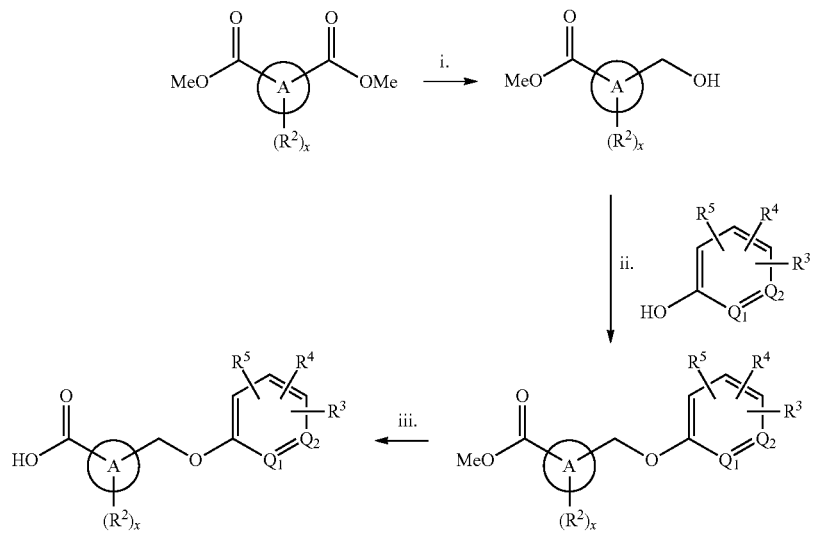

Reagents: (i) $NaBH_4$, DCM, MeOH; (ii) $PPh_3$, $NEt_3$, DEAD, THF; (iii) NaOH, solvent (THF, MeOH, or DMF).

Step 9-1. Synthesis of methyl 4-bromo-6-(hydroxymethyl)picolinate (INT 9-A)

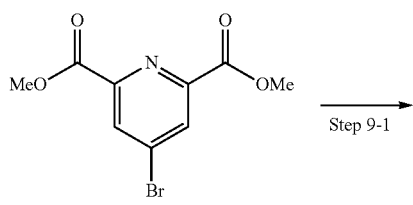

Step 9-2. Synthesis of methyl 4-bromo-6-((2-chloro-4-(trifluoromethyl)phenoxy)-methyl)picolinate (INT 9-B)

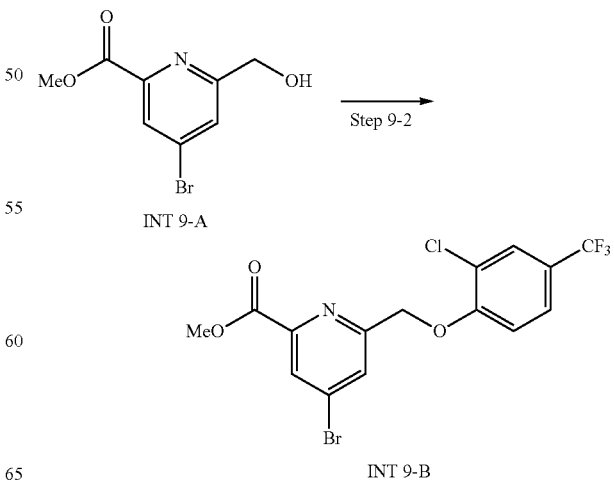

To a stirring solution of 2-chloro-4-(trifluoromethyl)phenol (87.9 mg, 0.447 mmol) in THF (10 mL) were added methyl 4-bromo-6-(hydroxymethyl) picolinate (INT 9-A) (100 mg, 0.406 mmol), triphenylphosphine (107 mg, 0.406 mmol) and TEA (56.7 µL, 406 µmol). The reaction mixture was cooled to 0° C. and diisopropyl azodicarboxylate (82.2 mg, 80.0 µL, 0.406 mmol) was added dropwise. The reaction mixture was stirred at 0° C. for 30 minutes, warmed to room temperature and stirred overnight. The reaction mixture was concentrated in vacuo to afford a crude product that was purified by SiO$_2$ chromatography (EA/hexanes) to afford 94 mg (55%) of methyl 4-bromo-6-((2-chloro-4-(trifluoromethyl)phenoxy)methyl)picolinate (INT 9-B) as an off-white solid. LCMS-ESI (m/z) calculated for C$_{15}$H$_{10}$BrClF$_3$NO$_3$: 422.95; m/z not observed, t$_R$=6.73 min. (Method 1).

Step 9-3. Synthesis of 4-bromo-6-((2-chloro-4-(trifluoromethyl)phenoxy)methyl)picolinic acid Compound 9-1)

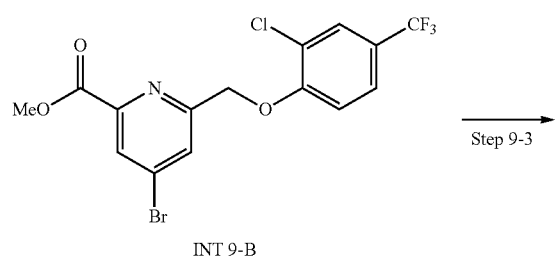

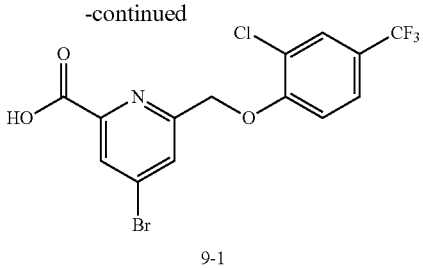

To a stirring solution of methyl 4-bromo-6-((2-chloro-4-(trifluoromethyl)phenoxy)methyl)picolinate (INT 9-B) (94.5 mg, 223 µmol) in THF (2 mL) was added 1M NaOH (1 mL, 1.11 mmol). The reaction mixture was heated at 60° C. overnight, cooled and acidified with 3M HCl. The mixture was extracted with EA and Et$_2$O, and the combined organics were dried (Na$_2$SO$_4$), filtered and concentrated in vacuo to afford 77.6 mg (85%) of 4-bromo-6-((2-chloro-4-(trifluoromethyl)phenoxy)methyl)picolinic acid (Compound 9-1) as a white solid. LCMS-ESI (m/z) calculated for C$_{14}$H$_{18}$BrClF$_3$NO$_3$: 408.93. found 410.0 [M+H]$^+$, t$_R$=10.7 min. (Method 3).

The compounds listed in Table 9 were made using the procedures of Scheme 9:

TABLE 9

| Structure | Cpd No. | Purity RT (min) | MW | Observed m/z | Ion | Purity Method |
|---|---|---|---|---|---|---|
| 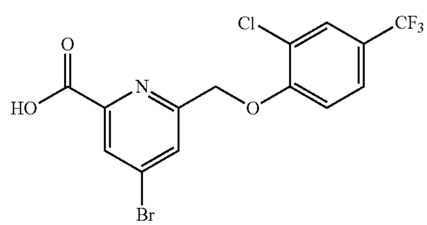 [SMILES: O=C(O)c1cc(Br)cc(COc2ccc(C(F)(F)F)cc2Cl)n1] | 9-1 | 10.73 | 410.57 | 412.0 | [M + H]$^+$ | 3 |
| 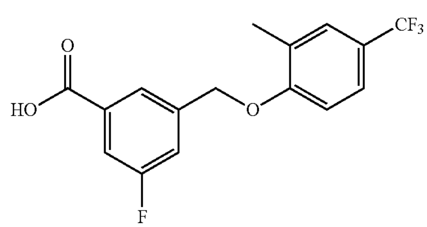 [SMILES: Cc1cc(C(F)(F)F)ccc1OCc1cc(F)cc(C(=O)O)c1] | 9-2 | 10.758 | 328.26 | 327 | [M − H]$^+$ | 4 |
| 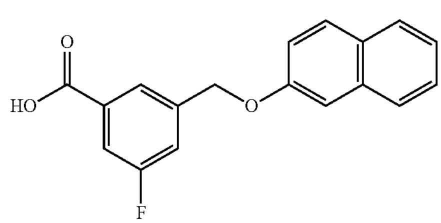 [SMILES: O=C(O)c1cc(F)cc(COc2ccc3ccccc3c2)c1] | 9-3 | 10.281 | 296.30 | 295.2 | [M − H]$^+$ | 4 |

Example 10

Synthesis of Compound 10-1

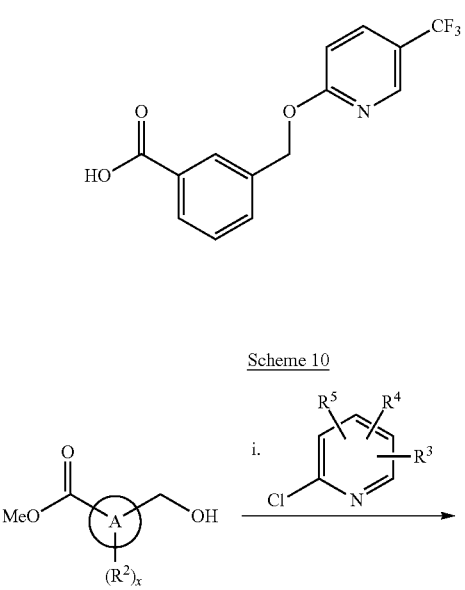

10-1

Scheme 10

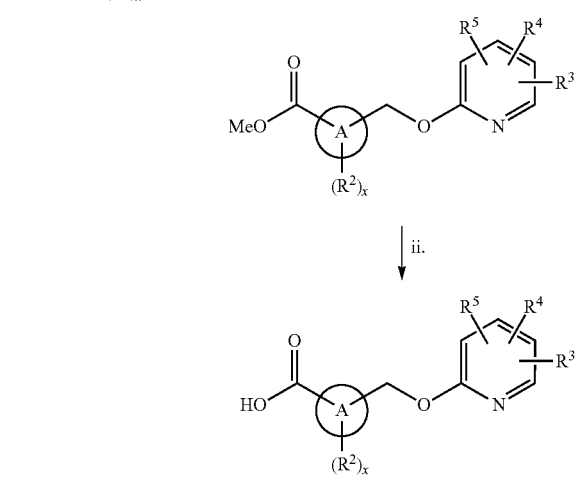

Reagents: (i) KOtBu, dioxane; (ii) NaOH, solvent (THF, MeOH, or DMF).

Step 10-1. Synthesis of methyl 3-(((5-(trifluoromethyl)pyridin-2-yl)oxy)methyl)-benzoate (INT 10-A)

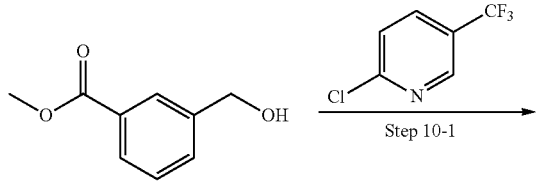

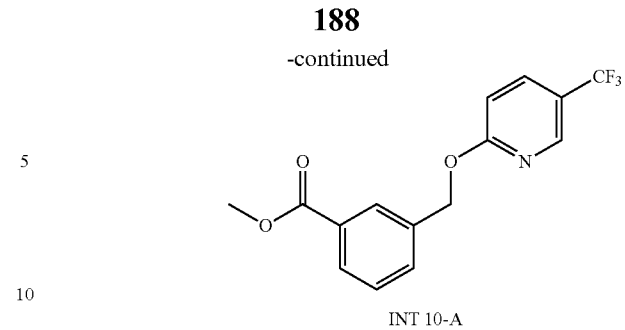

INT 10-A

Into a pressure vessel containing a solution of methyl 3-(hydroxymethyl) benzoate (499 mg, 3.00 mmol) in 1,4-Dioxane (9 mL) were added 2-chloro-5-(trifluoromethyl) pyridine (363 mg, 2.00 mmol) and potassium tert-butoxide (337 mg, 3.00 mmol). The vessel was sealed, and the reaction mixture was heated and stirred overnight at 90° C., then cooled to room temperature. The reaction mixture was partitioned between Et$_2$O and H$_2$O. The phases were separated and the aqueous layer was further extracted with diethyl ether (2×). The organic phases were combined, washed with brine, dried (Na$_2$SO$_4$), filtered, and concentrated under reduced pressure. The resulting colorless oil was purified by flash SiO$_2$ chromatography (EA/hexanes) to yield 177 mg (28.4%) of methyl 3-(((5-(trifluoromethyl)pyridin-2-yl)oxy)methyl)benzoate (INT 10-A) as a colorless oil. LCMS-ESI (m/z) calculated for C$_{15}$H$_{12}$F$_3$NO$_3$: 311.1. found 312.1 [M+H]$^+$, t$_R$=6.25 min. (Method 1). $^1$H NMR (500 MHz, DMSO-d6) δ 8.608 (s, 1H), 8.114 (dd, J=8.5, 2.5 Hz, 1H), 8.050 (s, 1H), 7.934 (d, J=7.5 Hz, 1H), 7.753 (d, J=8.0 Hz, 1H), 7.551 (t, J=7.5 Hz, 1H), 7.129 (d, J=9.0 Hz, 1H), 5.512 (s, 2H), 3.858 (s, 3H). $^{19}$F NMR (470 MHz, DMSO-d6) δ 60.140 (s).

Step 10-2. Synthesis of 3-(((5-(trifluoromethyl)pyridin-2-yl)oxy)methyl)benzoic acid (Compound 10-1)

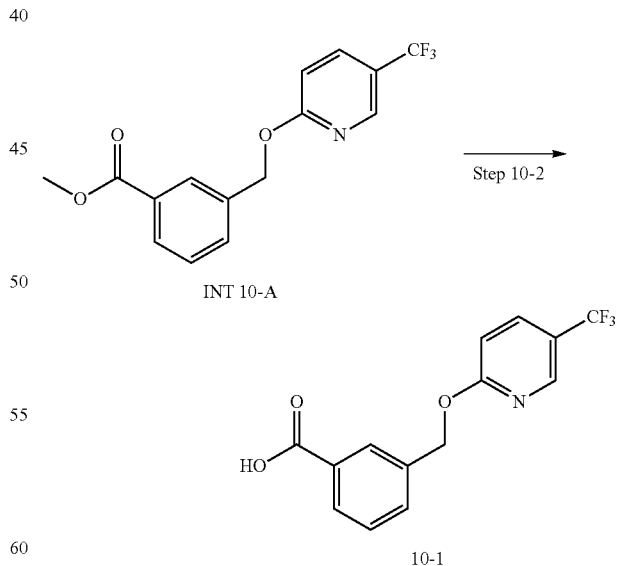

A 20 mL vial containing a stirring solution of methyl 3-(((5-(trifluoromethyl)pyridin-2-yl)oxy)methyl)benzoate (INT 10-A) (177 mg, 0.569 mmol) in THF (6 mL) was charged with 1M NaOH (2.27 mL, 2.27 mmol). After stirring for 12 h at 50° C. the reaction mixture was concentrated in vacuo and the residue was dissolved in H₂O and acidified to pH 4-5 using 3M HCl. The resulting white precipitate was extracted with Et₂O (3×). The combined organic layers were washed with brine, dried (Na₂SO₄) and concentrated in vacuo to yield 151 mg (89.3%) of 3-(((5-(trifluoromethyl)pyridin-2-yl)oxy)methyl)benzoic acid (Compound 10-1) as a white solid. LCMS-ESI (m/z) calculated for $C_{14}H_{11}F_3NO_3$: 297.2. found 298.1 $[M+H]^+$, $t_R$=9.33 min. (Method 3). ¹H NMR (500 MHz, DMSO-d₆) δ 13.006 (br s, 1H), 8.595 (s, 1H), 8.100 (dd, J=9.0, 2.5 Hz, 1H), 8.015 (s, 1H), 7.900 (d, J=8.0 Hz, 1H), 7.702 (d, 8.0 Hz, 1H), 7.522 (t, J=7.5 Hz, 1H), 7.115 (d, J=8.5 Hz, 1H), 5.493 (s, 2H). ¹⁹F NMR (470 MHz, DMSO-d6) δ 60.126 (s).

The compound listed in Table 10 was made using the procedures of Scheme 10:

TABLE 10

| Structure | Cpd No. | Purity RT (min) | MW | Observed m/z | Ion | Purity Method |
|---|---|---|---|---|---|---|
| 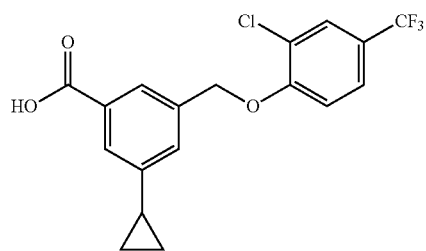 | 10-1 | 9.33 | 297.23 | 298.2 | $[M + H]^+$ | 3 |

Example 11

Synthesis of Compound 11-1

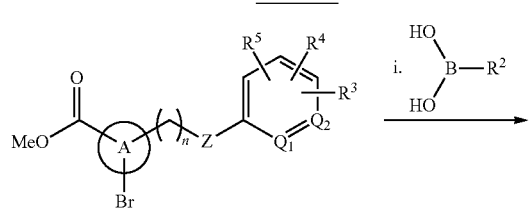

11-1

Scheme 11

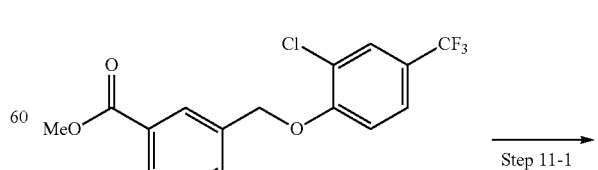

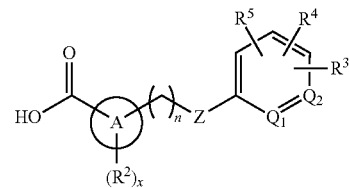

Reagents (i) tricyclohexyl phosphine, Pd(OAc)₂, cyclopropylboronic acid, potassium phosphate, toluene; (ii) NaOH, solvent (THF, MeOH, or DMF).

Step 11-1. Synthesis of methyl 3-((2-chloro-4-(trifluoromethyl)phenoxy)methyl)-5-cyclopropylbenzoate (INT 11-B)

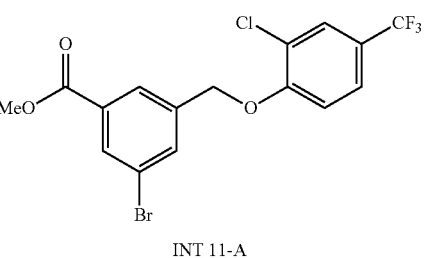

INT 11-A

-continued

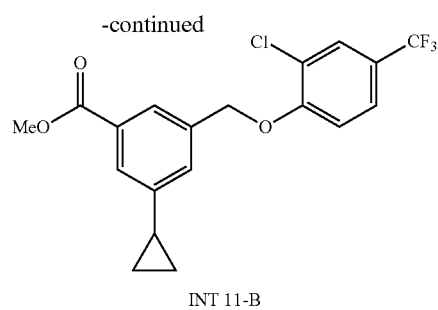

INT 11-B

To a degassed solution of methyl 3-bromo-5-((2-chloro-4-(trifluoromethyl)phenoxy)m)methyl)benzoate (INT 11-A) (200 mg, 472 μmol, prepared via Scheme 2 from methyl 3-bromo-5-(hydroxymethyl)benzoate and 2-chloro-4-(trifluoromethyl)phenol)), tricyclohexyl phosphine (6.62 mg, 23.6 μmol), potassium phosphate (230 mg, 1.09 mmol), and cyclopropylboronic acid (52.7 mg, 614 μmol) in toluene (4 mL) was added palladium diacetate (5.30 mg, 23.6 μmol). The reaction vial was capped and heated at 100° C. overnight. The reaction was further degassed and additional tricyclohexyl phosphine (6.62 mg, 23.6 μmol), cyclopropylboronic acid (52.7 mg, 614 μmol), and palladium diacetate (5.30 mg, 23.6 μmol) were added. After heating at 100° C. for 4 h, the reaction mixture was filtered through Celite rinsing with EA and concentrated in vacuo. The residue was taken up in EA, washed with sat. sodium bicarbonate and brine, dried ($Na_2SO_4$), filtered, and concentrated in vacuo to afford crude material that was purified by $SiO_2$ chromatography (EA/hexanes) to afford 132 mg (72%) of methyl 3-((2-chloro-4-(trifluoromethyl)phenoxy)methyl)-5-cyclopropylbenzoate (INT 11-B). LCMS-ESI (m/z) calculated for $C_{19}H_{16}ClF_3O_3$: 384.1; no m/z observed, $t_R$=7.02 min. (Method 1). $^1$H NMR (500 Hz, DMSO-d6) δ 7.86 (d, J=2.5, 1H), 7.85 (s, 1H), 7.71 (dd, J=8.8, 2.5, 1H), 7.64 (s, 1H), 7.46, (s, 1H), 7.41 (d, J=9.0, 1H), 5.35 (s, 2H), 3.85 (s, 3H), 2.07-2.02 (m, 1H), 1.03-1.00 (m, 2H), 0.73-0.70 (m, 2H).

Step 11-2 Synthesis of 3-((2-chloro-4-(trifluoromethyl)phenoxy)methyl)-5-cyclopropylbenzoic acid (Compound 11-1)

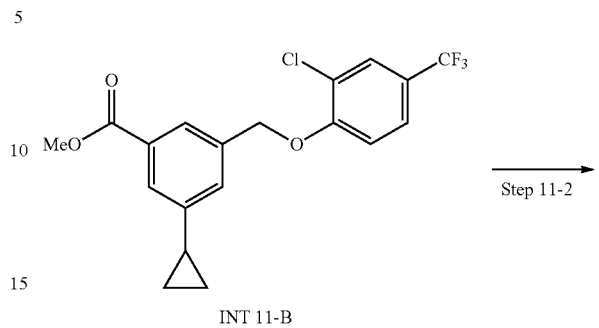

To a stirring solution of methyl 3-((2-chloro-4-(trifluoromethyl)phenoxy)methyl)-5-cyclopropylbenzoate (INT 11-B, 132 mg, 0.343 mmol) in THF (2 mL) was added 1M NaOH (2 mL, 1.72 mmol). After heating at 60° C. overnight, the reaction mixture was cooled and acidified with 3M HCl. The mixture was extracted with EA and $Et_2O$, dried ($Na_2SO_4$), filtered, concentrated in vacuo. The crude solid was purified by reversed phase HPLC to afford 71.2 mg (56%) of 3-((2-chloro-4-(trifluoromethyl)phenoxy)methyl)-5-cyclopropylbenzoic acid (Compound 11-1) as a white solid. LCMS-ESI (m/z) calculated for $C_{18}H_{14}ClF_3O_3$: 370.7. found 393.1 [M+Na]$^+$, $t_R$=11.25 min. (Method 3). $^1$H NMR (500 Hz, DMSO-d$_6$) δ 13.00 (s, 1H), 7.87 (s, 1H), 7.82 (s, 1H), 7.71 (d, J=8.0, 1H), 7.62 (s, 1H), 7.43-7.41 (m, 2H), 5.34 (s, 2H), 2.04 (m, 1H), 1.01 (d, J=7.0, 2H), 0.72-0.71 (m, 2H).

The compound listed in the Table 11 was made using the procedures of Scheme 11.

TABLE 11

| Structure | Cpd No. | Purity RT (min) | MW | Observed m/z | Ion | Purity Method |
|---|---|---|---|---|---|---|
| (structure shown) | 11-1 | 11.25 | 370.75 | 393.1 | [M + Na]$^+$ | 3 |

Example 12

Synthesis of Compound 12-1

12-1

Scheme 12

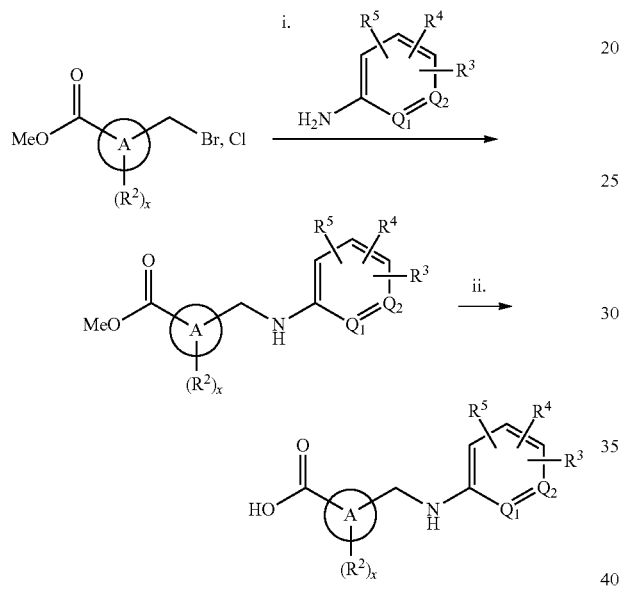

Reagents: (i) NaH, DMF; (ii) NaOH, solvent (THF, MeOH, or DMF).

Step 12-1. Synthesis of methyl 3-(((2,4-dichlorophenyl)amino)methyl)benzoate (INT 12-A)

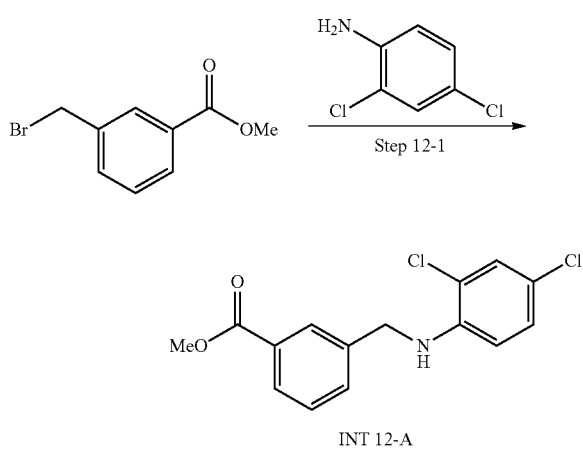

To a stirring solution of methyl 3-(bromomethyl)benzoate (300 mg, 1.31 mmol) and 2,4-dichloroaniline (0.23 g, 1.44 mmol) in DMF (2 mL) at 0° C. was added NaH (60% in mineral oil, 38 mg, 0.95 mmol). After 1 at 0° C. the mixture was diluted with $H_2O$ (20 mL) and extracted with EA (2×50 mL). The organic layers were combined, washed with brine, dried ($Na_2SO_4$), filtered, and concentrated to provide a crude product that was purified by $SiO_2$ chromatography to afford 230 mg (56%) of methyl 3-(((2,4-dichlorophenyl) amino)methyl)benzoate (INT 12-A) that was 30% pure and used without further purification. LCMS-ESI (m/z) calculated for $C_{15}H_{13}C_{12}NO_2$: 310.2. found 311.2 $[M+H]^+$, $t_R$=5.7 min. (Method 11).

Step 12-2. Synthesis of 3-(((2,4-dichlorophenyl)amino)methyl)benzoic acid (Compound 12-1)

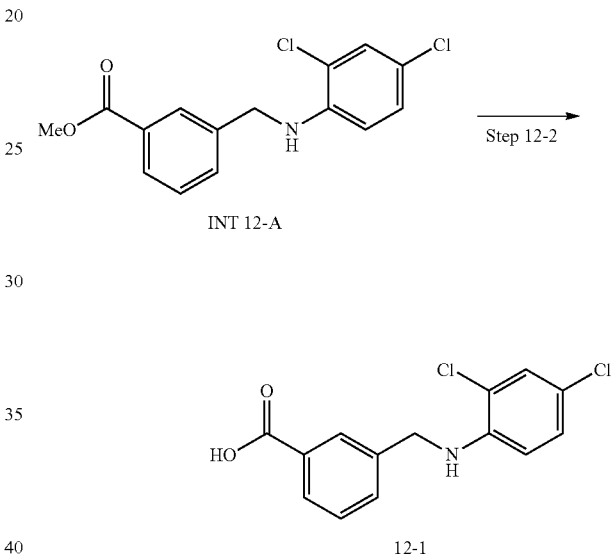

To a stirring solution of crude methyl 3-(((2,4-dichlorophenyl) amino)methyl)benzoate (INT 12-A) (230 mg, 0.74 mmol) in MeOH (3 mL) was added a solution of NaOH (290 mg, 7.4 mmol) in $H_2O$ (1 mL). The reaction was heated to reflux for 2, cooled to rt and concentrated in vacuo to remove the MeOH. The aqueous layer was acidified to pH 2 with 4N HCl(aq) and extracted with EA (2×50 mL). The combined organic layers were washed with $H_2O$, brine, dried ($MgSO_4$), filtered and concentrated in vacuo to provide a crude material that was purified by $SiO_2$ chromatography to provide 5 mg (2.3%) of 3-(((2,4-dichlorophenyl)amino) methyl)benzoic acid (Compound 12-1). LCMS-ESI (m/z) calculated for $C_{14}H_{11}C_{11}NO_2$: 296.2. found 296.5 $[M+H]^+$, $t_R$=13.88 min. (Method 9). $^1H$ NMR (400 MHz, DMSO-$d_6$) δ 7.88 (s, 1H), 7.76 (d, J=8 Hz, 1H), 7.42 (d, J=8 Hz, 1H), 7.35 (m, 2H), 7.06 (d, J=8 Hz, 1H), 6.51 (d, J=8 Hz, 1H), 6.39 (t, J=8 Hz, 1H), 4.43 (d, J=4 Hz, 2H).

The compounds listed in Table 12 were made using the procedures of Scheme 12.

TABLE 12
| Structure | Cpd No. | Purity RT (min) | MW | Observed m/z | Ion | Purity Method |
|---|---|---|---|---|---|---|
| 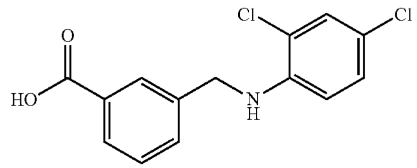 [SMILES: O=C(O)c1cccc(CNc2ccc(Cl)cc2Cl)c1] | 12-1 | 13.88 | 296.2 | 296.5 | [M + H]⁺ | 10 |
| 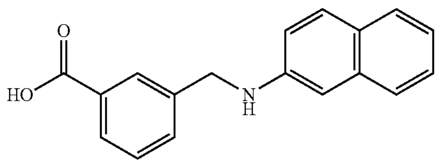 [SMILES: O=C(O)c1cccc(CNc2ccc3ccccc3c2)c1] | 12-2 | 0.787 | 277.3 | 275.9 | [M + H]⁺ | 6 |
| 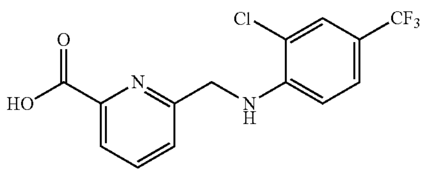 [SMILES: O=C(O)c1cccc(CNc2ccc(C(F)(F)F)cc2Cl)n1] | 12-3 | 0.913 | 330.7 | 331.1 | [M + H]⁺ | 6 |
| 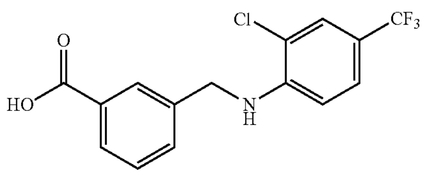 [SMILES: O=C(O)c1cccc(CNc2ccc(C(F)(F)F)cc2Cl)c1] | 12-4 | 0.984 | 329.7 | 330.1 | [M + H]⁺ | 6 |
Example 13
Synthesis of Compound 13-1
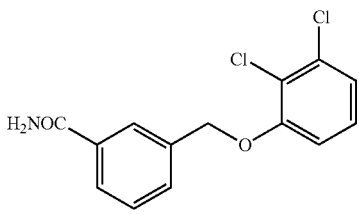 [SMILES: NC(=O)c1cccc(COc2cccc(Cl)c2Cl)c1]
13-1
Scheme 13
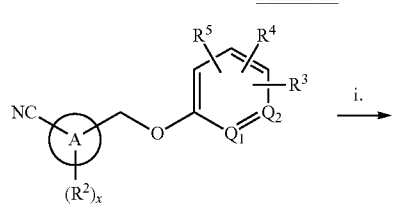
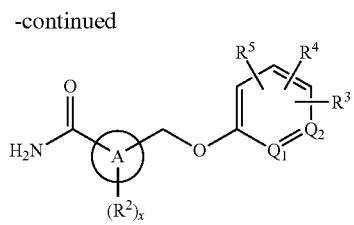
Reagents (i) NaOH, MeOH, heat.
Step 13-1. Synthesis of 3-((2,3-dichlorophenoxy)methyl)benzamide (Compound 13-1)
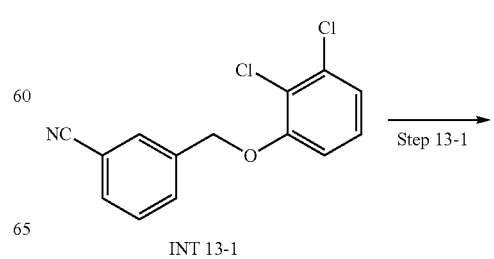
INT 13-1

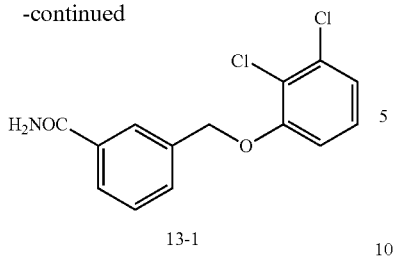

13-1

To a stirring solution INT 13-1 (0.3 g, 1.1 mmol, prepared via Scheme 3 from 3-(bromomethyl)benzonitrile and 2,3-dichlorophenol) in MeOH (5 mL) was added to a solution of NaOH (0.34 g, 8.6 mmol) in $H_2O$ (5 mL). After heating for 4 h at 90° C., the reaction mixture was cooled to room temperature and the resulting solid was collected and washed with $H_2O$ (10 mL). The material was dried under high vacuum to provide 68.8 mg (21%) of 3-((2,3-dichlorophenoxy)methyl)benzamide (Compound 13-1). LCMS-ESI (m/z) calculated for $C_{14}H_{11}Cl_2NO_2$: 296.2. found 297.2 [M+H]$^+$, $t_R$=11.8 min. (Method 10). $^1$H NMR (400 MHz, CDCl$_3$) δ 7.92 (s, 1H), 7.78 (d, J=8 Hz, 1H), 7.65 (d, J=8 Hz, 1H), 7.50 (t, J=8 Hz, 1H), 7.10 (m, 2H), 6.86 (d, J=8 Hz, 1H), 6.22 (bs, 1H), 5.59 (bs, 1H), 5.21 (s, 2H).

The compound listed in Table 13 was made using the procedures of Scheme 13.

TABLE 13

| Structure | Cpd No. | Purity RT (min) | MW | observed m/z | Ion | Purity Method |
|---|---|---|---|---|---|---|
| 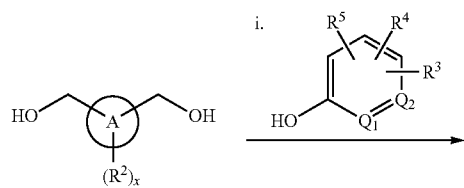 | 13-1 | 11.83 | 296.15 | 296.5 | [M − H]$^+$ | 4 |

Example 14

Synthesis of Compound 14-1

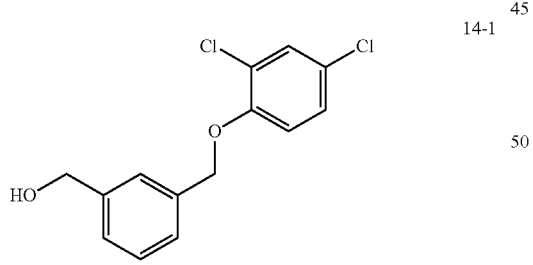

Scheme 14

Reagents: (i) PPh$_3$, NEt$_3$, DIAD, THF.

Step 14-1. Synthesis of (3-((2,4-dichlorophenoxy)methyl)phenyl)methanol (Compound 14-1)

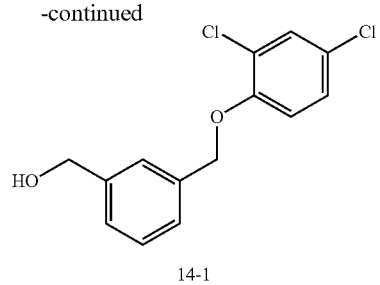

To a stirring solution of 2,4-dichlorophenol (324 mg, 1.99 mmol) in THF (15 mL) were added 1,3-phenylenedimethanol (250 mg, 1.81 mmol), triphenylphosphine (475 mg, 1.81 mmol), and TEA (183 mg, 252 μL, 1.81 mmol). The reaction mixture was cooled to 0° C. and diisopropyl azodicarboxylate (356 μL, 1.81 mmol) was added dropwise. The reaction mixture was stirred at 0° C. for 30 minutes, warmed to room temperature, and stirred overnight. The reaction mixture was concentrated in vacuo to afford crude product that was purified by SiO$_2$ chromatography (EA/hexanes) to afford 90.9 mg (17.7%) of (3-((2,4-dichlorophenoxy)methyl)phenyl)methanol (Compound 14-1) as an off-white solid. LCMS-ESI (m/z) calculated for $C_{14}H_{12}Cl_2O_2$: 282.0. found 282.21 [M+H]$^+$, $t_R$=10.08 min. (Method 3).

The compound listed in Table 14 was made using the procedures of Scheme 14:

TABLE 14

| Structure | Cpd No. | Purity RT (min) | MW | Observed m/z | Ion | Purity Method |
|---|---|---|---|---|---|---|
| 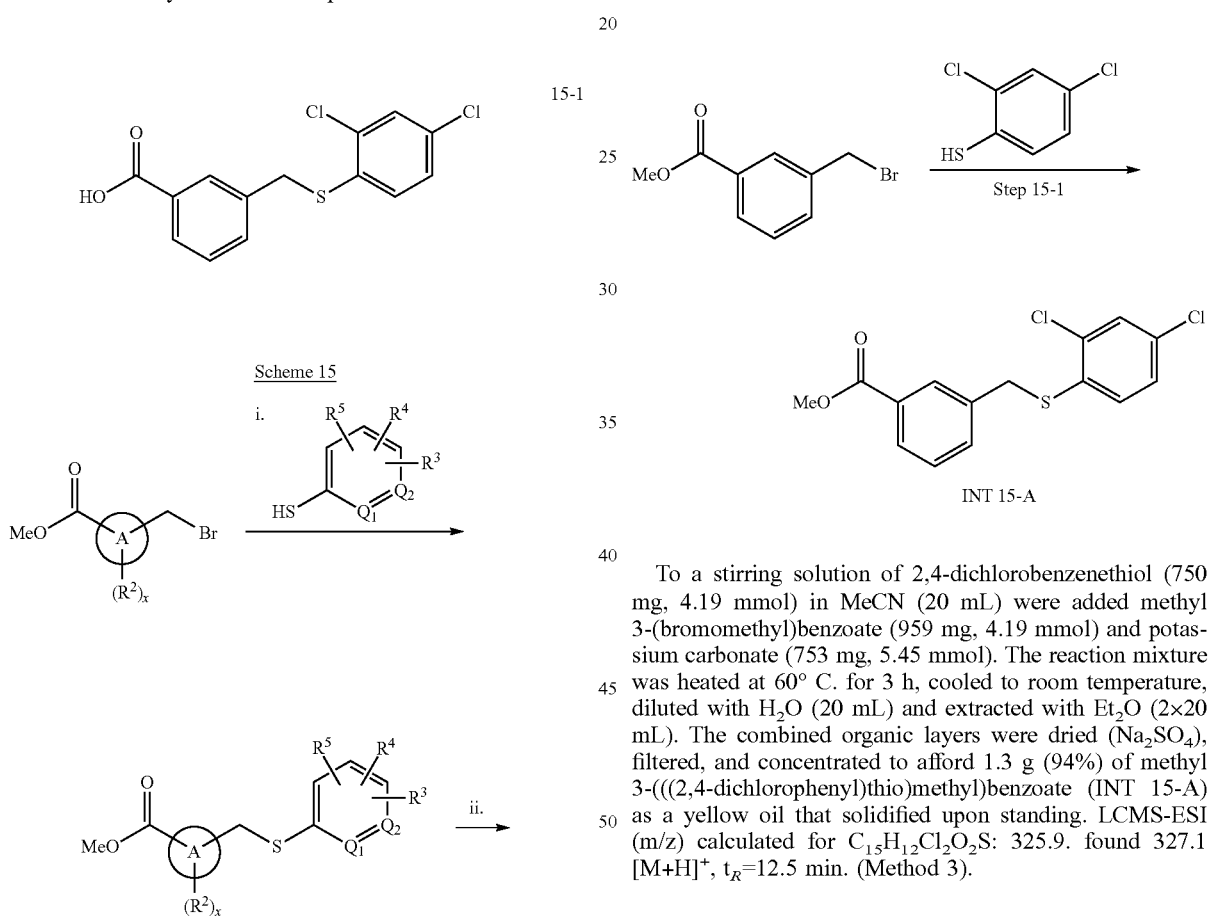 | 14-1 | 10.05 | 283.15 | 283.0 | [M − H]⁺ | 4 |

(Table 14 structure: 2,4-dichlorophenyl ether of (3-(hydroxymethyl)phenyl)methanol)

Example 15

Synthesis of Compound 15-1

Scheme 15

Reagents: (i) Base (Na₂CO₃, K₂CO₃, KO^tBu), solvent (THF or DMF); ii. NaOH, solvent (THF, MeOH or DMF).

Step 15-1. Synthesis of methyl 3-(((2,4-dichlorophenyl)thio)methyl)benzoate (INT 15-A)

To a stirring solution of 2,4-dichlorobenzenethiol (750 mg, 4.19 mmol) in MeCN (20 mL) were added methyl 3-(bromomethyl)benzoate (959 mg, 4.19 mmol) and potassium carbonate (753 mg, 5.45 mmol). The reaction mixture was heated at 60° C. for 3 h, cooled to room temperature, diluted with H₂O (20 mL) and extracted with Et₂O (2×20 mL). The combined organic layers were dried (Na₂SO₄), filtered, and concentrated to afford 1.3 g (94%) of methyl 3-(((2,4-dichlorophenyl)thio)methyl)benzoate (INT 15-A) as a yellow oil that solidified upon standing. LCMS-ESI (m/z) calculated for $C_{15}H_{12}Cl_2O_2S$: 325.9. found 327.1 [M+H]⁺, $t_R$=12.5 min. (Method 3).

Step 15-2. Synthesis of 3-(((2,4-dichlorophenyl)thio)methyl)benzoic acid (15-1)

-continued

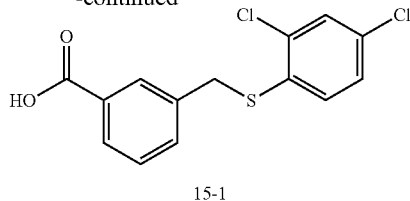

15-1

To a stirring solution of methyl 3-(((2,4-dichlorophenyl)thio)methyl)benzoate (INT 15-A) (250 mg, 0.764 mmol) in THF (3 mL) was added 1M NaOH (4 mL, 3.82 mmol). The reaction mixture was heated at 60° C. for 3 h, the aqueous layer extracted with EA (2×5 mL), dried (Na$_2$SO$_4$), filtered and concentrated to give a crude solid that was purified by reversed phase HPLC to afford 240.3 mg (99%) of 3-(((2,4-dichlorophenyl)thio)methyl)benzoic acid (Compound 15-1) as an off-white solid. LCMS-ESI (m/z) calculated for C$_{14}$H$_{10}$Cl$_2$O$_2$S: 311.97. found 313.1 [M+Na]$^+$, t$_R$=10.59 min. (Method 3).

The compound listed in Table 15 was made using the procedures of Scheme 15.

TABLE 15

| Structure | Cpd No. | Purity RT (min) | MW | Observed m/z | Ion | Purity Method |
|---|---|---|---|---|---|---|
| 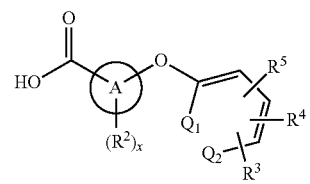 | 15-1 | 10.59 | 313.19 | 313.1 | [M − H]$^+$ | 4 |

-continued

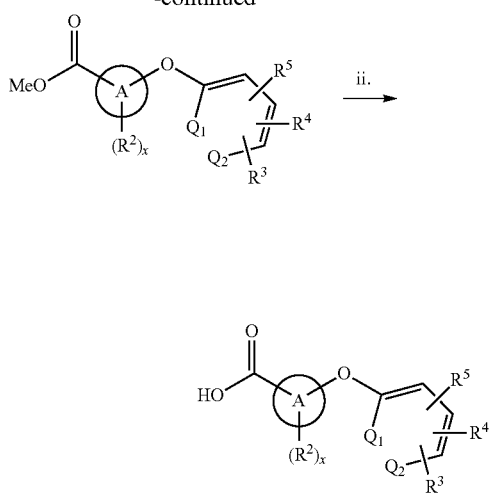

Reagents: (i) Base, Cu(OAc)$_2$, DCM; ii. NaOH, solvent (THF, MeOH or DMF).

Example 16

Synthesis of Compound 16-1 and Other Representative Compounds

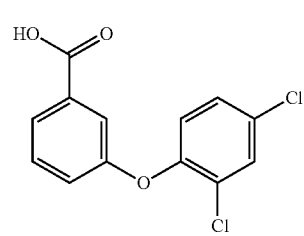 [SMILES: O=C(O)c1cccc(Oc2ccc(Cl)cc2Cl)c1]

16-1

Scheme 16

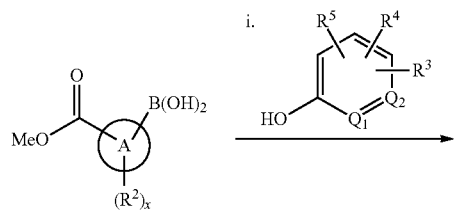

Step 16-1. Synthesis of methyl 3-(2,4-dichlorophenoxy)benzoate (INT 16-A)

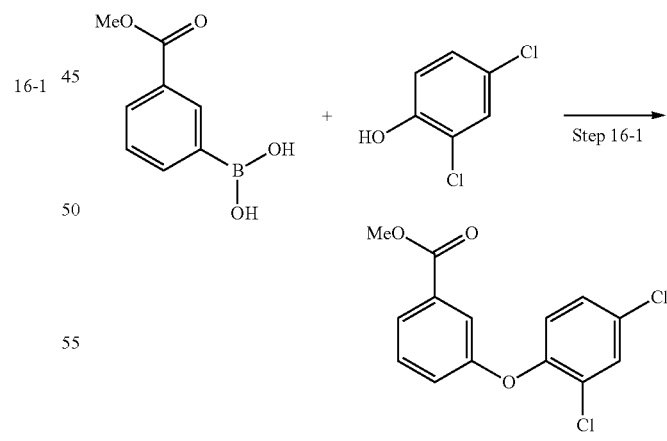

INT 16-A

To a stirring solution of (3-(methoxycarbonyl)phenyl)boronic acid (221 mg, 1.2 mmol) and 2,4-dichlorophenol (100 mg, 0.61 mmol) in anhydrous DCM (5 mL) were added Cu(OAc)$_2$ (111 mg, 0.61 mmol) and TEA (0.86 mL, 0.61 mmol). After stirring overnight, the reaction mixture was filtered, concentrated and purified by SiO$_2$ chromatography (EA/hexane) to afford 182 mg (27%) of methyl 3-(2,4-dichlorophenoxy) benzoate (INT 16-A). LCMS-ESI (m/z) calculated for $C_{14}H_{10}Cl_2O_3$: 296. found 297.5 $[M+H]^+$, $t_R$=5.96 min. (Method 11).

Step 16-2. Synthesis of 3-(2,4-dichlorophenoxy)benzoic acid (16-1)

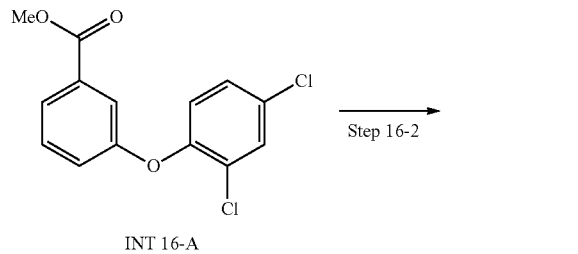

To a stirring solution of methyl 3-(2,4-dichlorophenoxy) benzoate (INT 16-A) (50 mg, 0.17 mmol) in MeOH (3 mL) was added 1M NaOH (67 mg, 1.68 mmol). The reaction mixture was heated at reflux for 2 h. The pH was adjusted to 2 by the addition of 4N HCl (aq) and was then extracted with EA. The organic layer was washed with brine, dried (MgSO$_4$), filtered and concentrated in vacuo to give a crude solid that was purified by SiO$_2$ chromatography (EA/hexanes) to afford 10 mg (21%) 3-(2,4-dichlorophenoxy) benzoic acid (Compound 16-1) as a white solid. LCMS-ESI (m/z) calculated for $C_{13}H_8Cl_2O_3$: 281.99. found 283.6 $[M+H]^+$, $t_R$=14.15 min. (Method 10).

The compounds listed in Table 16 were made using the procedures of Scheme 16.

Example 17

Synthesis of Compound 17-1, Compound I-31 and Other Representative Tetrazole Isostere Compounds

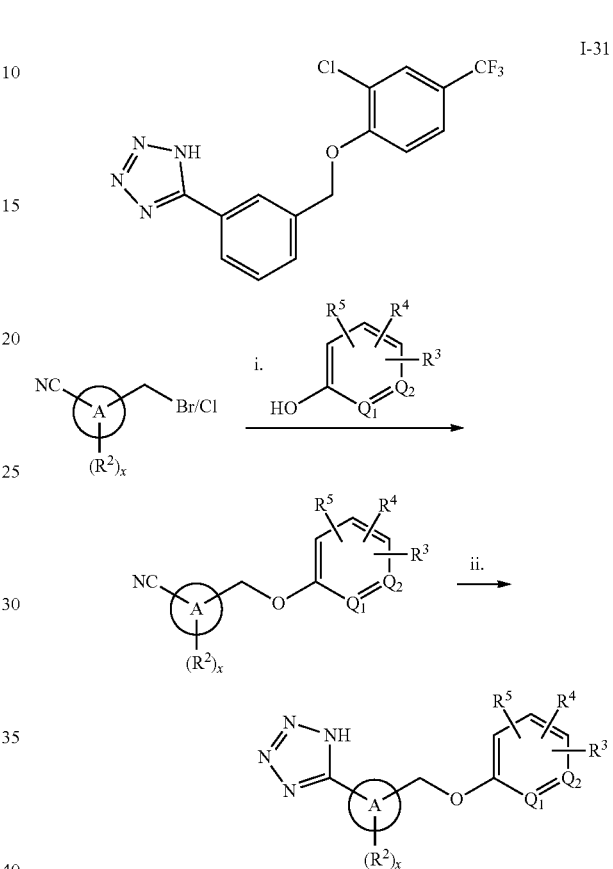

Reagents: (i) Base (Na$_2$CO$_3$, K$_2$CO$_3$, KO$^t$Bu), Solvent (Acetone, MeCN, DMF); (ii) NaN$_3$, NH$_4$Cl, DMF.

TABLE 16

| Structure | Cpd No. | Purity RT (min) | MW | observed m/z | Ion | Purity Method |
|---|---|---|---|---|---|---|
| HO-benzoic acid with 2,4-dichlorophenoxy | 16-1 | 14.15 | 283.10 | 283.6 | $[M-H]^+$ | 10 |
| Cl, O$_2$N-phenoxy benzoic acid | 16-2 | 13.46 | 293.66 | 294.4 | $[M-H]^+$ | 10 |

Step 17-1: 3-((2-chloro-4-(trifluoromethyl)phenoxy)methyl)benzonitrile (INT-17-1)

Step 17-2: 5-(3-((2-chloro-4-(trifluoromethyl)phenoxy)methyl)phenyl)-1H-1,2,3,4-tetrazole (INT-31)

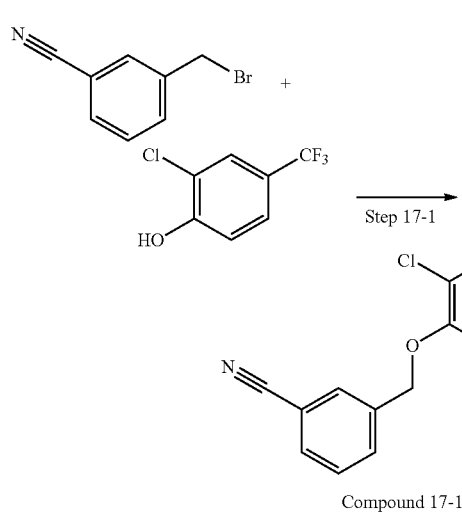

Compound 17-1

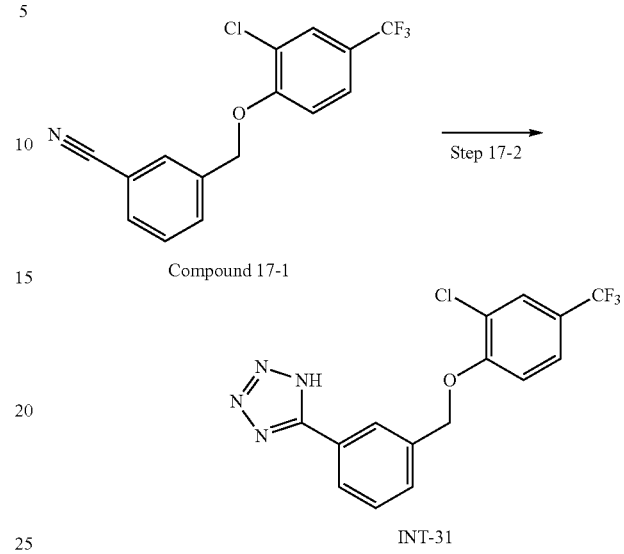

Compound 17-1

INT-31

A mixture of 3-(bromomethyl)benzonitrile (500 mg, 2.55 mmol), 2-chloro-4-(trifluoromethyl)phenol (0.551 g, 2.81 mmol), and $K_2CO_3$ (1.06 g, 7.65 mmol) in acetone (10.0 mL) was heated at 80° C. for 1 hour. The mixture was filtered, and the filtrate was concentrated under reduced pressure. The residue was purified by silica gel chromatography (40 g cartridge), eluting with a mixture of hexanes and EA to provide 750 mg (94%) of 3-((2-chloro-4-(trifluoromethyl)phenoxy)methyl)benzonitrile (Compound 17-1) as a solid. $^1$HNMR (400 MHz, DMSO) δ 7.96-7.92 (m, 1H), 7.90-7.87 (m, 1H), 7.87-7.80 (m, 2H), 7.72 (ddd, J=8.7, 2.3, 0.7 Hz, 1H), 7.66 (t, J=7.7 Hz, 1H), 7.43 (d, J=8.5 Hz, 1H), 5.38 (s, 2H); LCMS: m/z (ES−), [M−H]$^−$: 310.15; HPLC $t_R$=5.78 min. (Method 12).

A mixture of Compound 17-1 (100 mg, 0.321 mmol), $NaN_3$ (31.3 mg, 0.481 mmol), and $NH_4C_1$ (27.5 mg, 0.513 mmol) in DMF (1.00 mL) was heated at 130° C. for 12 hours. The mixture was cooled to room temperature and poured into 2M HCl at 0° C. The mixture was filtered, and the solid was dried to provide 5-(3-((2-chloro-4-(trifluoromethyl)-phenoxy)methyl)phenyl)-1H-1,2,3,4-tetrazole (INT-31) as a solid (102 mg, 90%). $^1$HNMR (400 MHz, CD$_3$OD) δ 8.17 (s, 1H$_1$), 8.00 (d, J=7.8 Hz, 1H$_1$), 7.72 (dd, J=8.1, 5.0 Hz, 2H), 7.67-7.53 (in, 2H), 7.33 (d, J=8.7 Hz, 1H), 5.37 (s, 2H); LCMS: calculated for $C_{15}H_{10}ClF_3N_4O$: 354. found 355.06, [M−H]$^+$, $t_R$=4.35 min. (Method 12).

The compounds listed in Table 17 were made using the procedures of Scheme 17.

TABLE 17

| Structure | Cpd No. | Purity RT (min) | MW | observed m/z | Ion | Purity Method |
|---|---|---|---|---|---|---|
| 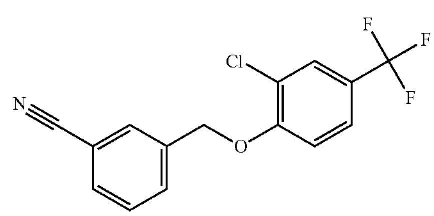 [SMILES: N#Cc1cccc(COc2ccc(C(F)(F)F)cc2Cl)c1] | 17-1 | 5.76 | 311.69 | 309.99 | [M − H]$^+$ | 12 |
| 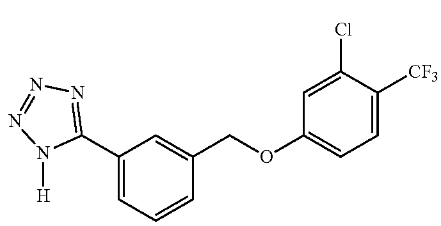 [SMILES: FC(F)(F)c1ccc(OCc2cccc(-c3nnn[nH]3)c2)cc1Cl] | 17-2 | 9.89 | 354.72 | 355.1 | [M + H]$^+$ | 3 |

TABLE 17-continued

| Structure | Cpd No. | Purity RT (min) | MW | observed m/z | Ion | Purity Method |
|---|---|---|---|---|---|---|
| 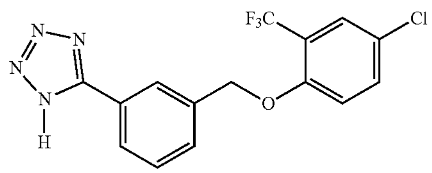 [SMILES: FC(F)(F)c1cc(Cl)ccc1OCc1cccc(-c2nnn[nH]2)c1] | 17-3 | 9.98 | 354.72 | 355 | [M + H]⁺ | 3 |
| 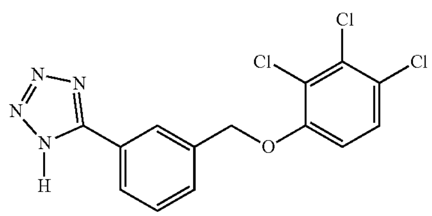 [SMILES: Clc1ccc(OCc2cccc(-c3nnn[nH]3)c2)c(Cl)c1Cl] | 17-4 | 10.34 | 355.60 | 355 | [M + H]⁺ | 3 |
| 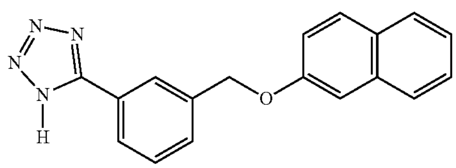 [SMILES: c1cc(COc2ccc3ccccc3c2)cc(-c2nnn[nH]2)c1] | 17-5 | 9.49 | 302.34 | 303.2 | [M + H]⁺ | 3 |
| 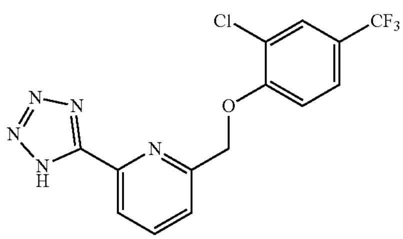 [SMILES: FC(F)(F)c1ccc(OCc2cccc(-c3nnn[nH]3)n2)c(Cl)c1] | 17-6 | 9.792 | 355.71 | 356.1 | [M + H]⁺ | 3 |
| 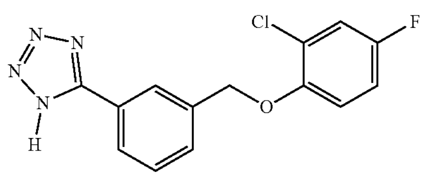 [SMILES: Fc1ccc(OCc2cccc(-c3nnn[nH]3)c2)c(Cl)c1] | 17-7 | 8.991 | 304.71 | 303 | [M + H]⁺ | 3 |
| 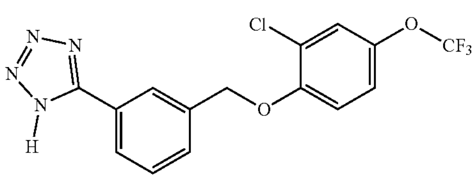 [SMILES: FC(F)(F)Oc1ccc(OCc2cccc(-c3nnn[nH]3)c2)c(Cl)c1] | 17-8 | 10.167 | 370.72 | 369 | [M − H]⁺ | 4 |
| 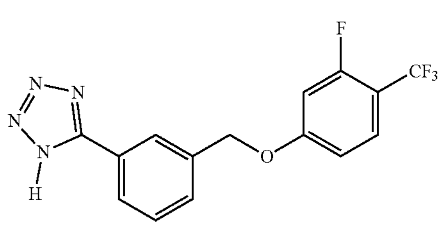 [SMILES: Fc1cc(OCc2cccc(-c3nnn[nH]3)c2)ccc1C(F)(F)F] | 17-9 | 9.557 | 338.27 | 337.2 | [M − H]⁺ | 4 |

TABLE 17-continued
| Structure | Cpd No. | Purity RT (min) | MW | observed m/z | Ion | Purity Method |
|---|---|---|---|---|---|---|
| 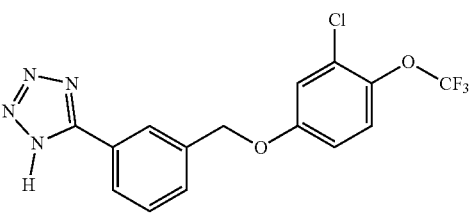 [SMILES: FC(F)(F)Oc1ccc(OCc2cccc(-c3nnn[nH]3)c2)cc1Cl] | 17-10 | 10.263 | 370.72 | 369 | [M − H]⁺ | 4 |
| 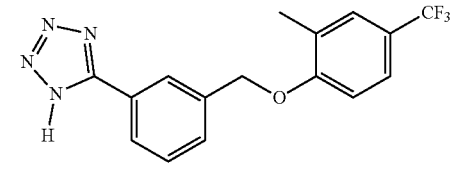 [SMILES: Cc1cc(C(F)(F)F)ccc1OCc1cccc(-c2nnn[nH]2)c1] | 17-11 | 10.06 | 334.30 | 333.2 | [M − H]⁺ | 4 |
| 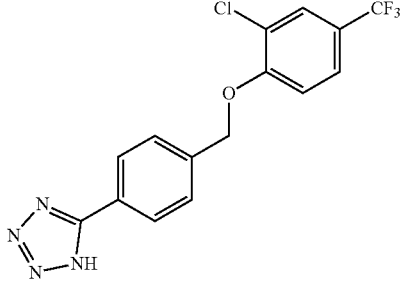 [SMILES: FC(F)(F)c1ccc(OCc2ccc(-c3nnn[nH]3)cc2)c(Cl)c1] | 17-12 | 9.905 | 354.72 | 355.1 | [M + H]⁺ | 3 |
| 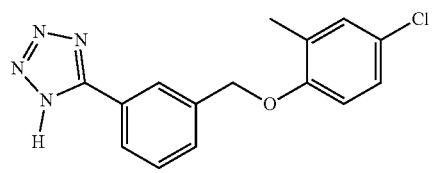 [SMILES: Cc1cc(Cl)ccc1OCc1cccc(-c2nnn[nH]2)c1] | 17-13 | 9.879 | 300.75 | 300.1 | [M + H]⁺ | 3 |
| 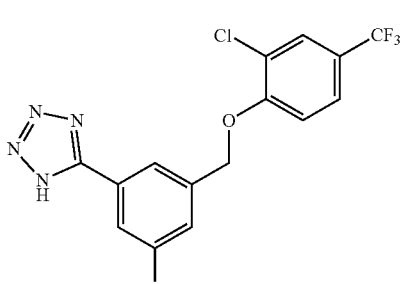 | 17-14 | 10.482 | 372.71 | 373.1 | [M + H]⁺ | 3 |
| 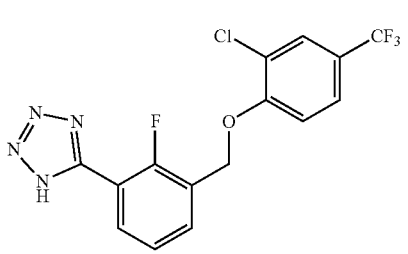 [SMILES: Fc1c(COc2ccc(C(F)(F)F)cc2Cl)cccc1-c1nnn[nH]1] | 17-15 | 10.09 | 372.71 | 373.1 | [M + H]⁺ | 3 |

TABLE 17-continued

| Structure | Cpd No. | Purity RT (min) | MW | observed m/z | Ion | Purity Method |
|---|---|---|---|---|---|---|
| 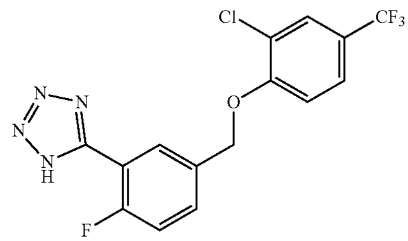 [SMILES: Fc1ccc(COc2ccc(C(F)(F)F)cc2Cl)cc1-c1nnn[nH]1] | 17-16 | 10.04 | 372.71 | 373.1 | [M + H]+ | 3 |

Example 18

General Synthesis of Representative Arylsulfonamide Isostere Compounds

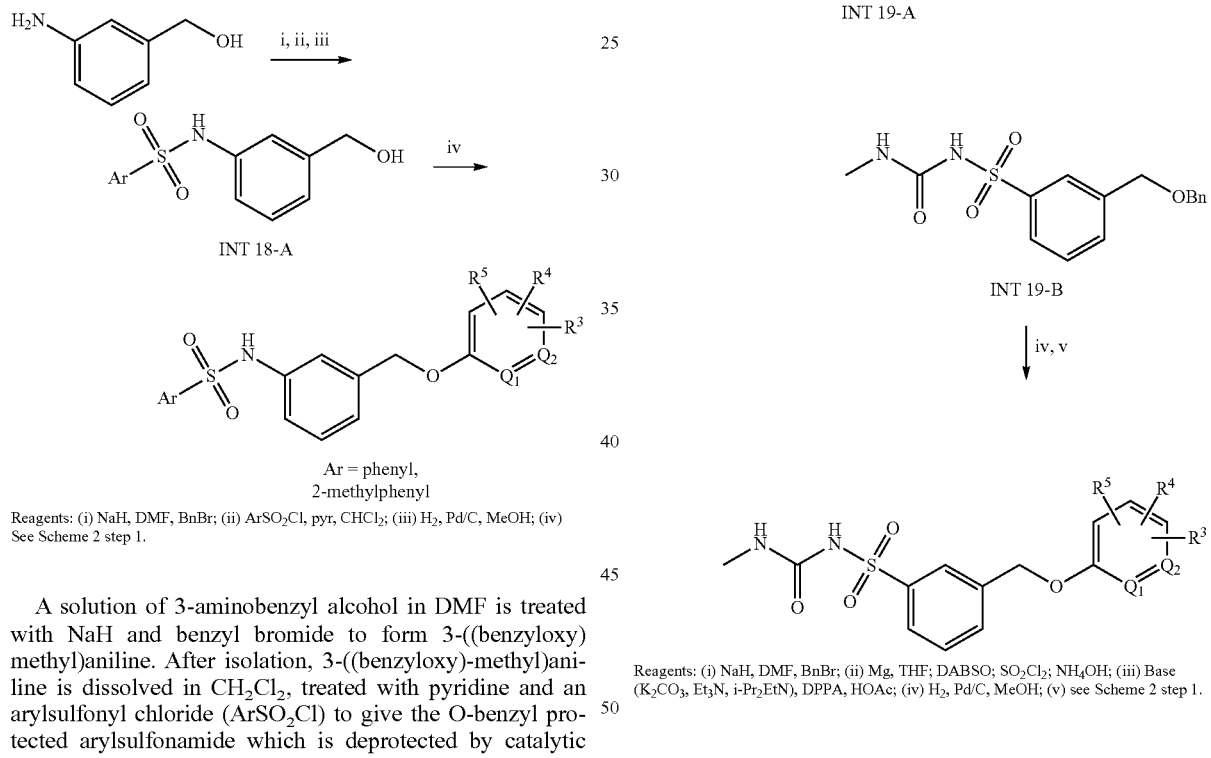

Ar = phenyl, 2-methylphenyl

Reagents: (i) NaH, DMF, BnBr; (ii) ArSO$_2$Cl, pyr, CHCl$_2$; (iii) H$_2$, Pd/C, MeOH; (iv) See Scheme 2 step 1.

A solution of 3-aminobenzyl alcohol in DMF is treated with NaH and benzyl bromide to form 3-((benzyloxy)methyl)aniline. After isolation, 3-((benzyloxy)-methyl)aniline is dissolved in CH$_2$Cl$_2$, treated with pyridine and an arylsulfonyl chloride (ArSO$_2$Cl) to give the O-benzyl protected arylsulfonamide which is deprotected by catalytic hydrogenation to give alcohol Intermediate 18-A. Preparation of the final compound is accomplished according to the Mitsunobu conditions described in Scheme 2, step 1.

Example 19

General Synthesis of Representative Sulfonylurea Isostere Compounds

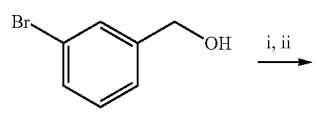

Reagents: (i) NaH, DMF, BnBr; (ii) Mg, THF; DABSO; SO$_2$Cl$_2$; NH$_4$OH; (iii) Base (K$_2$CO$_3$, Et$_3$N, i-Pr$_2$EtN), DPPA, HOAc; (iv) H$_2$, Pd/C, MeOH; (v) see Scheme 2 step 1.

A solution of 3-bromobenzyl alcohol in DMF is treated with NaH and benzylbromide to form 1-((benzyloxy)methyl)-3-bromobenzene that is converted to a Grignard reagent in a separate step by dissolving in dry THF and treating with Mg. The Grignard reagent is reacted with DABSO, sulfuryl chloride and ammonium hydroxide according to Woolven, H. et al. (*Org. Lett.* 13:4876, 2011) to provide the O-benzyl protected sulfonamide, Intermediate 19-A. INT 19-A is treated with base, DPPA and acetic acid according to the method of Lockhurst, C. A. et al. (*Tet. Lett.* 48:8878, 2007) to provide the O-benzyl protected sulfonylurea, Intermediate 19-B. INT 19-B is deprotected by catalytic hydrogenation to give the free alcohol intermediate that is converted to the final compound according to the Mitsunobu conditions described in Scheme 2, step 1.

Example 20

General Synthesis of Representative N-Acylsulfonamide Isostere Compounds

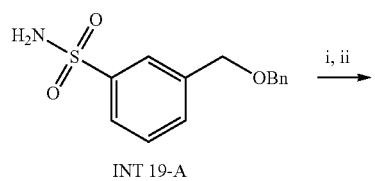

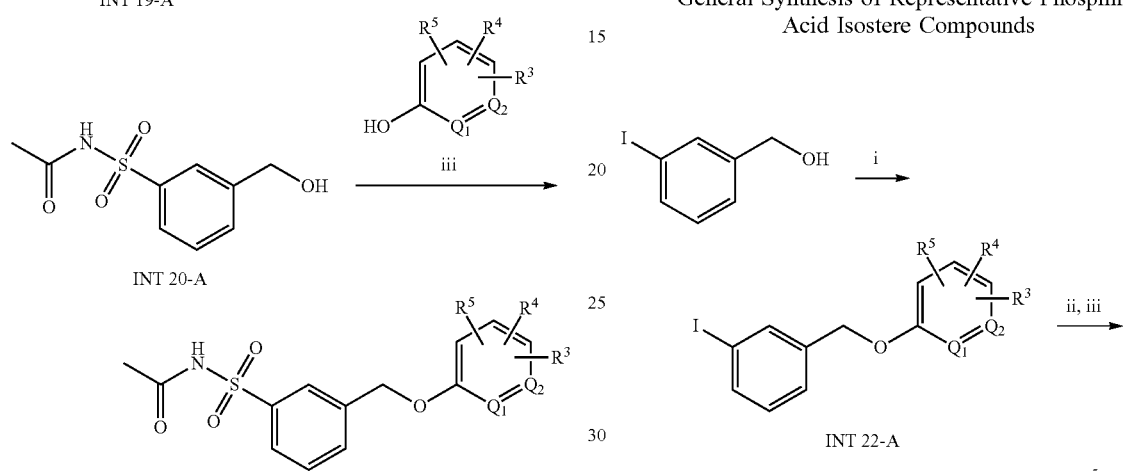

Reagents: (i) ZnCl$_2$, Ac$_2$O; (ii) H$_2$, Pd/C, MeOH; (iii) See Scheme 2 step 1.

Intermediate 19-A (see Example 19) is reacted with ZnCl$_2$ and acetic anhydride (Ac$_2$O) according to Pham, M. V. et al. (*Angew. Chem I. E.* 51:10610, 2012) to provide an O-benzyl protected N-acylsulfonamide intermediate that is deprotected by catalytic hydrogenation to give the free alcohol, Intermediate 20-A. The alcohol is converted to the final compound according to the Mitsunobu conditions described in Scheme 2, step 1.

Example 21

General Synthesis of Representative N-hydroxyamide Isostere Compounds

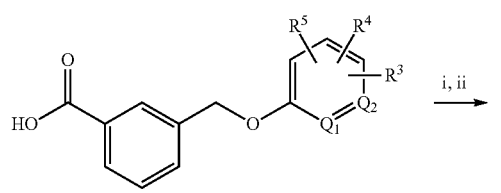

Reagents: (i) EtCO$_2$Cl, NMM, DMF; (ii) NH$_2$OH MeOH.

A compound of Formula (I) wherein A is phenyl and R is carboxylic acid is dissolved in DMF and cooled to 0° C. Ethyl chloroformate (1.2 eq.) and N-methyl morpholine (1.3 eq.) are added successively and mixture is stirred 10 minutes. Hydroxylamine (2 eq.) in methanol is added and the reaction is allowed to warm to room temperature and stir overnight. Routine workup and purification gives the desired N-hydroxyamide product.

Example 22

General Synthesis of Representative Phosphinc Acid Isostere Compounds

Reagents: (i) see Scheme 2 step 1; (ii) methyl phosphinate, Pd(OAc)$_2$, PPh$_3$, NMM, MeCN; (iii) HCl, H$_2$O.

3-Iodobenzyl alcohol is converted to Intermediate 22-A according to the Mitsunobu conditions described in Scheme 2, step 1. The aryl iodide is converted to an alkylphosphinate using a palladium catalyzed cross coupling reaction (Pd(OAc)$_2$ and PPh$_3$ as ligand) described by Grady, H. L. ("Preparation of arylphosphinic acid derivatives as building blocks for binding sites", Retrospective Theses and Dissertations, 10373, 1992) that uses methyl phosphinate in acetonitrile in the presence of NMM as a base. The aryl phosphinic acid product is obtained from hydrolysis of the alkylphosphinate in aqueous HCl.

Example 23

General Synthesis of Representative Phosphonic Acid Isostere Compounds

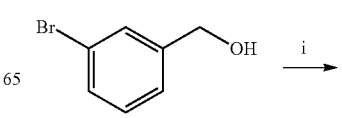

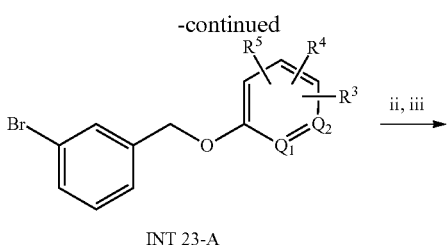

INT 23-A

Reagents: (i) see Scheme 2 step 1; (ii) HPO(Oi-Pr)₂, Pd(OAc)₂, CM-Phos, t-BuOH/iPrOH, DIPEA; (iii) HCl, H₂O.

3-Bromobenzyl alcohol is converted to Intermediate 23-A according to the Mitsunobu conditions described in Scheme 2, step 1. The aryl bromide is converted to a dialkylphosphonate using a palladium catalyzed cross coupling reaction (Pd(OAc)₂ and CM-Phos as ligand) described by Fu, C. W. et al. (*Org. Lett.* 17:5906, 2015) that uses diisopropylphosphite in alcohol solvent with DIPEA as a base. The aryl phosphonic acid product is achieved from hydrolysis of the dialkylphosphonate in aqueous HCl.

Example 24

General Synthesis of Representative Pyrrolidine-2,4-dione Isostere Compounds

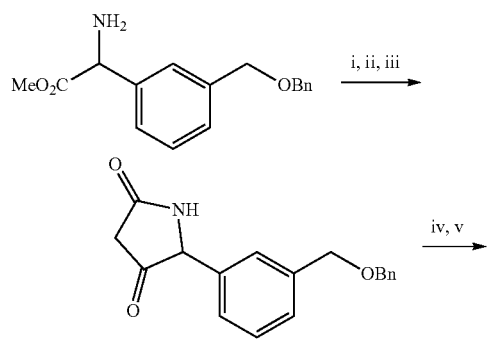

INT 24-A

Reagents: (i) Ethylmalonyl chloride, CH₂Cl₂ Et₃N; (ii) KHMDS, toluene; (iii) HBr, water; (iv) H₂, Pd/C, MeOH; (v) see Scheme 2 step 1.

Conversion of the starting phenyl glycine amino acid derivative to the Pyrrolidine-2,4-dione is accomplished by a three-step addition/cyclization/decarboxylation sequence described in WO2007/063010, to give Intermediate 24-A. This intermediate is deprotected by catalytic hydrogenation to give the free alcohol that is converted to the final compound according to the Mitsunobu conditions described in Scheme 2, step 1. The starting material, amino acid methyl ester can be prepared in various ways known to those skilled in the art; for example from 3-((benzyloxy)methyl)benzaldehyde (described below) by a Strecker amino acid synthesis and esterification.

Example 25

General Synthesis of Representative Furan-2,4-dione Isostere Compounds

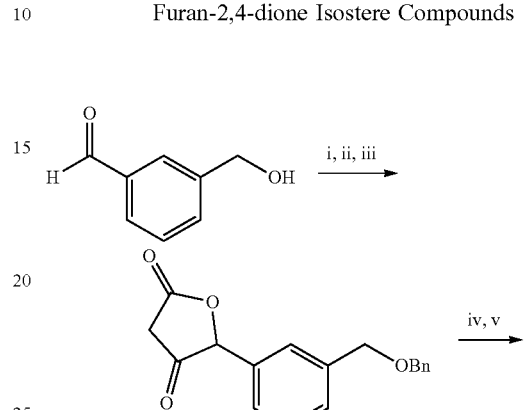

INT 25-A

Reagents: (i) NaH, DMF, BnBr; (ii) LDA, THF, MeO~~~~~CO₂Me; (iii) HBr, water; (iv) H₂, Pd/C, MeOH; (v) see Scheme 2 step 1.

Commercially available 3-hydroxymethyl benzaldehyde is reacted with NaH and benzylbromide to form 3-((benzyloxy)methyl)benzaldehyde. This intermediate is converted to the cyclopentane-1,3-dione in a two-step sequence described in WO2007/063010, to give Intermediate 25-A. This intermediate is deprotected by catalytic hydrogenation to give the free alcohol that is converted to the final compound according to the Mitsunobu conditions described in Scheme 2, step 1.

Example 26

General Synthesis of Representative Cyclopentane-1,3-dione Isostere Compounds

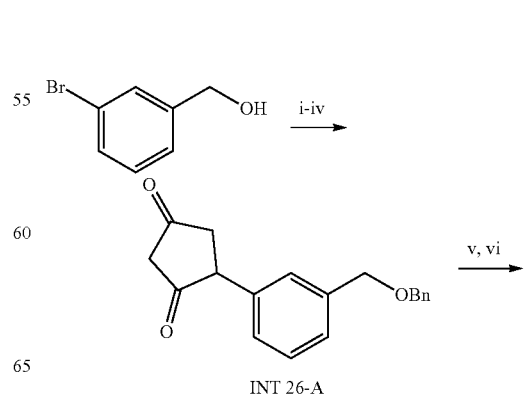

INT 26-A

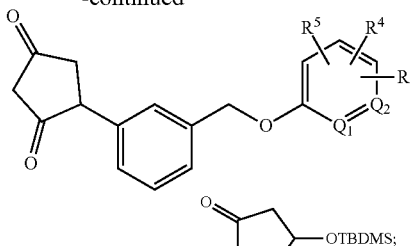

Reagents: (i) NaH, DMF, BnBr; (ii) *t*-BuLi, Et₂O; CuI;
(iii) HF/pyridine, CH₃CN; (iv) Jones reagent, acetone; (v) H₂, Pd/C, MeOH; (vi) see Scheme 2 step 1.

A solution of 3-bromobenzyl alcohol in DMF is treated with NaH and benzylbromide to form 1-((benzyloxy)methyl)-3-bromobenzene. This intermediate is converted to the cyclopentane-1,3-dione in a three-step, conjugate addition/deprotection/oxidation sequence described by Lassalas, P. et al. (*ACS Med. Chem. Lett.* 8:864, 2017) to give Intermediate 26-A. This intermediate is deprotected by catalytic hydrogenation to give the free alcohol that is converted to the final compound according to the Mitsunobu conditions described in Scheme 2, step 1.

Example 27

General Synthesis of Representative Difluorophenol Isostere Compounds

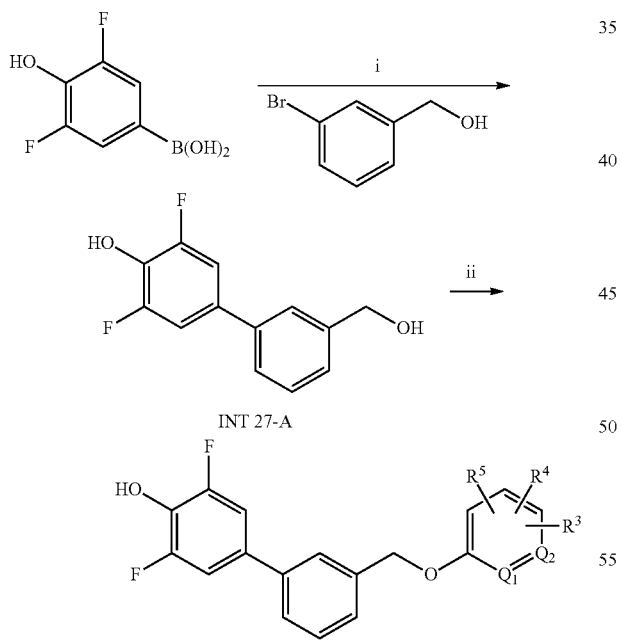

Reagents: (i) see Scheme 11 step 1; (ii) see Scheme 2 step 1.

3-Bromobenzyl alcohol and commercially available 4-hydroxy-3,5-difluorophenylboroic acid are coupled according to the Suzuki coupling method described in Example 11 to give Intermediate 27-A that is converted to the final compound according to the Mitsunobu conditions described in Scheme 2, step 1.

Example 28

General Synthesis of Representative 3-Substituted 5-Oxo-Thiadiazole Isostere Compounds

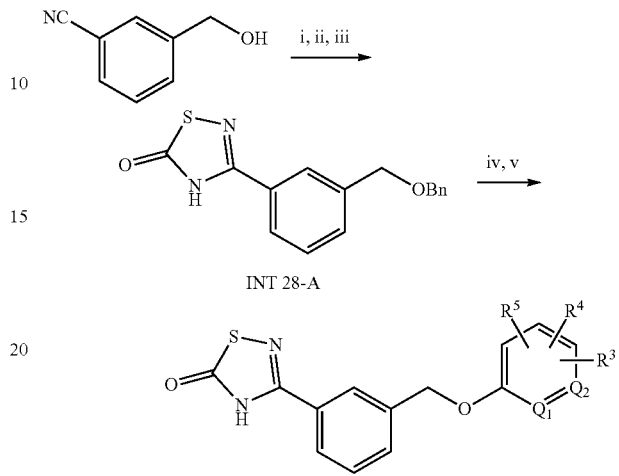

Reagents: (i) NaH, DMF, BnBr; (ii) NH₂OH·HCl, Et₃N, EtOH; (iii) TCDI, THF; BF₃—OEt₂/THF; (iv) H₂, Pd/C, MeOH; (v) see Scheme 2 step 1.

A solution of 3-cyanobenzyl alcohol in DMF is treated with NaH and benzylbromide to form 3-((benzyloxy)methyl)benzonitrile. The aryl cyanide is then converted to the 3-Substituted 5-Oxo-Thiadiazole in two steps according to Kohara, Y. et al. (*J. Hetercyclic Chem.* 37:1419, 2000) to give Intermediate 28-A. This intermediate is deprotected by catalytic hydrogenation to give the free alcohol that is converted to the final compound according to the Mitsunobu conditions described in Scheme 2, step 1.

Example 29

General Synthesis of Representative 3-Substituted Oxadiazolone Isostere Compounds

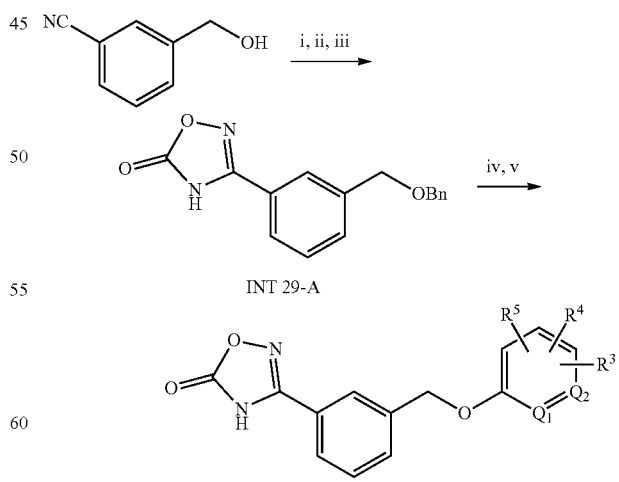

Reagents: (i) NaH, DMF, BnBr; (ii) NH₂OH·HCl, Et₃N, EtOH; (iii) CDI, DBU, 1,4-dioxane; (iv) H₂, Pd/C, MeOH; (v) see Scheme 2 step 1.

A solution of 3-cyanobenzyl alcohol in DMF is treated with NaH and benzylbromide to form 3-((benzyloxy)

methyl)benzonitrile. The aryl cyanide is then converted to the 3-substituted oxadiazolone in two steps according to Yu, X. et al. (*Org. Lett.* 18:5412, 2-016) to give Intermediate 29-A. This intermediate is deprotected by catalytic hydrogenation to give the free alcohol that is converted to the final compound according to the Mitsunobu conditions described in Scheme 2, step 1.

Commercially available 3-hydroxymethyl benzaldehyde is reacted with NaH and benzylbromide to form 3-((benzyloxy)methyl)benzaldehyde. The resulting ether aldehyde is converted to the mandelate according to Sirimanne and Patterson (*J. Label. Cmpd. Radiopharm.* 33:725, 1993) to first give a mandelic acid derivative that is esterified giving Intermediate 30-A. Intermediate 30-A is converted to the thiazolidine-2,4-dione according to Koyama et al. (*Biorg. Med. Chem. Lett.* 13:1801, 2003) and catalytic hydrogenation allows deprotection of the alcohol to give Intermediate 30-B. Alcohol 30-B is converted to the final compound according to the Mitsunobu conditions described in Scheme 2, step 1.

Example 30

General Synthesis of Representative Thiazolidine 2,4-dione Isostere Compounds

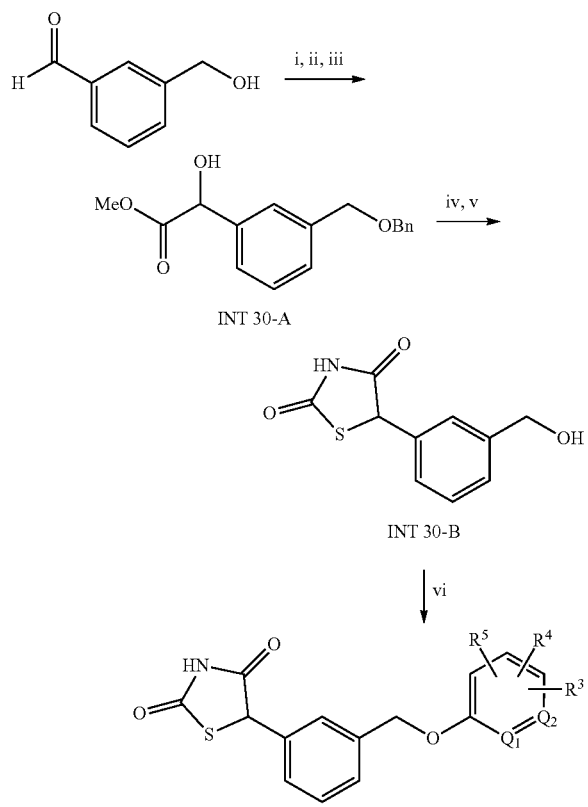

Reagents: (i) NaH, DMF, BnBr; (ii) ZnI₂, TMSCN; HCl (conc); (iii) MeOH, cat. Salicylaldehyde; (iv) SOCl₂, pyridine; thiourea, NaOAc, EtOH; HCl(aq), EtOH; (v) H₂, Pd/C, MeOH; (vi) see Scheme 2 step 1.

Example 31

Alternative Synthesis of Compound 1-56 and Synthesis of 31-2

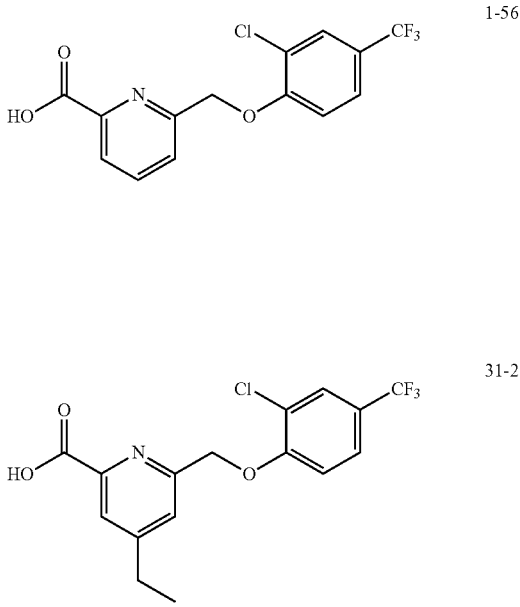

Scheme 31

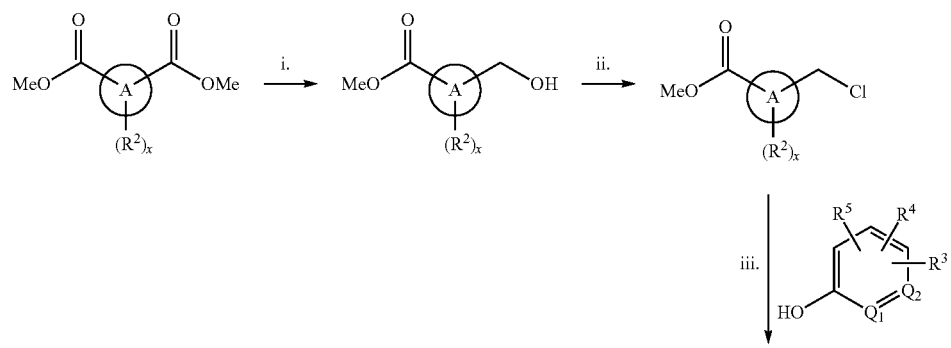

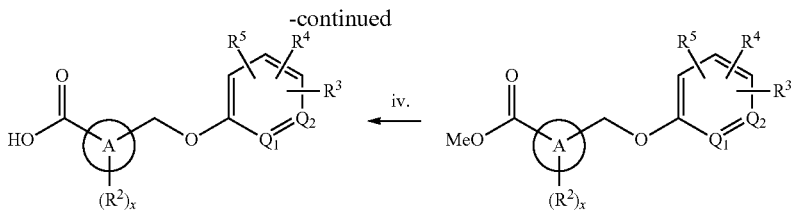

Reagents: (i) NaBH₄, DCM, MeOH; (ii) SOCl₂, DCM; (iii) K₂CO₃, CH₃CN (iv) NaOH, solvent (THF, MeOH, or DMF).

Step 31-1. Synthesis of methyl 6-(hydroxymethyl)picolinate (INT 31-A)

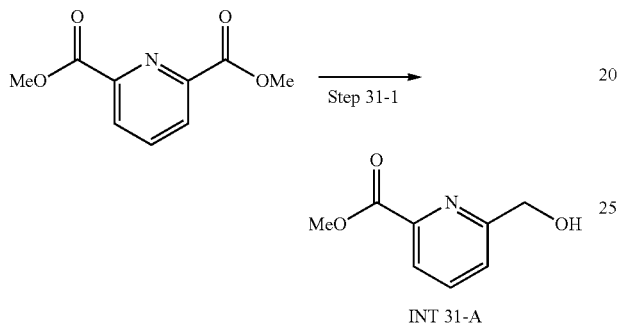

To a stirring solution of dimethyl pyridine-2,6-dicarboxylate (20 g, 102.5 mmol) in MeOH (20 mL) at 0° C. was added sodium borohydride (5.81 g, 153.7 mmol) in 3 portions. The reaction mixture was warmed to room temperature and stirred for 1 h. The reaction mixture was diluted with NH₄Cl (aq) (10 mL) and extracted with EA (3×500 mL) and EA (10 mL). The combined organic layers were dried (Na₂SO₄), concentrated in vacuo and purified by SiO₂ chromatography (10% MeOH in EA/hexanes) to afford 12 g, (70%) of methyl 6-(hydroxymethyl)pyridine-2-carboxylate (INT 31-A) as a white solid. TLC (EA): $R_f$=0.60.

Step 31-2. Synthesis of methyl 6-(chloromethyl)picolinate (INT 31-B)

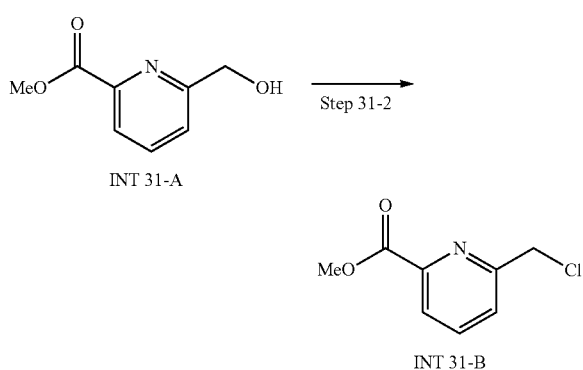

A flask containing a stirring solution of INT 31-A (5.00 g, 29.9 mmol) in DCM (62.5 mL) was charged with thionyl chloride (4.36 mL, 59.8 mmol) at room temperature. After stirring for 14 h, the reaction mixture was charged dropwise with saturated aqueous K₂CO₃ to adjust the pH to 10-11. The organic layer was collected, and the aqueous layer was back-extracted 2× with DCM. The organic layers were combined, washed with brine, dried (Na₂SO₄) and purified by SiO₂ chromatography (EA/hexanes) to provide 3.9 g (69.7%) of methyl 6-(chloromethyl)picolinate (INT 31-B) as a colorless oil that solidified upon standing to yield a white crystalline powder. LCMS-ESI (m/z) calculated for C₈H₈ClNO₂: 185.61; m/z 186.1 (M+H)⁺, $t_R$=3.64 min. (Method 1). ¹H NMR (500 MHz, DMSO-d6) δ 8.09-7.99 (m, 2H), 7.81 (dd, J=7.5, 1.3 Hz, 1H), 4.86 (s, 2H), 3.89 (s, 3H).

Step 31-3. Synthesis of methyl 6-((2-chloro-4-(trifluoromethyl)phenoxy)methyl)picolinate (Compound 31-C)

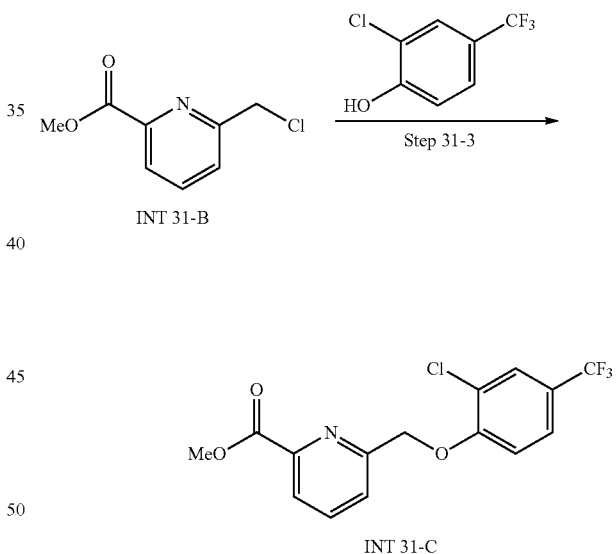

A flask containing INT 31-C (3.861 g, 20.8 mmol) was charged with a solution of 2-chloro-4-(trifluoromethyl)phenol (4.497 g, 22.9 mmol) in MeCN (70 mL), followed by K₂CO₃ (4.312 g, 31.2 mmol) and potassium iodide (345.3 mg, 2.08 mmol). The resulting suspension was heated to 60° C. After stirring for 16 hours, the reaction mixture was cooled to room temperature, diluted with H₂O and extracted 3× with Et₂O. The organic layers were combined, washed with brine, dried (Na₂SO₄) and purified by SiO₂ chromatography (EA/hexanes) to yield 6.64 g, (92.4%) of methyl 6-((2-chloro-4-(trifluoromethyl)phenoxy)methyl)picolinate (INT 31-C) as a white solid. LCMS-ESI (m/z) calculated for C₁₅H₁₁ClF₃NO₃: 345.70. found 346.1 [M+H]⁺, $t_R$=5.99 min. (Method 1).

Step 31-4. Synthesis of 6-((2-chloro-4-(trifluoromethyl)phenoxy)methyl)picolinic acid (Compound 1-56)

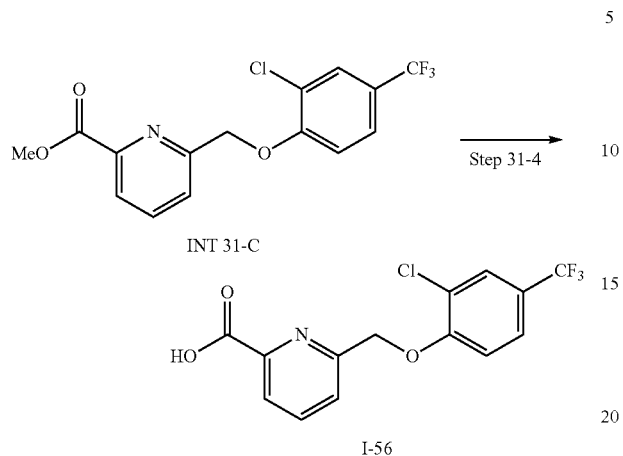

A flask containing a stirred solution of INT 31-C (500 mg, 1.45 mmol) in THF (7.23 mL) was charged with 1M NaOH (7.23 mL, 7.23 mmol). After stirring for 17 h at 50° C., the mixture was diluted with THF and H$_2$O, however no distinct layers were observed. Et$_2$O was added to effect separation of the organic and aqueous layers. The aqueous layer was collected and acidified to pH 3-4 using 3M HCl. The resulting white precipitate was extracted 3× with Et$_2$O, and the combined organic extracts were washed with brine, dried (Na$_2$SO$_4$) and concentrated under reduced pressure to yield 310 mg (64.6%) of 6-((2-chloro-4-(trifluoromethyl)phenoxy)methyl)picolinic acid (Compound 1-56) as a white solid. LCMS-ESI (m/z) calculated for C$_{14}$H$_9$ClF$_3$NO$_3$: 331.68. found 332.1 [M+H]$^+$, t$_R$=5.34 min. (Method 1).

Synthesis of Compound 31-2

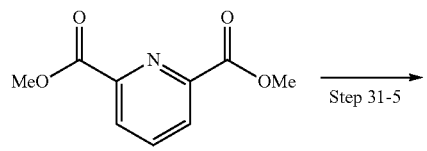

Step 31-5. Synthesis of dimethyl 4-ethylpyridine-2,6-dicarboxylate (INT 31-D)

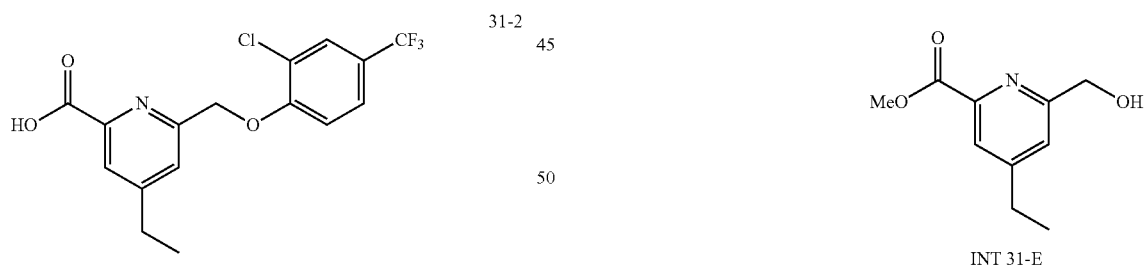

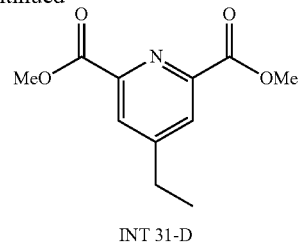

To a solution of dimethyl pyridine-2,6-dicarboxylate (10 g, 51.2 mmol) and propanal (18.7 mL, 256.2 mmol) in H$_2$SO$_4$ (100 mL) were added FeSO$_4$ (5.70 g, 20.49 mmol) and 30% H$_2$O$_2$ (9.9 mL, 102.5 mmol) dropwise 15 min. After stirring at 0° C. for 15 min, the mixture was diluted with saturated K$_2$CO$_3$(aq) and extracted with EA. The organic layer was dried (Na$_2$SO$_4$), concentrated in vacuo and purified by SiO$_2$ chromatography (petroleum ether/EA) to afford 4.5 g (39%) of dimethyl 4-ethylpyridine-2,6-dicarboxylate (INT 31-D) as a yellow solid. TLC (3:1 petroleum ether: EA): R$_f$-0.6. $^1$H NMR (400 MHz, CDCl$_3$) δ 8.13-8.20 (m, 2H) 4.00-4.03 (m, 6H) 2.78-2.87 (m, 2H) 1.29-1.37 (m, 3H).

Step 31-6. Synthesis of methyl 4-ethyl-6-(hydroxymethyl)picolinate (INT 31-E)

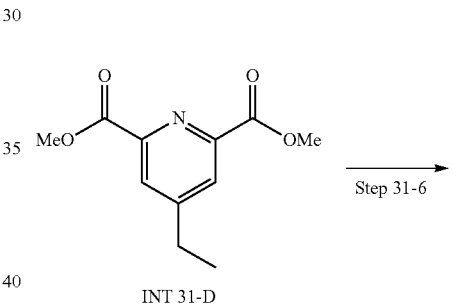

To a solution of INT-31-D (4.5 g, 20.2 mmol) in MeOH (80 mL) and DCM (20 mL) was added NaBH$_4$ (1.14 g, 30.24 mmol) at 0° C. After stirring for 12 h at 20° C., the mixture was diluted with saturated aq. NH$_4$Cl and extracted with EA. The organic layer was dried (Na$_2$SO$_4$), concentrated in vacuo and purified by SiO$_2$ chromatography (petroleum ether/EA) to afford 2.8 g (71%) of methyl 4-ethyl-6-(hydroxymethyl) picolinate (INT 31-E) as a yellow solid. TLC (1:1 petroleum ether: EA): R$_f$=0.4. $^1$H NMR (400 MHz, CDCl$_3$) δ 7.84-7.93 (m, 1H) 7.34-7.43 (m, 1H) 4.79-4.86 (m, 2H) 3.93-4.00 (m, 3H) 2.68-2.77 (m, 2H) 1.27 (t, J=7.64 Hz, 3H).

Step 31-7. Synthesis of methyl 6-(chloromethyl)-4-ethylpicolinate (INT 31-F)

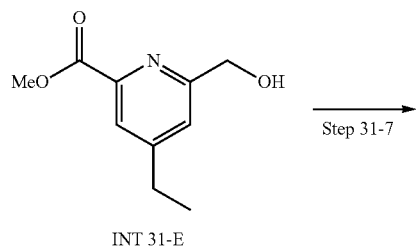

INT 31-E

↓ Step 31-7

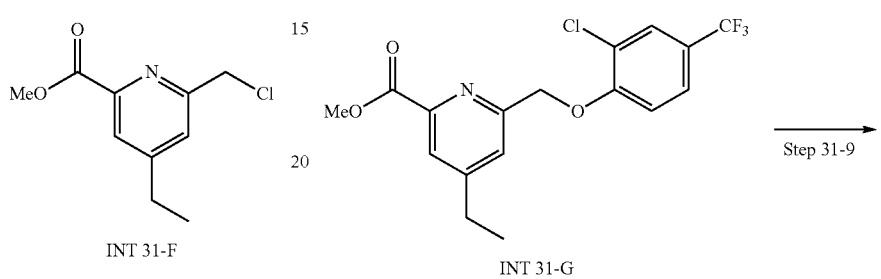

INT 31-F

To a solution of INT-31-E (2.8 g, 14.34 mmol) in DCM (100 mL) at 0° C. was added SOCl$_2$ (14.01 mL, 193 mmol). After 1.5 h the reaction mixture was concentrated to provide 2.5 g (82%) of methyl 6-(chloromethyl)-4-ethylpicolinate (INT-31F) as a yellow oil that was used in the next step without any further purification. LCMS-ESI (m/z) calculated for $C_{10}H_{12}ClNO_2$: 213.66. found 214.0 [M+H]$^+$, $t_R$=0.842 min. (Method 6).

Step 31-8. Synthesis of methyl 6-((2-chloro-4-(trifluoromethyl)phenoxy)methyl)-4-ethylpicolinate (INT 31-G)

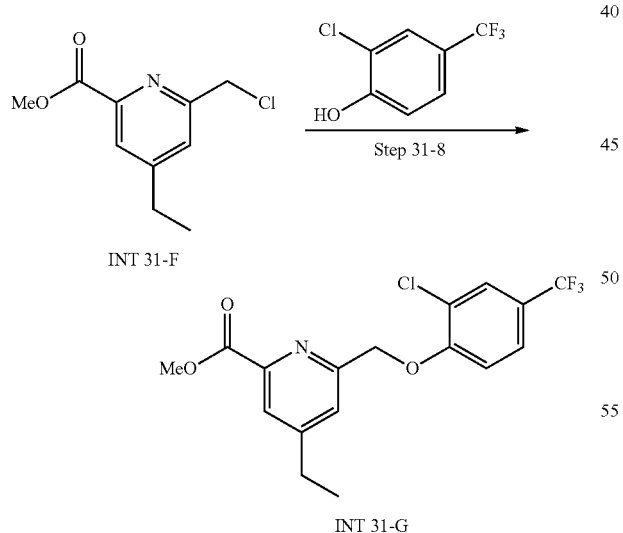

INT 31-F

INT 31-G

To a solution of INT-31-F (2.5 g, 11.70 mmol) and 2-chloro-4-(trifluoromethyl)phenol (2.0 g, 10.18 mmol) in MeCN (160 mL) was added K$_2$CO$_3$ (4.85 g, 35.10 mmol). The suspension was stirred at 80° C. for 12 h, cooled and filtered to collect a residue that was purified by SiO$_2$ chromatography (PE:EA) to provide 4 g (82%) of methyl 6-((2-chloro-4-(trifluoromethyl)phenoxy)methyl)-4-ethylpicolinate (INT-31-G) as a light yellow solid. TLC (3:1 petroleum ether: EA): R$_f$=0.55. $^1$H NMR (400 MHz, CDCl$_3$) δ ppm 1.32 (t, J=7.58 Hz, 3H) 2.79 (q, J=7.62 Hz, 2H) 4.03-4.05 (m, 3H) 5.40 (s, 2H) 7.06 (d, J=8.56 Hz, 1H) 7.50 (dd, J=8.68, 1.59 Hz, 1H) 7.67-7.74 (m, 2H) 7.97 (s, 1H).

Step 31-9. Synthesis of 6-((2-chloro-4-(trifluoromethyl)phenoxy)methyl)-4-ethylpicolinic acid (Compound 31-2)

31-2

A solution of INT-31-G (3.4 g, 9.1 mmol) and LiOH—H$_2$O (1.15 g, 27.3 mmol) in THF (5 mL) and H$_2$O (1 mL) was stirred at 30° C. for 12 hr. The reaction mixture was acidified with 1N HCl to pH 6, then extracted into EA. The combined organic extracts were dried (Na$_2$SO$_4$), concentrated and dissolved into MeCN. H$_2$O was added to create a white precipitate that was collected by filtration and washed with H$_2$O. The resulting filter cake was lyophilized to provide 1.93 g (58%) of 6-((2-chloro-4-(trifluoromethyl)phenoxy)methyl)-4-ethylpicolinic acid (Compound 31-2) as a white solid. LCMS-ESI (m/z) calculated for $C_{16}H_{13}ClF_3NO_3$: 359.7. found 360.0 [M+H]$^+$, $t_R$=0.95 min. (Method 5-95AB_R_220&254.1 cm). $^1$H NMR (400 MHz, CDCl$_3$) δ ppm 8.07 (s, 1H) 7.76 (s, 1H) 7.72 (d, J=1.88 Hz, 1H) 7.53 (dd, J=8.63, 1.63 Hz, 1H) 7.06 (d, J=8.63 Hz, 1H) 5.34 (s, 2H) 2.84 (q, J=7.63 Hz, 2H) 1.33 (t, J=7.57 Hz, 3H).

Example 32

Synthesis of Compound 32-1

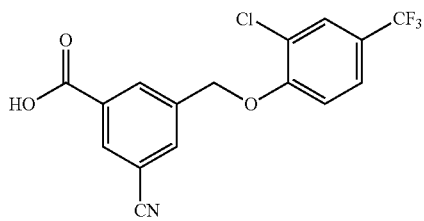

Thionyl chloride (7 mL) was added to 3-(methoxycarbonyl)-5-methylbenzoic acid (1.5 g, 7.7 mmol). After stirring at reflux for 1 h, the reaction mixture was dissolved and concentrated 3 times with toluene. The residue was dissolved in DCM (5 mL) and added to $NH_4OH$ (5 mL) at 0° C., giving a white precipitate. The reaction mixture was stirred for 5 min at 0° C. $H_2O$ and EA were added, and the mixture was filtered to give 1.40 g of a white solid. To the filtered solid was added $POCl_3$ (4.7 mL) and the reaction mixture was heated at 100° C. for 1 h. The reaction mixture was cooled, concentrated in vacuo dissolved in DCM, and treated with sat. $NaHCO_3$. The mixture was extracted with EA (2×20 mL), dried ($Na_2SO_4$), filtered and concentrated in vacuo to afford 1.15 g of crude material. The crude material was purified by $SiO_2$ chromatography (EA/hexanes) to afford 952 mg (70%) of methyl 3-cyano-5-methylbenzoate Scheme 32

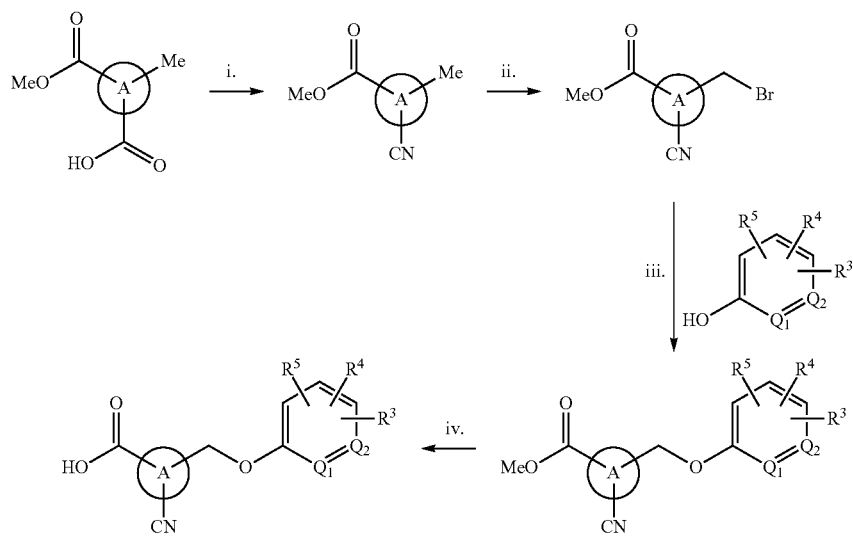

Reagents: (i) Thionyl-Cl, POCl₃, MeOH; (ii) SOCl₂, DCM; (iii) K₂CO₃, CH₃CN (iv) NaOH, solvent (THF, MeOH, or DMF).

Step 32-1. Synthesis of methyl 3-cyano-5-methylbenzoate (INT 32-A)

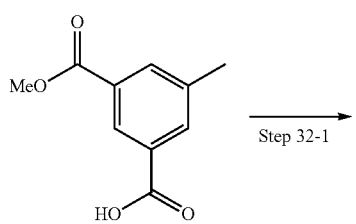

(INT 32-A) as a white solid. LCMS-ESI (m/z) calculated for $C_{10}H_9NO_2$: 175.19. found 176.2 $[M+H]^+$, $t_R$=4.87 min. (Method 1). $^1H$ NMR (500 MHz, $CDCl_3$) δ 8.12 (br s, 1H), 8.07 (br s, 1H), 7.63 (br s, 1H), 3.94 (s, 3H), 2.45 (s, 3H).

Step 32-2. Synthesis of methyl 3-(bromomethyl)-5-cyanobenzoate (INT 32-B)

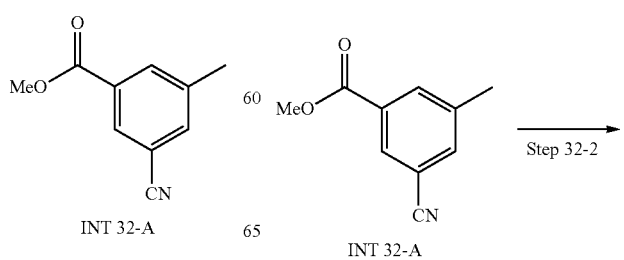

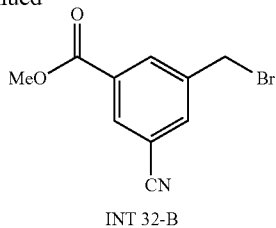

INT 32-B

To a stirring solution of INT 32-A (0.50 g, 2.9 mmol) in CCl$_4$ (10 mL) were added NBS (0.56 g, 3.1 mmol) and AIBN (94 mg, 0.57 mmol). The reaction mixture was heated to 77° C. (reflux) for 4 h then concentrated in vacuo and purified by SiO$_2$ chromatography (EA/hexanes) to afford 247 mg (34%) of methyl 3-(bromomethyl)-5-cyanobenzoate (INT 32-B) as a white solid. LCMS-ESI (m/z) calculated for C$_{10}$H$_8$BrNO$_2$: 254.08; m/z 255.2 (M+H)$^+$, t$_R$=5.05 min. (Method 1).

Step 32-3. Synthesis of methyl 3-((2-chloro-4-(trifluoromethyl)phenoxy)methyl)-5-cyanobenzoate (INT 32-C)

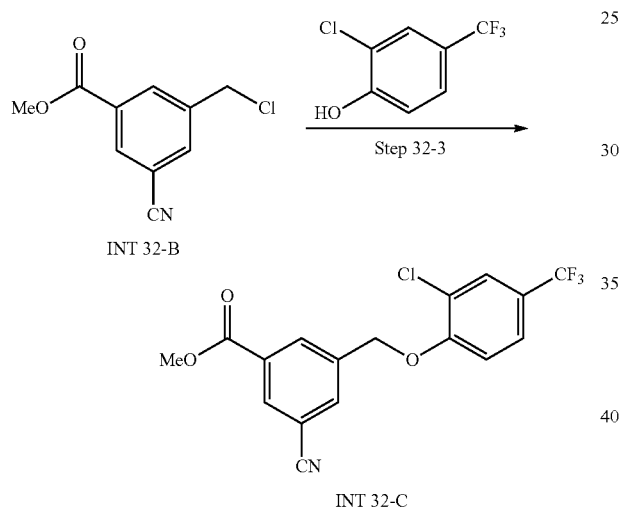

INT 32-C

To a stirred solution of INT 32-B (124 mg, 488 µmol) in MeCN (3 mL) were added 2-chloro-4-(trifluoromethyl)phenol (95.9 mg, 488 µmol) and K$_2$CO$_3$ (87.7 mg, 634 µmol). After heating at 60° C. for 12 h, the reaction mixture was cooled to RT and diluted with H$_2$O (6 mL). The aqueous layer was extracted with Et$_2$O (2×6 mL) and EA (6 mL), dried (Na$_2$SO$_4$), filtered through Celite, and concentrated in vacuo to afford 146.1 mg (81%) of methyl 3-((2-chloro-4-(trifluoromethyl)phenoxy)methyl)-5-cyanobenzoate (INT 32-C) as a beige solid. LCMS-ESI (m/z) calculated for C$_{17}$H$_{11}$ClF$_3$NO$_3$: 369.72. found 370.0 [M+H]$^+$, t$_R$=6.39 min. (Method 1).

Step 32-3. Synthesis of 3-((2-chloro-4-(trifluoromethyl)phenoxy)methyl)-5-cyanobenzoic acid (Compound 32-1)

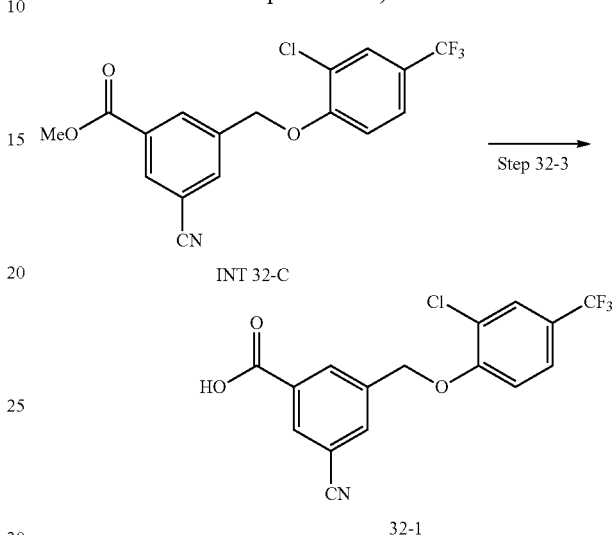

32-1

A vial containing a stirring solution of INT 32-C (146.1 mg, 395.2 µmol) in MeOH (2 mL) and THF (2 mL) was charged with solid NaOH (79 mg, 1.98 mmol). After stirring at 50° C. for 12 h, the reaction mixture was diluted with H$_2$O and acidified to pH 4-5 using 3M HCl. The resulting white precipitate was extracted with Et$_2$O (3×10 mL) and EA (2×10 mL). The organic layers were combined, washed with brine, dried (Na$_2$SO$_4$) and concentrated under reduced pressure to give a crude solid that was purified by reversed phase HPLC (H$_2$O/CH$_3$CN). Lyophilization of the combined pure fractions provided 82.6 mg (590%) of 3-((2-chloro-4-(trifluoromethyl)phenoxy)methyl)-5-cyanobenzoic acid (Compound 32-1) as a white solid. LCMS-ESI (m/z) calculated for C$_{16}$H$_9$ClF$_3$NO$_3$: 355.0. found 354.0 [M–H]$^+$, t$_R$=10.07 mo. (Method 4). $^1$H NMR (500 MHz, DMSO-d6) δ 13.60 (br s, 1H), 8.36 (s, 1H), 8.29 (s, 1H), 8.18 (s, 1H), 7.89 (s, 1H), 7.74 (dd, J=8.5, 2.0 Hz, 1H), 7.43 (d, J=9.0 Hz, 1H), 5.46 (s, 2H).

The compounds listed in Table 32 were made using the procedures of Scheme 32.

TABLE 32

| Structure | Cpd No. | Purity RT (min) | MW | observed m/z | Ion | Purity Method |
|---|---|---|---|---|---|---|
| ![structure] | 32-1 | 10.067 | 355.70 | 354 | [M – H]$^+$ | 4 |

TABLE 32-continued
| Structure | Cpd No. | Purity RT (min) | MW | observed m/z | Ion | Purity Method |
|---|---|---|---|---|---|---|
| 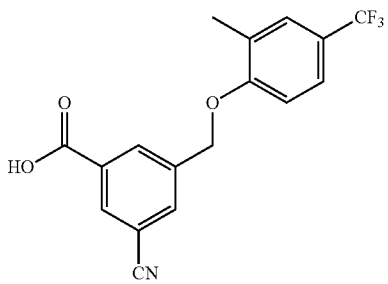 [SMILES: N#Cc1cc(COc2ccc(C(F)(F)F)cc2Cl)cc(C(=O)O)c1] | 32-2 | 10.142 | 335.28 | 334 | [M − H]⁺ | 4 |
| 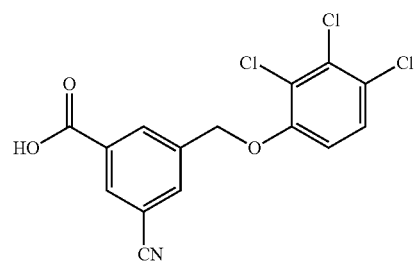 [SMILES: N#Cc1cc(COc2ccc(Cl)c(Cl)c2Cl)cc(C(=O)O)c1] | 32-3 | 4.42 | 356.58 | 353.95 | [M − H]⁺ | 12 |
| 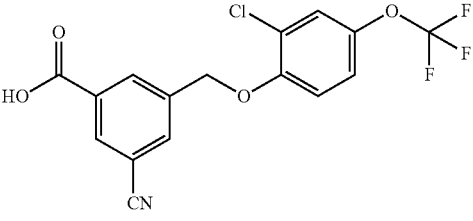 [SMILES: N#Cc1cc(COc2ccc(OC(F)(F)F)cc2Cl)cc(C(=O)O)c1] | 32-4 | 4.4 | 371.70 | 370.01 | [M − H]⁺ | 12 |
| 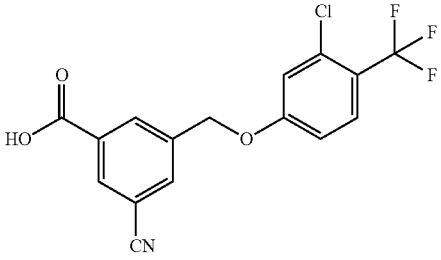 [SMILES: N#Cc1cc(COc2ccc(C(F)(F)F)c(Cl)c2)cc(C(=O)O)c1] | 32-5 | 4.3 | 355.70 | 354.01 | [M − H]⁺ | 12 |
Example 33
Synthesis of Compound 33-1
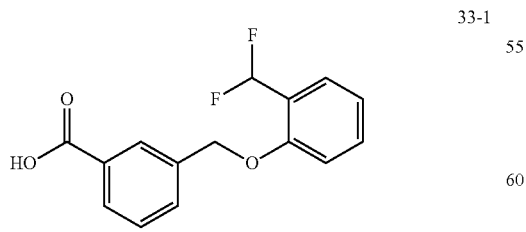
33-1

Scheme 33

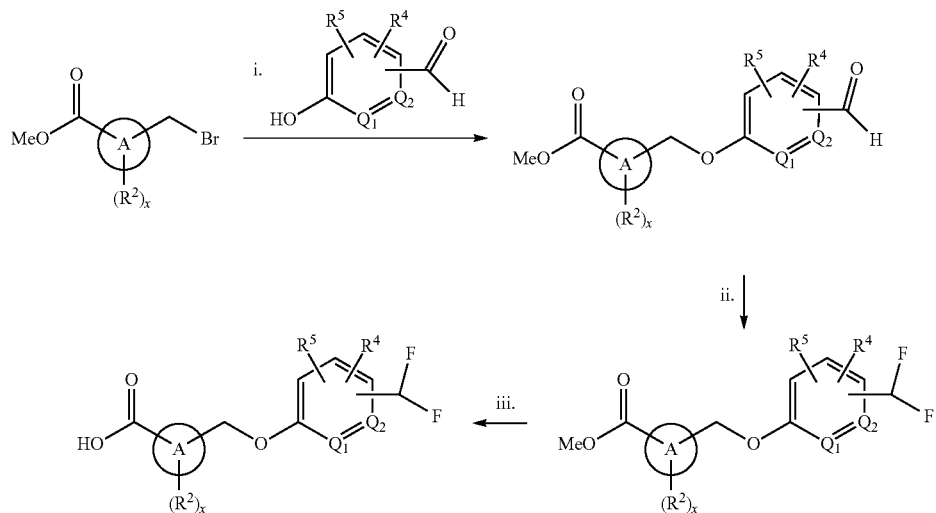

Reagents: (i) Base (Na₂CO₃, K₂CO₃, KOᵗBu), solvent (THF or DMF); ii. Diethylaminosulfur trifluoride, DCM; iii. NaOH, solvent (THF, MeOH or DMF).

Step 33-1. Synthesis of methyl 3-((2-formylphenoxy)methyl)benzoate (INT 33-A)

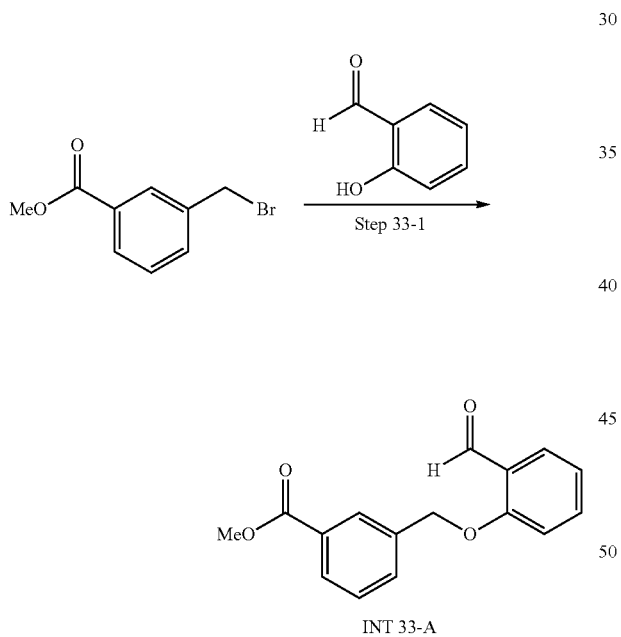

To a stirring solution of methyl 3-(bromomethyl) benzoate (300 mg, 1.31 mmol) in MeCN (6 mL) were added 2-hydroxybenzaldehyde (160 mg, 1.31 mmol) and K₂CO₃ (235 mg, 1.70 mmol). After heating at 60° C. for 18 h, the mixture was cooled to RT, diluted with H₂O (6 mL), and the aqueous layer was extracted with Et₂O (2×6 mL) and EA (6 mL). The combined organic layers were dried (Na₂SO₄), filtered through Celite, and purified by SiO₂ chromatography (EA/hexanes) to afford 315 mg (89%) of methyl 3-((2-formylphenoxy)methyl)benzoate (INT 33-A) as a white solid. LCMS-ESI (m/z) calculated for $C_{16}H_{14}O_4$: 270.1. found 271.5 (M+H)⁺, $t_R$=5.4 min. (Method 1).

Step 33-2. Synthesis of methyl 3-((2-(difluoromethyl)phenoxy)methyl)benzoate (INT 33-B)

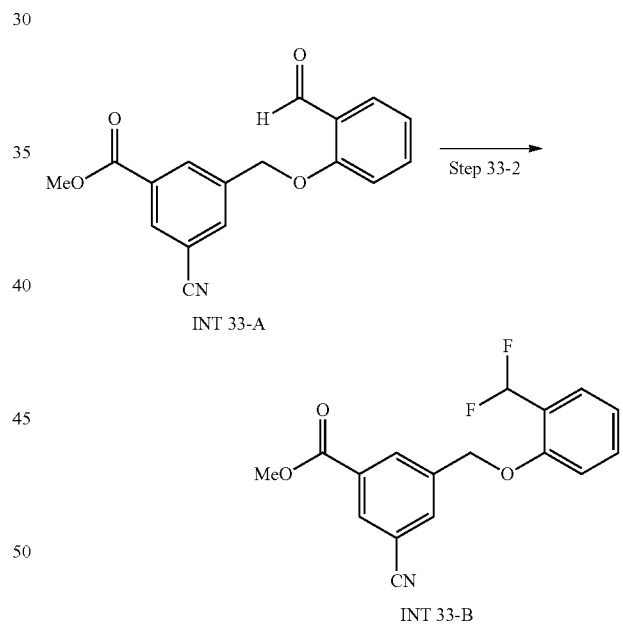

Into a stirring solution of INT 33-A (50 mg, 0.18 mmol) in DCM (2 mL) was added diethylaminosulfur trifluoride (0.12 mL, 0.92 mmol). After heating at 40° C. overnight, additional diethylaminosulfur trifluoride (0.12 mL, 0.92 mmol) was added and the reaction mixture was stirred at 40° C. overnight. The reaction mixture was cooled to RT, diluted with H₂O, and extracted with DCM (3×5 mL). The combined organic extracts were dried (Na₂SO₄), filtered, concentrated in vacuo, and purified by SiO₂ chromatography EA/hexanes) to provide 28.7 mg (53%) of methyl 3-((2-(difluoromethyl)phenoxy)methyl)benzoate (INT 33-B). LCMS-ESI (m/z) calculated for $C_{16}H_{14}F_2O_3$: 292.28. found 273.2 (M+H)⁺, $t_R$=5.94 min. (Method 1). ¹H NMR (500

MHz, CDCl$_3$) δ 8.09 (s, 1H), 8.03-8.01 (m, 1H), 7.65-7.63 (m, 1H), 7.60 (d, J=10 Hz, 1H), 7.48 (d, J=10.0 Hz, 1H), 7.41-7.39 (m, 1H), 7.06 (t, J=10.0 Hz, 1H), 7.02 (t, J=55 Hz, 1H), 6.99-6.97 (m, 1H), 5.17 (s, 2H), 3.94 (s, 3H).

Step 33-3. Synthesis of 3-((2-(difluoromethyl)phenoxy)methyl)benzoic acid (Compound 33-1)

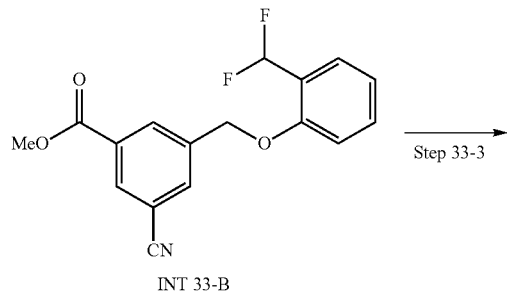

INT 33-B

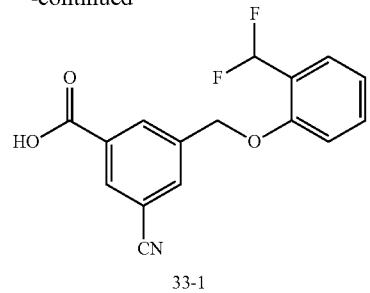

33-1

Into a stirring solution of INT 33-B (28.7 mg, 98.2 μmol) in THF (2 mL) was added 1M NaOH (0.5 mL, 491 μmol). The reaction mixture was heated at 60° C. overnight, concentrated in vacuo, diluted with 3M HCl, and extracted (EA and Et$_2$O). The combined organic layers were dried (Na$_2$SO$_4$), filtered and concentrated in vacuo to afford 20.0 mg (730%) of 3-((2-(difluoromethyl)phenoxy)methyl)benzoic acid (Compound 33-1) as a white solid. LCMS-ESI (m/z) calculated for C$_{15}$H$_{12}$F$_2$O$_3$: 278.3. found 277.2 [M−H]$^+$, t$_R$=8.02 min. (Method 4). $^1$H NMR (500 MHz, DMSO-d6) δ 12.99 (br s, 1H), 8.05 (s, 1H), 7.91 (d, J=7.5 Hz, 1H), 7.73 (d, J=7.0 Hz, 1H), 7.54-7.45 (m, 3H), 7.26-7.04 (m, 3H), 5.30 (s, 2H).

The compounds listed in Table 33 were made using the procedures of Scheme 33.

TABLE 33

| Structure | Cpd No. | Purity RT (min) | MW | observed m/z | Ion | Purity Method |
|---|---|---|---|---|---|---|
| ![structure] | 33-1 | 8.02 | 278.25 | 277.2 | [M − H]$^+$ | 4 |
| ![structure] | 33-2 | 8.761 | 278.25 | 277.2 | [M − H]$^+$ | 4 |
| ![structure] | 33-3 | 9.3 | 312.70 | 311 | [M − H]$^+$ | 4 |

TABLE 33-continued

| Structure | Cpd No. | Purity RT (min) | MW | observed m/z | Ion | Purity Method |
|---|---|---|---|---|---|---|
| 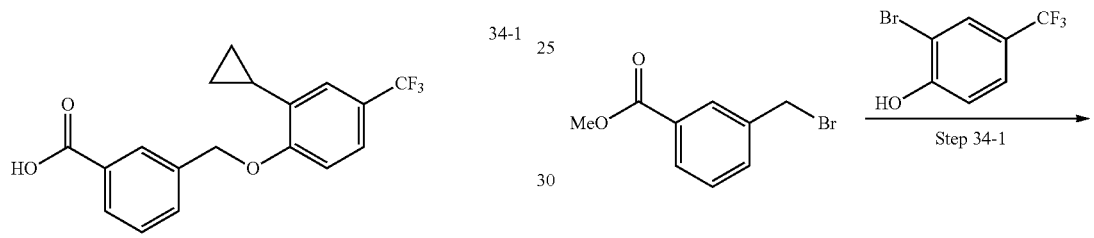 | 33-4 | 8.8 | 296.25 | 295 | [M − H]⁺ | 4 |

Example 34

Synthesis of Compound 34-1

Step 34-1. Synthesis of methyl 3-((2-bromo-4-(trifluoromethyl)phenoxy)methyl)benzoate (INT 34-A)

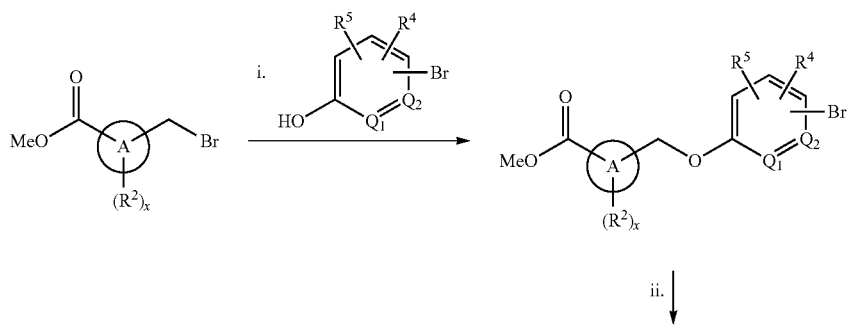

Scheme 34

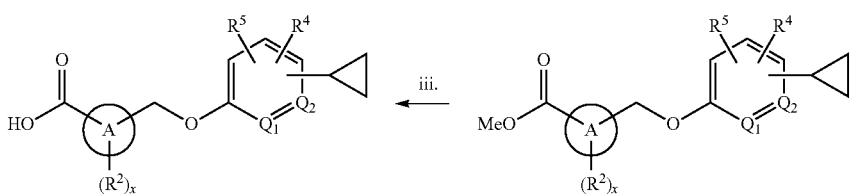

Reagents: (i) Base (Na₂CO₃, K₂CO₃, KOᵗBu), solvent (THF or DMF);
ii. Tricyclohexylphosphine, potassium phosphate, Pd(OAc)₂, boronic acid, toluene;
iii. NaOH, solvent (THF, MeOH or DMF).

-continued

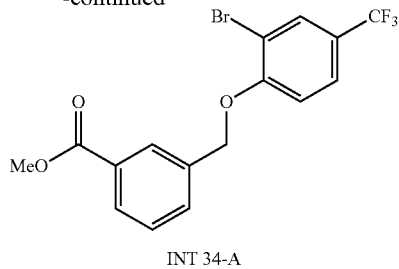

INT 34-A

A vial containing a stirring solution of 2-bromo-4-(trifluoromethyl)phenol (316 mg, 1.31 mmol) in MeCN (5 mL) was charged with methyl 3-(bromomethyl)benzoate (300 mg, 1.31 mmol) and $K_2CO_3$ (235 mg, 1.70 mmol). The resulting yellow suspension was stirred at 60° C. for 16 hours, cooled to room temperature, diluted with $H_2O$ and extracted 3× with $Et_2O$. The organic layers were combined, washed with brine, concentrated under reduced pressure, and purified by $SiO_2$ chromatography (EA/hexanes) to yield 451 mg (88.5%) of methyl 3-((2-bromo-4-(trifluoromethyl)phenoxy)methyl)benzoate (INT 34-A) as a white solid. LCMS-ESI (m/z) calculated for $C_{16}H_{12}BrF_3O_3$: 389.2. found 391.0 (M+H)$^+$, $t_R$=6.7 min. (Method 1).

Step 34-2. Synthesis of methyl 3-((2-cyclopropyl-4-(trifluoromethyl)phenoxy)methyl) benzoate (INT 34-B)

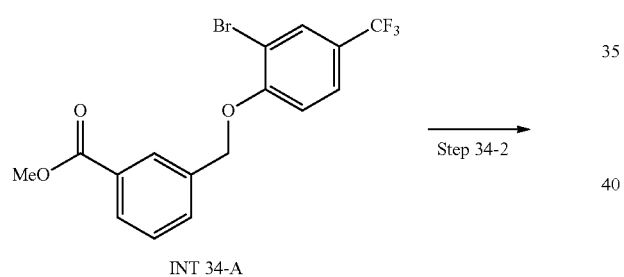

INT 34-A

INT 34-B

A 15 mL pressure tube containing a mixture of INT 34-A (300 mg, 771 μmol) in toluene (4 mL) was charged with potassium phosphate (491 mg, 2.31 mmol), tricyclohexylphosphine (32.4 mg, 116 μmol), cyclopropylboronic acid (132 mg, 1.54 mmol), and palladium (II) acetate (17.3 mg, 77.1 μmol). The tube was sealed, and the resulting orange suspension was stirred at 100° C. for 13.5 hours, then cooled to room temperature and partitioned between $Et_2O$ and $H_2O$. The aqueous layer was back-extracted with $Et_2O$ (2×). The organic layers were combined, washed with brine, dried ($Na_2SO_4$), concentrated under reduced pressure and purified by $SiO_2$ chromatography (EA/hexanes) to provide 201 mg (74%) of methyl 3-((2-cyclopropyl-4-(trifluoromethyl)phenoxy)methyl)benzoate (INT 34-B). LCMS-ESI (m/z) calculated for $C_{19}H_{17}F_3O_3$: 350.34. found 373.2 (M+Na)$^+$, $t_R$=6.8 min. (Method 1). $^1$H NMR (500 MHz, DMSO-d6) δ 8.11 (s, 1H), 7.93 (d, J=7.7 Hz, 1H), 7.78 (d, J=7.4 Hz, 1H), 7.58 (t, J=7.7 Hz, 1H), 7.49 (dd, J=8.2, 2.0 Hz, 1H), 7.21 (d, J=8.6 Hz, 1H), 7.15 (d, J=2.3 Hz, 1H), 5.34 (s, 2H), 3.86 (s, 3H), 2.18 (tt, J=8.5, 5.3 Hz, 1H), 1.01-0.91 (m, 2H), 0.76-0.69 (m, 2H).

Step 34-3. Synthesis of 3-((2-cyclopropyl-4-(trifluoromethyl)phenoxy)methyl)benzoic acid (Compound 34-1)

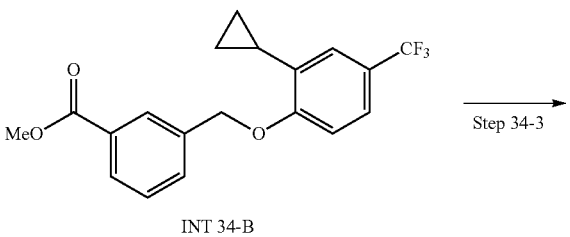

INT 34-B

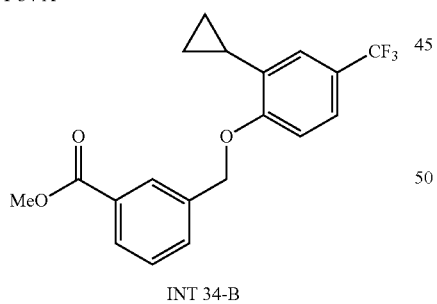

34-1

Into a stirring solution of INT 34-B (195 mg, 557 μmol) in THF (5 mL) was a solution of 1M NaOH (2.23 mL, 2.23 mmol). The solution was stirred overnight at 50° C. for 12.5 hours, concentrated under reduced pressure, dissolved in $H_2O$ and acidified to pH 4-5 using 3M HCl. The resulting white precipitate was extracted 3× into $Et_2O$. The organic layers were combined, washed with brine, dried ($Na_2SO_4$) and concentrated under reduced pressure to yield a crude product that was purified by prep HPLC ($CH_3CN/H_2O$ containing 0.1% formic acid) to afford 66 mg (35%) 3-((2-cyclopropyl-4-(trifluoromethyl)phenoxy)methyl)benzoic acid (Compound 34-1) as a white solid. LCMS-ESI (m/z) calculated for $C_{18}H_{15}F_3O_3$: 336.3. found 335.2 [M−H]$^+$, $t_R$=10.83 min. (Method 4). $^1$H NMR (499 MHz, DMSO-d$_6$) δ 13.03 (s, 1H), 8.09 (s, 1H), 7.91 (d, J=7.8 Hz, 1H), 7.74 (d, J=7.7 Hz, 1H), 7.55 (t, J=7.7 Hz, 1H), 7.50 (dd, J=8.7, 2.3 Hz, 1H), 7.21 (d, J=8.6 Hz, 1H), 7.15 (d, J=2.3 Hz, 1H), 5.33 (s, 2H), 2.18 (tt, J=8.5, 5.3 Hz, 1H), 0.99-0.91 (m, 2H), 0.76-0.69 (m, 2H). $^{19}$F NMR (376 MHz, DMSO-d$_6$) δ−59.98.

Example 35

Synthesis of Compound 35-1

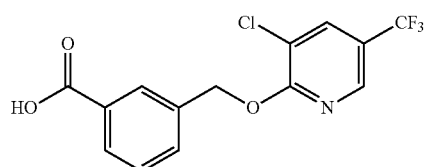

35-1

Scheme 35

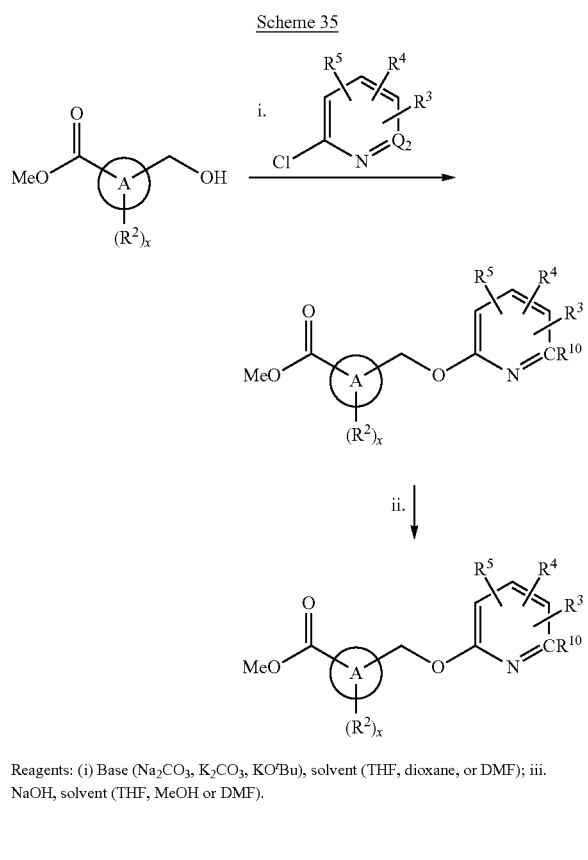

Reagents: (i) Base (Na₂CO₃, K₂CO₃, KOᵗBu), solvent (THF, dioxane, or DMF); iii. NaOH, solvent (THF, MeOH or DMF).

Step 35-1. Synthesis of methyl 3-(((3-chloro-5-(trifluoromethyl)pyridin-2-yl)oxy)methyl)benzoate (INT 35-A)

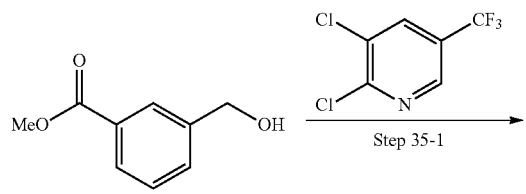

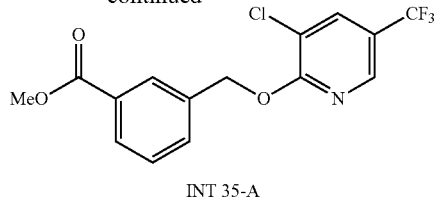

INT 35-A

Into a 48 mL pressure vessel containing a solution of 2,3-dichloro-5-(trifluoromethyl)pyridine (433 mg, 2.01 mmol) in 1,4-Dioxane (9 mL) were added methyl 3-(hydroxymethyl)benzoate (500 mg, 3.01 mmol) and potassium tert-butoxide (338 mg, 3.01 mmol). The vessel was sealed, the reaction mixture was heated and at 90° C. for 15.5 hours, and then cooled to room temperature. The reaction mixture was partitioned between Et₂O and H₂O. The phases were separated, and the aqueous layer was extracted with Et₂O (2×). The organic phases were combined, washed with brine, dried (Na₂SO₄), concentrated and purified by SiO₂ chromatography (EA/hexanes) to yield 198 mg (28.6%) of methyl 3-(((3-chloro-5-(trifluoromethyl)pyridin-2-yl)oxy)methyl) benzoate (INT 35-A) as a white solid. LCMS-ESI (m/z) calculated for $C_{15}H_{11}ClF_3NO_3$: 345.7. found 346.1 (M+H)⁺, $t_R$=6.6 min. (Method 1). ¹H NMR (500 MHz, DMSO-d6) δ 8.59 (dd, J=2.2, 1.1 Hz, 1H), 8.44 (d, J=1.9 Hz, 1H), 8.09 (t, J=1.8 Hz, 1H), 7.94 (dt, J=7.7, 1.5 Hz, 1H), 7.76 (dt, J=7.6, 1.5 Hz, 1H), 7.57 (t, J=7.7 Hz, 1H), 5.60 (s, 2H), 3.86 (s, 3H).

Step 35-2. Synthesis of 3-(((3-chloro-5-(trifluoromethyl)pyridin-2-yl)oxy)methyl)benzoic acid (Compound 35-1)

A 20 mL vial containing a stirring solution of INT 35-A (190 mg, 550 μmol) in THF (5 mL) was charged with 1M NaOH (2.20 mL, 2.20 mmol). After stirring for 22.5 hours at 50° C., the reaction mixture was concentrated under reduced pressure, the resulting residue was dissolved in H₂O and acidified to pH 4-5 using 3M HCl. The resulting white precipitate was extracted with Et₂O (3×). The organic layers were combined, washed with brine, dried (Na₂SO₄) and concentrated under reduced pressure to yield 150 mg (82.3%) of 3-(((3-chloro-5-(trifluoromethyl) pyridin-2-yl) oxy)methyl)benzoic acid (Compound 35-1) as a white powder. LCMS-ESI (m/z) calculated for $C_{14}H_9ClF_3NO_3$: 331.7. found 333.2 (M+Na)⁺, $t_R$=10.1 min. (Method 3). ¹H NMR (500 MHz, DMSO-d6) δ 13.05 (s, 1H), 8.60 (d, J=1.1 Hz, 1H), 8.44 (d, J=2.2 Hz, 1H), 8.06 (s, 1H), 7.92 (d, J=7.8 Hz, 1H), 7.73 (d, J=7.7 Hz, 1H), 7.54 (t, J=7.7 Hz, 1H), 5.59 (s, 2H). $^{19}$F NMR (376 MHz, DMSO-d$_6$) δ−60.02.

Example 36

Synthesis of Compound 36-1

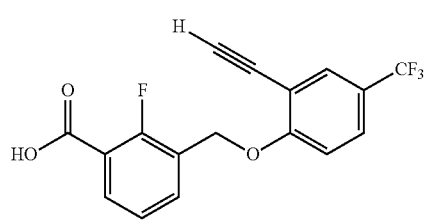

Scheme 36

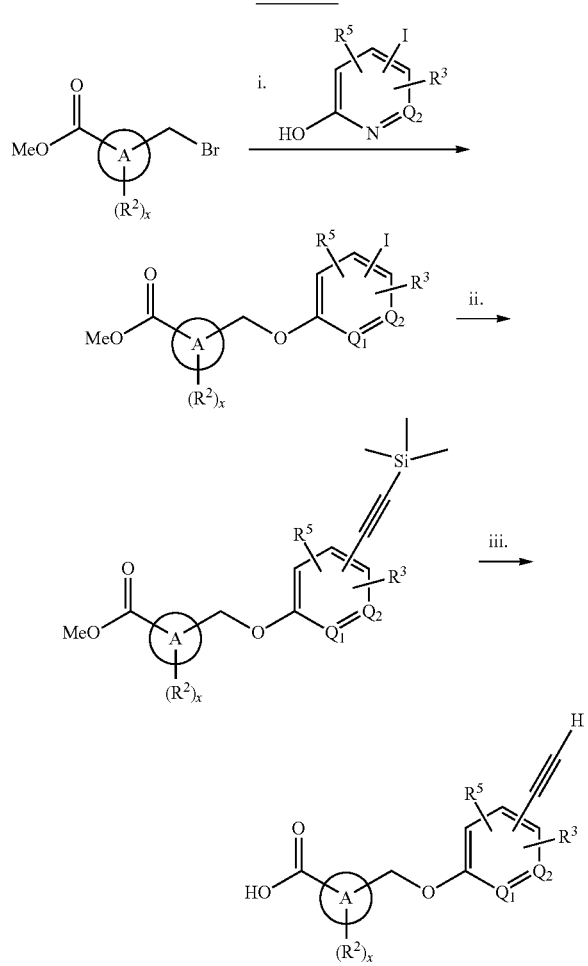

Reagents: (i) Base (Na$_2$CO$_3$, K$_2$CO$_3$, KO$^t$Bu), solvent (THF, dioxane, or DMF); (ii). ethynyl(trimethyl)silane, dichloropalladium, triphenylphosphine, CuI, TEA, THF; (iii). NaOH, solvent (THF, MeOH or DMF).

Step 36-1. Synthesis of methyl 2-fluoro-3-((2-iodo-4-(trifluoromethyl)phenoxy)-methyl)benzoate (INT 36-A)

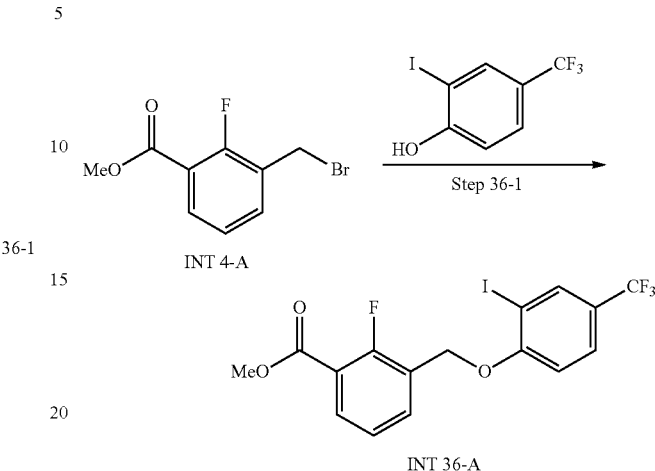

Into a solution of INT 4-A (300 mg, 1.21 mmol) and 2-iodo-4-(trifluoromethyl)phenol (349.72 mg, 1.21 mmol) in CH$_3$CN (10 mL) was added K$_2$CO$_3$ (218.17 mg, 1.58 mmol). After stirring at 60° C. for 12 h, the reaction mixture was filtered and the filtrate was concentrated to provide 500 mg (91%) of methyl 2-fluoro-3-((2-iodo-4-(trifluoromethyl) phenoxy)methyl)benzoate (INT 36-A) that was used without further purification. LCMS-ESI (m/z) calculated for C$_{16}$H$_{11}$F$_4$IO$_3$: 454.16. found 454.9 (M+H)$^+$, t$_R$=1.04 min. (Method 6).

Step 36-2. Synthesis of methyl 2-fluoro-3-((4-(trifluoromethyl)-2-((trimethylsilyl) ethynyl)phenoxy) methyl)benzoate (INT 36-B)

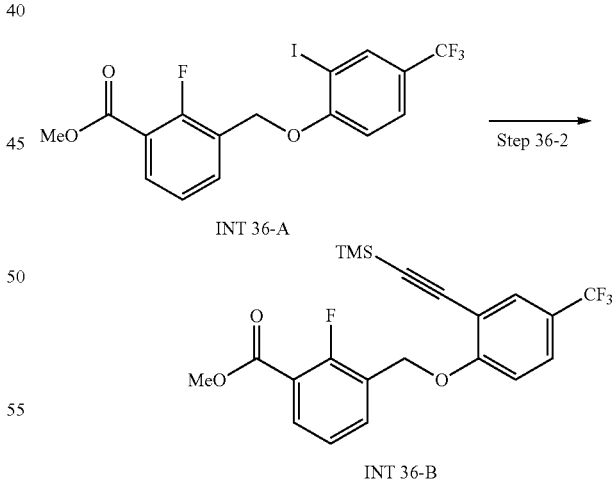

Into a solution of INT 36-A (500 mg, 1.10 mmol) in THF (10 mL) were added ethynyl(trimethyl)silane (167.7 μL, 1.21 mmol), dichloropalladium triphenyl phosphine (77.28 mg, 110.09 μmol), CuI (20.97 mg, 110.09 μmol) and TEA (459.72 μL, 3.30 mmol). After stirring at 40° C. 12 h, the mixture was poured into H$_2$O (20 mL) and extracted with EA (3×20 mL). The organic layer was dried (Na$_2$SO$_4$), concentrated, and purified by SiO$_2$ chromatography(PE,EA)

to provide 200 mg (42%) of methyl 2-fluoro-3-((4-(trifluoromethyl)-2-((trimethylsilyl) ethynyl)phenoxy)methyl)benzoate (INT 36-B) as a white solid. TLC (5:1 PE:EA, $R_f$=0.7)$^1$H NMR (400 MHz, CDCl$_3$) δ 7.95-7.90 (m, 2H), 7.74 (s, 1H), 7.57-7.53 (m, 1H), 7.33-7.27 (m, 1H), 7.05-7.01 (m, 1H), 5.29 (s, 2H), 3.96 (s, 3H), 0.31-0.27 (m, 9H).

Step 36-3. Synthesis of 3-((2-ethynyl-4-(trifluoromethyl)phenoxy)methyl)-2-fluorobenzoic acid (Compound 36-1)

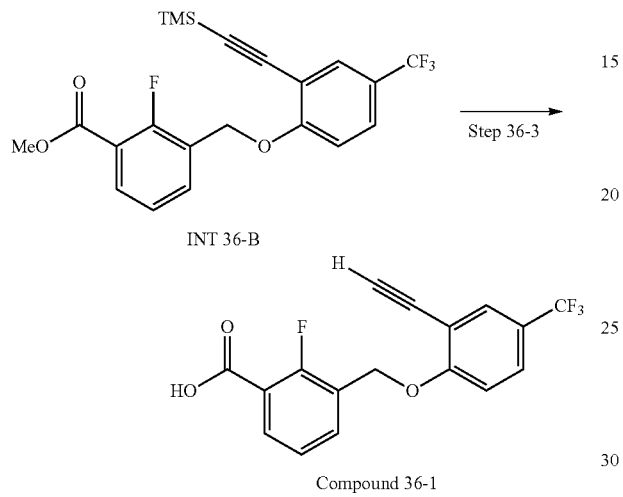

Into a suspension of INT 36-B (185 mg, 0.44 mmol) in MeOH (5 mL) and H$_2$O (5 mL), and THF (5 mL) was added NaOH (52.3 mg, 1.4 mmol). After stirring at 30° C. for 1.5 h, the reaction mixture was concentrated, dissolved in MeOH (5 mL), filtered and purified by prep-HPLC (H$_2$O/CH$_3$CN with formic acid) to provide 59 mg (48%) of 3-((2-ethynyl-4-(trifluoromethyl)phenoxy)methyl)-2-fluorobenzoic acid (Compound 36-1) as a white solid. LCMS-ESI (m/z) calculated for C$_{17}$H$_{10}$F$_4$O$_3$: 338.3. found 339.1 (M+Na)$^+$, $t_R$=0.786 min. (Method 6). $^1$H NMR (400 MHz, DMSO-d6) δ ppm 4.44 (s, 1H) 5.38 (s, 2H) 7.36 (t, J=7.69 Hz, 1H) 7.43 (d, J=8.50 Hz, 1H) 7.75-7.84 (m, 3H) 7.88 (td, J=7.38, 1.75 Hz, 1H).

Example 37

Synthesis of Compound 37-1

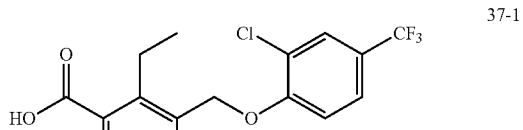

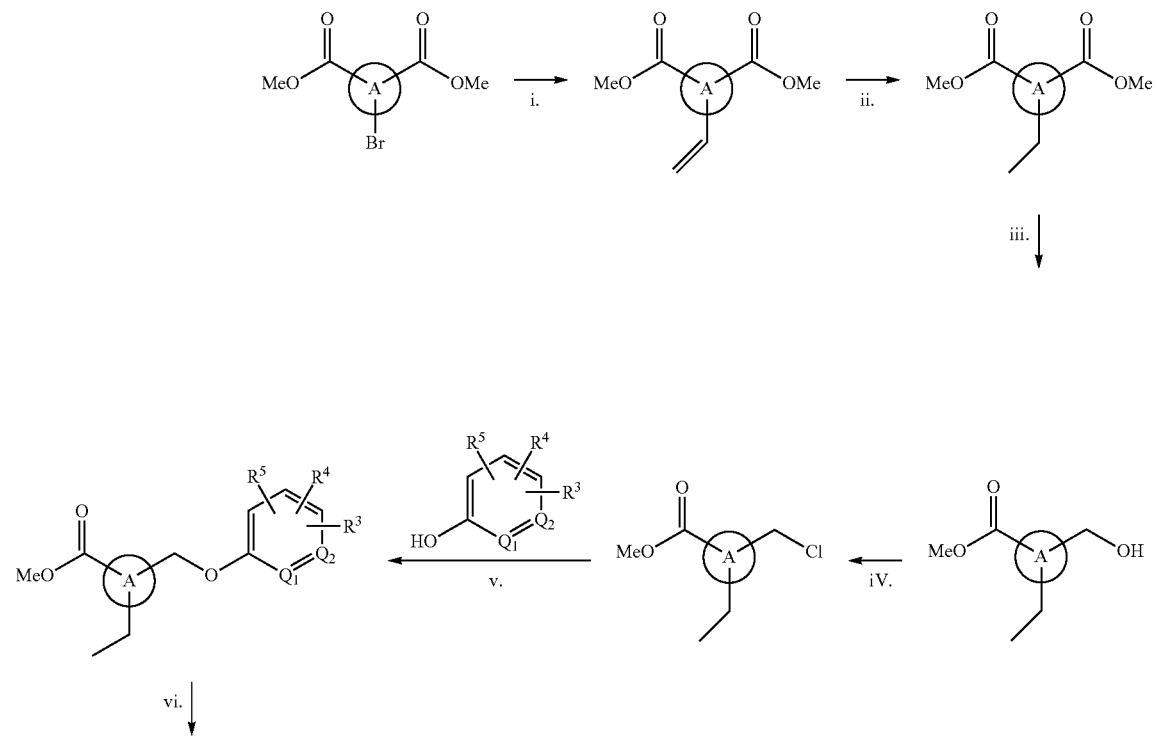

Scheme 37

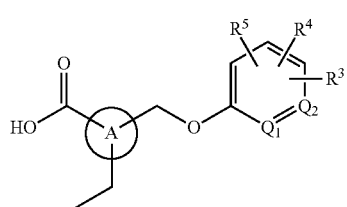

Reagents: (i) dioxaborolane or boronic acid, Pd(dppf)Cl$_2$—CH$_2$Cl$_2$, dioxane; (ii) H$_2$, Pd/C, MeOH; (iii) NaBH$_4$, MeOH; (iv) SOCl$_2$, DCM; (v) Base (Na$_2$CO$_3$, K$_2$CO$_3$, KO$^t$Bu), solvent (THF, dioxane, or DMF); (iv). NaOH, solvent (THF, MeOH or DMF).

Step 37-1. Synthesis of methyl 3-(hydroxymethyl)-2-vinylbenzoate (INT 37-A)

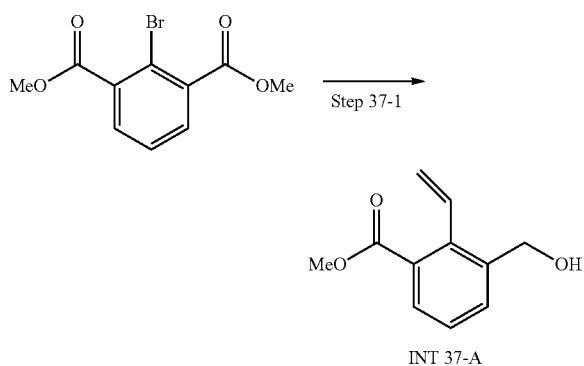

To a suspension of dimethyl 2-bromobenzene-1,3-dicarboxylate (1 g, 3.66 mmol) and Na$_2$CO$_3$ (776.25 mg, 7.32 mmol) in 1,4-dioxane (20 mL) and H$_2$O (4 mL) was added 4,4,5,5-tetramethyl-2-vinyl-1,3,2-dioxaborolane (683.25 µL, 4.03 mmol). The reaction mixture was treated with Pd(dppf)Cl$_2$—CH$_2$Cl$_2$ (149.5 mg, 183.1 µmol) and stirred at 100° C. for 12 hr. The mixture was filtered. The filtrate was partitioned between EA (30 ml) and H$_2$O (30 ml). The aqueous layer was back-extracted with EA (30 ml). The combined organic extracts were dried (Na$_2$SO$_4$), filtered, and concentrated under vacuum to provide a residue that was purified by SiO$_2$ chromatography to provide 680 mg (84.3%) of methyl 3-(hydroxymethyl)-2-vinylbenzoate (INT 37-A) as a colorless oil. TLC (5:1 PE:EA): R$_f$=0.7.

Step 37-2. Synthesis of methyl 2-ethyl-3-(hydroxymethyl)benzoate (INT 37-B)

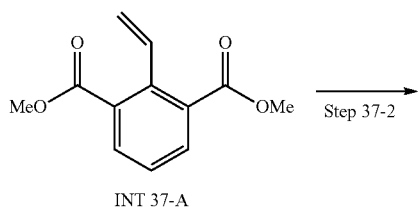

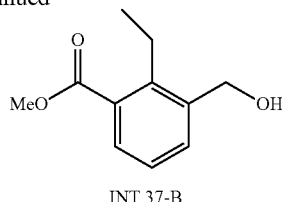

H$_2$ (15 psi) was bubbled into a solution of INT 37-A (680 mg, 3.09 mmol), Pd/C (70 mg, 308.8 umol, 10% purity) in MeOH (10 mL) at 30° C. for 12 hr. The reaction mixture was filtered and the filtrate was concentrated to give a crude product that was purified by SiO$_2$ chromatography (EA/PE) to provide 560 mg (81.6%) of methyl 2-ethyl-3-(hydroxymethyl)benzoate (INT 37-B) as a colorless oil. TLC (5:1 PE:EA): R$_f$=0.4. $^1$H NMR (400 MHz, CDCl$_3$) δ ppm 1.25 (t, J=7.40 Hz, 3H) 3.15 (q, J=7.46 Hz, 2H) 3.92 (s, 6H) 7.30 (t, J=7.76 Hz, 1H) 7.85 (d, J=7.70 Hz, 2H).

Step 37-3. Synthesis of methyl 2-ethyl-3-(hydroxymethyl)benzoate (INT 37-C)

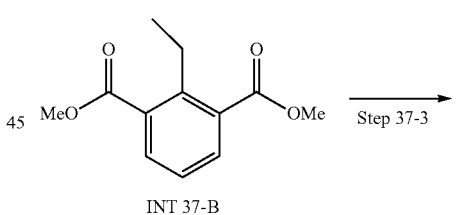

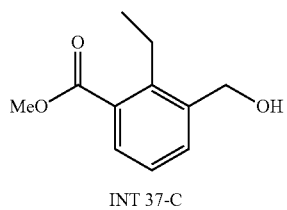

Into a solution of INT 37-B (0.4 g, 1.80 mmol) in THF (10 mL) at 0° C. were added NaBH$_4$ (102.13 mg, 2.70 mmol) and MeOH (2 mL). After stirring 12 h at 70° C., the mixture was poured into saturated NH$_4$Cl (aq. 20 mL) and extracted with EA (3×20 mL). The combined organic layers were dried (Na$_2$SO$_4$), concentrated, and purified by prep-TLC to provide 170 mg (48.6%) of methyl 2-ethyl-3-(hydroxymethyl) benzoate (INT 37-C) as a yellow oil. TLC (5:1 PE:EA): R$_f$=0.5.

Step 37-4. Synthesis of methyl 3-(chloromethyl)-2-ethylbenzoate (INT 37-D)

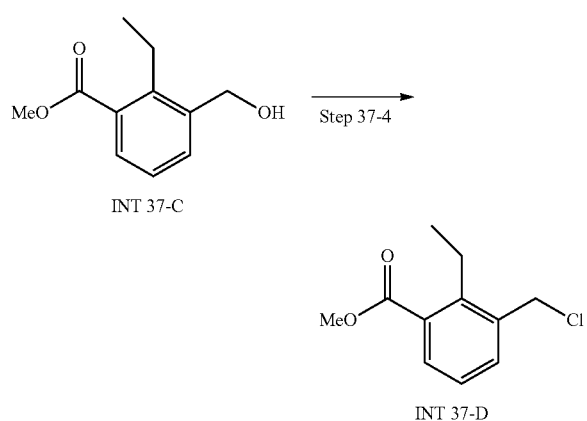

Into a solution of INT 37-C (70 mg, 360.4 μmol) in DCM (2 mL) was added SOCl₂ (130.7 μL, 1.80 mmol) at 0° C. After stirring at 30° C. for 1 h, the reaction mixture was concentrated in vacuo to provide 72 mg (94%) of methyl 3-(chloromethyl)-2-ethyl-benzoate (INT 37-D) as brown gum that was used in the next step without further purification. TLC (5:1 PE:EA): $R_f$=0.7.

Step 37-5. Synthesis of methyl 3-((2-chloro-4-(trifluoromethyl)phenoxy)methyl)-2-ethylbenzoate (INT 37-E)

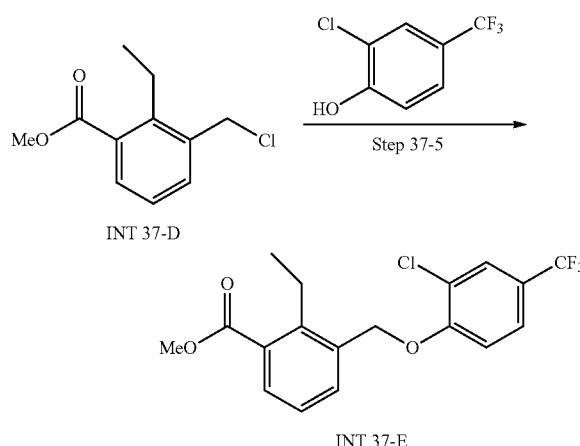

Into a suspension of INT 37-D (70 mg, 329.15 μmol) and K₂CO₃ (136.47 mg, 987.44 μmol) in CH₃CN (2 mL) was added 2-chloro-4-(trifluoromethyl)phenol (71.16 mg, 362.06 μmol, 1.1 eq). After stirring at 80° C. for 12 h the reaction mixture was filtered and the filtrate was concentrated in vacuo to provide a residue that was purified by SiO₂ chromatography (EA/PE) to provide 59 mg (48%) of methyl 3-((2-chloro-4-(trifluoromethyl)phenoxy)methyl)-2-ethyl-benzoate (INT 37-E) as a light yellow gum. TLC (10:1 PE:EA): $R_f$=0.75. LCMS-ESI (m/z) calculated for $C_{18}H_{16}ClF_3O_3$: 372.7. found 373.4 (M+H)⁺, $t_R$=1.14 min. (Method 6). ¹H NMR (400 MHz, CDCl₃) δ 7.78 (dd, J=1.3, 7.8 Hz, 1H), 7.66-7.63 (m, 1H), 7.62 (s, 1H), 7.46 (dd, J=1.6, 8.7 Hz, 1H), 7.30-7.22 (m, 1H), 7.03 (d, J=8.6 Hz, 1H), 5.22 (s, 2H), 3.89 (s, 3H), 2.97 (q, J=7.5 Hz, 2H), 1.23 (t, J=7.5 Hz, 3H).

Step 37-6. Synthesis of 3-((2-chloro-4-(trifluoromethyl)phenoxy)methyl)-2-ethylbenzoic acid (Compound 37-1)

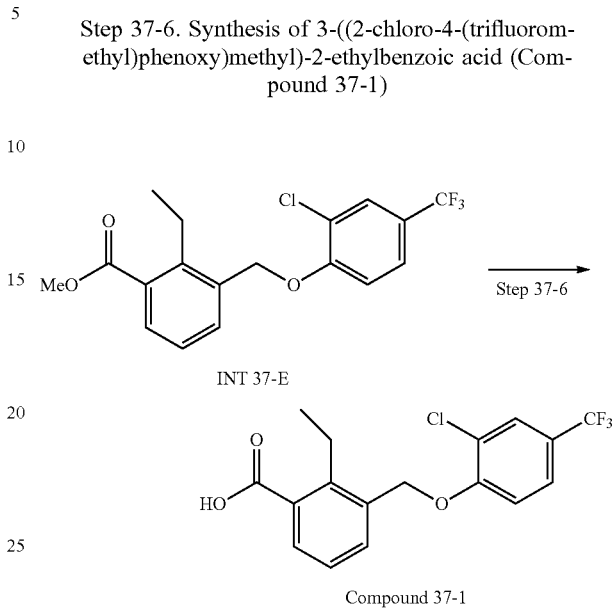

Into a solution of INT 37-E (156 mg, 418.5 umol) in THF (3 mL), MeOH (1 mL) and H₂O (1 mL) was add NaOH (42.92 mg, 1.07 mmol). After stirring at 50° C. for 12 h, the mixture was acidified with 3M hydrochloride acid then partitioned between EA (10 ml) and H₂O (10 ml). The organic layer was dried (Na₂SO₄) filtered and concentrated in vacuo. The resulting residue was purified by prep-HPLC (H₂O (0.225% FA)-CH₃CN) to provide 144 mg (77%) of 3-((2-chloro-4-(trifluoromethyl)phenoxy)methyl)-2-ethyl-benzoic acid (Compound 37-1). LCMS-ESI (m/z) calculated for $C_{17}H_{14}ClF_3O_3$: 358.7. found 357.0 (M–H)⁺, $t_R$=0.95 min. (Method 8). ¹H NMR (400 MHz, CDCl₃) δ 8.02 (dd, J=1.1, 7.8 Hz, 1H), 7.74 (d, J=7.0 Hz, 1H), 7.69 (d, J=2.1 Hz, 1H), 7.52 (dd, J=1.7, 8.7 Hz, 1H), 7.36 (t, J=7.8 Hz, 1H), 7.09 (d, J=8.6 Hz, 1H), 5.28 (s, 2H), 3.12 (q, J=7.5 Hz, 2H), 1.31 (t, J=7.5 Hz, 3H

Example 38

Synthesis of Compound 38-1

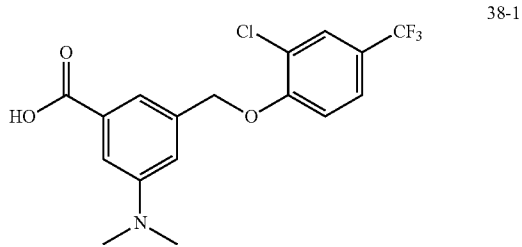 [SMILES: CN(C)c1cc(COc2ccc(C(F)(F)F)cc2Cl)cc(C(=O)O)c1]

Scheme 38

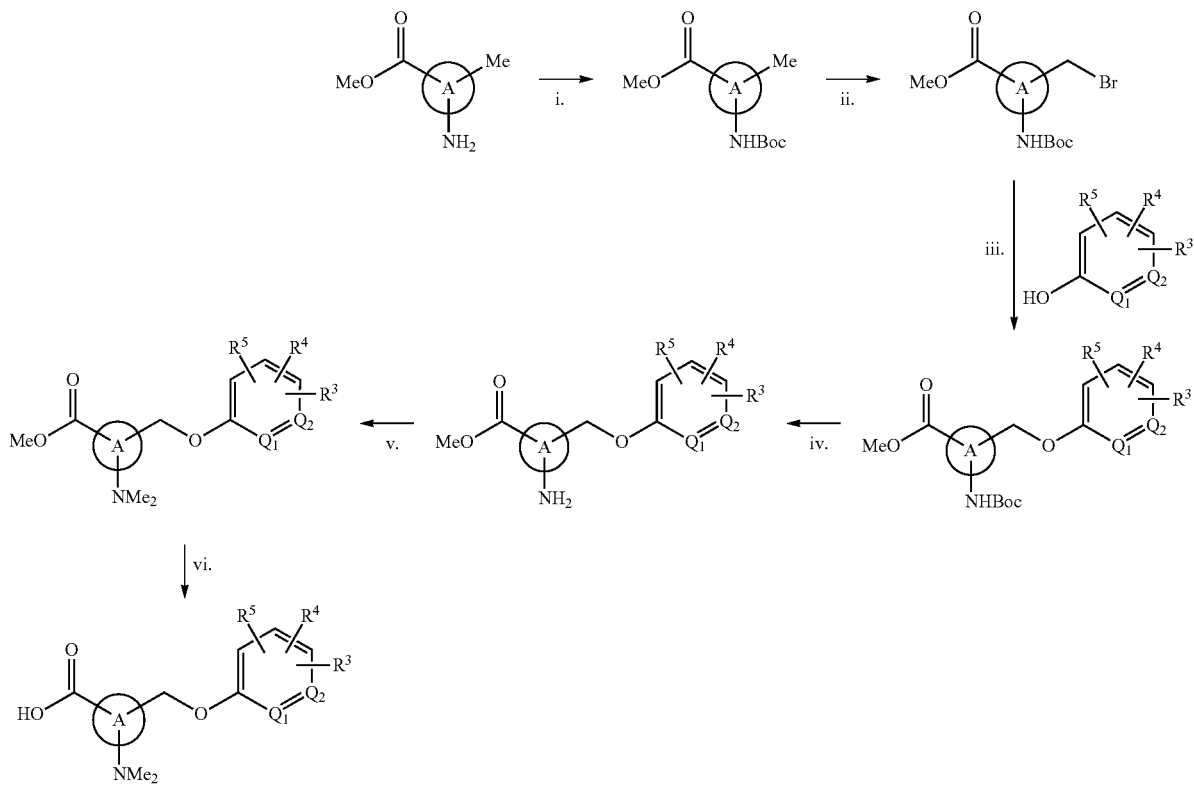

Reagents: (i) Boc₂O, DMAP, CH₃CN; (ii) NBS, AIBN or BPO, CCl₄; (iii) Base (Na₂CO₃, K₂CO₃, KOtBu), solvent (THF, dioxane, or DMF); (iv) Acid (HCl, TFA), solvent (Dioxanes, THF); (v) MeI, K₂CO₃, CH₃CN; (vi) NaOH, solvent (THF, MeOH or DMF).

Step 38-1 Synthesis of methyl 3-((tert-butoxycarbonyl)amino)-5-methylbenzoate (INT 38-A)

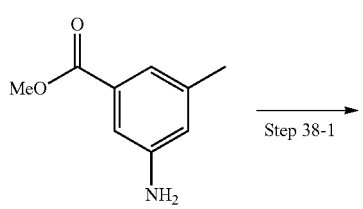

Into a solution of methyl 3-amino-5-methyl-benzoate (1 g, 6.05 mmol, 1), di-tert-butyl dicarbonate (2.64 g, 12.11 mmol) and TEA (1.69 mL, 12.11 mmol) in CH₃CN (15 mL) was added 4-dimethylamino pyridine (73.96 mg, 605.37 µmol). The reaction mixture was stirred at 50° C. for 12 h then filtered. The filtrate was concentrated and the residue was purified by SiO₂ chromatography (EA/PE) to provide 850 mg (53%) of methyl 3-((tert-butoxycarbonyl)amino)-5-methylbenzoate (INT 38-A) as a yellow gum. TLC (5:1 PE:EA): $R_f$=0.7. ¹H NMR (400 MHz, CDCl₃) δ ppm 1.46 (s, 9H) 2.40 (s, 3H) 3.91 (s, 3H) 7.28 (s, 1H) 7.75 (s, 1H) 7.82 (s, 1H).

Step 38-2 Synthesis of methyl 3-(bromomethyl)-5-((tert-butoxycarbonyl)amino)benzoate (INT 38-B)

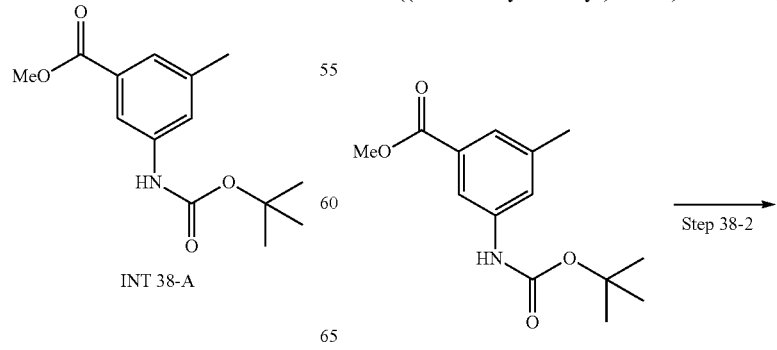

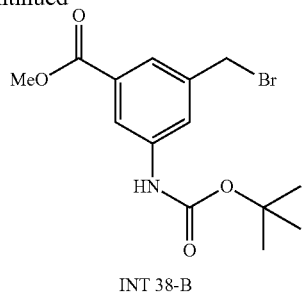

INT 38-B

Into a solution of INT 38-A (750 mg, 2.83 mmol) and NBS (604 mg, 3.39 mmol) in CCl$_4$ (10 mL) was added AIBN (46 mg, 282 μmol). After stirring at 80° C. for 12 h, the reaction mixture was filtered purified by SiO$_2$ chromatography (EA/PE) to provide 800 mg (82%) of methyl 3-(bromomethyl)-5-((tert-butoxycarbonyl)amino)benzoate (INT 38-B) as a brown gum. TLC (10:1 PE:EA): R$_f$=0.45.

Step 38-3 Synthesis of methyl 3-((tert-butoxycarbonyl)amino)-5-((2-chloro-4-(trifluoromethyl)phenoxy)methyl)benzoate (INT 38-C)

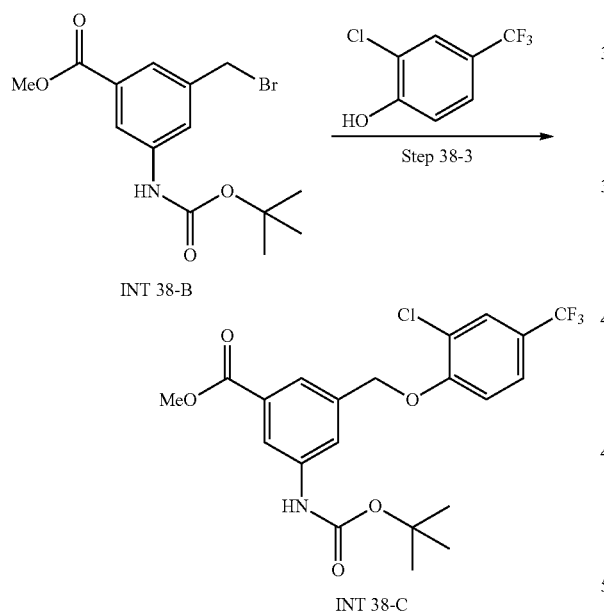

Into a suspension of INT 38-B (560 mg, 1.63 mmol) and K$_2$CO$_3$ (674.57 mg, 4.88 mmol) in CH$_3$CN (10 mL) was added 2-chloro-4-(trifluoromethyl)phenol (351.76 mg, 1.79 mmol). After stirring at 80° C. for 12 h, the reaction mixture was filtered, concentrated, and purified by SiO$_2$ chromatography to provide 140 mg (18%) of methyl 3-((tert-butoxycarbonyl)amino)-5-((2-chloro-4-(trifluoromethyl)phenoxy)methyl)benzoate (INT 38-C) as a light yellow gum. TLC (10:1 PE:EA): R$_f$=0.60. LCMS-ESI (m/z) calculated for C$_{21}$H$_{21}$ClF$_3$NO$_5$: 459.85. found 458 (M−H)$^+$, t$_R$=1.12 min (Method 6). $^1$H NMR (400 MHz, DMSO-d6) δ 9.72 (s, 1H), 8.15 (s, 1H), 7.87 (d, J=1.9 Hz, 1H), 7.78 (s, 1H), 7.72-7.68 (m, 2H), 7.39 (d, J=8.9 Hz, 1H), 5.35 (s, 2H), 3.85 (s, 3H), 1.48 (s, 9H).

Step 38-4 Synthesis of methyl 3-amino-5-((2-chloro-4-(trifluoromethyl)phenoxy)methyl) benzoate (INT 38-D)

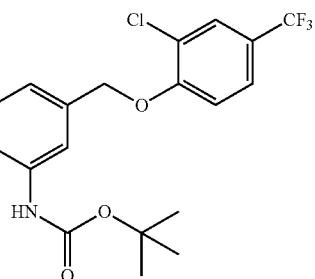

INT 38-C

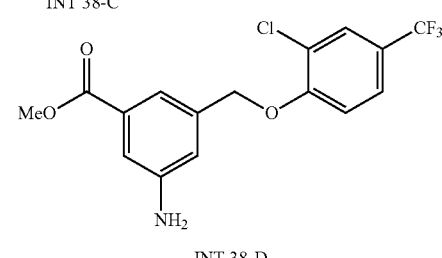

INT 38-D

A solution of INT 38-C (60 mg, 130.48 μmol) in HCl/dioxane (4 M, 1 mL) was stirred at 30° C. for 1 hr. The reaction mixture was concentrated in vacuo to give 55 mg of crude methyl 3-amino-5-((2-chloro-4-(trifluoromethyl)phenoxy)methyl)benzoate (INT 38-D) as a gray solid that was used into the next step without further purification. TLC (10:1 PE:EA): R$_f$=0.65.

Step 38-5 Synthesis of methyl 3-((2-chloro-4-(trifluoromethyl)phenoxy)methyl)-5-(dimethylamino)benzoate (INT 38-E)

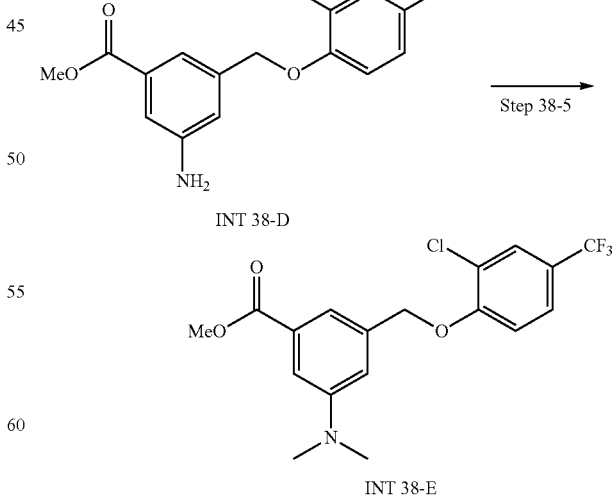

Into a suspension of INT 38-D (50 mg, 138.99 μmol) and K$_2$CO$_3$ (38.42 mg, 278 umol) in MECN (3 mL) was added MeI (17.31 uL, 277.99 umol). The reaction mixture was stirred at 30° C. for 12 h, filtered and purified by SiO₂ chromatography to provide 12 mg (22%) of methyl 3-((2-chloro-4-(trifluoromethyl)phenoxy)methyl)-5-(dimethylamino)benzoate (INT 38-E) as a light yellow gum. TLC (5:1 PE:EA): $R_f$=0.8. LCMS-ESI (m/z) calculated for $C_{18}H_{17}ClF_3NO_3$: 387.8. found 388 (M–H)⁺, $t_R$=0.99 min (Method 6). ¹H NMR (400 MHz, CDCl₃) δ ppm 7.66 (d, J=1.88 Hz, 1H) 7.46 (dd, J=8.63, 1.63 Hz, 1H) 7.42 (s, 1H) 7.36 (s, 1H) 7.00-7.06 (m, 2H) 5.21 (s, 2H) 3.92 (s, 3H) 3.02 (s, 6H).

Step 38-6 Synthesis of 3-((2-chloro-4-(trifluoromethyl)phenoxy)methyl)-5-(dimethylamino) benzoic acid (Compound 38-1)

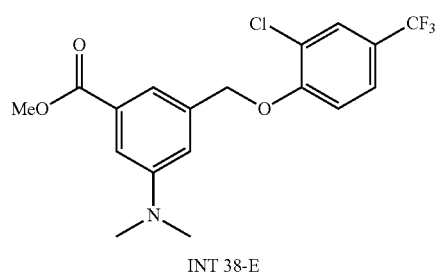

INT 38-E

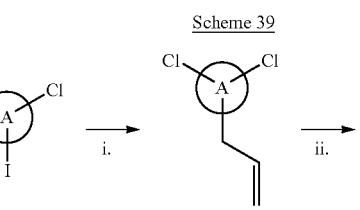

Compound 38-1

To a solution of INT 38-E (12 mg, 30.95 μmol) in THF (1 mL), MeOH (0.5 mL) and H₂O (0.5 mL) was added NaOH (4.95 mg, 123.78 μmol). After stirring at 50° C. for 4 h, the mixture was acidified with 3M hydrochloride acid. The mixture was partitioned between EA (10 ml) and H₂O (10 ml) and the resulting organic layer was dried (Na₂SO₄), filtered, and purified by prep-HPLC (H₂O(0.225% FA)-CH₃CN) to provide 3.6 mg (31%) of 3-((2-chloro-4-(trifluoromethyl)phenoxy)methyl)-5-(dimethylamino)benzoic acid (Compound 38-1) as a white solid. LCMS-ESI (m/z) calculated for $C_{17}H_{15}ClF_3NO_3$: 373.76. found 374.1 (M+H)⁺, $t_R$=0.93 min (Method 6). ¹H NMR (400 MHz, CDCl₃) δ 7.67 (d, J=1.8 Hz, 1H), 7.50-7.44 (m, 2H), 7.41 (s, 1H), 7.09-7.02 (m, 2H), 5.23 (s, 2H), 3.03 (s, 6H).

Example 39

Synthesis of Compound 39-1

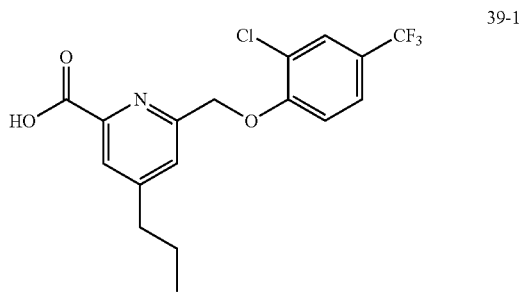 [SMILES: CCCc1cc(COc2ccc(C(F)(F)F)cc2Cl)nc(C(=O)O)c1]

39-1

Scheme 39

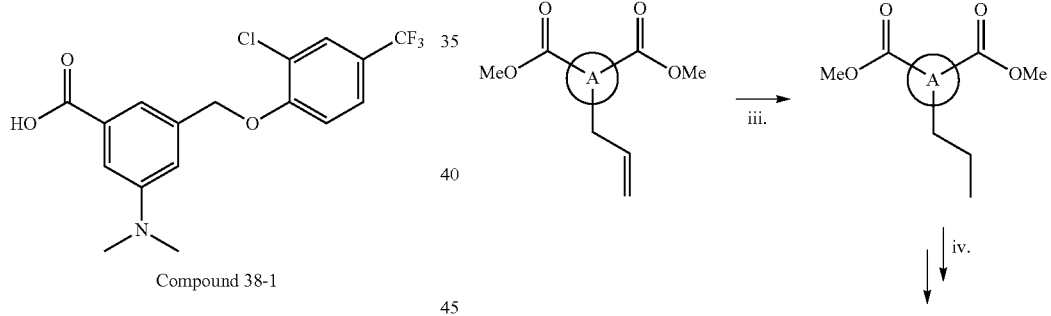

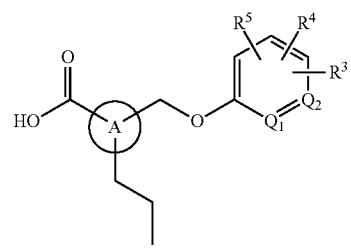

Reagents: (i) ⁱPrMgCl—LiCl, 3-bromoprop-1-ene, CuCN, THF; (ii) Pd(dppf)Cl₂, CO (gas), TEA, MeOH, DCM; (iii) Pd/C, H₂ (gas), MeOH; (ii) See Scheme 31.

Step 39-1. Synthesis of 4-allyl-2,6-dichloropyridine (INT 39-A)

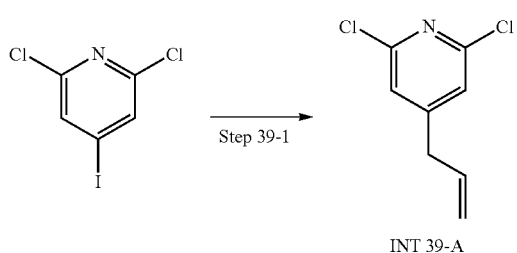

Into a mixture of ⁱPrMgCl—LiCl (1 M, 12.78 mL) in THF (100 mL) at −60° C. was added 2,6-dichloro-4-iodopyridine (2.8 g, 10.22 mmol). The mixture was stirred at −60° C. for 0.5 h, then 3-bromoprop-1-ene (1.55 g, 12.78 mmol) and CuCN (1.14 g, 12.78 mmol) were added and the mixture was stirred for 16 h at 25° C. The reaction mixture was quenched by the addition of $H_2O$ (100 mL) and extracted with EA (3×50 mL). The combined organic layers were dried and concentrated to give a residue that was purified by prep-TLC (PE) to provide 1.4 g (73%) of 4-allyl-2,6-dichloropyridine (INT 39-A) as a yellow oil. TLC (PE): $R_f$=0.50.

Step 39-2. Synthesis of dimethyl 4-allylpyridine-2,6-dicarboxylate (INT 39-B)

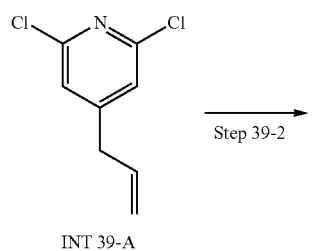

Into a solution of INT 39-A (1.4 g, 7.44 mmol) Pd(dppf) $C_{12}$—$CH_2Cl_2$ (3.04 g, 3.72 mmol) and TEA (6.22 mL, 44.67 mmol) in MeOH (10 mL) was bubbled CO gas (20.85 g, 744.47 mmol). The mixture was stirred at 70° C. for 12 h then filtered. The resulting residue was purified by $SiO_2$ chromatography (EA/PE) to provide 1.75 g (60%) of dimethyl 4-allylpyridine-2,6-dicarboxylate (INT 39-B) as a black solid. TLC (1:1 EA:PE): $R_f$=0.50.

Step 39-3. Synthesis of dimethyl 4-propylpyridine-2,6-dicarboxylate (INT 39-C)

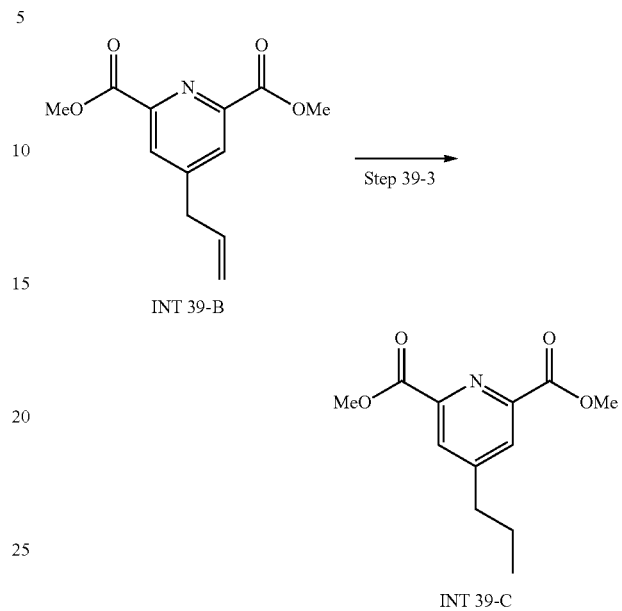

A solution of INT 39-B (2.9 g, 12.33 mmol) and Pd/C (0.3 g, 1.23 mmol, 10% purity) in MeOH (80 mL) was stirred at 25° C. for 12 h under $H_2$ (50 psi). The reaction mixture was filtered and concentrated to give a residue that was purified by $SiO_2$ chromatography (EA) to provide 2.5 g (85%) of dimethyl 4-propylpyridine-2,6-dicarboxylate (INT 39-C) as a yellow solid. TLC (1:1 EA:PE): $R_f$=0.80. $^1$H NMR (400 MHz, $CDCl_3$) δ ppm 8.14 (s, 2H) 4.02 (s, 6H) 2.76 (t, J=7.64 Hz, 2H) 1.75 (sxt, J=7.46 Hz, 2H)$_{0.98}$ (t, J=7.34 Hz, 3H).

Step 39-4. Synthesis of 6-((2-chloro-4-(trifluoromethyl)phenoxy)methyl)-4-propylpicolinic acid (Compound 39-1)

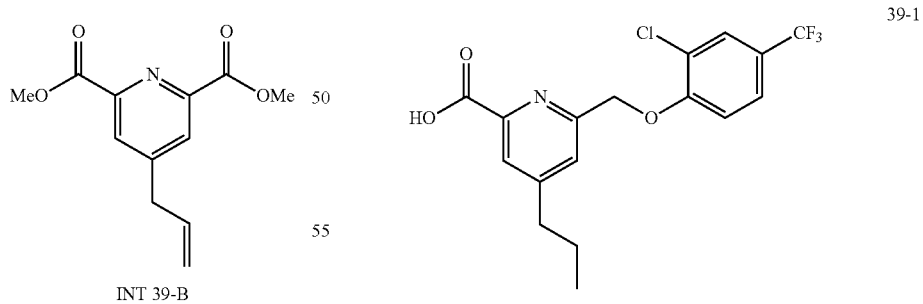

The synthesis of Compound 39-1 was completed from INT 39-C as demonstrated in Scheme 31. LCMS-ESI (m/z) calculated for $C_{17}H_{15}ClF_3NO_3$: 373.76. found 373.8 (M+H)⁺, $t_R$=0.786 min. (Method 6). $^1$H NMR (400 MHz, DMSO-d6) δ 7.85-7.91 (m, 2H) 7.71 (dd, J=8.76, 1.63 Hz, 1H) 7.61 (s, 1H) 7.45 (d, J=8.63 Hz, 1H), 5.42 (s, 2H) 2.70 (t, J=7.50 Hz, 2H) 1.62 (m, J=7.40 Hz, 2H) 0.87 (t, J=7.32 Hz, 3H).

Example 40

Synthesis of Compound 40-1

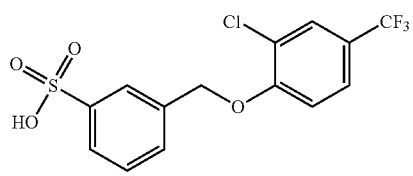

40-1

Scheme 40

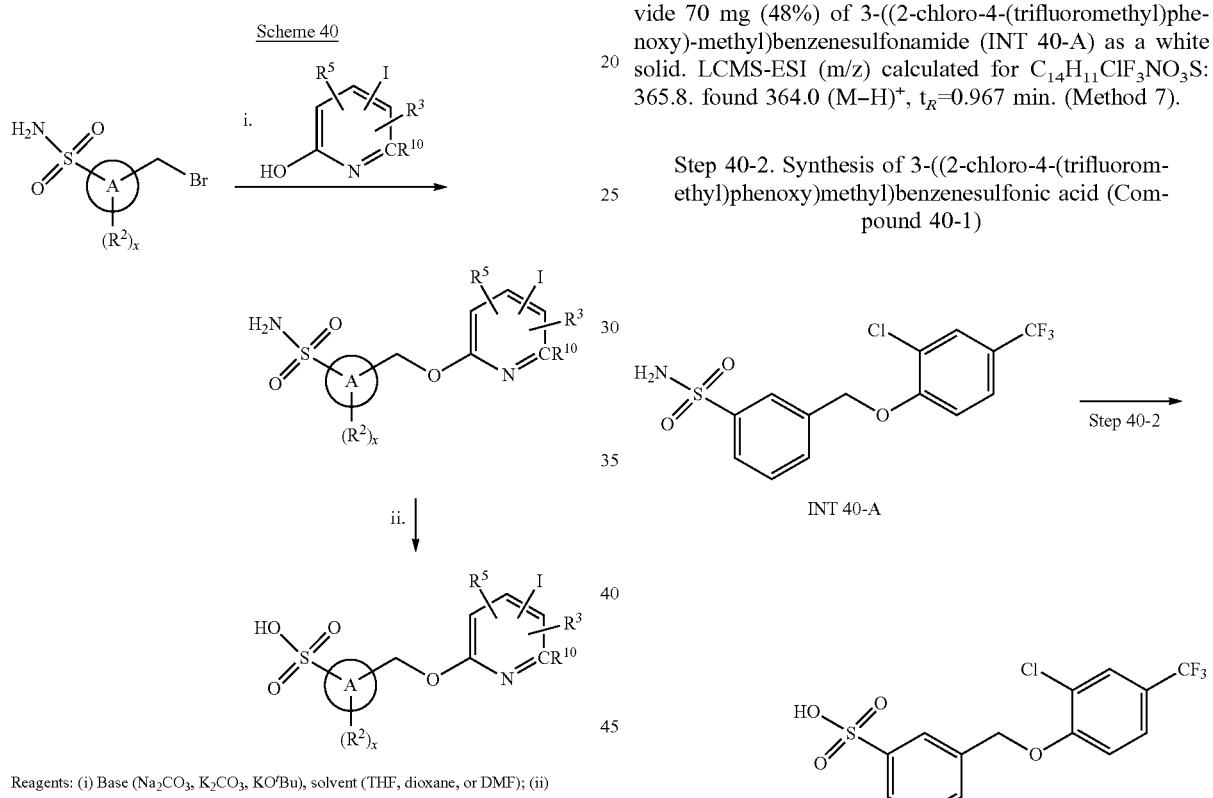

Reagents: (i) Base (Na₂CO₃, K₂CO₃, KOᵗBu), solvent (THF, dioxane, or DMF); (ii) NaOH, solvent (THF, MeOH or DMF).

Step 40-1. Synthesis of 3-((2-chloro-4-(trifluoromethyl)phenoxy)methyl) benzenesulfonamide INT 40-A)

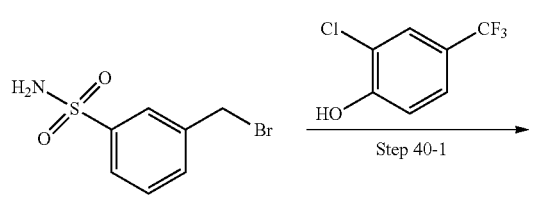

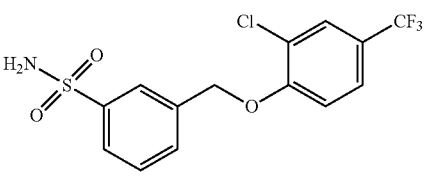

INT 40-A

To a solution of 3-(bromomethyl) benzenesulfonamide (100 mg, 400 μmol) in CH₃CN (3 mL) were added 2-chloro-4-(trifluoromethyl)phenol (78.6 mg, 400 μmol) and K₂CO₃ (111 mg, 800 μmol). After stirring at 30° C. for 12 h, the mixture was concentrated to give a crude product that was purified by prep-HPLC (H₂O(0.225% FA)/CH₃CN) to provide 70 mg (48%) of 3-((2-chloro-4-(trifluoromethyl)phenoxy)-methyl)benzenesulfonamide (INT 40-A) as a white solid. LCMS-ESI (m/z) calculated for $C_{14}H_{11}ClF_3NO_3S$: 365.8. found 364.0 (M–H)⁺, $t_R$=0.967 min. (Method 7).

Step 40-2. Synthesis of 3-((2-chloro-4-(trifluoromethyl)phenoxy)methyl)benzenesulfonic acid (Compound 40-1)

To a solution of INT 40-A (30 mg, 82 μmol) in THF (3 mL) were added HCl (2 M, 41.01 μL) and NaNO₂ (9.6 mg, 139 μmol). After stirring at 40° C. for 12 h, the mixture was concentrated to give a crude product that was purified by prep-HPLC (H₂O(0.1% TFA)/CH₃CN) to provide 2.6 mg (8.5%) of 3-((2-chloro-4-(trifluoromethyl)phenoxy)-methyl)benzenesulfonic acid (Compound 40-1) as brown gum. LCMS-ESI (m/z) calculated for $C_{14}H_{10}ClF_3O_4S$: 366.7. found 365.0 (M–H)⁺, $t_R$=0.708 min. (Method 7).

Example 41

Synthesis of Compound 41-1

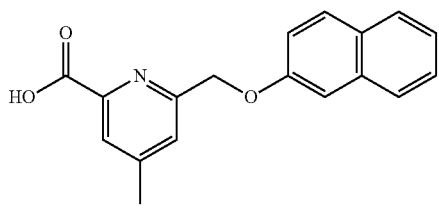

41-1

Scheme 41

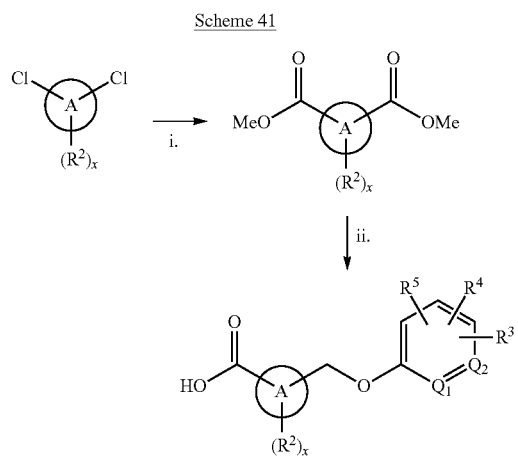

Reagents: (i) Pd(dppf)Cl₂—CH₂Cl₂, CO (gas), TEA, (ii) See Scheme 31.

Step 41-1. Synthesis of dimethyl 4-methylpyridine-2,6-dicarboxylate (INT 41-A)

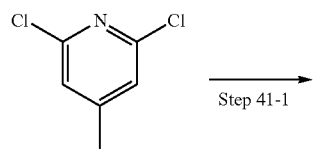

Step 41-1

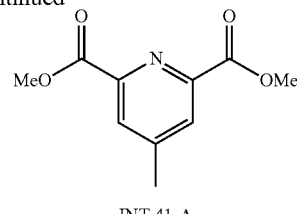

INT 41-A

To a solution of 2,6-dichloro-4-methyl-pyridine (1 g, 6.17 mmol) in DMF (20 mL) and MeOH (10 mL) were added Pd(dppf)Cl₂—CH₂Cl₂ (504.05 mg, 617.22 μmol) and TEA (3.44 mL, 24.69 mmol). After stirring at 80° C. under an atmosphere of CO (50 PSI) for 16 h, the reaction mixture was filtered, concentrated, diluted with H₂O and extracted with EA (2×50 mL). The combined organic layers were dried (Na₂SO₄), filtered, concentrated, and purified by SiO₂ chromatography (EA/PE) to provide 900 mg (68%) of dimethyl 4-methylpyridine-2,6-dicarboxylate (INT 41-A) as a yellow solid. TLC (2:1 EA:PE): $R_f$=0.20. LCMS-ESI (m/z) calculated for $C_{10}H_{11}NO_4$: 209.2. found 210.6 (M+H)⁺, $t_R$=0.756 min. (Method 7). ¹H NMR (400 MHz, DMSO-d6) δ 8.12 (d, J=0.7 Hz, 2H), 3.91 (s, 6H), 2.49-2.48 (s, 3H).

Step 41-2. Synthesis of 4-methyl-6-((naphthalen-2-yloxy)methyl)picolinic acid (Compound 41-1)

Compound 41-1

4-methyl-6-((naphthalen-2-yloxy)methyl)picolinic acid (Compound 41-1) was synthesized following Scheme 31 (Steps i-iv) from INT 41-A and naphthalen-2-ol, obtained as a white solid. LCMS-ESI (m/z) calculated for $C_{18}H_{15}NO_3$: 293.3. found 294.2 (M+H)⁺, $t_R$=0.789 min. (Method 7). ¹H NMR (400 MHz, DMSO-d6) δ 12.93-13.50 (m, 1H) 7.77-7.90 (m, 4H) 7.64 (s, 1H) 7.42-7.50 (m, 2H) 7.33-7.40 (m, 1H) 7.30 (dd, J=8.94, 2.44 Hz, 1H) 5.22-5.41 (m, 2H) 2.38-2.45 (m, 3H).

The compounds listed in Table 41 were made using the procedures of Scheme 41.

TABLE 41

| Structure | Cpd No. | Purity RT (min) | MW | observed m/z | Ion | Purity Method |
|---|---|---|---|---|---|---|
| 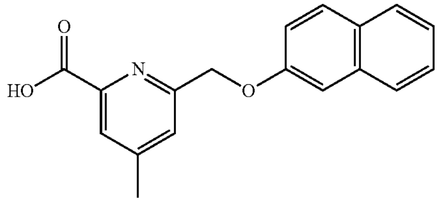 [SMILES: Cc1cc(COc2ccc3ccccc3c2)nc(C(=O)O)c1] | 41-1 | 0.715 | 293.32 | 293.9 | [M + H]⁺ | 6 |

TABLE 41-continued

| Structure | Cpd No. | Purity RT (min) | MW | observed m/z | Ion | Purity Method |
|---|---|---|---|---|---|---|
| 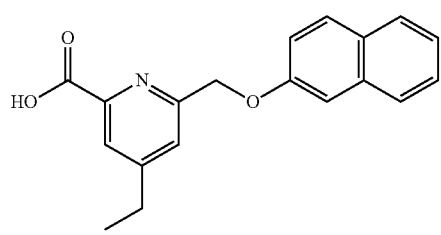 | 41-2 | 0.913 | 345.70 | 346 | [M + H]⁺ | 6 |

Example 42

Synthesis of Compound 42-1

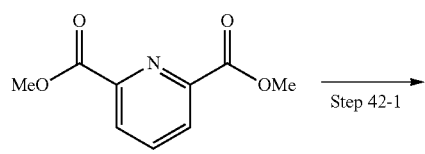
42-1

Scheme 42

Reagents: (i) Aldehyde, aq. H₂SO₄, FeSO₄, 30% H₂O₂; (ii). See Scheme 31.

Step 42-1. Synthesis of dimethyl 4-ethylpyridine-2,6-dicarboxylate (INT 42-A)

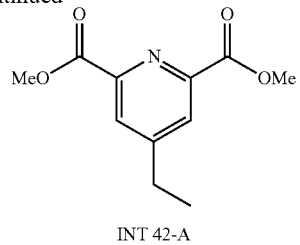

INT 42-A

To a solution of dimethyl pyridine-2,6-dicarboxylate (10 g, 51.2 mmol) and propanal (18.65 mL, 256.2 mmol) in $H_2SO_4$ (100 mL) were added $FeSO_4$ (5.70 g, 20.49 mmol) and 30% $H_2O_2$ (9.85 mL, 102.47 mmol) dropwise over 15 min. After stirring at 0° C. for 15 min, the mixture was diluted with saturated $K_2CO_3$(aq) and extracted with EA (3×200 mL). The combined organic layers were dried ($Na_2SO_4$), concentrated, purified by $SiO_2$ chromatography (EA/PE) to provide 4.5 g (39%) of dimethyl 4-ethylpyridine-2,6-dicarboxylate (INT 42-A) as a yellow solid. TLC (3:1 EA:PE): $R_f$=0.60. $^1$H NMR (400 MHz, CDCl₃) δ 8.13-8.20 (m, 2H) 4.00-4.03 (m, 6H) 2.78-2.87 (m, 2H) 1.29-1.37 (m, 3H).

Step 42-2. Synthesis of 4-ethyl-6-((naphthalen-2-yloxy)methyl)picolinic acid (Compound 42-1)

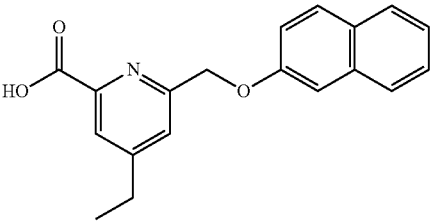

Compound 42-1

4-ethyl-6-((naphthalen-2-yloxy) methyl) picolinic acid (Compound 42-1) was synthesized following Scheme 31 (Steps i-iv) from INT 42-A and naphthalen-2-ol, and was obtained as a light yellow solid. LCMS-ESI (m/z) calculated for $C_{19}H_{17}NO_3$: 307.4. found 307.9 (M+H)⁺, $t_R$=0.743 min. (Method 6). $^1$H NMR (400 MHz, DMSO-d6) δ 12.82-13.61 (m, 1H) 7.78-7.91 (m, 4H) 7.68 (s, 1H) 7.43-7.50 (m, 2H) 7.33-7.39 (m, 1H) 7.31 (dd, J=8.88, 2.50 Hz, 1H) 5.26-5.41 (m, 2H) 2.74 (q, J=7.63 Hz, 2H) 1.13-1.30 (m, 3H).

The compounds listed in Table 42 were made using the procedures of Scheme 42.

TABLE 42
| Structure | Cpd No. | Purity RT (min) | MW | observed m/z | Ion | Purity Method |
|---|---|---|---|---|---|---|
| 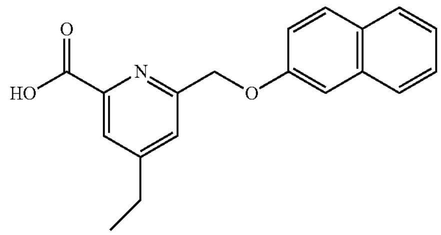 [SMILES: CCc1cc(COc2ccc3ccccc3c2)nc(C(=O)O)c1] | 42-1 | 0.754 | 307.35 | 307.9 | [M + H]⁺ | 6 |
| 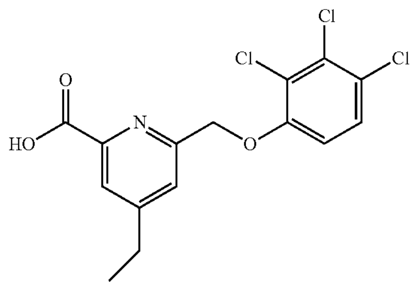 [SMILES: CCc1cc(COc2ccc(Cl)c(Cl)c2Cl)nc(C(=O)O)c1] | 42-2 | 0.828 | 360.62 | 359.8 | [M − H]⁺ | 6 |
| 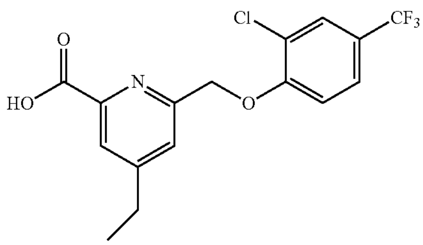 [SMILES: CCc1cc(COc2ccc(C(F)(F)F)cc2Cl)nc(C(=O)O)c1] | 42-3 | 1.007 | 359.73 | 360.2 | [M + H]⁺ | 6 |
Example 43
Synthesis of Compound 43-1
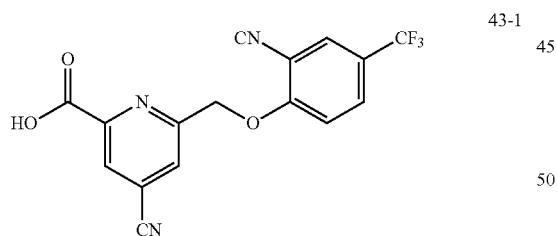
Scheme 43
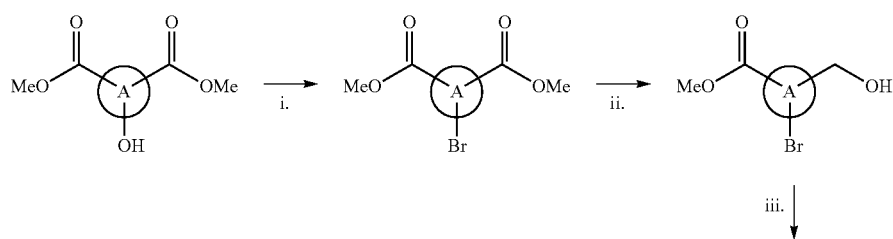

-continued

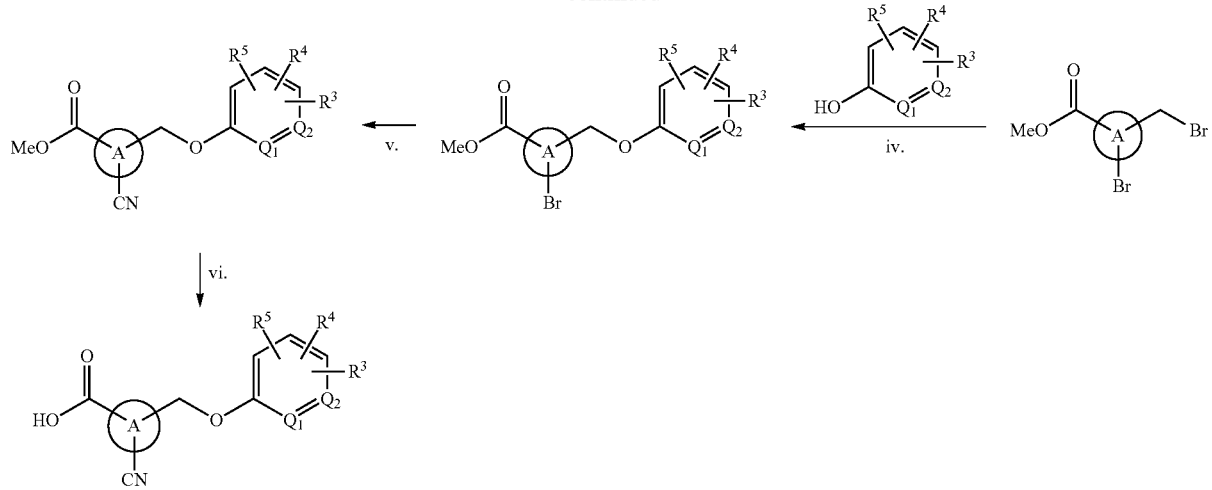

Reagents: (i) PBr₃, Br₂, hexanes; (ii) NaBH₄, MeOH, DCM; (iii) PBr₃, CHCl₃; (iv) Base (Na₂CO₃, K₂CO₃, KOᵗBu), solvent (THF, dioxane, or DMF); (iv). Zn(CN)₂, Pd(PPh₃)₄, DMF; (v) NaOH, solvent (THF, MeOH or DMF).

Step 43-1. Synthesis of dimethyl 4-bromopyridine-2,6-dicarboxylate (INT 43-A)

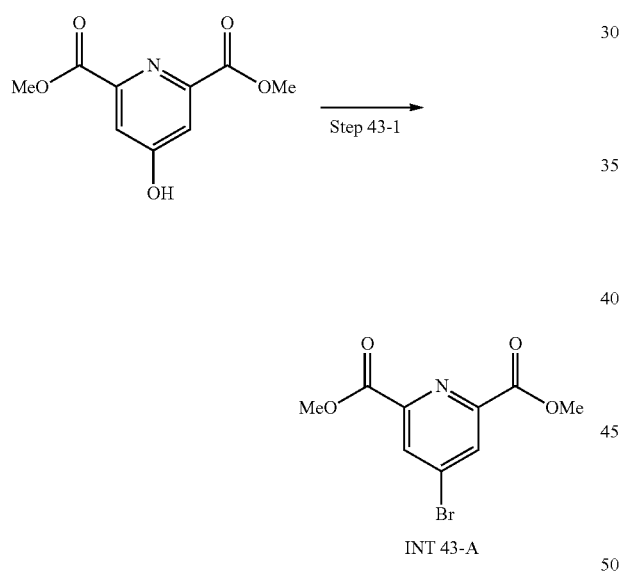

PBr₃ (1.61 mL, 16.9 mmol) was added to a solution of Br₂ (700 µL, 13.7 mmol) in hexanes (10.0 mL) at 0° C. The mixture was stirred at 22° C. for 1 h. 4-Hydroxypyridine-2,6-dicarboxylic acid (1.00 g, 5.46 mmol) was added, and the mixture was stirred at 90° C. for 6 h. The mixture was cooled and diluted with CHCl₃ (50 mL). Anhydrous MeOH (50 mL) was added dropwise at 0° C., and the mixture was stirred at 22° C. for 1 h. The mixture was concentrated, and the residue was dissolved in DCM (50 mL) and diluted with sat. aq. NaHCO₃ (50 mL). The aq. phase was extracted with DCM (4×50 mL), and the combined organic layers were dried (Na₂SO₄), filtered, and concentrated under reduced pressure. The residue was purified by SiO₂ chromatography (EA/hexanes) to provide 924 mg (62%) of dimethyl 4-bromopyridine-2,6-dicarboxylate (INT 43-A) as a solid. LCMS-ESI (m/z) calculated for $C_9H_8BrNO_4$: 274.07. found 276.1 (M+H)⁺, $t_R$=2.04 min. (Method 13).

Step 43-2. Synthesis of methyl 4-bromo-6-(hydroxymethyl)pyridine-2-carboxylate (INT 43-B)

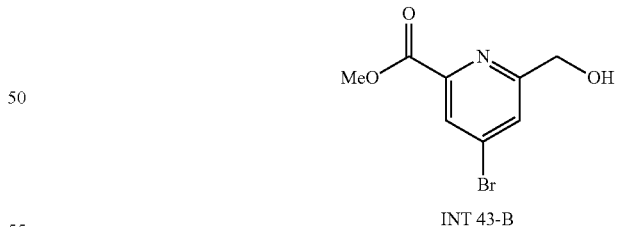

NaBH₄ (191 mg, 5.06 mmol) was added to a solution of INT 43-A (924 mg, 3.37 mmol) in MeOH and DCM (4:1 v/v, 50 mL) at 0° C. The mixture was stirred at 0° C. for 30 min. Saturated aq. NaHCO₃ (50 mL) was added, and the aq. phase was extracted with DCM (4×30 mL). The combined organic layers were dried (Na₂SO₄), filtered, and concentrated to provide 690 mg (83%) of methyl 4-bromo-6-(hydroxymethyl)pyridine-2-carboxylate (INT 43-B) as a solid. LCMS-ESI (m/z) calculated for $C_8H_8BrNO_3$: 246.06. found 246.1 (M+H)⁺, $t_R$=1.78 min. (Method 13).

Step 43-3. Synthesis of methyl 4-bromo-6-(bromomethyl)pyridine-2-carboxylate (INT 43-C)

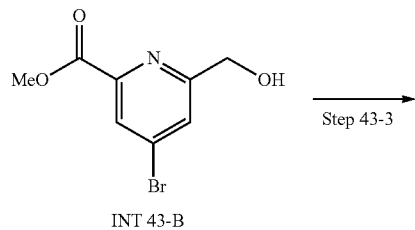

INT 43-B

PBr$_3$ (450 µL, 4.74 mmol) was added to a solution of INT 43-B (690 mg, 2.80 mmol) in CHCl$_3$ (35.0 mL) at 0° C. The mixture was stirred at 22° C. for 5 h, cooled to 0° C., and diluted with sat. aq. K$_2$CO$_3$ (25.0 mL). The aq. phase was extracted with EA (3×30 mL), and the combined organic layers were washed with brine (20 mL), dried (Na$_2$SO$_4$), filtered, and concentrated. The residue was purified by SiO$_2$ chromatography (EA/hexanes) to provide 700 mg (81%) of dimethyl 4-bromopyridine-2,6-dicarboxylate (INT 43-C) as a solid. LCMS-ESI (m/z) calculated for C$_8$H$_7$Br$_2$NO$_2$: 308.96. found 246.1 (M+H)$^+$, t$_R$=2.22 min. (Method 13).

Step 43-4. Synthesis of methyl 4-bromo-6-((2-chloro-4-(trifluoromethyl)phenoxy)methyl) pyridine-2-carboxylate (INT 43-D)

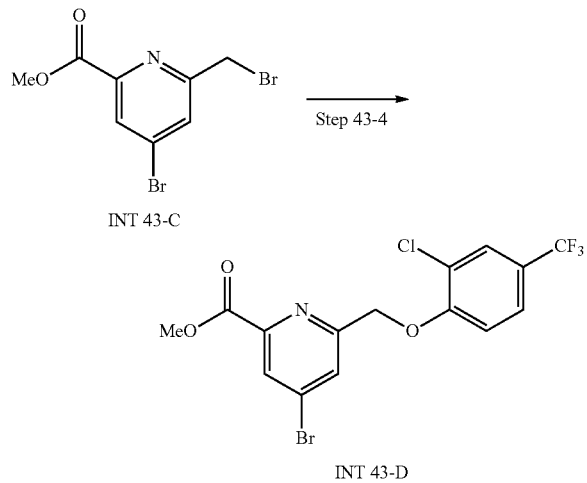

2-Chloro-4-(trifluoromethyl)phenol (490 mg, 2.49 mmol) and Cs$_2$CO$_3$ (1.48 g, 4.53 mmol) were added to a solution of INT 43-C (700 mg, 2.27 mmol) in anhydrous DMF (5 mL) at 22° C. The mixture was stirred at 50° C. for 18 h, cooled to rt, and diluted with H$_2$O (25 mL). The aq. phase was extracted with EA (3×30 mL), and the combined organic layers were washed with brine (20 mL), dried (Na$_2$SO$_4$), filtered, and concentrated. The residue was purified by SiO$_2$ chromatography (EA/hexanes) to provide 750 mg (78%) of methyl 4-bromo-6-((2-chloro-4-(trifluoromethyl)phenoxy)methyl)pyridine-2-carboxylate (INT 43-D) as a solid. LCMS-ESI (m/z) calculated for C$_{15}$H$_{10}$BrClF$_3$NO$_3$: 422.95. found 424.4 (M+H)$^+$, t$_R$=2.78 min. (Method 13).

Step 43-5. Synthesis of methyl 4-bromo-6-((2-chloro-4-(trifluoromethyl)phenoxy)methyl) pyridine-2-carboxylate (INT 43-E)

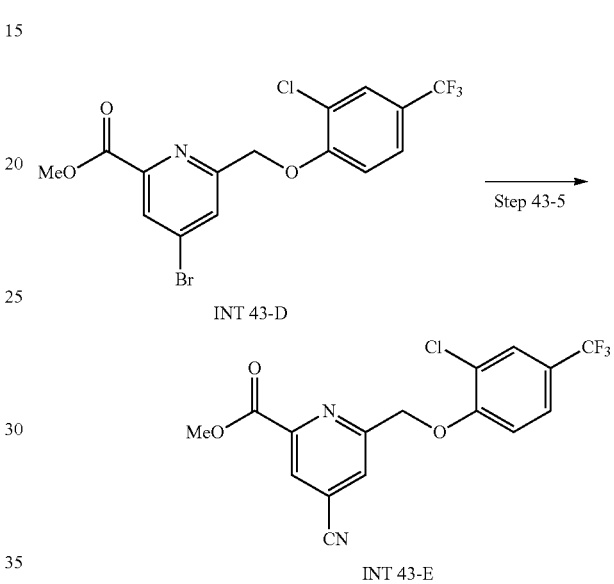

Zn(CN)$_2$ (59.7 mg, 0.509 mmol) and Pd(PPh$_3$)$_4$ (44.1 mg, 0.038 mmol) were added to a solution of INT 43-D (108 mg, 0.254 mmol) in degassed DMF (2.00 mL) at 22° C. The mixture was purged with N$_2$ for 5 min and stirred at 150° C. for 6 h. The mixture was concentrated, and the residue was purified by SiO$_2$ chromatography (EA/hexanes) to provide 74 mg (79%) of methyl 4-bromo-6-((2-chloro-4-(trifluoromethyl)phenoxy)methyl)pyridine-2-carboxylate (INT 43-E) as a solid. LCMS-ESI (m/z) calculated for C$_{16}$H$_{10}$ClF$_3$N$_2$O$_3$: 370.03; m/z not observed)$^+$, t$_R$=2.78 min. (Method 13).

Step 43-6. Synthesis of 6-((2-chloro-4-(trifluoromethyl)phenoxy)methyl)-4-cyano-pyridine-2-carboxylic acid (Compound 43-1)

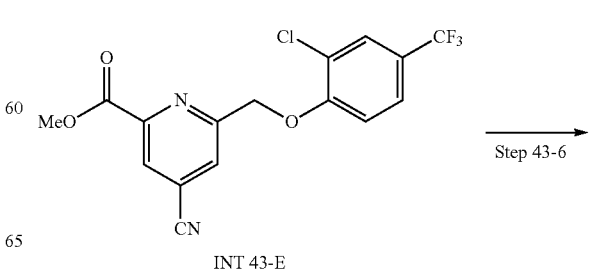

INT 43-E

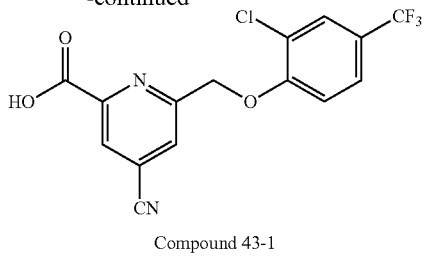

Compound 43-1

Aqueous 2 M NaOH (299 μL 0.150 mmol) was added to a solution of INT 43-E (74.0 mg, 0.20 mmol) in MeOH (1 mL) and THF (1 mL) at 22° C. The mixture was stirred at 22° C. for 2 h and concentrated. The residue was acidified with aq. 2 M HCl (pH 2) and diluted with $H_2O$ (10 mL). The aq. phase was extracted with EA (3×10 mL), and the combined organic layers were washed with brine (10 mL), dried ($Na_2SO_4$), filtered, and concentrated. The residue was purified by reverse phase chromatography ($H_2O$ (+0.1% formic acid)/$CH_3CN$) to provide 63 mg (89%) of 6-((2-chloro-4-(trifluoromethyl)phenoxy) methyl)-4-cyano-pyridine-2-carboxylic acid (Compound 43-1) as a solid. LCMS-ESI (m/z) calculated for $C_{15}H_8ClF_3N_2O_3$: 356.7. found 357.1 (M+H)$^+$, $t_R$=3.91 min. (Method 12). $^1$H NMR (500 MHz, DMSO-d6) δ 13.84 (br s, 1H), 8.39 (d, J=1.4 Hz, 1H), 8.17 (d, J=1.4 Hz, 1H), 7.92 (d, J=2.2 Hz, 1H), 7.73 (dd, J=2.3, 8.7 Hz, 1H), 7.48 (d, J=8.7 Hz, 1H), 5.51 (s, 2H).

Example 44

Synthesis of Compound 44-1

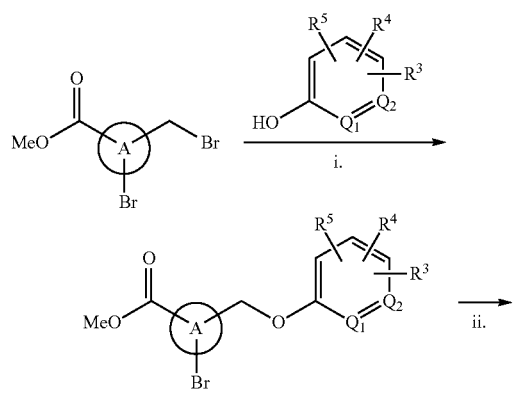

44-1

Scheme 44

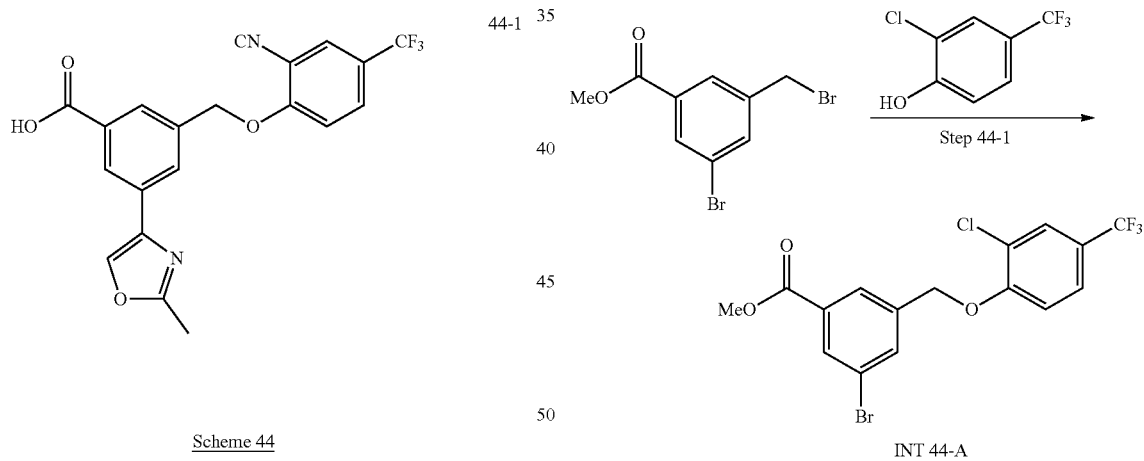

Reagents: (i) Base ($Na_2CO_3$, $K_2CO_3$, KO$^t$Bu), solvent (THF, dioxane, or DMF); (ii) 2-methyloxazole, Pd(PPh$_3$)$_4$, KOAc, DMF; (v) NaOH, solvent (THF, MeOH or DMF).

Step 44-1. Synthesis of methyl 3-bromo-5-((2-chloro-4-(trifluoromethyl)phenoxy)methyl) benzoate (INT 44-A)

INT 44-A

A mixture of methyl 3-bromo-5-(bromomethyl)benzoate (3.60 g, 11.7 mmol), 2-chloro-4-(trifluoromethyl)phenol (1.48 mL, 11.1 mmol) and $K_2CO_3$ (4.85 g, 35.1 mmol) in acetone (30 mL) was stirred at 90° C. for 1 h. The mixture was filtered, and the filtrate was concentrated. The residue was purified by $SiO_2$ chromatography (EA/hexanes) to provide 2.36 g (48%) of methyl 3-bromo-5-((2-chloro-4-(trifluoromethyl)phenoxy)methyl)benzoate (INT 44-A) as a solid. LCMS-ESI (m/z) calculated for $C_{16}H_{11}BrClF_3O_3$: 423.61. found 442.2 (M+$H_2O$)$^+$, $t_R$=3.29 min (Method 13). $^1$H NMR (400 MHz, CDCl$_3$) δ 8.18-8.13 (m, 1H), 8.05 (tt, J=1.5, 0.7 Hz, 1H), 7.84 (td, J=1.7, 0.8 Hz, 1H), 7.68 (dt, J=2.3, 0.7 Hz, 1H), 7.52-7.45 (m, 1H), 7.06-6.94 (m, 1H), 5.20 (s, 2H), 3.94 (s, 3H).

Step 44-2. Synthesis of methyl 3-((2-chloro-4-(trifluoromethyl)phenoxy)methyl)-5-(2-methyloxazol-5-yl)benzoate (INT 44-B)

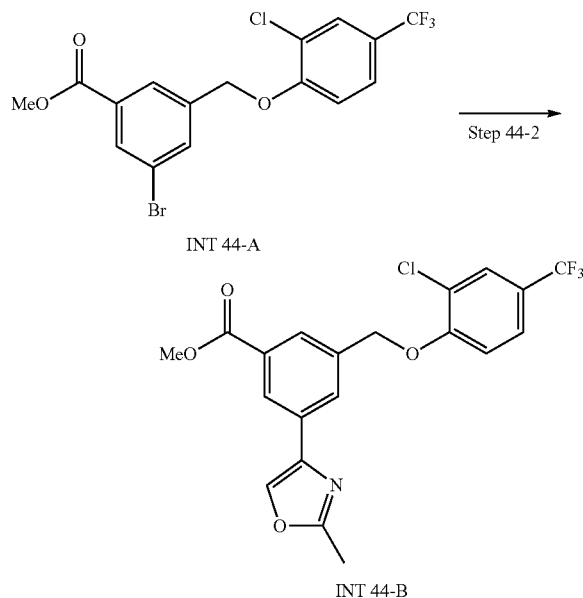

A mixture of INT 44-A (150 mg, 0.354 mmol), 2-methyloxazole (58.0 μL, 0.708 mmol), Pd(PPh₃)₄ (41.0 mg, 0.035 mmol), and KOAc (70.0 mg, 0.708 mmol) in DMF (4.00 mL) was stirred at 110° C. for 16 h. The mixture was cooled and diluted with H₂O (20 mL). The aq. phase was extracted with EA (3×20.0 mL), and the combined organic layers were washed with brine (20 mL), dried (MgSO₄), filtered, and concentrated. The residue was purified by SiO₂ chromatography (EA/hexanes) to provide 98 mg (65%) of methyl 3-((2-chloro-4-(trifluoromethyl)phenoxy)methyl)-5-(2-methyloxazol-5-yl)benzoate (INT 44-B) as a solid. LCMS-ESI (m/z) calculated for C₂₀H₁₅ClF₃NO₄: 425.06. found 426.25 (M+H)⁺, t$_R$=2.79 min (Method 13). ¹H NMR (500 MHz, CDCl₃) δ 8.25 (t, J=1.6 Hz, 1H), 8.07-8.03 (m, 1H), 7.95-7.89 (m, 1H), 7.71-7.65 (m, 1H), 7.49 (ddd, J=8.7, 2.3, 0.8 Hz, 1H), 7.33 (s, 1H), 7.08-7.00 (m, 1H), 5.26 (s, 2H), 3.97 (s, 3H), 2.56 (s, 3H).

Step 44-3. Synthesis of 3-((2-chloro-4-(trifluoromethyl)phenoxy)methyl)-5-(2-methyloxazol-5-yl)benzoic acid (Compound 44-1)

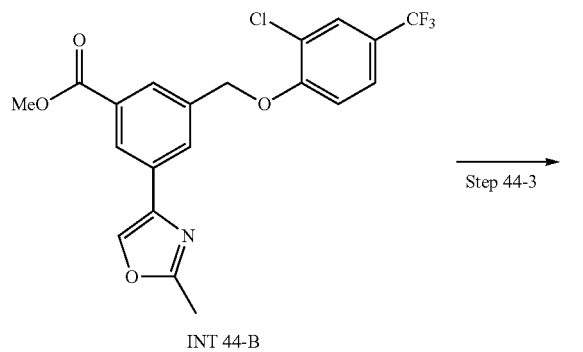

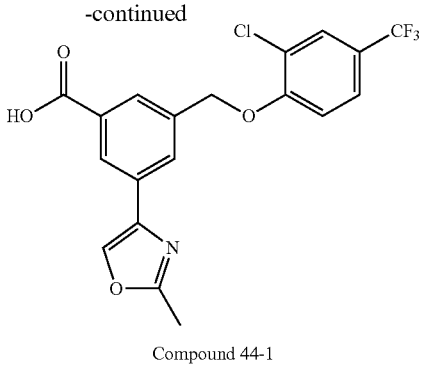

Compound 44-1

A solution of NaOH (1 M in H₂O, 676 μL, 0.676 mmol) was added to a mixture of INT 44-B (96.0 mg, 0.225 mmol) in THF and H₂O (3:1 v/v, 4.00 mL). The mixture was stirred at 22° C. for 4 h. The mixture was acidified with aq. 1 M HCl (pH 2) and diluted with EA (20 mL). The aq. phase was extracted with EA (2×30 mL), and the combined organic layers were washed with brine (20 mL), dried (MgSO₄), filtered, and concentrated. The residue was purified by SiO₂ chromatography (MeOH/DCM) to provide 77.5 mg (83%) of 3-((2-chloro-4-(trifluoromethyl)phenoxy)methyl)-5-(2-methyloxazol-5-yl) benzoic acid (Compound 44-1) as a solid. LCMS-ESI (m/z) calculated for C₁₉H₁₃ClF₃NO₄: 411.05. found 412.2 (M+H)⁺, t$_R$=4.59 min (Method 12). ¹H NMR (500 MHz, DMSO-d6) δ 13.35 (s, 1H), 8.17 (dd, J=1.7 Hz, 1H), 8.04-7.98 (m, 2H), 7.88 (d, J=2.3 Hz, 1H), 7.73 (dd, J=8.9, 2.3 Hz, 1H), 7.66 (s, 1H), 7.45 (d, J=8.7 Hz, 1H), 5.43 (s, 2H), 2.50 (s, 3H).

Example 45

Synthesis of Compounds 45-1 and 45-2

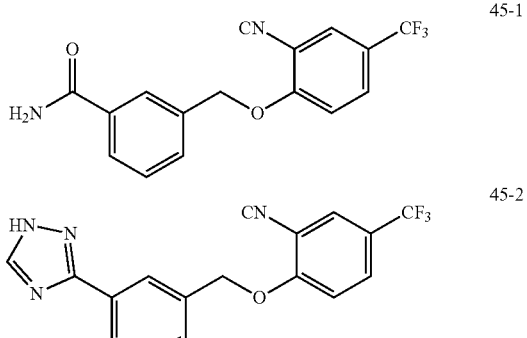

Scheme 45

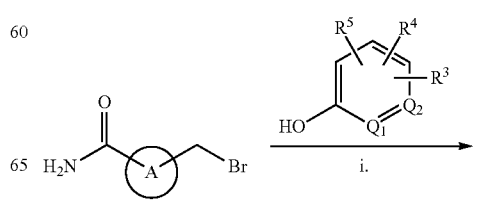

-continued

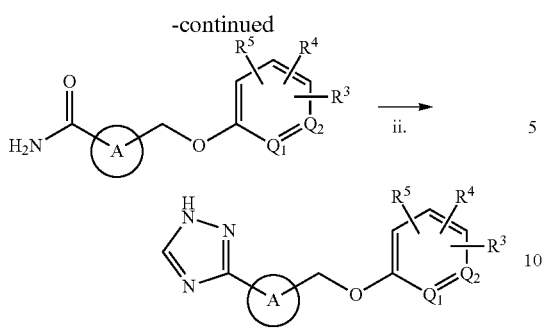

Reagents: (i) Base (NaH, Na$_2$CO$_3$, K$_2$CO$_3$, KO$^t$Bu), solvent (THF, dioxane, or DMF); (ii). dimethylformamide dimethyl acetal, N$_2$H$_4$—H$_2$O, AcOH.

Step 45-1. Synthesis of 3-((2-chloro-4-(trifluoromethyl)phenoxy)methyl)benzamide (Compound 45-1)

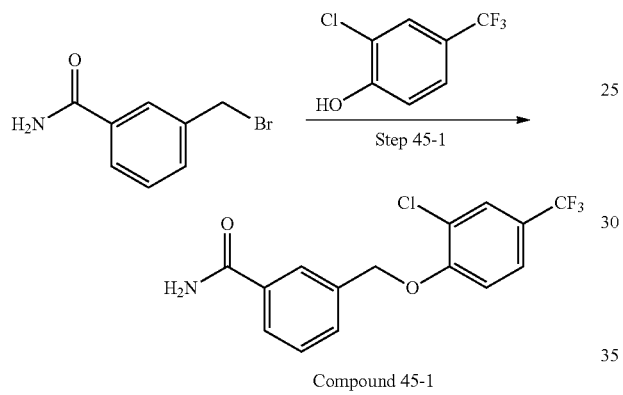

Compound 45-1

Into a solution of 3-(bromomethyl) benzamide (254 mg, 1.29 mmol) in DMF (5 mL) at 0° C. was added NaH. After the reaction mixture was stirred and allowed to warm to RT over 30 min, 2-chloro-4-(trifluoromethyl)phenol (250 mg, 1.17 mmol) was added. After 4 h, the reaction mixture was diluted with EA and washed with H$_2$O, 1 M HCl, 1 M NaOH, H$_2$O, brine, dried (Na$_2$SO$_4$), filtered and concentrated. The resulting crude residue was purified by reverse phase SiO$_2$ chromatography (MeOH/H$_2$O) to provide material that was triturated with MeOH/H$_2$O, filtered, and dried in vacuo to provide 260 mg (67%) of 3-((2-chloro-4-(trifluoromethyl)phenoxy)methyl)benzamide (Compound 45-1). LCMS-ESI (m/z) calculated for C$_{15}$H$_{11}$ClF$_3$NO$_2$: 329.04. found 330.1 (M+H)$^+$, t$_R$=12.14 min (Method 10). $^1$H NMR (300 MHz, CDCl$_3$) δ 7.96 (s, 1H), 7.80 (d, J=7.7 Hz, 1H), 7.69 (s, 1H), 7.68 (d, J=8.3 Hz, 1H), 7.54 (d, J=7.7 Hz, 1H), 7.51 (d, J=6.6 Hz, 1H), 7.05 (d, J=8.7 Hz, 1H), 6.11 (bs, 1H), 5.69 (bs, 1H), 5.28 (s, 2H).

Step 45-2. Synthesis of 3-(3-((2-chloro-4-(trifluoromethyl)phenoxy)methyl)phenyl)-1H-1,2,4-triazole (Compound 45-2)

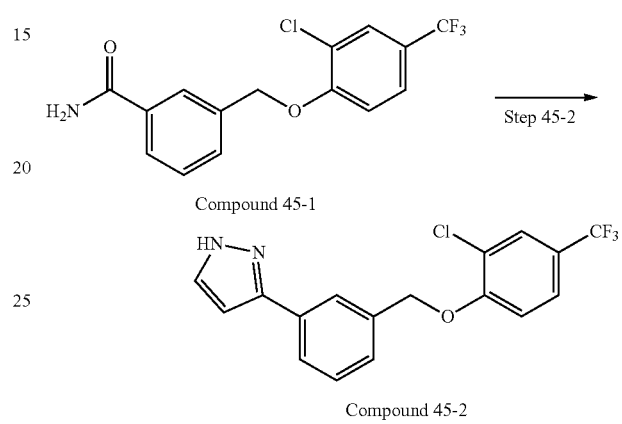

A solution of Compound 45-1 (260 mg, 0.079 mmol) in dimethylformamide dimethyl acetal (4 mL) was heated at 120° C. for 2 h. The reaction mixture was cooled to RT and concentrated in vacuo. The resulting residue was dissolved in AcOH (4 mL) and N$_2$H$_4$—H$_2$O (47 mg, 0.946 mmol) was added dropwise. After stirring at 90° C. for 2 h, the mixture was concentrated, diluted with Et$_2$O and cooled to 0° C. The resulting precipitate was collected by filtration and purified by SiO$_2$ chromatography (EA/hexane) to provide 125 mg (45%) of 3-((2-chloro-4-(trifluoromethyl)phenoxy)m)methyl)benzamide (Compound 45-2). LCMS-ESI (m/z) calculated for C$_{16}$H$_{11}$ClF$_3$N$_3$O: 353.05. found 354.5 (M+H)$^+$, t$_R$=13.56 min (Method 10). $^1$H NMR (300 MHz, CDCl$_3$) δ 8.30 (s, 1H), 8.16 (s, 1H), 8.04 (d, J=7.5 Hz, 1H), 7.76 (d, J=2.9 Hz, 1H), 7.56-7.44 (m, 3H), 7.03 (d, J=8.6 Hz, 1H), 5.24 (s, 2H).

The compounds listed in Table 45 were made using the procedures of Scheme 45.

TABLE 45

| Structure | Cpd No. | RT (min) | MW | observed m/z | Ion | Purity Method |
|---|---|---|---|---|---|---|
| ![structure] | 45-1 | 13.13 | 329.70 | 330.1 | [M + H]$^+$ | 10 |

TABLE 45-continued

| Structure | Cpd No. | Purity RT (min) | MW | observed m/z | Ion | Purity Method |
|---|---|---|---|---|---|---|
| 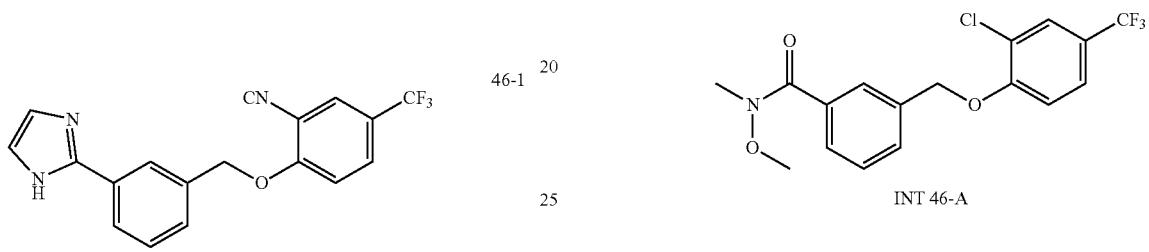 | 45-2 | 13.56 | 353.73 | 354.5 | [M + H]⁺ | 10 |

Example 46

Synthesis of Compound 46-1

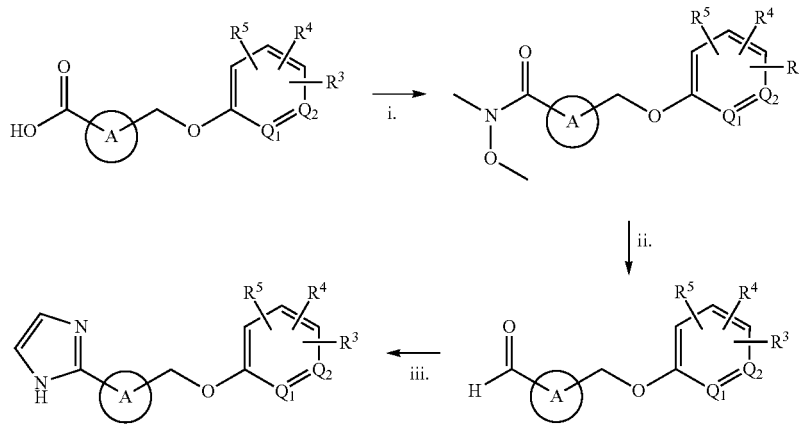

Scheme 46

Reagents: (i) N,O-dimethylhydroxylamine hydrochloride, HATU, DIPEA, DMF; (ii) DIBAL, THF, -78° C.; (iii) oxalaldehyde, NH₄OH, EtOH Step 46-1. Synthesis of 3-((2-chloro-4-(trifluoromethyl)phenoxy)methyl)-N-methoxy-N-methyl benzamide (INT 46-A)

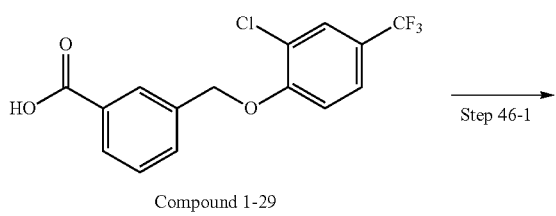

Into a solution of Compound 1-29 (500 mg, 1.51 mmol) in DMF (10 mL) were added N,O-dimethylhydroxylamine hydrochloride (161 mg, 1.66 mmol), HATU (632 mg, 1.66 mmol), and DIPEA (585 mg, 4.5 mmol). After the reaction mixture was stirred for 18 h, the reaction mixture was acidified with TFA and purified by reverse phase SiO₂ chromatography (MeOH/H₂O, 0/1% TFA) to provide 530 mg (94%) of 3-((2-chloro-4-(trifluoromethyl)phenoxy)methyl)-N-methoxy-N-methylbenzamide (INT 46-A). LCMS-ESI (m/z) calculated for $C_{17}H_{15}ClF_3NO_3$: 373.07; m/z not observed; $t_R$=6.2 min (Method 11).

Step 46-2. Synthesis of 3-((2-chloro-4-(trifluoromethyl)phenoxy)methyl)benzaldehyde (INT 46-B)

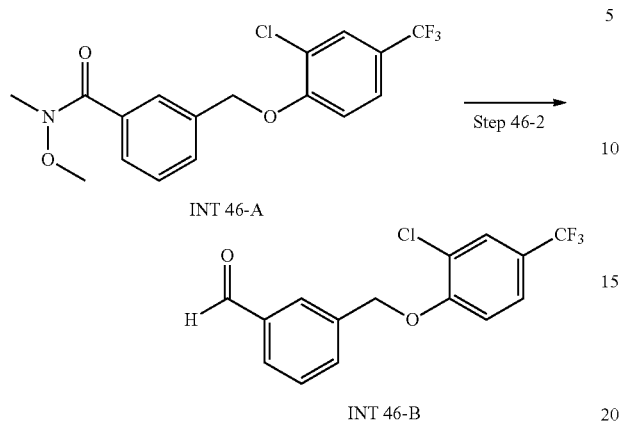

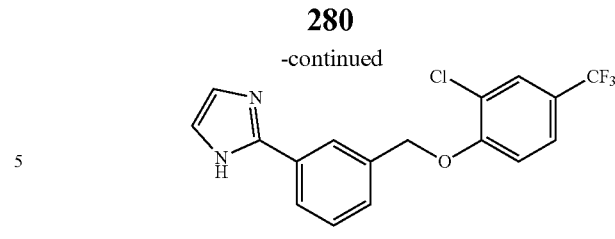

Compound 46-1

Into a solution of INT 46-A (1000 mg, 2.68 mmol) in THF (10 mL) at −78° C. was added DIBAL (3.21 mL of 1M/THF solution, 3.21 mmol). After the reaction mixture was stirred for 30 min, H$_2$O was added and the solution was extracted EA, dried (Na$_2$SO$_4$), and purified by SiO$_2$ chromatography (EA/hexanes) to provide 600 mg (71.1%) of 3-((2-chloro-4-(trifluoromethyl)phenoxy)methyl)benzaldehyde (INT 46-B). LCMS-ESI (m/z) calculated for C$_{15}$H$_{10}$ClF$_3$O$_2$: 314.03; m/z not observed, t$_R$=6.3 min (Method 11).

Step 46-3. Synthesis of 2-(3-((2-chloro-4-(trifluoromethyl)phenoxy)methyl)phenyl)-1H-imidazole (Compound 46-1)

Into a solution of INT 46-B (100 mg, 0.32 mmol) in EtOH (5 mL) at 0° C. were added oxalaldehyde (0.04 mL of 8.8M/H$_2$O solution, 0.35 mmol) and NH$_4$OH (0.053 mL of 29% solution in EtOH, 0.44 mmol). After stirring for 48 h, the mixture was concentrated and purified by SiO$_2$ chromatography (EA/hexanes) to provide 40 mg (35%) of 2-(3-((2-chloro-4-(trifluoromethyl)phenoxy)methyl)phenyl)-1H-imidazole (Compound 46-1) as a white solid. LCMS-ESI (m/z) calculated for C$_{17}$H$_{12}$ClF$_3$N$_2$O: 352.74. found 353.2 (M+H)$^+$, t$_R$=11.97 min (Method 10). $^1$H NMR (400 MHz, DMSO-d6) δ 12.6 (s, 1H), 8.08 (s, 1H), 8.00-7.75 (m, 2H), 7.72 (d, J=6 Hz, 1H), 7.60-7.35 (m, 3H), 7.26 (bs, 1H), 7.04 (bs, 1H), 5.38 (s, 2H).

Example 47

Synthesis of Compound 47-1

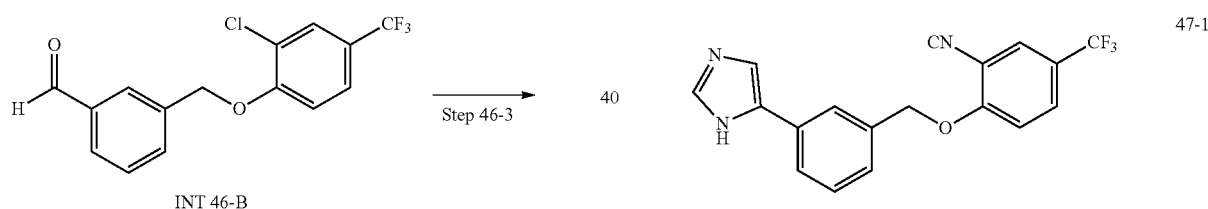

47-1

Scheme 47

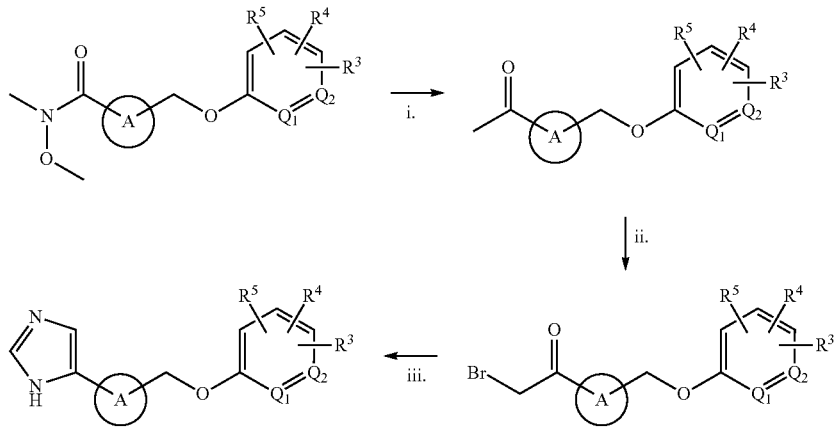

Reagents: (i) MeMgBr, Et$_2$O; (ii) Br$_2$, DCM; (iii) formamide.

Step 47-1. Synthesis of 1-(3-((2-chloro-4-(trifluoromethyl)phenoxy)methyl)phenyl)ethan-1-one INT 47-A)

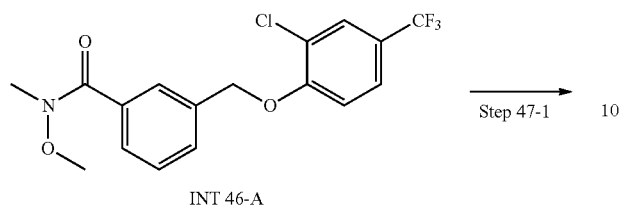

INT 46-A

Into a solution of INT 46-A (480 mg, 1.28 mmol) in Et$_2$O (20 mL) was added MeMgBr (0.557 mL of 3M solution in Et$_2$O, 1.67 mmol). After the reaction mixture was stirred for 6 h, the reaction mixture was quenched with 0.1 m HCl (50 mL) and extracted into EA. The resulting organic layer was washed with brine, dried (Na$_2$SO$_4$), filtered, concentrated, and purified by SiO$_2$ chromatography (EA/hexanes) to provide 224 mg (53%) of 1-(3-((2-chloro-4-(trifluoromethyl) phenoxy)methyl)phenyl)ethan-1-one (INT 47-A). LCMS-ESI (m/z) calculated for C$_{17}$H$_{15}$ClF$_3$NO$_3$: 373.07; m/z not observed; $t_R$=6.2 min (Method 11).

Step 47-2. Synthesis of 2-bromo-1-(3-((2-chloro-4-(trifluoromethyl)phenoxy)methyl) phenyl)ethan-1-one (INT 47-B)

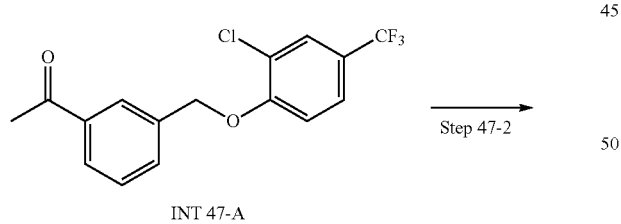

Into a solution of INT 47-A (224 mg, 0.68 mmol) in DCM (15 mL) was added Br$_2$ (0.035 mL, 0.68 mmol). After the reaction mixture was stirred for 30 min, the reaction mixture was quenched with NH$_4$C$_1$ (aq) and extracted into DCM. The resulting organic layer was washed with NaHCO$_3$ (sat, aq), water and brine, dried (Na$_2$SO$_4$), concentrated, and purified by SiO$_2$ chromatography (EA/hexanes) to provide 140 mg (50%) of 2-bromo-1-(3-((2-chloro-4-(trifluoromethyl)phenoxy)methyl)phenyl)ethan-1-one (INT 47-B). LCMS-ESI (m/z) calculated for C$_{16}$H$_{11}$BrClF$_3$O$_2$: 405.96. found 407.2 (M+H)$^+$; $t_R$=5.529 min (Method 11).

Step 47-3. Synthesis of 5-(3-((2-chloro-4-(trifluoromethyl)phenoxy)methyl)phenyl)-1H-imidazole (Compound 47-1)

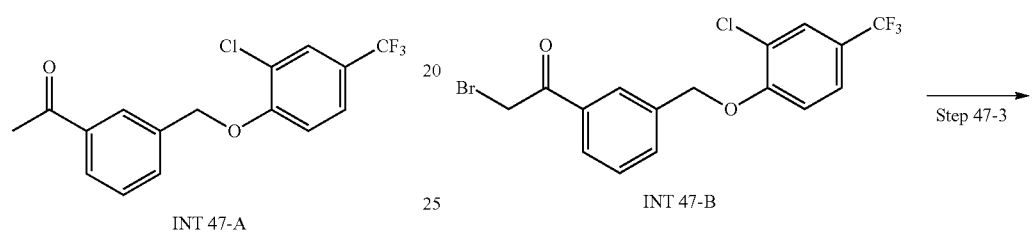

Compound 47-1

A solution of INT 47-B (100 mg, 0.3 mmol) in formamide (5 mL) was stirred for 4 h at 170° C., the reaction mixture was concentrated and purified by reverse-phase C$_{18}$ chromatography (H$_2$O/MeOH) to provide 6 mg (5%) of 5-(3-((2-chloro-4-(trifluoromethyl)phenoxy)methyl)phenyl)-1H-imidazole (Compound 47-1). LCMS-ESI (m/z) calculated for C$_{17}$H$_{12}$ClF$_3$N$_2$O: 352.06. found 353.4 (M+H)$^+$; $t_R$=12.14 min (Method 10).

Example 48

Synthesis of Compound 48-1

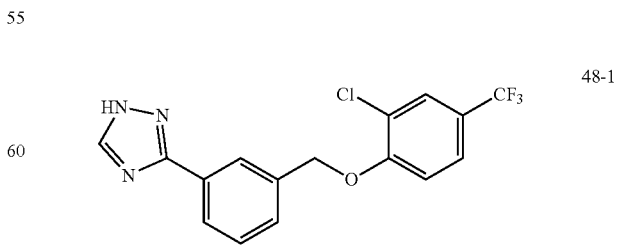

48-1

Scheme 48

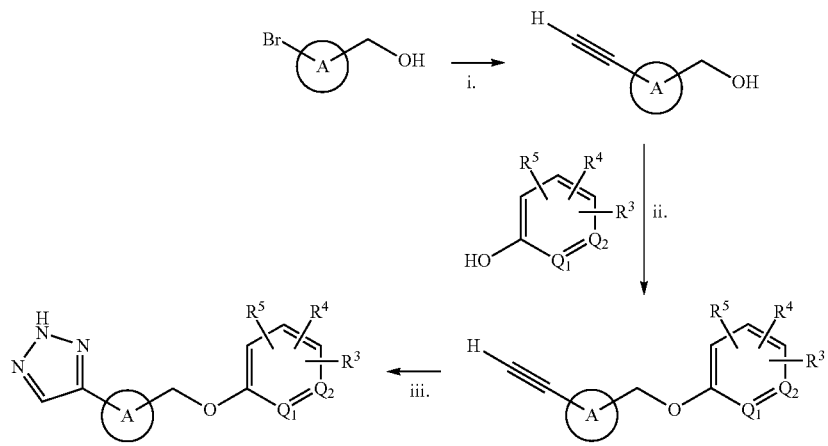

Reagents: (i) ethynyltrimethylsilane, Pd(OAc)$_2$, PPh$_3$; (ii) DEAD, PPh$_3$, THF; (iii) CuI, TMSN$_3$, DMF, EtOH.

Step 48-1. Synthesis of (3-ethynylphenyl)methanol (INT 48-A)

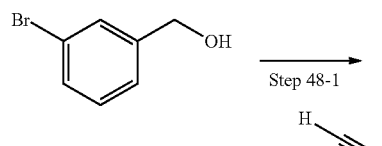

Into a solution of (3-ethynylphenyl) methanol (1.5 g, 8.02 mmol) in TEA (8 mL) were added ethynyltrimethylsilane (1.58 g, 16 mmol), palladium acetate (180 mg, 0.8 mmol), and PPh$_3$ (422 mg, 1.6 mmol). After stirring for 1 h at 95° C., the reaction mixture was filtered through Celite and washed with EA. The resulting organic layer was washed with H$_2$O (3×) and brine, dried (Na$_2$SO$_4$), filtered, concentrated, and purified by SiO$_2$ chromatography (EA/hexanes) to provide 800 mg (76%) of (3-ethynylphenyl)methanol (INT 48-A). LCMS-ESI (m/z) calculated for C$_9$H$_8$O: 132.06. found 133.3 (M+H)$^+$, $t_R$=3.1 min (Method 11).

Step 48-2. Synthesis of 2-chloro-1-((3-ethynylbenzyl)oxy)-4-(trifluoromethyl)benzene (INT 48-B)

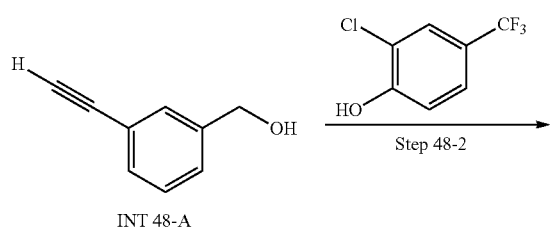

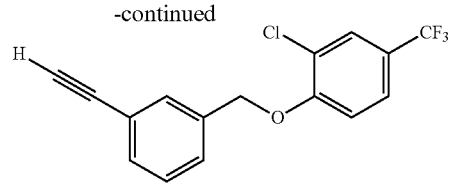

Into a solution of DEAD (55 mg of 40% solution, 2.7 mmol) in THF (3 mL) at 0° C. were added PPh$_3$ (71.2 mg, 2.7 mmol) and INT 48-A (30 mg, 8.02 mmol). After the reaction mixture was stirred for 1 h, the reaction mixture was concentrated and purified by SiO$_2$ chromatography (EA/hexanes) to provide 65 mg (93%) of crude 2-chloro-1-((3-ethynylbenzyl)oxy)-4-(trifluoromethyl)benzene (INT 48-B) that was carried onto the next step without further purification.

Step 48-3. Synthesis of 4-(3-((2-chloro-4-(trifluoromethyl)phenoxy)methyl)phenyl)-2H-1,2,3-triazole (Compound 48-1)

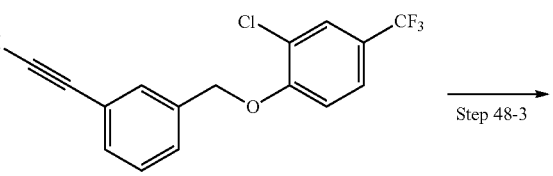

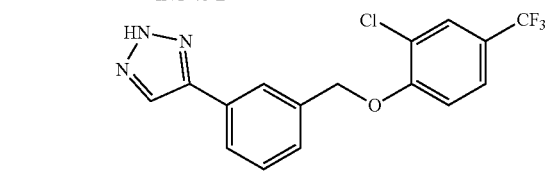

Into a solution of INT 48-B (65 mg, 2 mmol) in DMF (8 mL) and EtOH (1 mL) was added CuI (122 mg, 0.64 mmol). The mixture was purged with $N_2$ and $TMSN_3$ (741 mg, 6.4 mmol) was added. After stirring for 18 h at 120° C., the reaction mixture was filtered over Celite, concentrated, and purified by $SiO_2$ chromatography (EA/hexanes) and reverse-phase chromatography (MeOH/$H_2O$ with 0.1% TFA) to provide 65 mg (93%) of 4-(3-((2-chloro-4-(trifluoromethyl)phenoxy)methyl)phenyl)-2H-1,2,3-triazole (Compound 48-1). LCMS-ESI (m/z) calculated for $C_{16}H_{11}ClF_3N_3O$: 353.05. found 354.4 (M+H)$^+$, $t_R$=5.39 min (Method 11).

Example 49

Synthesis of Compound 49-1

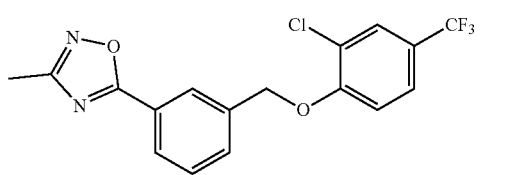

49-1

Scheme 49

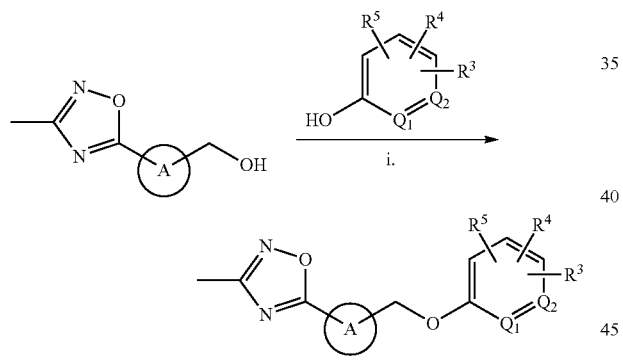

Reagents: (i) DEAD, PPh₃, THF.

Step 49-1. Synthesis of 5-(3-((2-chloro-4-(trifluoromethyl)phenoxy)methyl)phenyl)-3-methyl-1,2,4-oxadiazole (Compound 49-1)

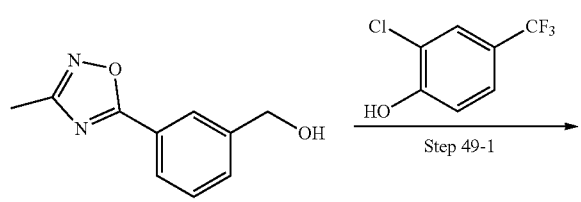

Step 49-1

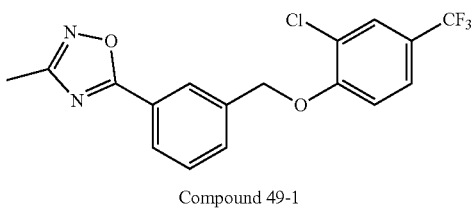

Compound 49-1

To a stirring solution of (3-(3-methyl-1,2,4-oxadiazol-5-yl)phenyl)methanol (500 mg, 2.6 mmol) in THF (5 mL) were added triphenylphosphine (830 mg, 3.1 mmol) and DEAD (911 μL of a 70% solution, 3.2 mmol). After stirring for 2 h, the reaction mixture was diluted with EA and washed with sat. NaHCO₃, H₂O, and brine, then dried (Na₂SO₄), concentrated and purified by SiO₂ chromatography (EA/hexane) to a residue that was triturated with MeOH/H₂O to afford 670 mg (69.1%) of 5-(3-((2-chloro-4-(trifluoromethyl)phenoxy)methyl)phenyl)-3-methyl-1,2,4-oxadiazole (Compound 49-1). LCMS-ESI (m/z) calculated for $C_{17}H_{12}ClF_3N_2O_2$: 368.05. found 369.1 (M+H)$^+$, $t_R$=14.59 min (50-95-4 min). $^1$H NMR (300 MHz, DMSO-d6) δ 8.23 (s, 1H), 8.08 (d, J=7.8 Hz, 1H), 7.89 (bs, 1H), 7.80 (d, J=6.5 Hz, 1H), 7.50-7.30 (m, 2H), 7.46 (d, J=8.5 Hz, 1H), 5.46 (s, 2H), 2.43 (s, 3H).

Example 50

Synthesis of Compound 50-1

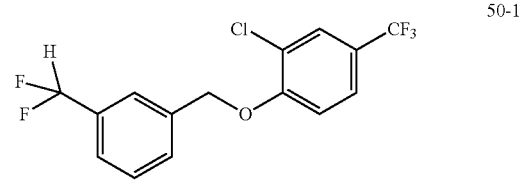 [SMILES: FC(F)c1cccc(COc2ccc(C(F)(F)F)cc2Cl)c1]

50-1

Scheme 50

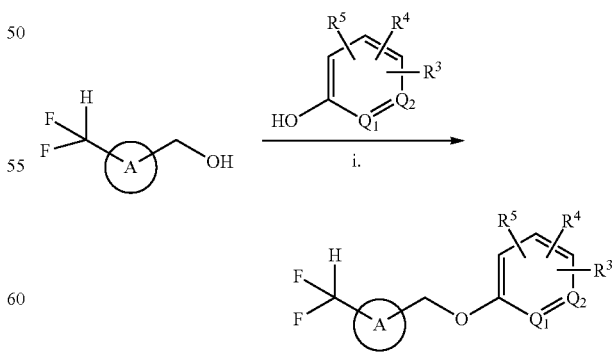

Reagents: (i) Na₂CO₃, DMF.

Step 50-1. Synthesis of 2-chloro-1-((3-(difluoromethyl)benzyl)oxy)-4-(trifluoromethyl) benzene (Compound 50-1)

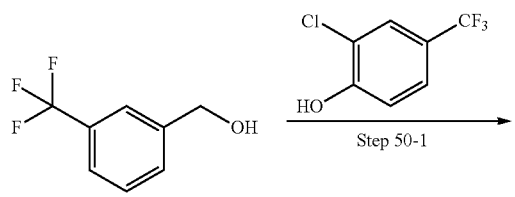

Compound 50-1

To a stirring solution of (3-(difluoromethyl)phenyl)methanol (500 mg, 2.26 mmol) in DMF (8 mL) were added 2-chloro-4-(trifluoromethyl)phenol (450 mg, 2.26 mmol) and $Na_2CO_3$ (720 mg, 6.79 mmol). After stirring for 18 h at 50° C., the reaction mixture was diluted with $H_2O$, extracted into EA, washed with $H_2O$ and brine. The organic layers were concentrated $SiO_2$ chromatography (EA/hexane) to afford 165 mg (22%) of 2-chloro-1-((3-(difluoromethyl)benzyl)oxy)-4-(trifluoromethyl)benzene (Compound 50-1). LCMS-ESI (m/z) calculated for $C_{15}H_{10}ClF_5O$: 336.03. found 359.2 (M+Na)$^+$, $t_R$=5.68 min (Method 11). $^1$H NMR (300 MHz, CDCl$_3$) 7.70 (s, 1H), 7.63 (s, 1H), 7.625-7.45 (m, 4H), 7.04 (d, J=8.6 Hz, 1H), 6.70 (t, $J_{H-F}$=56 Hz, 1H), 5.27 (s, 2H).

Example 52

Synthesis of Compound 52-1

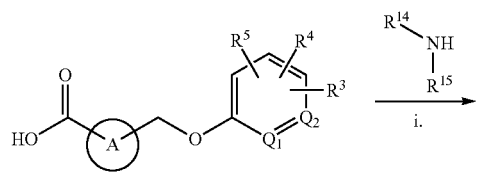

52-1

Scheme 52

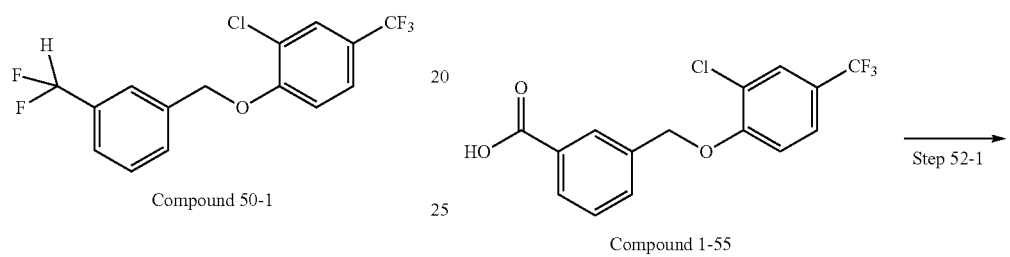

Reagents: (I) HATU, DIPEA, DMF.

Step 52-1. Synthesis of N-benzyl-3-((2-chloro-4-(trifluoromethyl)phenoxy)methyl) benzamide (Compound 52-1)

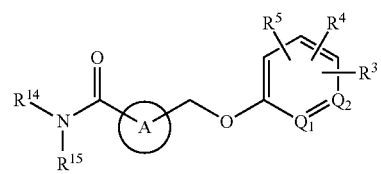

Compound 1-55

Compound 52-1

To a stirring solution of Compound 1-55 (113 mg, 0.34 mmol) in DMF (5 mL) were added HATU (137 mg, 0.36 mmol), DIPEA (126 mg, 0.98 mmol), and phenylmethanamine (35 mg, 0.33 mmol). After stirring for 16 h at rt, the reaction mixture was diluted with EA, washed with 30 mL each of $H_2O$, 1M HCl, 1 M NaOH, NaHCO$_3$ and brine. The organic layers were dried (Na$_2$SO$_4$), concentrated and purified by SiO$_2$ chromatography (EA/hexane) to afford 62 mg (54%) of N-benzyl-3-((2-chloro-4-(trifluoromethyl)phenoxy)methyl)benzamide (Compound 52-1). LCMS-ESI (m/z) calculated for $C_{22}H_{17}ClF_3NO_2$: 419.1. found 420.3 (M+H)$^+$, $t_R$=12.98 mi (Method 10). $^1$H NMR (400 MHz, DMSO-d6) δ 9.11 (s, 1H), 8.02 (s, 1H), 7.90-7.88 (m, 2H), 7.72 (d, J=8, 1H), 7.65 (d, J=8, 1H), 7.54 (t, J=8, 1H), 7.45 (d, J=8, 1H), 7.33 (t, J=4, 4H), 7.26 (d, J=4, 1H), 5.38 (s, 2H), 4.49 (d, J=4, 2H).

The compounds listed in Table 52 were made using the procedures of Scheme 52.

TABLE 52

| Structure | Cpd No. | Purity RT (min) | MW | observed m/z | Ion | Purity Method |
|---|---|---|---|---|---|---|
| 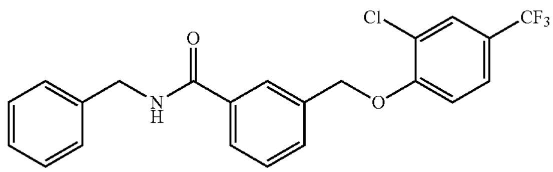 [SMILES: O=C(NCc1ccccc1)c1cccc(COc2ccc(C(F)(F)F)cc2Cl)c1] | 52-1 | 13.98 | 419.83 | 420.3 | [M + H]+ | 10 |
| 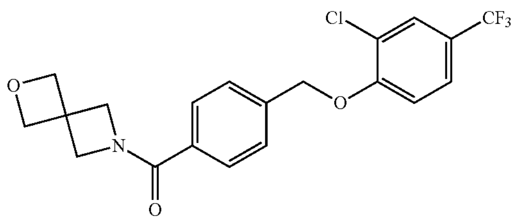 [SMILES: O=C(c1ccc(COc2ccc(C(F)(F)F)cc2Cl)cc1)N1CC2(COC2)C1] | 52-2 | 9.581 | 411.81 | 412.1 | [M + H]+ | 3 |
| 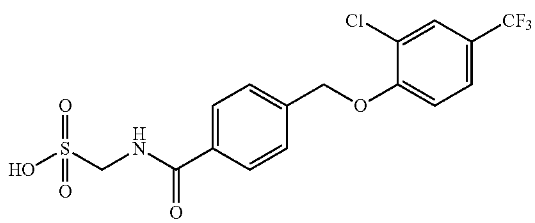 [SMILES: O=C(NCS(=O)(=O)O)c1ccc(COc2ccc(C(F)(F)F)cc2Cl)cc1] | 52-3 | 6.635 | 423.79 | 424 | [M + H]+ | 3 |
| 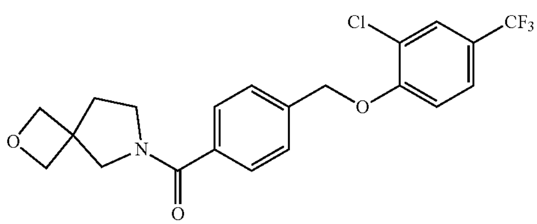 [SMILES: O=C(c1ccc(COc2ccc(C(F)(F)F)cc2Cl)cc1)N1CCC2(COC2)C1] | 52-4 | 9.748 | 425.83 | 426.1 | [M + H]+ | 3 |
| 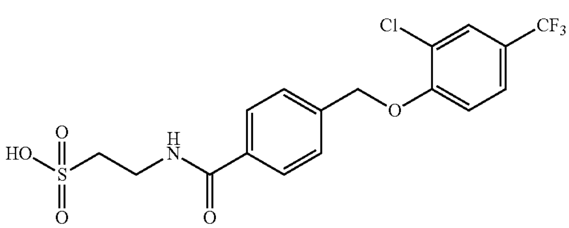 [SMILES: O=C(NCCS(=O)(=O)O)c1ccc(COc2ccc(C(F)(F)F)cc2Cl)cc1] | 52-5 | 6.747 | 437.81 | 438.1 | [M + H]+ | 3 |
| 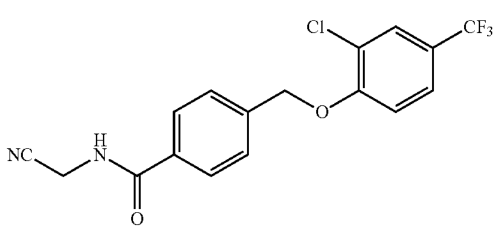 [SMILES: N#CCNC(=O)c1ccc(COc2ccc(C(F)(F)F)cc2Cl)cc1] | 52-6 | 10.113 | 368.74 | 369.1 | [M + H]+ | 3 |
| 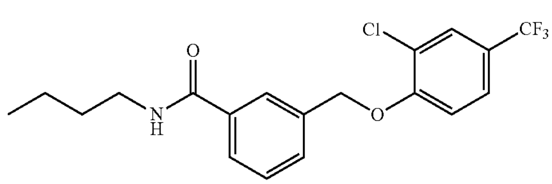 [SMILES: CCCCNC(=O)c1cccc(COc2ccc(C(F)(F)F)cc2Cl)c1] | 52-7 | 14.03 | 385.81 | 386.3 | [M + H]+ | 10 |

TABLE 52-continued

| Structure | Cpd No. | Purity RT (min) | MW | observed m/z | Ion | Purity Method |
|---|---|---|---|---|---|---|
| 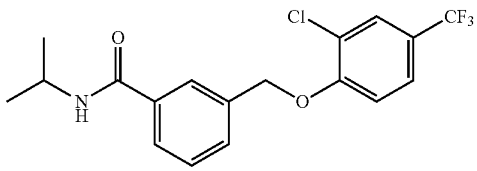 | 52-8 | 13.72 | 371.78 | 372 | [M + H]⁺ | 10 |
| 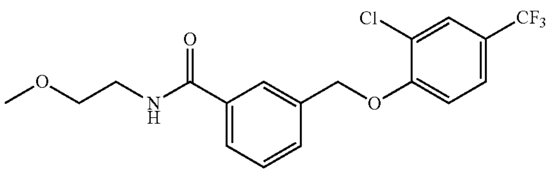 [SMILES: COCCNC(=O)c1cccc(COc2ccc(C(F)(F)F)cc2Cl)c1] | 52-9 | 13.45 | 387.78 | 388.4 | [M + H]⁺ | 10 |
| 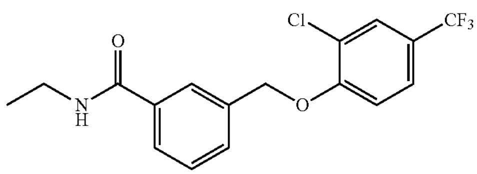 [SMILES: CCNC(=O)c1cccc(COc2ccc(C(F)(F)F)cc2Cl)c1] | 52-10 | 13.47 | 357.76 | 358.1 | [M + H]⁺ | 10 |
| 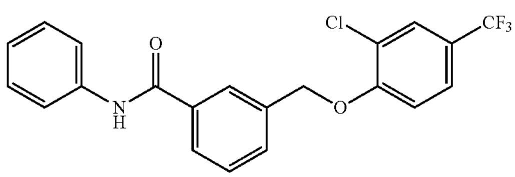 [SMILES: O=C(Nc1ccccc1)c1cccc(COc2ccc(C(F)(F)F)cc2Cl)c1] | 52-11 | 14.08 | 405.80 | 406.4 | [M + H]⁺ | 10 |
| 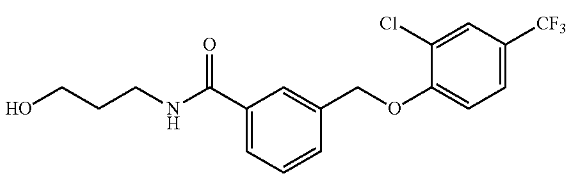 [SMILES: O=C(NCCCO)c1cccc(COc2ccc(C(F)(F)F)cc2Cl)c1] | 52-12 | 13.06 | 387.78 | 388.3 | [M + H]⁺ | 10 |
| 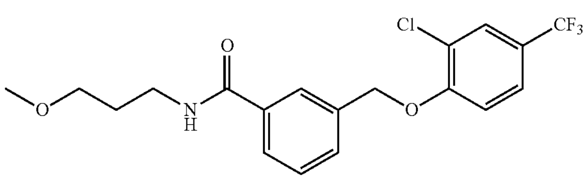 [SMILES: COCCCNC(=O)c1cccc(COc2ccc(C(F)(F)F)cc2Cl)c1] | 52-13 | 13.57 | 401.81 | 402.5 | [M + H]⁺ | 10 |
| 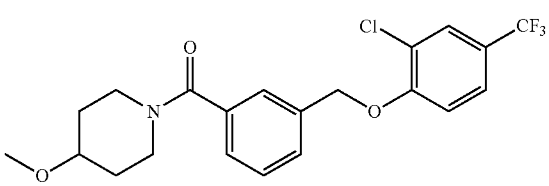 [SMILES: COC1CCN(C(=O)c2cccc(COc3ccc(C(F)(F)F)cc3Cl)c2)CC1] | 52-14 | 13.72 | 427.85 | 428.5 | [M + H]⁺ | 10 |
| 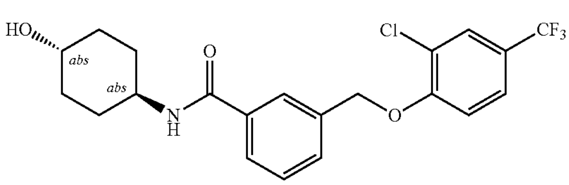 [SMILES: O=C(N[C@H]1CC[C@H](O)CC1)c1cccc(COc2ccc(C(F)(F)F)cc2Cl)c1] | 52-15 | 13.36 | 427.85 | 428.5 | [M + H]⁺ | 10 |

TABLE 52-continued

| Structure | Cpd No. | Purity RT (min) | MW | observed m/z | Ion | Purity Method |
|---|---|---|---|---|---|---|
| 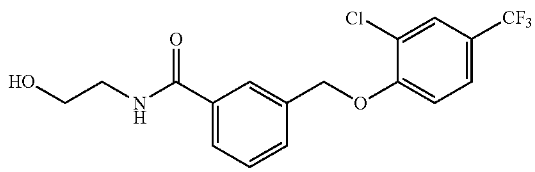 [SMILES: O=C(NCCO)c1cccc(COc2ccc(C(F)(F)F)cc2Cl)c1] | 52-16 | 12.93 | 373.76 | 374.4 | [M + H]⁺ | 10 |
| 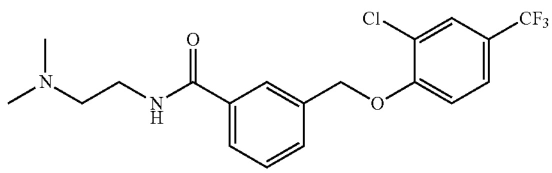 [SMILES: CN(C)CCNC(=O)c1cccc(COc2ccc(C(F)(F)F)cc2Cl)c1] | 52-17 | 12.04 | 400.83 | 401.4 | [M + H]⁺ | 10 |
| 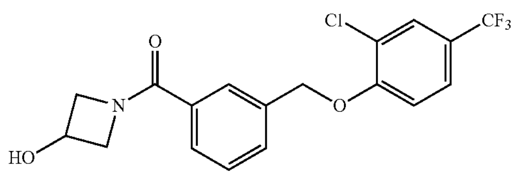 [SMILES: O=C(c1cccc(COc2ccc(C(F)(F)F)cc2Cl)c1)N1CC(O)C1] | 52-18 | 12.97 | 385.77 | 386.3 | [M + H]⁺ | 10 |
| 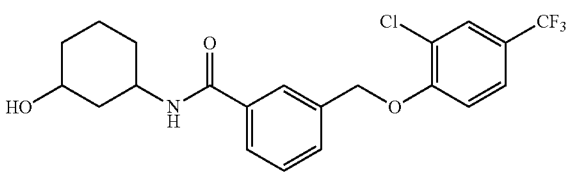 [SMILES: O=C(NC1CCCC(O)C1)c1cccc(COc2ccc(C(F)(F)F)cc2Cl)c1] | 52-19 | 13.4 | 427.85 | 428.5 | [M + H]⁺ | 10 |
| 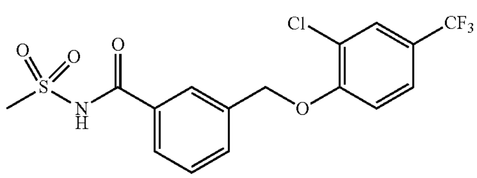 [SMILES: CS(=O)(=O)NC(=O)c1cccc(COc2ccc(C(F)(F)F)cc2Cl)c1] | 52-20 | 12.81 | 407.79 | 408.4 | [M + H]⁺ | 10 |
| 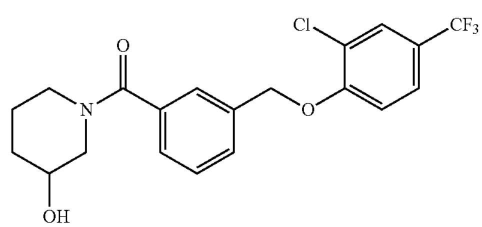 [SMILES: O=C(c1cccc(COc2ccc(C(F)(F)F)cc2Cl)c1)N1CCCC(O)C1] | 52-21 | 13.17 | 413.82 | 414.5 | [M + H]⁺ | 10 |
| 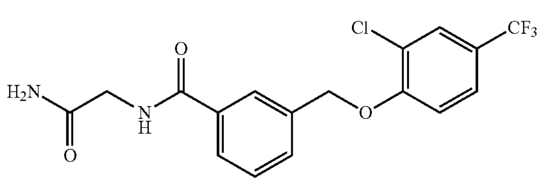 [SMILES: NC(=O)CNC(=O)c1cccc(COc2ccc(C(F)(F)F)cc2Cl)c1] | 52-22 | 12.76 | 386.76 | 387.4 | [M + H]⁺ | 10 |
| 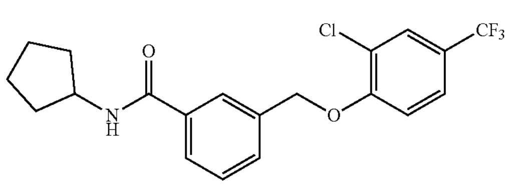 [SMILES: O=C(NC1CCCC1)c1cccc(COc2ccc(C(F)(F)F)cc2Cl)c1] | 52-23 | 14.11 | 397.82 | 398.4 | [M + H]⁺ | 10 |

TABLE 52-continued
| Structure | Cpd No. | Purity RT (min) | MW | observed m/z | Ion | Purity Method |
|---|---|---|---|---|---|---|
| 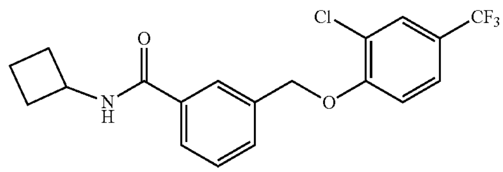 [SMILES: O=C(NC1CCC1)c1cccc(COc2ccc(C(F)(F)F)cc2Cl)c1] | 52-24 | 13.91 | 383.80 | 384.2 | [M + H]+ | 10 |
| 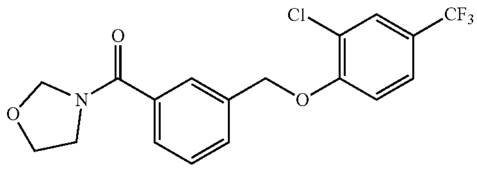 [SMILES: O=C(c1cccc(COc2ccc(C(F)(F)F)cc2Cl)c1)N1CCOC1] | 52-25 | 13.4 | 385.77 | 386.3 | [M + H]+ | 10 |
| 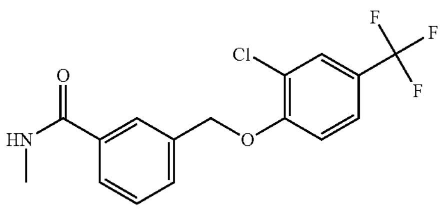 [SMILES: CNC(=O)c1cccc(COc2ccc(C(F)(F)F)cc2Cl)c1] | 52-26 | 4.73 | 343.73 | 344.066 | [M + H]+ | 12 |
| 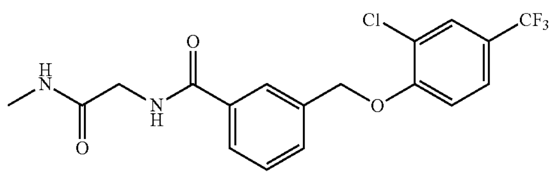 [SMILES: CNC(=O)CNC(=O)c1cccc(COc2ccc(C(F)(F)F)cc2Cl)c1] | 52-27 | 12.93 | 400.78 | 401.3 | [M + H]+ | 10 |
| 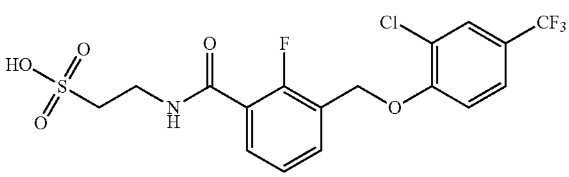 [SMILES: O=C(NCCS(=O)(=O)O)c1cccc(COc2ccc(C(F)(F)F)cc2Cl)c1F] | 52-28 | 0.854 | 455.8 | 456 | [M + H]+ | 6 |
Example 53
Synthesis of Compound 53-1
Scheme 53
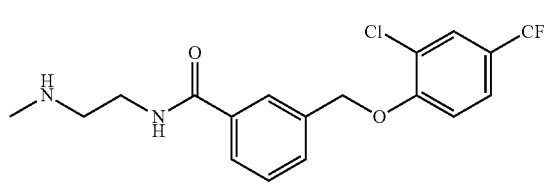
53-1
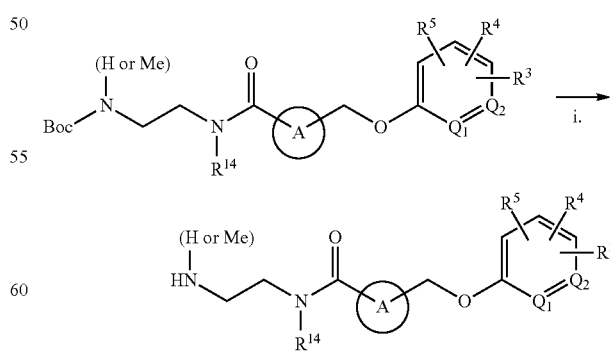
Reagents: (i) TFA, DCM.

Step 53-1. Synthesis of 3-((2-chloro-4-(trifluoromethyl)phenoxy)methyl)-N-(2-(methylamino)ethyl)benzamide (Compound 53-1)

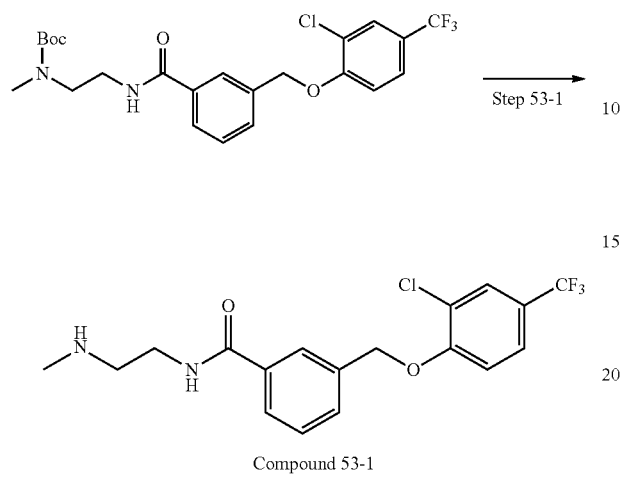

Compound 53-1

A solution of tert-butyl (2-(3-((2-chloro-4-(trifluoromethyl)phenoxy)m)methyl)benzamido) ethyl) (methyl)carbamate (50 mg, 0.099 mmol) (prepared from Compound 1-55 and tert-butyl (2-aminoethyl)(methyl)carbamate via Scheme 52) in 1:1 DCM: TFA (5 mL) was stirred for 16 h at rt. The reaction mixture was concentrated, dissolved in H$_2$O/CH$_3$CN and lyophilized to afford 30 mg (60%) of 3-((2-chloro-4-(trifluoromethyl)phenoxy)methyl)-N-(2-(methylamino)ethyl)benzamide (Compound 53-1). LCMS-ESI (m/z) calculated for C$_{18}$H$_{18}$ClF$_3$N$_2$O$_2$: 386.1. found 387.4 (M+H)$^+$, t$_R$=12.98 min (Method 10).

The compounds listed in Table 53 were made using the procedures of Scheme 53.

Example 54

Synthesis of Compound 54-1

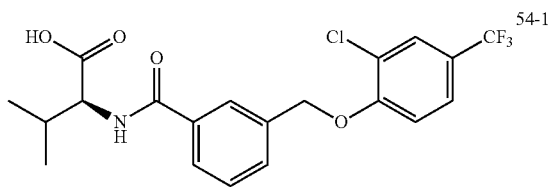 [SMILES: CC(C)[C@H](NC(=O)c1cccc(COc2ccc(C(F)(F)F)cc2Cl)c1)C(=O)O]

Scheme 54

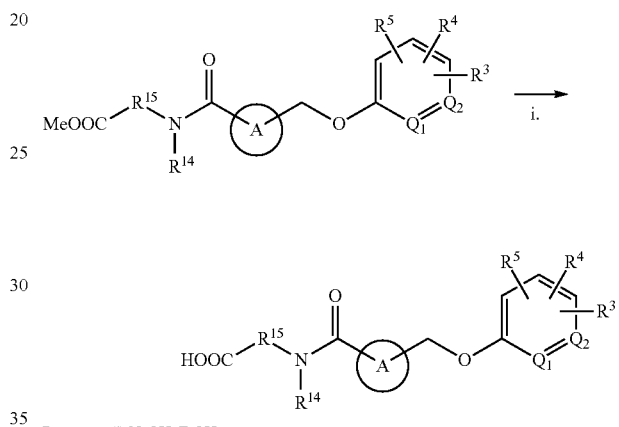

Reagents: (i) NaOH, EtOH.

TABLE 53

| Structure | Cpd No. | Purity RT (min) | MW | observed m/z | Ion | Purity Method |
|---|---|---|---|---|---|---|
| ![structure] Cl, CF$_3$ | 53-1 | 13.64 | 386.80 | 387.4 | [M + H]$^+$ | 10 |
| ![structure] H$_2$N, Cl, CF$_3$ | 53-2 | 11.85 | 372.77 | 373.3 | [M + H]$^+$ | 10 |

Step 54-1. Synthesis of (3-((2-chloro-4-(trifluoromethyl)phenoxy)methyl)benzoyl)-L-valine (Compound 54-1)

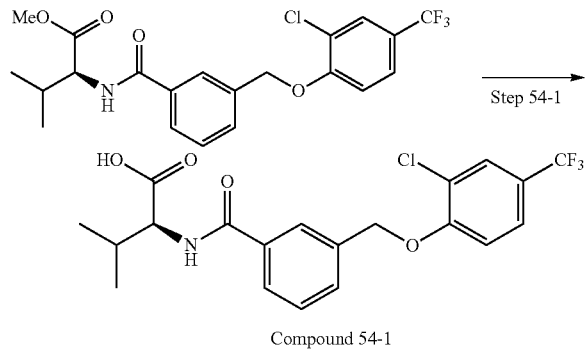

Compound 54-1

Into a solution of methyl (3-((2-chloro-4-(trifluoroethyl)phenoxy)-methyl)benzoyl)-L-valinate (250 mg, 0.56 mmol) (prepared from Compound 1-55 and methyl L-valinate via Scheme 52) in EtOH (5 mL) was added 2M NaOH (1.12 g, 1.1 mmol). After stirring for 16 h at rt, the reaction mixture was diluted with EA and acidified with 1M HCl. The organic layer was collected and washed with brine, dried ($Na_2SO_4$), concentrated, and purified with reverse-phase $SiO_2$ chromatography (MeOH/$H_2O$, with 0.1% formic acid) to afford 36 mg (15%) of (3-((2-chloro-4-(trifluoromethyl)phenoxy)methyl)benzoyl)-L-valine (Compound 54-1). LCMS-ESI (m/z) calculated for $C_{20}H_{19}ClF_3NO_4$: 429.1. found 430.6 $(M+H)^+$, $t_R$=5.31 min (Method 11).

The compounds listed in Table 54 were made using the procedures of Scheme 54.

TABLE 54

| Structure | Cpd No. | Purity RT (min) | MW | observed m/z | Ion | Purity Method |
|---|---|---|---|---|---|---|
| 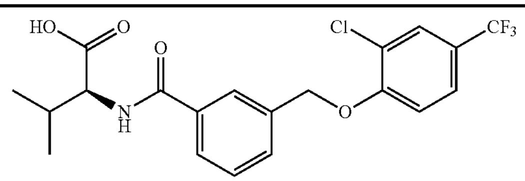 | 54-1 | 13.63 | 429.82 | 430.3 | $[M + H]^+$ | 10 |
| 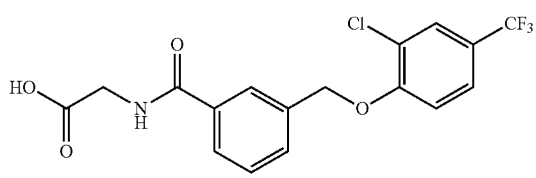 [SMILES: O=C(O)CNC(=O)c1cccc(COc2ccc(C(F)(F)F)cc2Cl)c1] | 54-2 | 13 | 387.74 | 388.3 | $[M + H]^+$ | 10 |
| 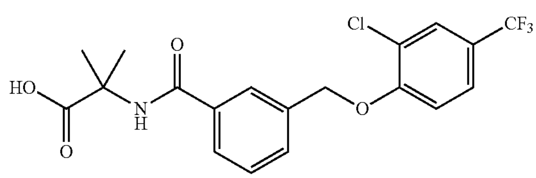 [SMILES: CC(C)(NC(=O)c1cccc(COc2ccc(C(F)(F)F)cc2Cl)c1)C(=O)O] | 54-3 | 13.27 | 415.79 | 416.5 | $[M + H]^+$ | 10 |
| 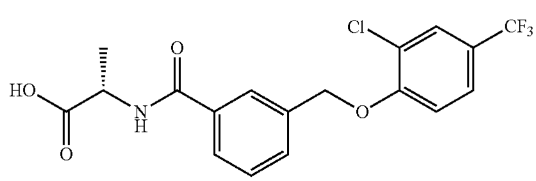 [SMILES: C[C@H](NC(=O)c1cccc(COc2ccc(C(F)(F)F)cc2Cl)c1)C(=O)O] | 54-4 | 13.15 | 401.77 | 402.6 | $[M + H]^+$ | 10 |
| 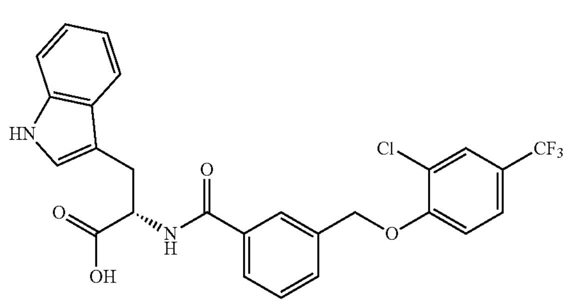 [SMILES: O=C(N[C@@H](Cc1c[nH]c2ccccc12)C(=O)O)c1cccc(COc2ccc(C(F)(F)F)cc2Cl)c1] | 54-5 | 13.62 | 516.90 | 517.2 | $[M + H]^+$ | 10 |

TABLE 54-continued

| Structure | Cpd No. | Purity RT (min) | MW | observed m/z | Ion | Purity Method |
|---|---|---|---|---|---|---|
| 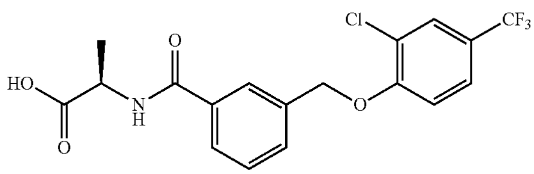 [SMILES: C[C@@H](NC(=O)c1cccc(COc2ccc(C(F)(F)F)cc2Cl)c1)C(=O)O] | 54-6 | 13.18 | 401.77 | 402.6 | [M + H]+ | 10 |
| 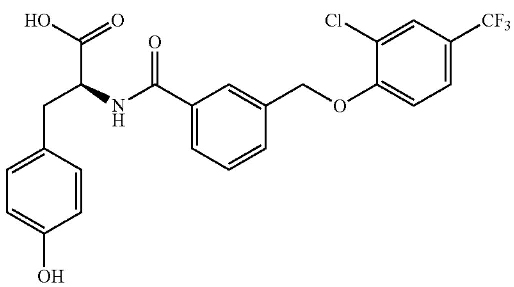 [SMILES: O=C(N[C@@H](Cc1ccc(O)cc1)C(=O)O)c1cccc(COc2ccc(C(F)(F)F)cc2Cl)c1] | 54-7 | 12.95 | 493.86 | 494.4 | [M + H]+ | 10 |
| 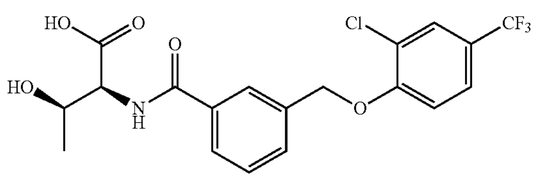 [SMILES: C[C@@H](O)[C@H](NC(=O)c1cccc(COc2ccc(C(F)(F)F)cc2Cl)c1)C(=O)O] | 54-8 | 12.89 | 431.79 | 432.2 | [M + H]+ | 10 |
| 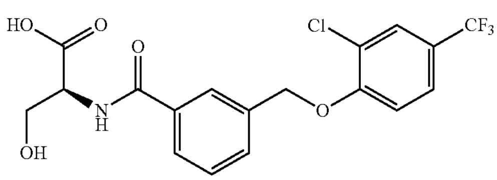 [SMILES: O=C(N[C@@H](CO)C(=O)O)c1cccc(COc2ccc(C(F)(F)F)cc2Cl)c1] | 54-9 | 12.71 | 417.77 | 418.5 | [M + H]+ | 10 |
| 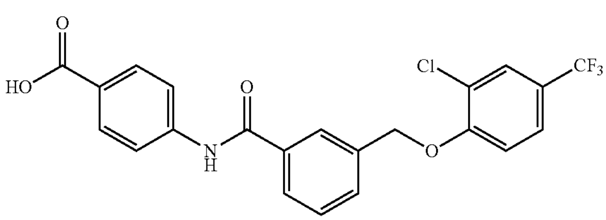 [SMILES: O=C(O)c1ccc(NC(=O)c2cccc(COc3ccc(C(F)(F)F)cc3Cl)c2)cc1] | 54-10 | 13.82 | 449.81 | 450.2 | [M + H]+ | 10 |
| 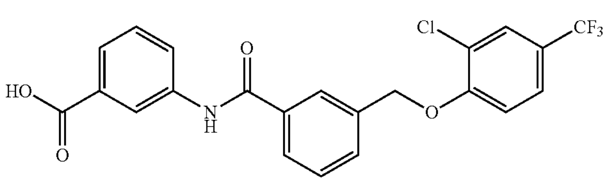 [SMILES: O=C(O)c1cccc(NC(=O)c2cccc(COc3ccc(C(F)(F)F)cc3Cl)c2)c1] | 54-11 | 13.61 | 449.81 | 450.2 | [M + H]+ | 10 |
| 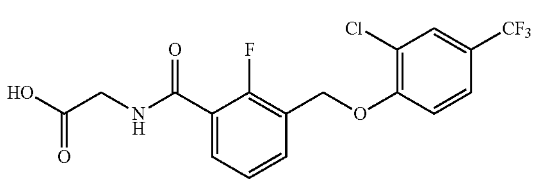 [SMILES: O=C(O)CNC(=O)c1cccc(COc2ccc(C(F)(F)F)cc2Cl)c1F] | 54-12 | 0.972 | 405.73 | 406 | [M + H]+ | 6 |

Example 55

Synthesis of Compound 55-1

Step 55-1. Synthesis of (3-((2-chloro-4-(trifluoromethyl)phenoxy)methyl)benzol)-L-asparagine (Compound 55-1)

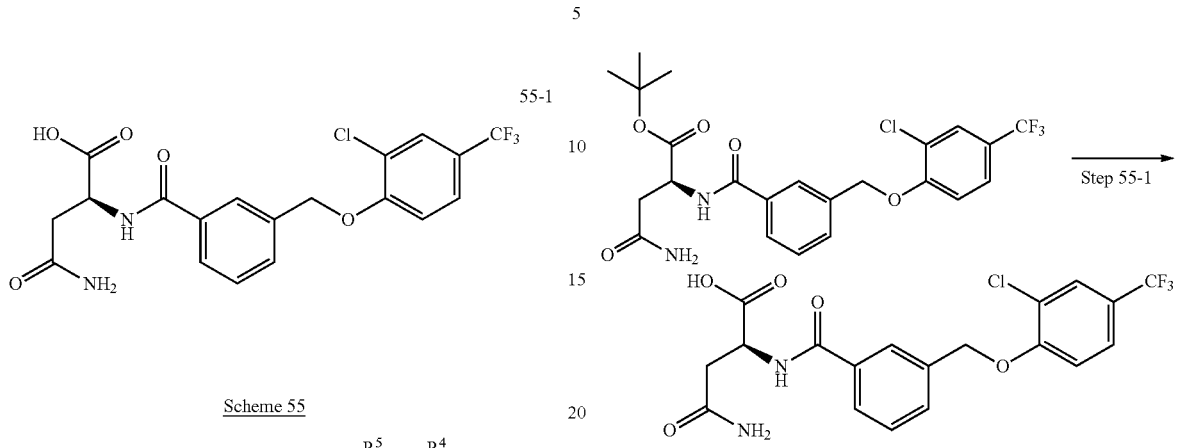

A solution of tert-butyl (3-((2-chloro-4-(trifluoromethyl)phenoxy)-methyl)benzoyl)-L-asparaginate (200 mg, 0.4 mmol) (prepared from Compound 1-55 and tert-butyl L-asparaginate via Scheme 52) in 1:1 TFA: DCM (5 mL) was stirred for 16 h at rt. The mixture was concentrated and purified using reverse-phase $SiO_2$ chromatography (MeOH/$H_2O$, with 0.100 formic acid) to afford 107 mg (60%) of (3-((2-chloro-4-(trifluoromethyl)phenoxy)methyl)benzoyl)-L-asparagine (Compound 55-1). LCMS-ESI (m/z) calculated for $C_{19}H_{16}ClF_3N_2O_5$: 444.1. found 445.4 $(M+H)^+$, $t_R$=4.70 min (Method 11).

The compounds listed in Table 55 were made using the procedures of Scheme 55.

Scheme 55

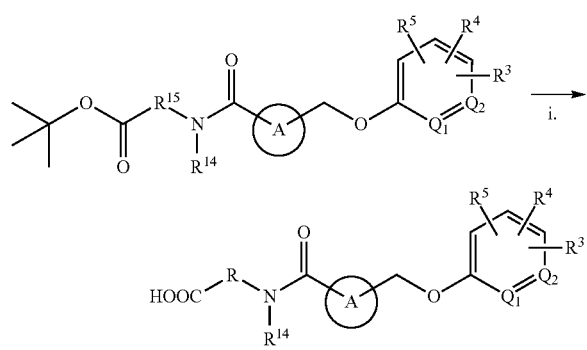

Reagents: (i) TFA, DCM.

TABLE 55

| Structure | Cpd No. | Purity RT (min) | MW | observed m/z | Ion | Purity Method |
|---|---|---|---|---|---|---|
| ![struct] | 55-1 | 12.54 | 444.79 | 445.4 | $[M + H]^+$ | 10 |
| ![struct] | 55-2 | 10.92 | 467.83 | 468.4 | $[M + H]^+$ | 10 |
| ![struct] | 55-3 | 12.58 | 458.82 | 459.4 | $[M + H]^+$ | 10 |

Example 56

Synthesis of Compound 56-1

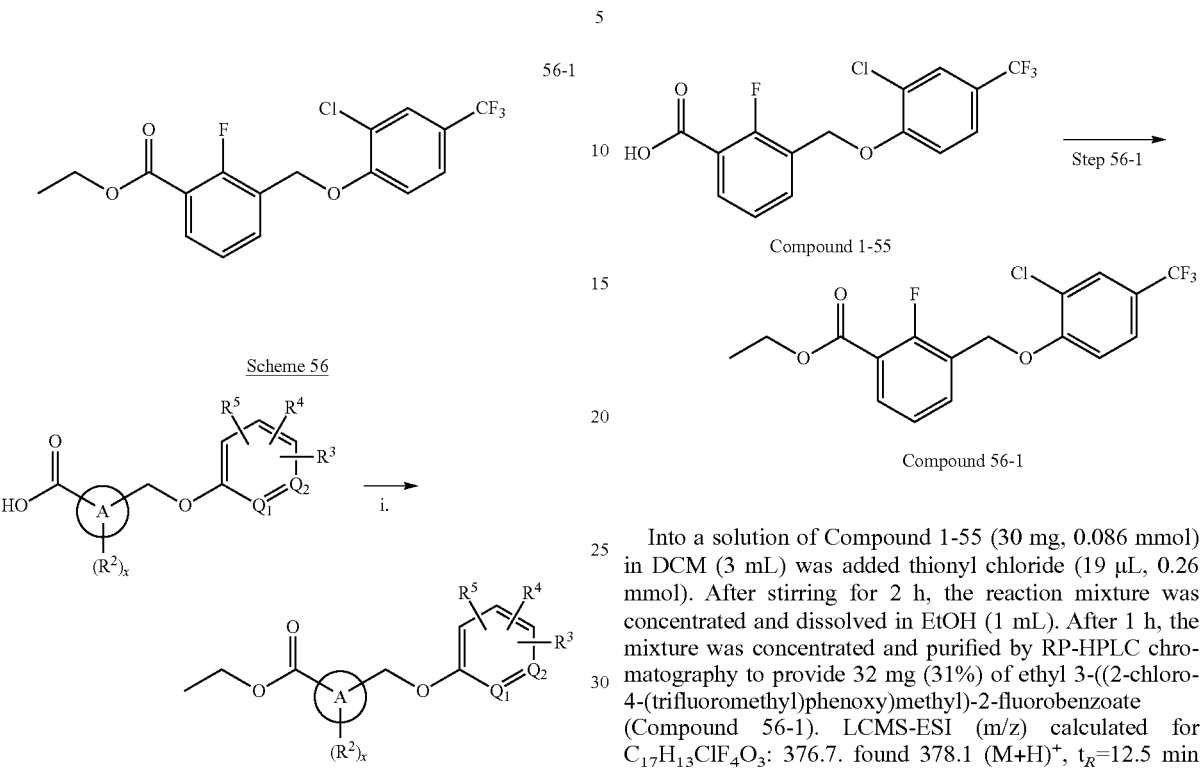

Scheme 56

Reagents: (i) Thionyl-Cl, EtOH, DCM.

Step 56-1. Synthesis of ethyl 3-((2-chloro-4-(trifluoromethyl)phenoxy)methyl)-2-fluorobenzoate (Compound 56-1)

Into a solution of Compound 1-55 (30 mg, 0.086 mmol) in DCM (3 mL) was added thionyl chloride (19 µL, 0.26 mmol). After stirring for 2 h, the reaction mixture was concentrated and dissolved in EtOH (1 mL). After 1 h, the mixture was concentrated and purified by RP-HPLC chromatography to provide 32 mg (31%) of ethyl 3-((2-chloro-4-(trifluoromethyl)phenoxy)methyl)-2-fluorobenzoate (Compound 56-1). LCMS-ESI (m/z) calculated for $C_{17}H_{13}ClF_4O_3$: 376.7. found 378.1 (M+H)$^+$, $t_R$=12.5 min (Escient purity).

The compounds listed in Table 56 were made using the procedures of Scheme 56.

TABLE 56

| Structure | Cpd No. | Purity RT (min) | MW | observed m/z | Ion | Purity Method |
|---|---|---|---|---|---|---|
| 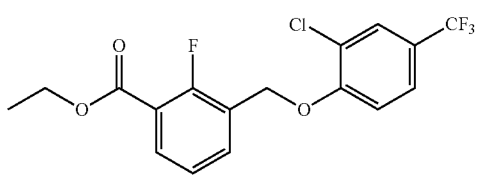 | 56-1 | 12.50 | 376.73 | 378.1 | [M + H]$^+$ | 3 |
| 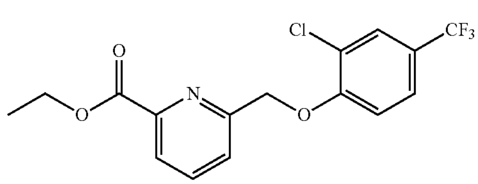 [SMILES: CCOC(=O)c1cccc(COc2ccc(C(F)(F)F)cc2Cl)n1] | 56-2 | 11.30 | 359.73 | 360.1 | [M + H]$^+$ | 3 |

Example 57

Synthesis of Compound 57-1

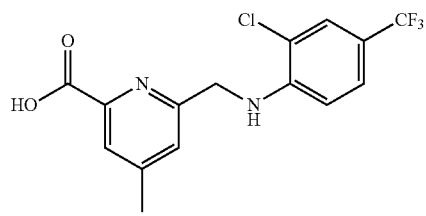

Into a solution of 2,6-dichloro-4-methyl-pyridine (6.8 g, 41.97 mmol) in DMF (100 mL) and MeOH (50 mL) were added Pd(dppf)Cl$_2$—CH$_2$Cl$_2$ (3.43 g, 4.20 mmol), TEA (23.37 mL. 167.9 mmol). The reaction was stirred at 80° C. under CO (1.18 g, 41.97 mmol, 50 Psi) for 16 h. The reaction mixture was filtered, concentrated diluted with H$_2$O (100 mL) and extracted with EA (2×100 mL). The organic layer was collected, dried, filtered, concentrated, and purified by SiO$_2$ chromatography (EA/Petroleum ether) to provide 6.7 g (76%) of dimethyl 4-methylpyridine-2,6-dicarboxylate (INT 57-1) as a yellow solid. LCMS-ESI (m/z) calculated for C$_{10}$H$_{11}$NO$_4$: 209.07. found 210.1 (M+H)$^+$, t$_R$=0.742 min (Method 6).

Scheme 57

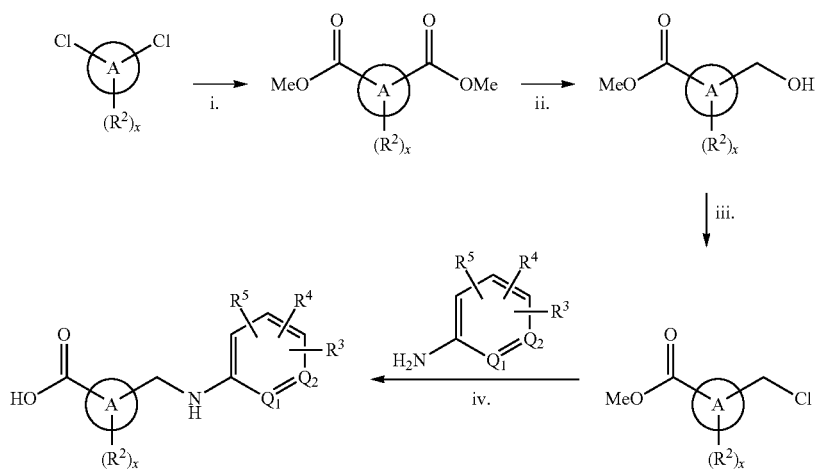

Reagents: (i) Pd(dppf)Cl$_2$—CH$_2$Cl$_2$, TEA, DMF, MeOH, CO; (ii) NaBH$_4$, MeOH, DCM; (iii) SOCl$_2$, DCM; (iv) NaOH, DMF

Step 57-1. Synthesis of dimethyl 4-methylpyridine-2,6-dicarboxylate (INT 57-1)

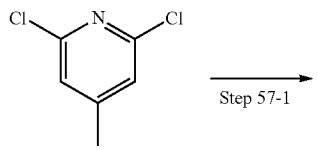

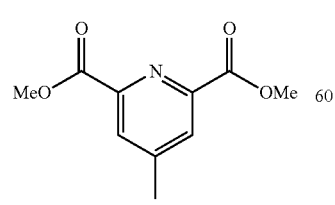

INT 57-1

Step 57-2. Synthesis of methyl 6-(hydroxymethyl)-4-methylpicolinate (INT 57-2)

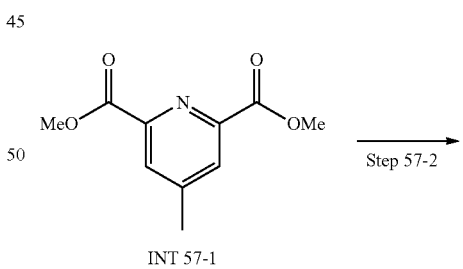

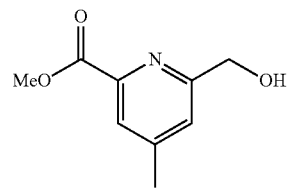

INT 57-2

Into a solution of INT 57-1 (6.7 g, 31.39 mmol) in MeOH (400 mL) and DCM (100 mL) at 0° C. was added NaBH$_4$ (1.78 g, 47.08 mmol) in small portions. After stirring for 12 h at 0° C., the reaction mixture was quenched by the addition of aqueous NH₄Cl (200 mL) and extracted into EA (3×200 mL). The combined organic layers were dried (Na₂SO₄), filtered, concentrated, and purified by SiO₂ chromatography to provide 3.7 g (64%) of methyl 6-(hydroxymethyl)-4-methylpicolinate (INT 57-2). LCMS-ESI (m/z) calculated for C₉H₁₁NO₃: 181.2. found 182.7 (M+H)⁺, t$_R$=0.323 min (Method 6). ¹H NMR (400 MHz, CDCl₃) δ 7.85 (s, 1H), 7.35 (s, 1H), 4.81 (s, 2H), 3.97 (s, 3H), 3.81-3.26 (m, 1H), 2.49-2.38 (s, 3H).

Step 57-3. Synthesis of methyl 6-(chloromethyl)-4-methylpicolinate (INT 57-3)

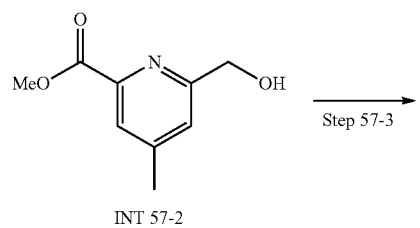

Into a solution of INT 57-2 (200 mg, 1.1 mmol) in DCM (7 mL) at 0° C. was added SOCl₂ (1 mL, 13.8 mmol). After stirring for 1.5 h at rt, the reaction mixture was concentrated to provide 32 mg (31%) of methyl 6-(chloromethyl)-4-methylpicolinate (INT 57-3) as a white solid that was used without further purification. LCMS-ESI (m/z) calculated for C₉H₁₀ClNO₂: 199.04. found 200.0 (M+H)⁺, t$_R$=0.755 min (Method 6).

Step 57-4. Synthesis of 6-(((2-chloro-4-(trifluoromethyl)phenyl)amino)methyl)-4-methylpicolinic acid (Compound 57-1)

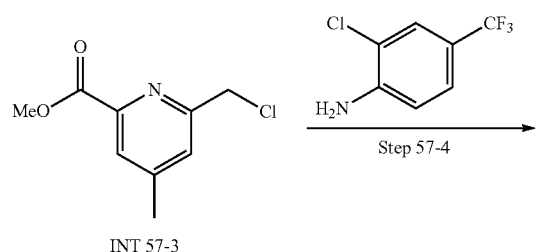

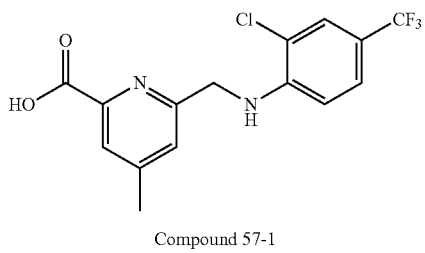

Compound 57-1

Into a solution of INT 57-3 (200 mg, 1.0 mmol) and 2-chloro-4-(trifluoromethyl) aniline (195.9 mg, 1.00 mmol) in DMF (3 mL) was added NaOH (400.7 mg, 10.02 mmol). The reaction mixture was stirred at 25° C. for 0.5 hr. The mixture was diluted with H₂O (10 mL), adjusted to pH=7 with HCl (36%), then filtered and concentrated to provide a residue that was purified by reverse-phase prep HPLC (H₂O/CH₃CN with 0.225% FA) to provide 2.2 mg (0.67%) of 6-(((2-chloro-4-(trifluoromethyl)phenyl)amino)methyl)-4-methylpicolinic acid (Compound 57-1) as a white solid. LCMS-ESI (m/z) calculated for C₁₅H₁₂ClF₃N₂O₂: 344.05. found 345.0 (M+H)⁺, t$_R$=0.873 min (Method 6). ¹H NMR (400 MHz, MeOD4) δ ppm 2.35-2.51 (s, 3H) 4.58-4.70 (s, 2H) 6.60-6.81 (m, 1H) 7.26-7.35 (m, 1H) 7.39-7.46 (m, 1H) 7.50-7.60 (s, 1H) 7.80-8.05 (s, 1H).

Example 58

Synthesis of Compounds 58-1 and 58-2

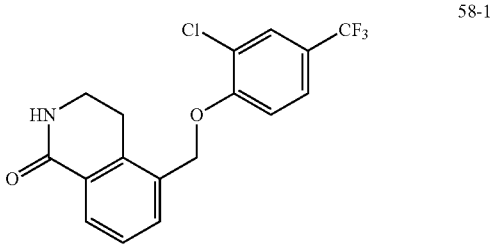

58-1

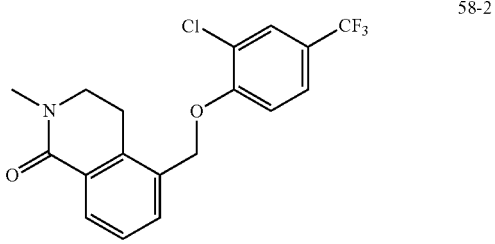

58-2

Scheme 58

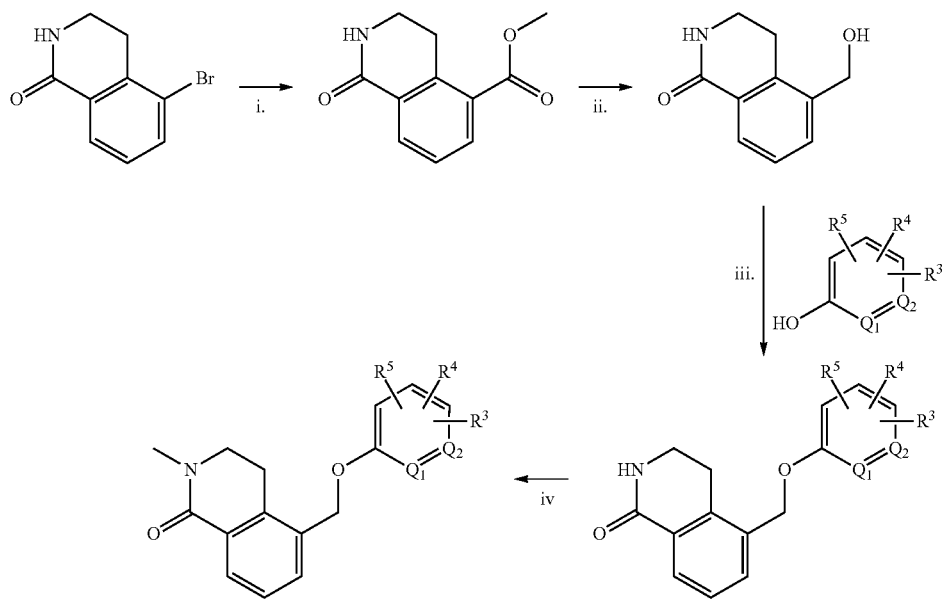

Reagents: (i) Pd(dppf)Cl$_2$·DCM, TEA, DMF, CO; (ii) LiBH$_4$, THF; (iii) DIAD, PPh$_3$, THF; (iv) NaH, THF, MeI.

Step 58-1. Synthesis of methyl 1-oxo-1,2,3,4-tetrahydroisoquinoline-5-carboxylate (INT 58-1)

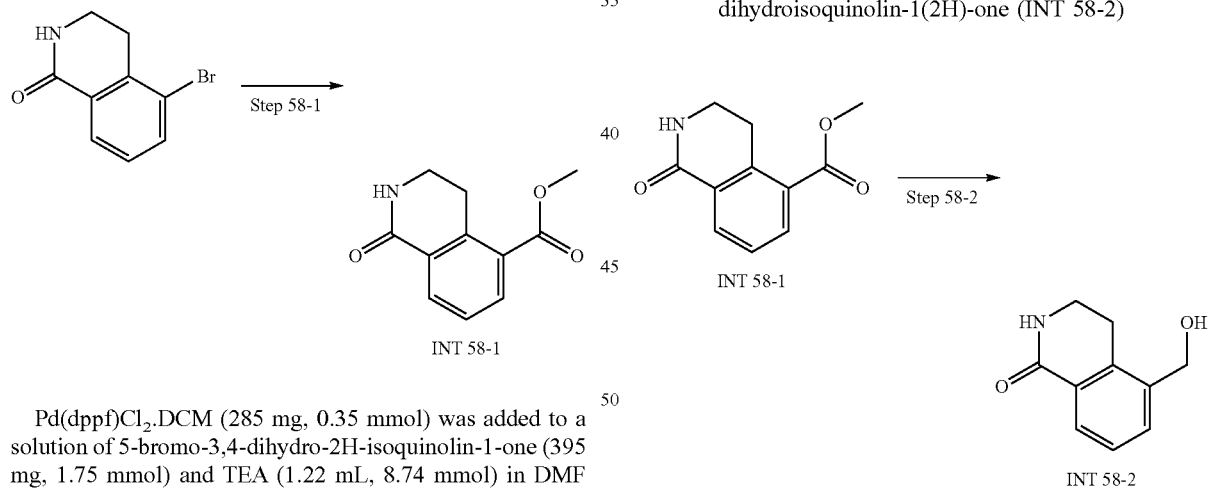

Pd(dppf)Cl$_2$.DCM (285 mg, 0.35 mmol) was added to a solution of 5-bromo-3,4-dihydro-2H-isoquinolin-1-one (395 mg, 1.75 mmol) and TEA (1.22 mL, 8.74 mmol) in DMF (6.00 mL) at 22° C. The mixture was evacuated and refilled with CO for 3 cycles. MeOH (3.08 mL) was added, and the mixture was heated to 85° C. under a CO atmosphere (1 atm) for 16 h. The mixture was diluted with EA (25 mL) and filtered through a pad of Celite. The filtrate was concentrated under reduced pressure. The residue was diluted with EA (100 mL) and H$_2$O (100 mL). The aq. phase was extracted with EA (3×25.0 mL). The combined organic layers were washed with brine (50 mL), dried (Na$_2$SO$_4$), filtered, and concentrated. The residue was purified by SiO$_2$ chromatography (hexanes and EA) to provide 285 mg (80%) of methyl 1-oxo-1,2,3,4-tetrahydroisoquinoline-5-carboxylate (INT 58-1). LCMS-ESI (m/z) calculated for C$_{11}$H$_{11}$NO$_3$: 205.07. found 205.74 (M+H)$^+$, t$_R$=1.82 min (Method 13). $^1$H NMR (400 MHz, CDCl$_3$) δ 8.30 (dd, J=7.7, 1.5 Hz, 1H), 8.09 (dd, J=7.8, 1.5 Hz, 1H), 7.42 (dd, J=7.8 Hz, 1H), 5.95 (s, 1H), 3.92 (s, 3H), 3.58-3.52 (m, 2H), 3.49-3.40 (m, 2H).

Step 58-2. Synthesis of 5-(hydroxymethyl)-3,4-dihydroisoquinolin-1(2H)-one (INT 58-2)

LiBH$_4$ (2 M in THF, 2.66 mL, 5.32 mmol) was added to a solution of INT 58-1 (182 mg, 0.887 mmol) in THF (5.00 mL) at 22° C. under N$_2$. The mixture was stirred at 22° C. for 20 h. The mixture was diluted with sat. aq. NH$_4$C$_1$ (10 mL). The aq. phase was extracted with EA (3×20 mL), and the combined organic phases were washed with brine (50 mL), dried (Na$_2$SO$_4$), filtered, and concentrated to provide 88 mg (56%) of 5-(hydroxymethyl)-3,4-dihydroisoquinolin-1(2H)-one (INT 58-2) as an oil. LCMS-ESI (m/z) calculated for C$_{10}$H$_{11}$NO$_2$: 177.08. found 178.13 (M+H)$^+$, t$_R$=1.39 min (Method 13). $^1$H NMR (500 MHz, CDCl$_3$) δ 8.07 (dd, J=7.8, 1.4 Hz, 1H), 7.52 (dd, J=7.6, 1.4 Hz, 1H), 7.36 (t, J=7.7 Hz, 1H), 5.95 (s, 1H), 4.75 (s, 2H), 3.57 (td, J=6.7, 2.9 Hz, 2H), 3.07 (t, J=6.6 Hz, 2H), 1.72 (s, 1H).

Step 58-3. Synthesis of 5-((2-chloro-4-(trifluoromethyl)phenoxy)methyl)-3,4-dihydroisoquinolin-1(2H)-one (Compound 58-1)

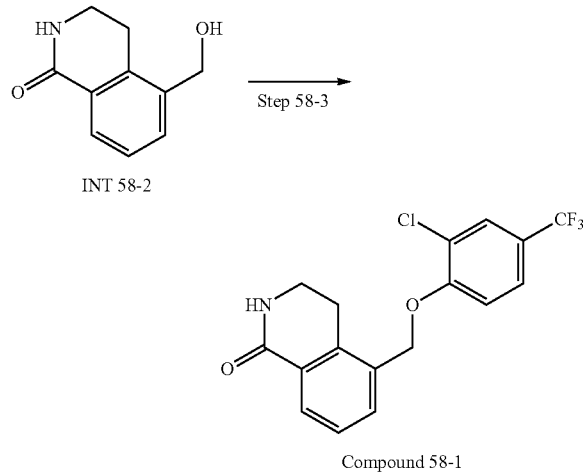

DIAD (108 μL, 0.55 mmol) was added to a mixture of INT 58-2 (88.0 mg, 0.497 mmol), 2-chloro-4-(trifluoromethyl)phenol (69.7 μL, 0.521 mmol), and PPh₃ (143 mg, 0.546 mmol) in THF (5.00 mL) at 0° C. under N₂. The mixture was stirred at 22° C. for 18 h. The mixture was concentrated, and the residue was purified by reverse phase chromatography (H₂O (+0.1% formic acid) and MeCN) to provide 32.7 mg (19%) of 5-((2-chloro-4-(trifluoromethyl)phenoxy)methyl)-3,4-dihydroisoquinolin-1(2H)-one (Compound 58-1) as a solid. LCMS-ESI (m/z) calculated for $C_{17}H_{13}ClF_3NO_2$: 355.06. found 356.07 (M+H)$^+$, $t_R$=4.69 min (Method 12). $^1$H NMR (500 MHz, CDCl₃) δ 8.00 (s, 1H), 7.90 (dd, J=7.8, 1.4 Hz, 1H), 7.88-7.85 (m, 1H), 7.73 (ddd, J=8.7, 2.3, 0.9 Hz, 1H), 7.68 (dd, J=7.6, 1.4 Hz, 1H), 7.52 (d, J=8.6 Hz, 1H), 7.40 (dd, J=7.6 Hz, 1H), 5.38 (s, 2H), 3.38 (td, J=6.6, 2.8 Hz, 2H), 2.96 (t, J=6.6 Hz, 2H).

Step 58-4. Synthesis of 5-((2-chloro-4-(trifluoromethyl)phenoxy)methyl)-2-methyl-3,4-dihydroisoquinolin-1(2H)-one (Compound 58-2)

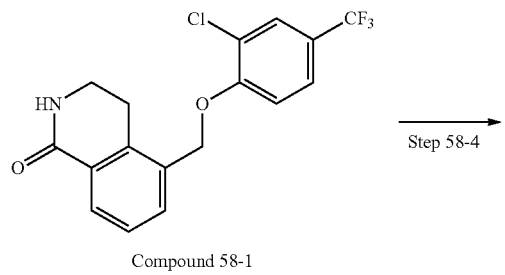

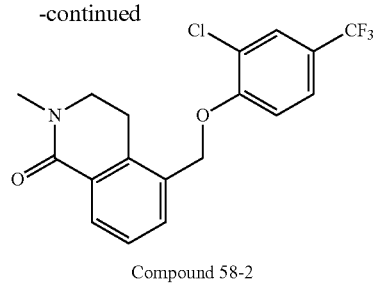

Compound 58-2

NaH (24.9 mg, 1.08 mmol) was added to a solution of Compound 58-1 (154 mg, 50% purity, 0.216 mmol) in THF (5.00 mL) at 0° C. under N₂. The mixture was stirred at 22° C. for 30 min. Iodomethane (67.4 μL, 1.08 mmol) was added, and the mixture was stirred at 70° C. for 1 h. The mixture was diluted with MeOH (10.0 mL) and concentrated. The product was purified by reverse phase chromatography (H₂O (+0.1% formic acid) and MeCN) to provide 60 mg (76%) of 5-((2-chloro-4-(trifluoromethyl)phenoxy)methyl)-2-methyl-3,4-dihydroisoquinolin-1(2H)-one (Compound 58-2) as an solid. LCMS-ESI (m/z) calculated for $C_{18}H_{15}ClF_3NO_2$: 369.77. found 370.08 (M+H)$^+$, $t_R$=5.08 min (Method 12). $^1$H NMR (500 MHz, CDCl₃) δ 8.00 (s, 1H), 7.92 (dd, J=7.8, 1.4 Hz, 1H), 7.86 (dd, J=2.3, 0.7 Hz, 1H), 7.73 (ddd, J=8.7, 2.3, 0.8 Hz, 1H), 7.66 (dd, J=7.6, 1.4 Hz, 1H), 7.52 (d, J=8.7 Hz, 1H), 7.39 (dd, J=7.7 Hz, 1H), 5.38 (s, 2H), 3.56 (t, J=6.7 Hz, 2H), 3.07-2.99 (m, 4H).

Example 59

Synthesis of Compound 59-1

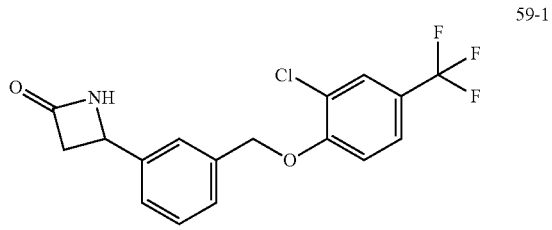 [SMILES: O=C1CC(c2cccc(COc3ccc(C(F)(F)F)cc3Cl)c2)N1]

Scheme 59

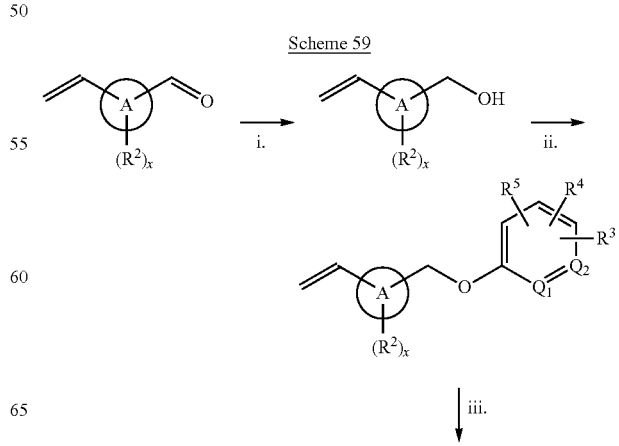

-continued

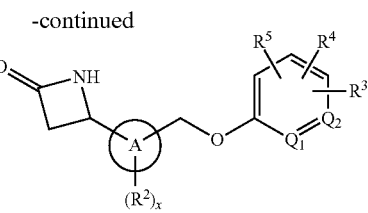

Reagents: (i) NaBH₄, MeOH; (ii) DIAD, PPh₃, THF; (iii) N-Chlorosulfonyl isocyanate, THF.

Step 59-1. Synthesis of (3-vinylphenyl)methanol (INT 59-1)

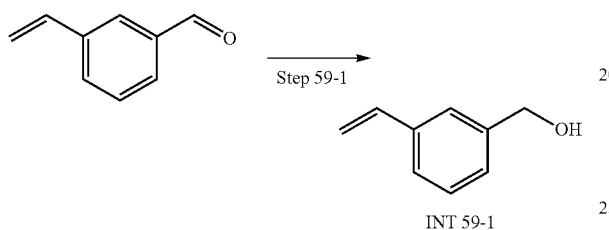

NaBH₄ (327 mg, 8.66 mmol) was slowly added to a solution of 3-vinylbenzaldehyde (1.00 mL, 7.87 mmol) in MeOH (20 mL) at 22° C. under $N_2$. The mixture was stirred at 22° C. for 1 h and concentrated under reduced pressure. The residue was purified by $SiO_2$ chromatography (EA/hexanes) to provide 1.05 g (99%) of (3-vinylphenyl) methanol (INT 59-1). LCMS-ESI (m/z) mass not observed, $t_R$=2.00 min (Method 13). ¹H NMR (400 MHz, CDCl₃) δ 7.42 (s, 1H), 7.37-7.30 (m, 2H), 7.26 (d, J=3.1 Hz, 1H), 6.73 (dd, J=17.6, 10.9 Hz, 1H), 5.78 (dd, J=17.6, 0.9 Hz, 1H), 5.27 (dd, J=10.9, 0.9 Hz, 1H), 4.70 (s, 2H), 1.67 (s, 1H).

Step 59-2. Synthesis of 2-chloro-4-(trifluoromethyl)-1-((3-vinylbenzyl)oxy)benzene (INT 59-2)

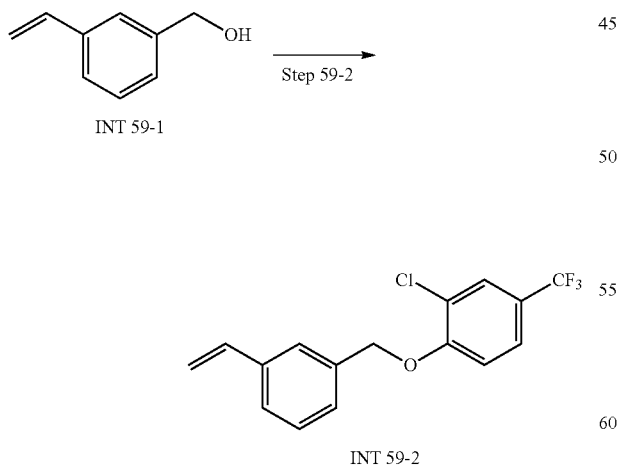

DIAD (1.29 mL, 6.56 mmol) was added dropwise to a mixture of INT 59-1 (800 mg, 5.96 mmol), 2-chloro-4-(trifluoromethyl)phenol (793 mL, 5.93 mmol), and PPh₃ (2.35 g, 8.94 mmol) in THF (15.0 mL) at 22° C. under $N_2$. The mixture was stirred at 22° C. for 6 h and concentrated. The residue was purified by $SiO_2$ chromatography (EA/hexanes) to provide 1.73 g (93%) of 2-chloro-4-(trifluoromethyl)-1-((3-vinylbenzyl)oxy)benzene (INT 59-2) as an oil. LCMS-ESI (m/z) mass not observed, $t_R$=2.95 min (Method 13). ¹H NMR (500 MHz, CDCl₃) δ 7.66 (dd, J=2.3, 0.7 Hz, 1H), 7.49 (s, 1H), 7.48-7.43 (m, 1H), 7.41-7.35 (m, 3H), 7.06-6.99 (m, 1H), 6.74 (dd, J=17.6, 10.9 Hz, 1H), 5.78 (dd, J=17.6, 0.9 Hz, 1H), 5.29 (dd, J=10.9, 0.8 Hz, 1H), 5.21 (s, 2H).

Step 59-3. Synthesis of 4-(3-((2-chloro-4-(trifluoromethyl)phenoxy)methyl)phenyl)azetidin-2-one (Compound 59-1)

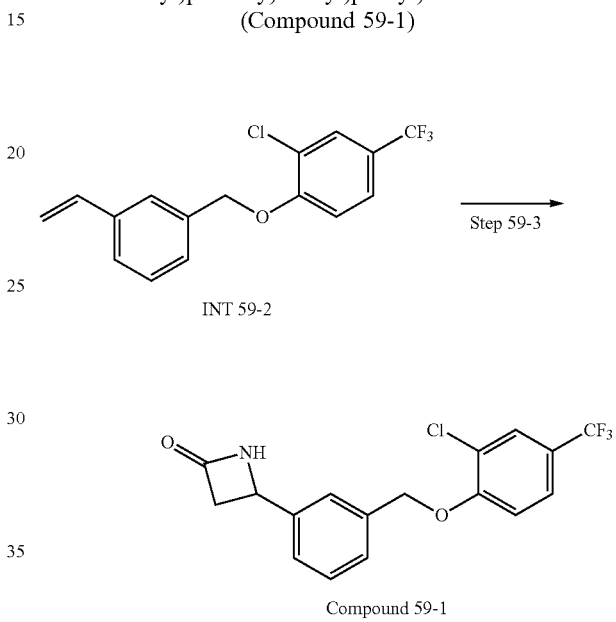

N-Chlorosulfonyl isocyanate (578 μL, 6.64 mmol) was added over 10 min to a solution of INT 59-2 (1.73 g, 5.53 mmol) in THF (5.00 mL) at 22° C. under $N_2$. The mixture was stirred at 22° C. for 16 h. The mixture was added over 20 min to a vigorously stirred mixture of $H_2O$ (10.0 mL), sodium carbonate (1.93 g, 18.3 mmol), and sodium sulfite (1.05 g, 8.30 mmol) at 0° C. The mixture was stirred at 22° C. for 2 h. The mixture was acidified with aq. 1 M HCl (pH~ 5) and diluted with EA (100 mL). The aq. phase was extracted with EA (3×50.0 mL), and the combined organic layers were dried (MgSO₄), filtered, and concentrated. The residue was purified by reverse phase chromatography ($H_2O$ (+0.1% formic acid) and MeCN (50-100%)) to provide 189 mg (10%) of 4-(3-((2-chloro-4-(trifluoromethyl)phenoxy)methyl)phenyl)azetidin-2-one (Compound 59-1) as an solid. LCMS-ESI (m/z) calculated for $C_{17}H_{13}ClF_3NO_2$: 355.06. found 356.07 (M+H)⁺, $t_R$=4.93 min (Method 12). ¹H NMR (500 MHz, CDCl₃) δ 8.41 (s, 1H), 7.86 (dd, J=2.3, 0.7 Hz, 1H), 7.75-7.67 (m, 1H), 7.50 (d, J=1.9 Hz, 1H), 7.48-7.38 (m, 3H), 7.36 (dt, J=6.8, 2.1 Hz, 1H), 5.33 (s, 2H), 4.67 (dd, J=5.3, 2.5 Hz, 1H), 3.36 (ddd, J=14.6, 5.3, 2.2 Hz, 1H), 2.67 (ddd, J=14.6, 2.5, 1.0 Hz, 1H).

Example 60

Synthesis of Compound 60-1

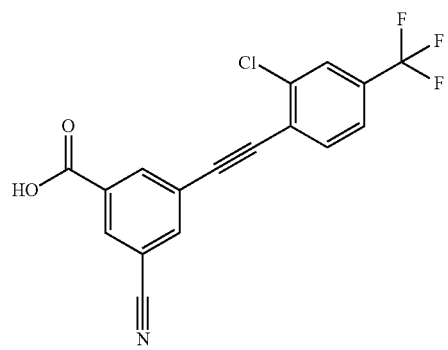

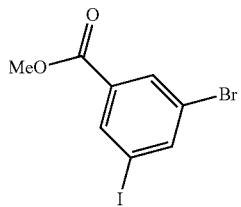

H₂SO₄ (600 µL, 11.3 mmol) was added to a solution of 3-bromo-5-iodo-benzoic acid (10.0 g, 30.6 mmol) in MeOH (65 mL). The mixture was stirred at 75° C. for 18 h. The mixture was cooled to 22° C. and concentrated. The residue was diluted in EA (100 mL), washed with sat. aq. NaHCO₃ (100 mL), dried (Na₂SO₄), filtered, and concentrated to provide 9.90 g (95%) of methyl 3-bromo-5-iodo-benzoate (INT 60-1) as a solid. LCMS-ESI (m/z) calculated for $C_8H_6BrIO_2$: 339.86. found 339.6 (M–H)⁺, $t_R$=2.72 min (Method 13).

Scheme 60

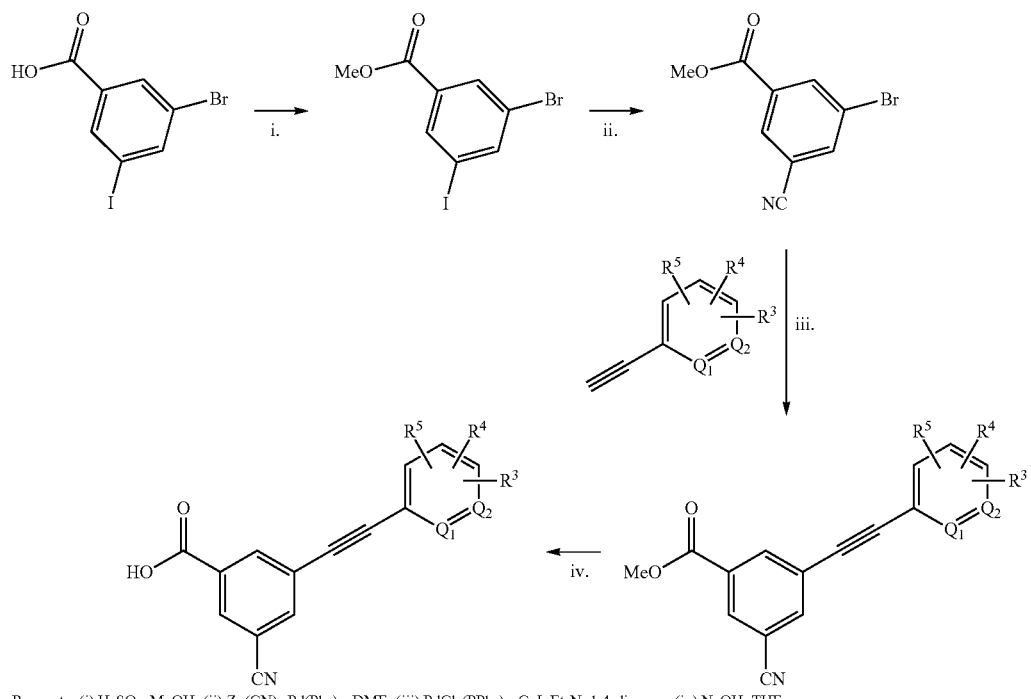

Reagents: (i) H₂SO₄, MeOH; (ii) Zn(CN)₂ Pd(Ph₃)₄; DMF; (iii) PdCl₂(PPh₃)₂, CuI, Et₃N, 1,4-dioxane; (iv) NaOH, THF.

Step 60-1. Synthesis of methyl 3-bromo-5-iodo-benzoate (INT 60-1)

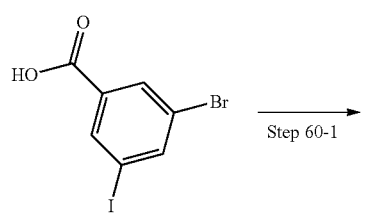

Step 60-2. Synthesis of methyl 3-bromo-5-cyanobenzoate (INT 60-2)

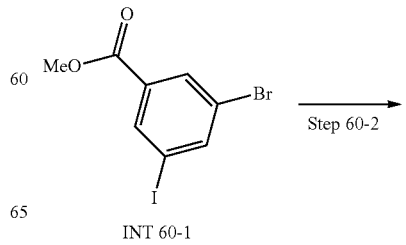

319
-continued

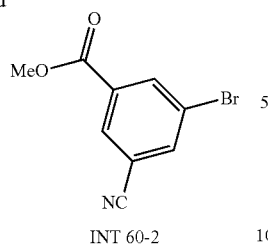

INT 60-2

Zinc cyanide (1.76 g, 15.0 mmol) and Pd(PPh$_3$)$_4$ (2.88 g, 2.49 mmol) were added to a solution of INT 60-1 (8.50 g, 2.49 mmol) in DMF (60 mL). The mixture was stirred at 80° C. for 2 h. The mixture was cooled to 22° C. and concentrated. The residue was diluted with EA (100 mL). The organic layer was washed with H$_2$O (3×50.0 mL) and brine (150 mL), dried (Na$_2$SO$_4$), filtered, and concentrated. The residue was purified by SiO$_2$ chromatography (EA/hexanes) to provide 3.00 g (50%) of methyl 3-bromo-5-cyanobenzoate (INT 60-2) as a solid. LCMS-ESI (m/z): mass not observed, t$_R$=2.38 min (Method 13).

Step 60-3. Synthesis of methyl 3-((2-chloro-4-(trifluoromethyl)phenyl)ethynyl)-5-cyanobenzoate (INT 60-3)

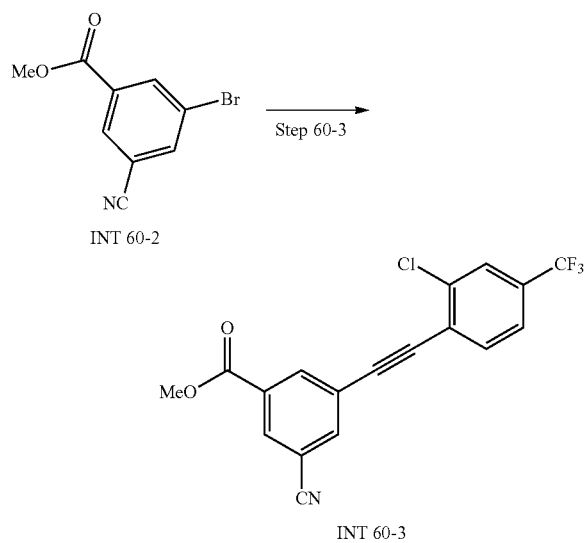

INT 60-3

2-Chloro-1-ethynyl-4-(trifluoromethyl)benzene (551 µL, 1.87 mmol), PdCl$_2$(PPh$_3$)$_2$ (132 mg, 0.19 mmol), and CuI (17.9 mg, 0.094 mmol) were added to a solution of INT 60-2 (225 mg, 0.94 mmol) in 1,4-dioxane (2 mL) and Et$_3$N (2.0 mL). The mixture was stirred at 80° C. for 24 h. The mixture was cooled to 22° C. and diluted with aq. sat. NH$_4$Cl (20 mL). The aq. phase was extracted with EA (3×50 mL), and the combined organic layers were concentrated. The residue was purified by SiO$_2$ chromatography (EA/hexanes) to provide 250 mg (73%) of methyl 3-((2-chloro-4-(trifluoromethyl)phenyl)ethynyl)-5-cyanobenzoate (INT 60-3) as a solid. LCMS-ESI (m/z) calculated for C$_{18}$H$_9$ClF$_3$NO$_2$: 363.03. found 365.5 (M+H)$^+$, t$_R$=2.92 min (Method 13). $^1$H NMR (400 MHz, CDCl$_3$) δ 8.42 (t, J=1.5 Hz, 1H), 8.30 (t, J=1.4 Hz, 1H), 8.00 (t, J=1.4 Hz, 1H), 7.72 (s, 1H), 7.68 (d, J=8.1 Hz, 1H), 7.54 (d, J=7.6 Hz, 1H), 3.99 (s, 3H).

320

Step 60-4. Synthesis of 3-((2-chloro-4-(trifluoromethyl)phenyl)ethynyl)-5-cyanobenzoic acid (Compound 60-1)

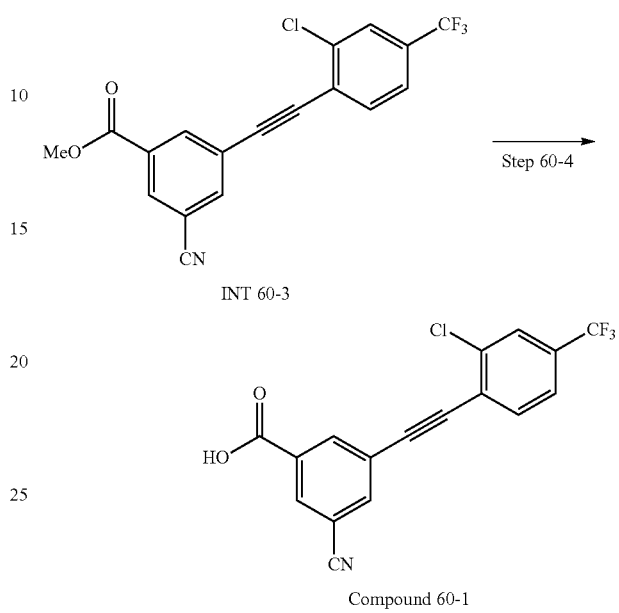

Aq. 2 M NaOH (165 µL, 0.330 mmol) was added to a solution of INT 60-3 (60.0 mg, 0.165 mmol) in THF (2 mL) at 22° C. The mixture was stirred at 22° C. for 12 h and concentrated. The residue was diluted with H$_2$O (10.0 mL) and acidified with aq. 2 M HCl (pH~ 2). The aq. phase was extracted with EA (3×20.0 mL), and the combined organic layers were dried (Na$_2$SO$_4$), filtered, and concentrated. The residue was purified by SiO$_2$ chromatography (MeOH/DCM) to provide 55.0 mg (95%) of 3-((2-chloro-4-(trifluoromethyl)phenyl)ethynyl)-5-cyanobenzoic acid (Compound 60-1) as a solid. LCMS-ESI (m/z) calculated for C$_{17}$H$_7$ClF$_3$NO$_2$: 349.01. found 348.49 (M−H)$^+$, t$_R$=4.55 min (Method 12). $^1$H NMR (400 MHz, DMSO-d6) δ 8.37-8.32 (m, 2H), 8.30 (s, 1H), 8.08 (s, 1H), 7.97 (d, J=8.0 Hz, 1H), 7.82 (dd, J=8.1, 1.1 Hz, 1H).

Example 61

Synthesis of Compound 61-1

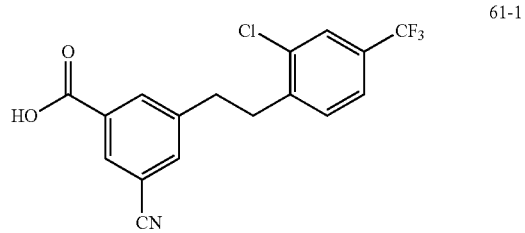 [SMILES: N#Cc1cc(CCc2ccc(C(F)(F)F)cc2Cl)cc(C(=O)O)c1]

Scheme 61

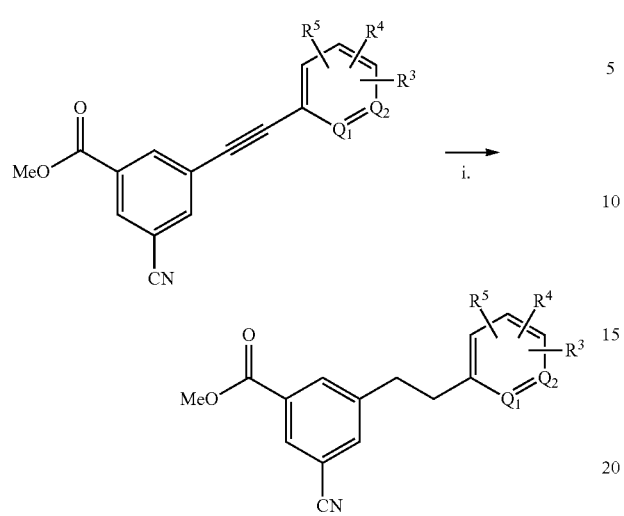

Reagents: (i) Pd/C, H₂, EA.

Step 61-1. Synthesis of methyl 3-(2-(2-chloro-4-(trifluoromethyl)phenyl)ethyl)-5-cyano-benzoate (INT 61-1)

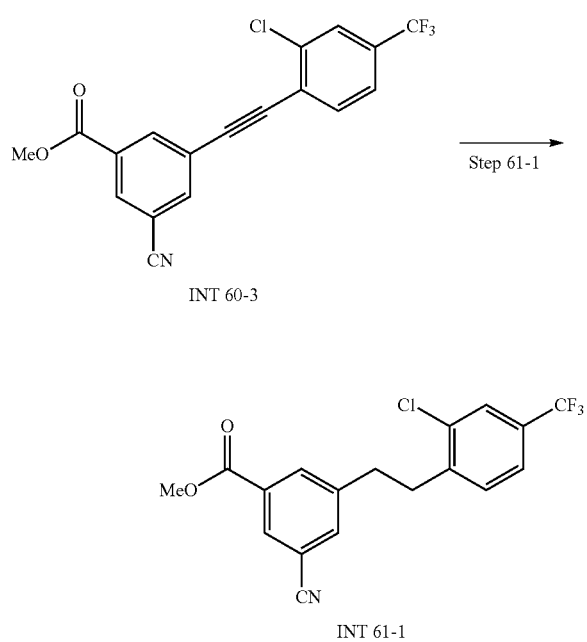

INT 60-3

INT 61-1

INT 60-3 (100 mg, 0.275 mmol) and Pd/C (100 mg, 0.0940 mmol) in EA (10.0 mL) were stirred under hydrogen (1 atm) at 22° C. for 4 h. The mixture was filtered through Celite, washing with EA (100 mL), and the filtrate was concentrated. The residue was purified by SiO₂ chromatography (EA/hexanes) to provide 101 mg (100%) methyl 3-[2-[2-chloro-4-(trifluoromethyl)phenyl]ethyl]-5-cyano-benzoate (INT 61-1) as a solid. LCMS-ESI (m/z) calculated for $C_{18}H_{13}ClF_3NO_2$: 367.06. found 367.3 (M–H)⁺, $t_R$=2.85 min (Method 13).

Step 61-2. Synthesis of 3-(2-chloro-4-(trifluoromethyl)phenethyl)-5-cyanobenzoic acid (Compound 61-2)

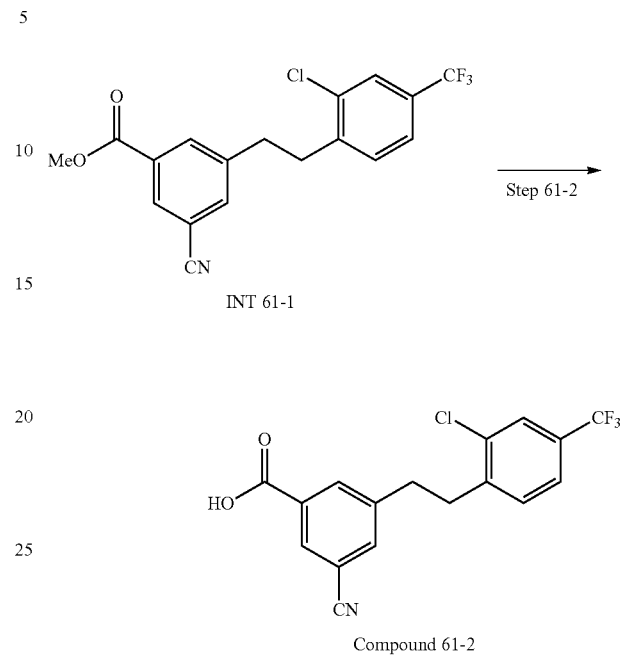

INT 61-1

Compound 61-2

A solution of 2 M NaOH (197 µL, 0.156 mmol) was added to a solution of INT 61-1 (60.0 mg, 0.156 mmol) in THF (2 mL). The mixture was stirred at 22° C. for 12 h and concentrated. The residue was acidified with 2 M HCl (pH ~2) and diluted with H₂O (10 mL). The aq. phase was extracted with EA (3×20 mL), and the combined organic layers were dried (Na₂SO₄), filtered, and concentrated. The residue was purified by reverse phase chromatography (H₂O (+0.1% formic acid) and ACN) to provide 47.0 mg (85%) of 3-(2-chloro-4-(trifluoromethyl)phenethyl)-5-cyanobenzoic acid (Compound 61-2) as a solid. LCMS-ESI (m/z) calculated for $C_{17}H_{11}ClF_3NO_2$: 353.04. found 352.1 (M–H)⁺, $t_R$=4.73 min (Method 12). ¹H NMR (500 MHz, DMSO-d6) δ 13.54 (s, 1H), 8.13 (t, J=1.5 Hz, 1H), 8.05 (t, J=1.6 Hz, 1H), 7.98 (t, J=1.6 Hz, 1H), 7.83 (d, J=1.2 Hz, 1H), 7.66 (dd, J=8.0, 1.3 Hz, 1H), 7.58 (d, J=8.0 Hz, 1H), 3.07 (dq, J=9.8, 6.3 Hz, 4H).

Example 62

Synthesis of Compound 62-1

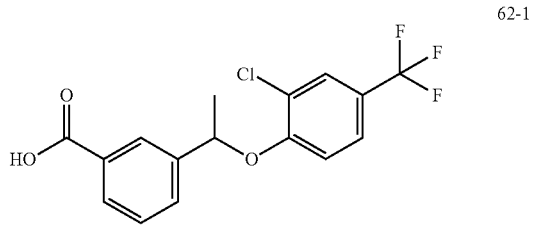 [SMILES: CC(Oc1ccc(C(F)(F)F)cc1Cl)c1cccc(C(=O)O)c1]

62-1

Scheme 62

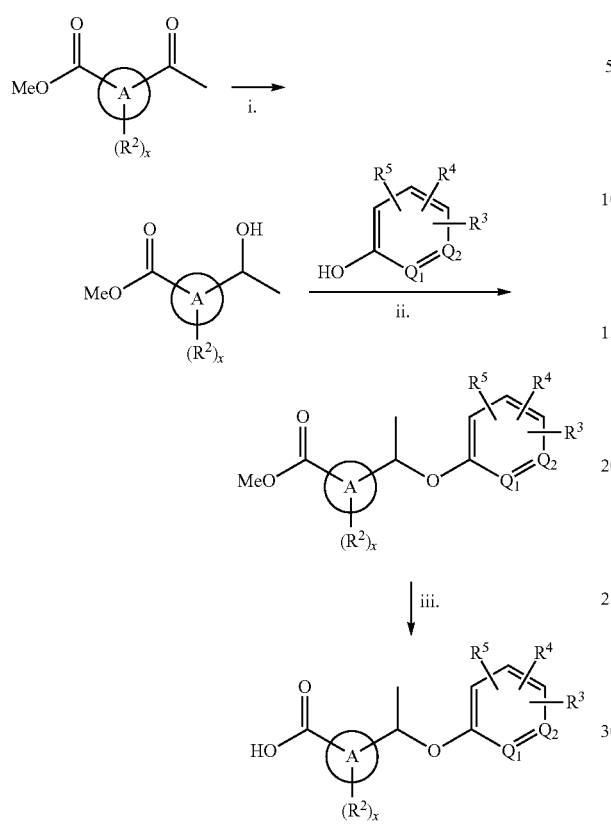

Reagents: (I) NaBH₄, EtOH; (ii) DIAD, PPh₃, THF; (iii) NaOH, MeOH, THF.

Step 62-1. Synthesis of methyl 3-(1-hydroxyethyl)benzoate (INT 62-1)

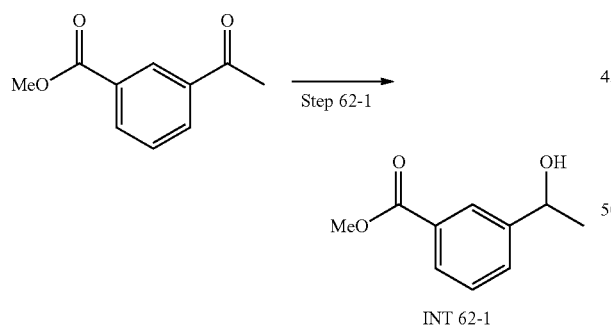

NaBH₄ (752 mg, 19.9 mmol) was added to a mixture of methyl 3-acetylbenzoate (1.18 g, 6.62 mmol) in EtOH (15.0 mL) at 22° C. The mixture was stirred at 0° C. for 30 min and at 22° C. for 1 h. The mixture was diluted with sat. aq. NH₄C₁ (30.0 mL). The aq. phase was extracted with EA (3×30.0 mL), and the combined organic layers were dried over Na₂SO₄, filtered, and concentrated. The residue was purified by SiO₂ chromatography (EA/hexanes) to provide the 830 mg (70%) of methyl 3-(1-hydroxyethyl) benzoate (INT 62-1) as a solid. LCMS-ESI (m/z) mass not observed, $t_R$=1.93 min (Method 12). ¹H NMR (400 MHz, CDCl₃) δ 8.05 (tt, J=1.8, 0.6 Hz, 1H), 7.98-7.92 (m, 1H), 7.59 (dddd, J=7.7, 1.8, 1.2, 0.6 Hz, 1H), 7.43 (tt, J=7.7, 0.4 Hz, 1H), 4.97 (q, J=6.5 Hz, 1H), 3.92 (s, 3H), 1.84 (s, 1H), 1.52 (d, J=6.5 Hz, 3H).

Step 62-2. Synthesis of methyl 3-(1-(2-chloro-4-(trifluoromethyl)phenoxy)ethyl)benzoate (INT 62-2)

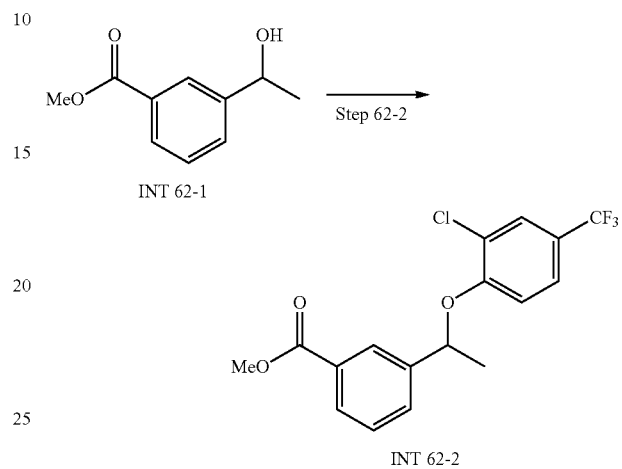

DIAD (981 μL, 4.98 mmol) was added to a mixture of INT 62-1 (816 mg, 4.53 mmol), 2-chloro-4-(trifluoromethyl)phenol (886 mg, 4.51 mmol), and PPh₃ (1.78 g, 6.79 mmol) in THF (25.0 mL) at 22° C. The mixture was stirred at 22° C. for 3 h. The mixture was concentrated, and the residue was purified by SiO₂ chromatography (EA/hexane) to provide 1.40 g (86%) of methyl 3-(1-(2-chloro-4-(trifluoromethyl)phenoxy)ethyl)benzoate (INT 62-2) as a solid. LCMS-ESI (m/z) calculated for C₁₇H₁₄ClF₃O₃: 358.06. found 357.06 (M–H)⁺, $t_R$=2.87 min (Method 13).

Step 62-3. Synthesis of 3-(1-(2-chloro-4-(trifluoromethyl)phenoxy)ethyl)benzoic acid (Compound 62-1)

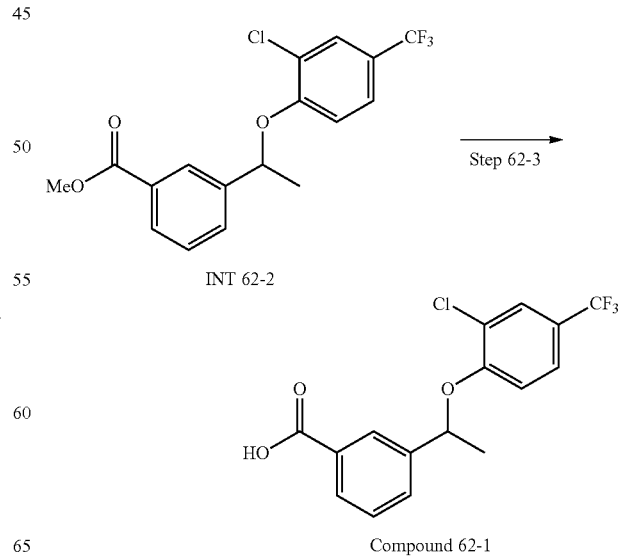

2 M NaOH (4.68 mmol, 2.34 mL) was added to a solution of INT 62-2 (1.40 g, 3.90 mmol) in MeOH (12 mL) and THF (12 mL) at 22° C. After 12 h, the mixture was concentrated, and the residue was diluted with H₂O (10.0 mL) and 2 M HCl (pH ~4). The aq. phase was extracted with EA (3×25.0 mL). The combined organic layers were dried (Na₂SO₄), filtered, and concentrated, and the residue was purified by SiO₂ chromatography (MeOH/DCM) to provide 1.34 g (99%) of 3-(1-(2-chloro-4-(trifluoromethyl)phenoxy)ethyl) benzoic acid (Compound 62-1) as a solid. LCMS-ESI (m/z) calculated for $C_{16}H_{12}ClF_3O_3$: 344.04. found 343.04 (M−H)⁺, $t_R$=5.17 min (Method 12). ¹H NMR (400 MHz, DMSO-d6) δ 13.04 (s, 1H), 8.03 (t, J=1.6 Hz, 1H), 7.90-7.84 (m, 1H), 7.82 (d, J=2.0 Hz, 1H), 7.71-7.64 (m, 1H), 7.60-7.54 (m, 1H), 7.50 (t, J=7.7 Hz, 1H), 7.24 (d, J=8.7 Hz, 1H), 5.89 (q, J=6.3 Hz, 1H), 1.62 (d, J=6.3 Hz, 3H).

Example 63

Synthesis of Compound 63-1

Step 63-1. Synthesis of tert-butyl N-((3-((2-chloro-4-(trifluoromethyl)phenoxy)methyl) phenyl)methyl) carbamate (INT 63-1)

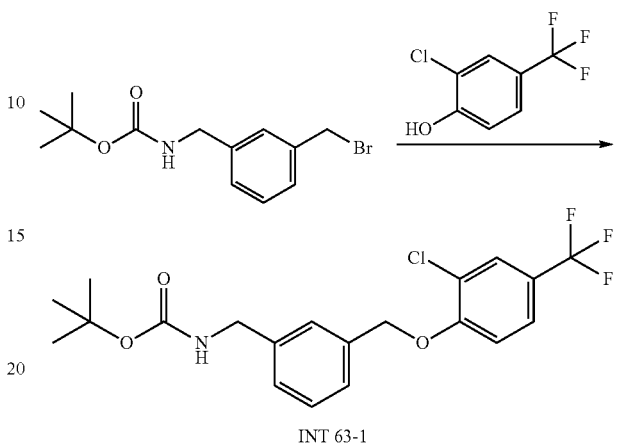

tert-Butyl N-((3-(bromomethyl)phenyl)methyl)carbamate (100 mg, 0.333 mmol) was added to a mixture of 2-chloro-4-(trifluoromethyl)phenol (50.0 μL, 0.366 mmol) and K₂CO₃ (51.0 mg, 0.366 mmol) in DMF (1 mL) at 22° C. under N₂. The mixture was stirred at 40° C. for 16 h. The mixture was diluted with H₂O (20 mL), and the aq. layer was extracted with DCM (3×20 mL). The combined organic layers were dried (MgSO₄), filtered, and concentrated. The residue was purified by SiO₂ chromatography (EA/hexanes)

Scheme 63

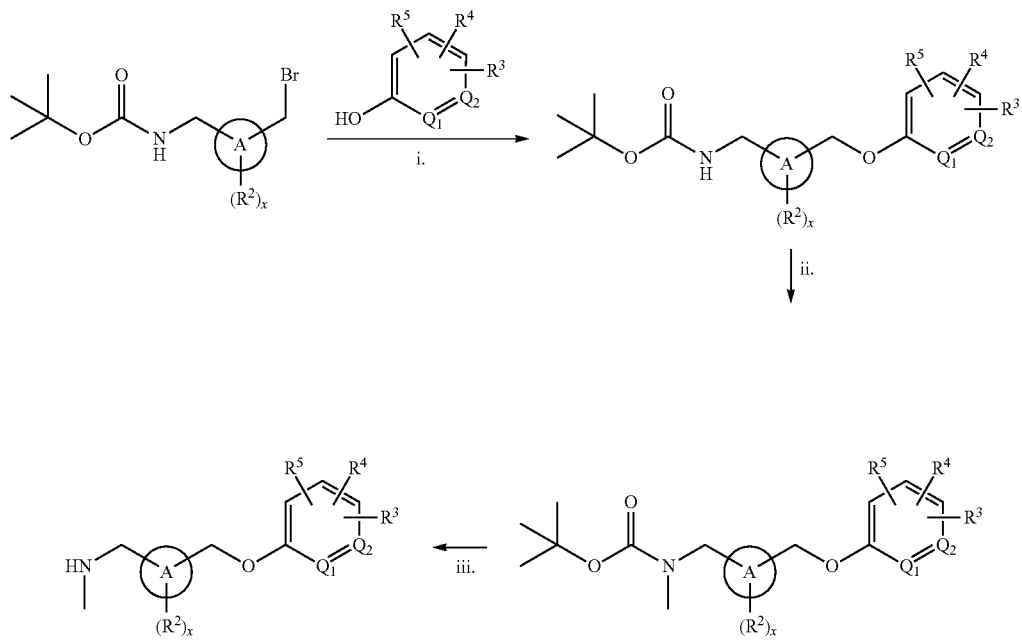

Reagents: (i) K₂CO₃, DMF; (ii) NaH, MeI, DMF; (iii) TFA, DCM.

to provide 122 mg (88%) of tert-butyl N-((3-((2-chloro-4-(trifluoromethyl)phenoxy)methyl)phenyl)methyl)carbamate (INT 63-1). LCMS-ESI (m/z) calculated for $C_{20}H_{21}ClF_3NO_3$: 415.12. found 414.17 (M+H)$^+$, $t_R$=2.86 min (Method 13). $^1$H NMR (400 MHz, CDCl$_3$) δ 7.66 (d, J=2.3 Hz, 1H), 7.45 (ddd, J=8.6, 2.2, 0.9 Hz, 1H), 7.40-7.33 (m, 3H), 7.28-7.27 (m, 1H), 7.01 (d, J=8.6 Hz, 1H), 5.20 (s, 2H), 4.86 (s, 1H), 4.34 (d, J=6.0 Hz, 2H), 1.46 (s, 9H).

Step 63-2. Synthesis of tert-butyl N-((3-((2-chloro-4-(trifluoromethyl)phenoxy)methyl) phenyl)methyl)-N-methyl-carbamate (INT 63-2)

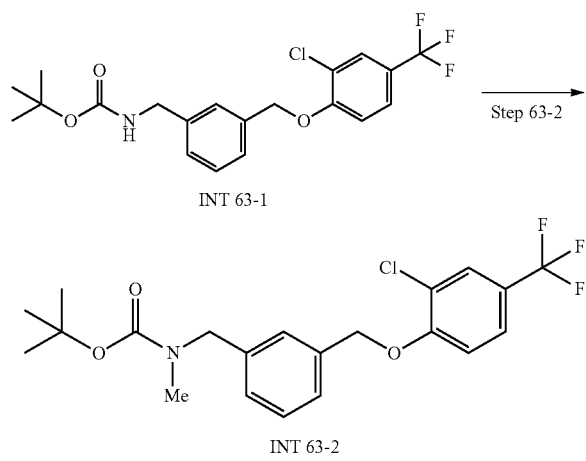

NaH (60 wt. %, 12.2 mg, 0.317 mmol) was added to a solution of INT 63-1 (120 mg, 0.289 mmol) in THF (2 mL) at 22° C. under N$_2$. The mixture was stirred at 22° C. for 15 min. Iodomethane (21.6 µL, 0.346 mmol) was added, and the mixture was stirred at 50° C. for 24 h. The mixture was concentrated, and the residue was purified by SiO$_2$ chromatography (EA/hexanes) to provide 71.2 mg (57%) of tert-butyl N-((3-((2-chloro-4-(trifluoromethyl)phenoxy)methyl)phenyl)methyl)-N-methyl-carbamate (INT 63-2). LCMS-ESI (m/z) calculated for $C_{21}H_{23}ClF_3NO_3$: 429.13. found 428.17 (M−H)$^+$, $t_R$=3.29 min (Method 13). $^1$H NMR (500 MHz, CDCl$_3$) δ 7.66 (d, J=2.2 Hz, 1H), 7.48-7.43 (m, 1H), 7.38-7.33 (m, 2H), 7.30 (s, 1H), 7.21 (s, 1H), 7.01 (d, J=8.6 Hz, 1H), 5.20 (s, 2H), 4.45 (s, 2H), 2.82 (d, J=26.0 Hz, 3H), 1.47 (d, J=15.5 Hz, 9H).

Step 63-3. Synthesis of 1-(3-((2-chloro-4-(trifluoromethyl)phenoxy)methyl)phenyl)-N-methylmethanamine (Compound 63-1)

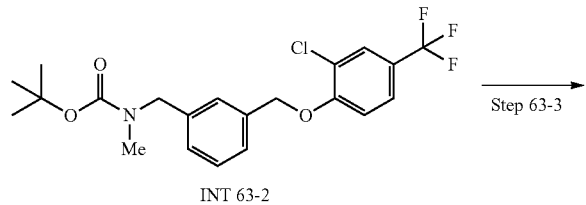

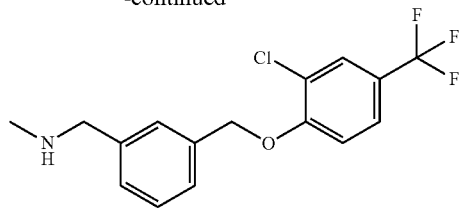

Compound 63-1

A solution of TFA (500 µL) was added dropwise to a solution of INT 63-2 (70.0 mg, 0.745 mmol) in DCM (1.5 mL). The mixture was stirred at 22° C. for 5 h. The mixture was basified with aq. 1 M NaOH (10 mL) and stirred at 22° C. for 15 min. The aq. phase was extracted with DCM (3×20 mL), and the combined organic layers were washed with brine (20 mL), dried (MgSO$_4$), filtered, and concentrated. The residue was purified by reverse phase chromatography (H$_2$O (+0.03% ammonium carbonate)/MeCN) to provide the free form as an oil. HCl (2 M in Et$_2$O, 121 µL, 0.121 mmol) was added to a solution of the free form (40.0 mg, 0.121 mmol) in Et$_2$O (2 mL) at 22° C. After 10 min, the mixture was concentrated to provide 42.2 mg (70%) of 1-(3-((2-chloro-4-(trifluoromethyl)phenoxy)methyl)phenyl)-N-methylmethanamine (Compound 63-1). LCMS-ESI (m/z) calculated for $C_{16}H_{15}ClF_3NO$: 329.08. found 330.09 (M+H)$^+$, $t_R$=3.87 min (Method 12). $^1$H NMR (500 MHz, CDCl$_3$) δ 8.98 (s, 2H), 7.88 (d, J=2.5 Hz, 1H), 7.71 (dd, J=8.7, 2.3 Hz, 1H), 7.59 (d, J=1.5 Hz, 1H), 7.54 (qd, J=4.0, 3.5, 1.6 Hz, 1H), 7.53-7.50 (m, 2H), 7.45 (d, J=8.7 Hz, 1H), 5.34 (s, 2H), 4.15 (s, 2H), 2.56 (s, 3H).

Example 64

Synthesis of Compound 64-1

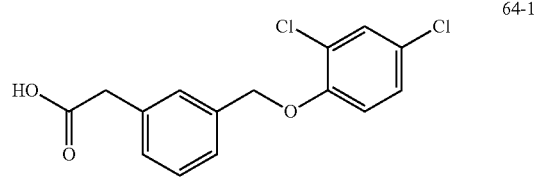 [SMILES: O=C(O)Cc1cccc(COc2ccc(Cl)cc2Cl)c1]

Scheme 64

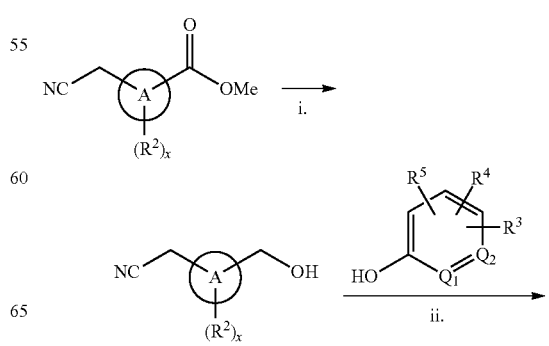

-continued

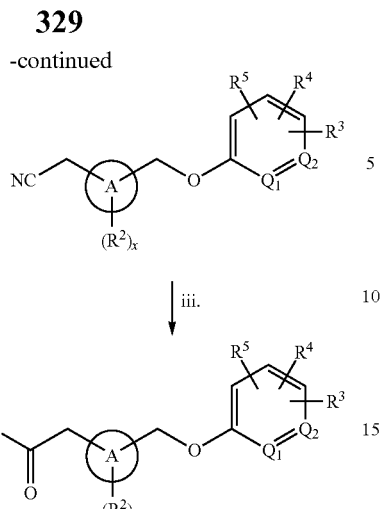

Reagents: (i) NaBH₄, DMF; (ii) DIAD, PPh₃, THF; (iii) NaOH, heat.

Step 64-1. Synthesis of
2-(3-(hydroxymethyl)phenyl)acetonitrile (INT 64-1)

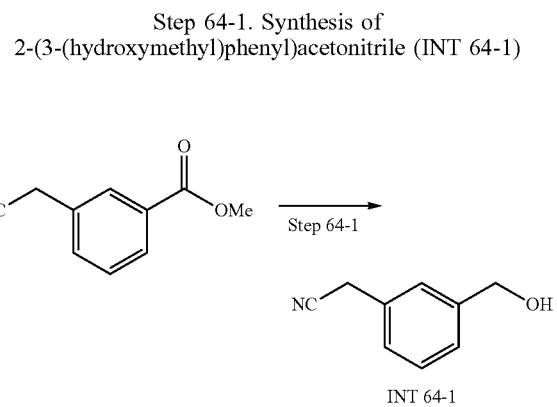

INT 64-1

To a solution of methyl 3-(cyanomethyl)benzoate (3 g, 17.1 mmol) in THF (150 ml) was added NaBH₄ (1.3 g, 34 mmol) in 5 portions. The mixture was heated to 80° C. and stirred for 30 min. After cooling to rt, MeOH was added dropwise and the mixture was stirred at 80° C. for 30 min and at rt for 16 h. The solution was quenched with H₂O (30 mL) and concentrated. The resulting residue was diluted with H₂O and extracted with EA. The organic layer was washed with H₂O then brine, dried (Na₂SO₄), filtered and concentrated. The resulting crude residue was purified by SiO₂ chromatography (EA/hexane) to provide 1.0 g (40%) of 2-(3-(hydroxymethyl)phenyl)acetonitrile (INT 64-1). LCMS-ESI (m/z) calculated for C₉H₉NO: 147.07. found 170.3 (M+H₂O)⁺, $t_R$=2 min (Method 11).

Step 64-2. Synthesis of 2-(3-((2,4-dichlorophenoxy)methyl)phenyl)acetonitrile (INT 64-2)

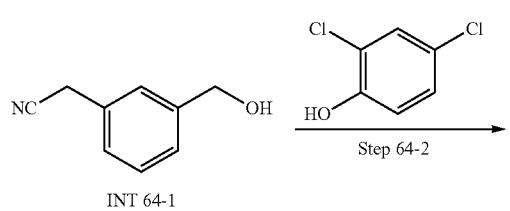

-continued

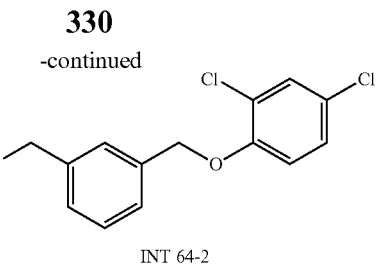

INT 64-2

To a solution of DIAD (495 mg, 2.4 mmol) in THF (10 mL) was added PPh₃ (641 mg, 2.4 mmol) and stirred for 10 min. A solution of INT 64-1 (300 mg, 0.2 mmol) in THF (5 mL) was then added followed by a solution of 2,4-dichlorophenol (332 mg, 2 mmol) in THF (5 mL). The reaction was stirred at rt for 16 h, diluted with EA and washed consecutive with saturated NaHCO₃(aq), and brine, then dried over (Na₂SO₄), filtered and concentrated. The resulting crude residue was purified twice by SiO₂ chromatography (EA/hex) to provide 0.21 g (35%) of 2-(3-((2,4-dichlorophenoxy)methyl)phenyl)acetonitrile (INT 64-2). ¹H NMR (400 MHz, CDCl₃) δ 7.27-7.5 (m, 5H), 7.16 (d, J=8 Hz, 1H), 6.87 (d, J=8 Hz, 1H), 5.13 (s, 2H), 3.77 (s, 2H).

Step 64-3. Synthesis of 2-(3-((2,4-dichlorophenoxy)methyl)phenyl)acetic acid (Compound 64-1)

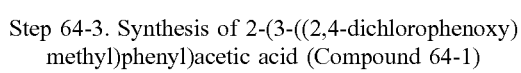

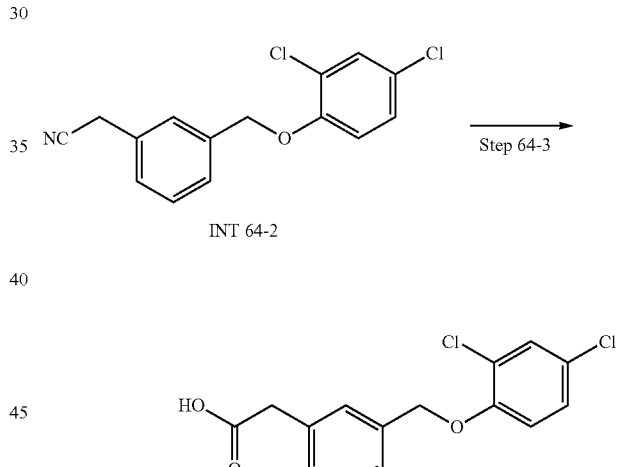

Compound 64-1

INT 64-2 (100 mg, 0.34 mmol) was dissolved in a solution of NaOH (aq, 2M, 5 mL) and heated to 130° C. in a sealed tube for 24 h. The reaction mixture was acidified with 1M HCl and extracted with EA. The organic layer was dried washed with brine, dried (Na₂SO₄), filtered and concentrated. The resulting residue was dried further under high vacuum to provide 20 mg (19%) of 2-(3-((2,4-dichlorophenoxy)methyl)phenyl)acetic acid (Compound 64-1). LCMS-ESI (m/z) mass not observed, $t_R$=13.8 min (Method 10). ¹H NMR (400 MHz, DMSO-d6) δ 7.60 (s, 1H), 7.40-7.30 (m, 4H), 7.30-7.20 (m, 2H), 5.20 (s, 2H), 3.59 (s, 2H).

Example 65

Synthesis of Compound 65-1

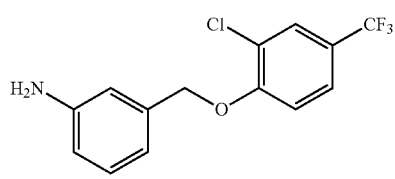

65-1

Scheme 65

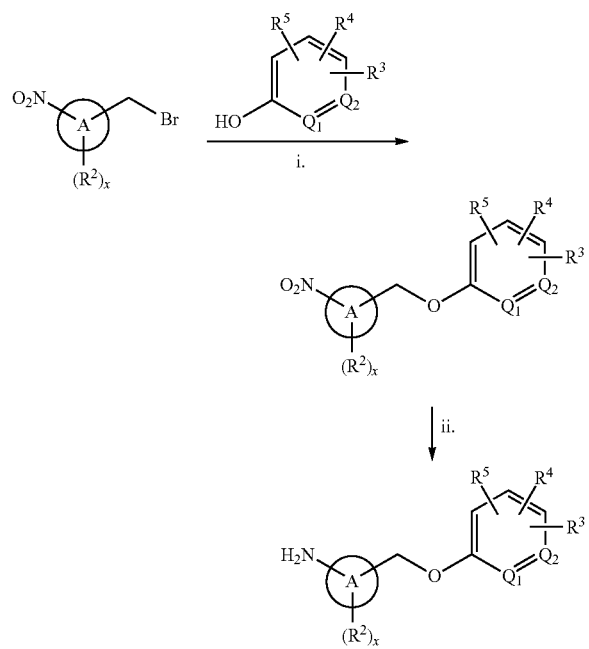

Reagents: (I) Na₂CO₃, DMF; (ii) Fe, HCl, MeOH

Step 65-1. Synthesis of 2-chloro-1-((3-nitrobenzyl) oxy)-4-(trifluoromethyl)benzene (INT 65-1)

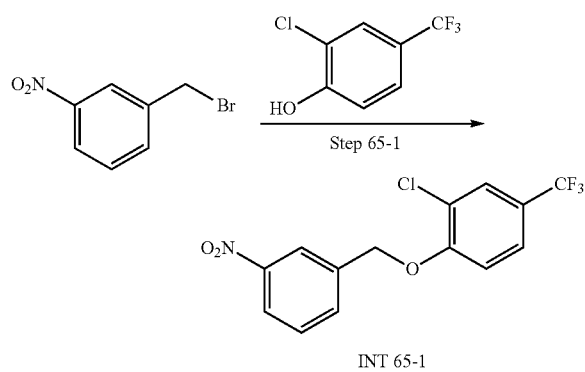

Into a 250 mL flask were added 1-(bromomethyl)-3-nitrobenzene (1.0 g, 4.37 mmol), 2-chloro-4-(trifluoromethyl)phenol (858 mg, 4.37 mmol), Na₂CO₃ (1.39 g, 13 mmol) and DMF (50 mL). After stirring at 50° C. for 18 h, the reaction was quenched with H₂O and extracted into EA. The organic layers were dried (Na₂SO₄), concentrated and purified by SiO₂ chromatography (EA/Hexane) to provide 1.0 g (69%) of 2-chloro-1-((3-nitrobenzyl) oxy)-4-(trifluoromethyl) benzene (INT 65-1). LCMS-ESI no mass observed, $t_R$=5.66 min (Method 11).

Step 65-2. Synthesis of 3-((2-chloro-4-(trifluoromethyl)phenoxy)methyl)aniline (Compound 65-1)

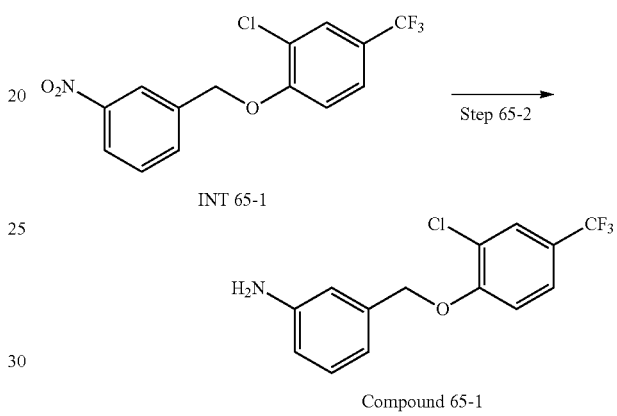

INT 65-1 (1.0 g, 3.02 mmol) was dissolved in MeOH (10 mL) and excess 2N HCl and Fe powder (210 mg, 3.77 mmol) were added. The reaction mixture was heated to 80° C. for 18 h, filtered through Celite, concentrated, and purified over SiO₂, (EA/hexane). The resulting material was further purified by reverse-phase chromatography (MeOH/H₂O with 0.1% formic acid) to provide 800 mg (60%) of 3-((2-chloro-4-(trifluoromethyl)phenoxy)methyl)aniline (Compound 65-1). LCMS-ESI (m/z) calculated for $C_{14}H_{11}ClF_3NO$: 301.05. found 302.1 (M+H)⁺, $t_R$=2 min (Method 11).

Example 66

MRGPRX4 Activity

HEK cells stably transfected to express human MRGPR X4 were maintained in an incubator at 37° C. with 5% CO₂ and grown in DMEM media with 10% fetal bovine serum (FBS) and 1% each of sodium pyruvate, Glutamax, penicillin/streptomycin, and Geneticin. HEK cells stably transfected to express mouse MRGPR A1 were maintained in the same incubator and grown in DMEM media with 10% FBS, 1% each of sodium pyruvate, Glutamax, penicillin/streptomycin, Geneticin, and 2.2 mg/mL Hygromycin.

Cells were plated in a 384-well assay plate at 20,000 cells per well in 12 μL of Opti-MEM and kept in an incubator overnight. On the day of the assay, compounds solubilized at 10 mM in DMSO were added as a 10-point curve (10 uM final top concentration with 1:3 serial dilutions) using a Tecan D300E digital dispenser. Agonists were diluted in assay buffer (final concentrations of 5.7 mM Tris-HCl, 43 mM NaCl, 50 mM LiCl, pH=8) and 2 μL of the appropriate agonist are added to each well. Final concentrations of agonists were 10 μM bilirubin, 20 μM deoxycholic acid, or 100 μM conjugated bilirubin (obtained from Lee Biosolutions, catalog #910-12). Final concentrations of DMSO were kept consistent across the plate. Plates were incubated in the dark for 1 h at 37° C. and then for 30 minutes at room temperature. IP-1 standards and HTRF detection reagents were added according to the IP-One—Gq Kit purchased from Cisbio (part number 62IPAPEJ) and incubated in the dark for 1 h at room temperature. The plate was read on a Molecular Devices SpectraMax iD5 plate reader. The HTRF ratio was calculated from the raw data and graphed using GraphPad Prism to calculate an $IC_{50}$ value for each compound.

Activity data for selected MRGPR X4 antagonists (versus 10 μM Bilirubin agonist) are displayed in Table 66A. The activity ranges are denoted as follows: "+++++" denotes antagonist activity <100 nM; "++++" denotes antagonist activity between 100 and 500 nM; "+++" denotes activity between 500 and 1000 nM; "++" denotes activity between 1000 and 2500 nM; and "+" denotes activity >2500 nM.

TABLE 66A

| Cpd No. | MRGPR4 Antagonist Activity |
| --- | --- |
| 1-1 | ++ |
| 1-2 | ++++ |
| 1-3 | ++ |
| 1-4 | + |
| 1-5 | ++++ |
| 1-6 | ++ |
| 1-7 | ++ |
| 1-8 | + |
| 1-9 | ++ |
| 1-10 | +++ |
| 1-11 | +++++ |
| 1-12 | +++++ |
| 1-13 | ++++ |
| 1-14 | ++ |
| 1-15 | ++ |
| 1-16 | +++++ |
| 1-17 | ++++ |
| 1-18 | +++++ |
| 1-19 | ++ |
| 1-20 | ++ |
| 1-21 | ++++ |
| 1-22 | + |
| 1-23 | +++ |
| 1-24 | + |
| 1-25 | + |
| 1-26 | ++ |
| 1-27 | + |
| 1-28 | ++++ |
| 1-29 | +++++ |
| 1-30 | +++++ |
| 1-31 | +++++ |
| 1-32 | ++ |
| 1-33 | ++ |
| 1-34 | + |
| 1-35 | ++++ |
| 1-36 | +++ |
| 1-37 | ++++ |
| 1-38 | ++++ |
| 1-39 | ++++ |
| 1-40 | ++ |
| 1-41 | ++++ |
| 1-42 | ++ |
| 1-43 | +++ |
| 1-44 | +++ |
| 1-45 | ++ |
| 1-46 | ++ |
| 1-47 | ++++ |
| 1-48 | + |
| 1-49 | +++ |
| 1-50 | ++ |
| 1-51 | ++ |
| 1-52 | + |
| 1-53 | +++ |
| 1-54 | + |
| 1-55 | +++++ |
| 1-56 | +++++ |
| 1-57 | ++++ |
| 1-58 | +++++ |
| 1-59 | +++++ |
| 1-60 | +++ |
| 1-61 | +++ |
| 1-62 | +++++ |
| 1-63 | +++++ |
| 1-64 | +++++ |
| 1-65 | +++++ |
| 1-66 | +++ |
| 1-67 | +++ |
| 1-68 | ++++ |
| 1-69 | +++ |
| 1-70 | ++ |
| 1-71 | +++ |
| 1-72 | +++ |
| 1-73 | +++++ |
| 1-74 | + |
| 1-75 | ++ |
| 1-76 | ++++ |
| 1-77 | ++ |
| 1-78 | +++++ |
| 1-79 | ++++ |
| 1-80 | ++++ |
| 1-81 | + |
| 1-82 | +++++ |
| 1-83 | ++++ |
| 1-84 | ++ |
| 1-85 | +++++ |
| 1-86 | +++ |
| 1-87 | ++ |
| 1-88 | ++ |
| 1-89 | ++++ |
| 1-90 | ++++ |
| 1-91 | +++ |
| 1-92 | ++ |
| 1-94 | ++ |
| 1-95 | ++++ |
| 1-96 | +++ |
| 1-97 | ++++ |
| 1-98 | +++ |
| 1-99 | ++++ |
| 1-100 | + |
| 1-101 | +++++ |
| 1-102 | ++ |
| 1-103 | +++++ |
| 1-108 | ++ |
| 1-109 | +++ |
| 1-110 | ++++ |
| 1-112 | +++++ |
| 1-113 | +++ |
| 1-114 | ++ |
| 1-115 | +++++ |
| 1-116 | +++ |
| 1-117 | +++ |
| 1-118 | +++++ |
| 1-119 | +++++ |
| 1-120 | +++++ |
| 1-121 | ++++ |
| 1-122 | ++++ |
| 1-123 | +++++ |
| 1-124 | +++++ |
| 1-125 | +++++ |
| 1-126 | ++ |
| 1-127 | +++++ |
| 1-128 | +++ |
| 1-129 | +++++ |
| 1-130 | ++++ |
| 1-131 | ++++ |
| 1-132 | +++++ |

TABLE 66A-continued

| Cpd No. | MRGPR4 Antagonist Activity |
| --- | --- |
| 1-133 | +++++ |
| 1-134 | ++++ |
| 1-135 | ++++ |
| 1-136 | +++++ |
| 1-137 | ++++ |
| 1-138 | + |
| 1-139 | + |
| 1-140 | ++ |
| 1-141 | ++ |
| 1-142 | ++++ |
| 1-143 | +++++ |
| 1-144 | + |
| 1-145 | ++++ |
| 1-146 | + |
| 1-147 | ++ |
| 1-148 | +++++ |
| 1-149 | +++++ |
| 1-150 | + |
| 1-151 | + |
| 1-152 | ++ |
| 1-153 | ++++ |
| 1-154 | ++++ |
| 2-1 | +++++ |
| 2-2 | +++++ |
| 2-3 | +++++ |
| 2-4 | +++++ |
| 3-1 | +++ |
| 3-2 | +++ |
| 3-3 | ++ |
| 3-4 | ++++ |
| 3-5 | ++++ |
| 3-6 | ++++ |
| 3-7 | ++ |
| 3-8 | ++ |
| 3-9 | ++ |
| 4-1 | +++++ |
| 4-2 | ++ |
| 4-3 | ++++ |
| 4-4 | +++++ |
| 4-5 | +++++ |
| 4-6 | ++++ |
| 4-7 | +++++ |
| 4-8 | ++++ |
| 4-9 | +++++ |
| 4-10 | +++++ |
| 4-11 | +++++ |
| 4-12 | +++++ |
| 4-13 | +++++ |
| 4-14 | +++++ |
| 4-15 | +++++ |
| 4-16 | ++++ |
| 4-17 | +++++ |
| 4-18 | +++++ |
| 4-19 | +++++ |
| 4-20 | ++++ |
| 4-21 | +++++ |
| 4-22 | ++++ |
| 4-23 | +++ |
| 4-24 | +++ |
| 4-25 | ++++ |
| 4-26 | +++++ |
| 4-27 | ++++ |
| 4-28 | +++++ |
| 4-29 | + |
| 5-1 | +++++ |
| 5-2 | ++ |
| 6-1 | ++ |
| 7-1 | ++++ |
| 8-1 | + |
| 8-2 | ++ |
| 8-3 | +++++ |
| 8-4 | +++ |
| 9-1 | +++++ |
| 9-2 | +++++ |
| 9-3 | +++++ |
| 10-1 | ++ |
| 11-1 | +++++ |
| 12-1 | ++++ |
| 12-2 | +++ |
| 12-3 | +++++ |
| 12-4 | +++++ |
| 13-1 | + |
| 14-1 | ++ |
| 15-1 | ++++ |
| 16-1 | ++ |
| 16-2 | + |
| 17-1 | ++++ |
| 17-2 | +++++ |
| 17-3 | ++++ |
| 17-4 | +++++ |
| 17-5 | +++++ |
| 17-6 | +++++ |
| 17-7 | +++++ |
| 17-8 | +++++ |
| 17-9 | +++++ |
| 17-10 | +++++ |
| 17-11 | +++++ |
| 17-12 | +++ |
| 17-13 | +++++ |
| 17-14 | +++++ |
| 17-15 | +++++ |
| 17-16 | +++++ |
| 32-1 | +++++ |
| 32-2 | +++++ |
| 32-3 | +++++ |
| 32-4 | +++++ |
| 32-5 | +++++ |
| 33-1 | + |
| 33-2 | ++++ |
| 33-3 | +++++ |
| 33-4 | ++++ |
| 34-1 | +++ |
| 35-1 | ++++ |
| 36-1 | +++ |
| 37-1 | ++ |
| 38-1 | ++++ |
| 39-1 | +++++ |
| 40-1 | +++ |
| 41-1 | +++++ |
| 41-2 | +++++ |
| 42-1 | +++++ |
| 42-2 | +++++ |
| 42-3 | +++++ |
| 43-1 | +++++ |
| 44-1 | ++++ |
| 45-1 | ++++ |
| 45-2 | +++ |
| 46-1 | ++++ |
| 47-1 | +++ |
| 48-1 | ++ |
| 49-1 | + |
| 50-1 | ++ |
| 52-1 | ++++ |
| 52-2 | + |
| 52-3 | ++++ |
| 52-4 | ++ |
| 52-5 | ++++ |
| 52-6 | ++++ |
| 52-7 | ++++ |
| 52-8 | ++++ |
| 52-9 | +++ |
| 52-10 | ++++ |
| 52-11 | ++++ |
| 52-12 | ++++ |
| 52-13 | +++++ |
| 52-14 | ++ |
| 52-15 | +++ |
| 52-16 | ++++ |
| 52-17 | +++ |
| 52-18 | +++ |
| 52-19 | +++ |
| 52-20 | ++++ |

TABLE 66A-continued

| Cpd No. | MRGPR4 Antagonist Activity |
|---|---|
| 52-21 | +++ |
| 52-22 | ++++ |
| 52-23 | ++++ |
| 52-24 | ++++ |
| 52-25 | +++ |
| 52-26 | ++++ |
| 52-27 | +++ |
| 53-1 | +++ |
| 53-2 | ++ |
| 54-1 | ++++ |
| 54-2 | +++++ |
| 54-3 | ++++ |
| 54-4 | +++++ |
| 54-5 | ++++ |
| 54-6 | +++ |
| 54-7 | ++++ |
| 54-8 | +++ |
| 54-9 | ++++ |
| 54-10 | +++ |
| 54-11 | + |
| 55-1 | ++++ |
| 55-2 | +++ |
| 55-3 | ++++ |
| 56-1 | ++++ |
| 56-2 | +++++ |
| 57-1 | +++++ |
| 58-1 | +++ |
| 58-2 | +++ |
| 59-1 | +++ |
| 60-1 | ++++ |
| 61-1 | ++++ |
| 62-1 | +++++ |
| 63-1 | ++++ |
| 64-1 | + |
| 65-1 | +++ |

Activity data for selected MRGPR X4 antagonists (versus 10 μM Bilirubin agonist, 20 μM deoxycholic acid, 100 μM conjugated bilirubin, 50 μM urobilin, or 20 μM obeticholic acid) are presented in Table 66B.

TABLE 66B

| Cpd No. | $IC_{50}$ (Bilirubin agonist) nM | $IC_{50}$ (Conjugated Bilirubin Agonist) nM | $IC_{50}$ (Deoxycholic Acid agonist) nM | $IC_{50}$ (Urobilin Agonist) nM | $IC_{50}$ (Obeticholic Acid Agonist) nM |
|---|---|---|---|---|---|
| 1-55 | 6 | 14 | 22 | 23 | 11 |
| 1-78 | 7 | 24 | 24 | 13 | 21 |
| 4-1 | 27 | 81 | 55 | ND | ND |
| 1-115 | 81 | 180 | 230 | ND | 47 |
| 1-18 | 57 | 130 | 130 | 230 | 40 |
| 1-29 | 20 | 46 | 46 | 16 | 25 |
| 1-56 | 28 | 32 | 30 | 21 | 24 |
| 1-65 | 9 | 17 | 28 | 21 | 23 |
| 1-85 | 20 | 29 | 30 | 41 | 15 |
| 4-10 | 16 | 21 | 22 | 35 | 15 |
| 4-11 | 24 | 41 | 63 | 35 | 25 |
| 1-101 | 17 | 12 | 75 | 91 | 22 |
| 42-3 | 16 | 28 | 16 | 21 | 7 |
| 17-4 | 5 | 7 | 6 | 6 | 8 |
| 1-31 | 10 | 9 | 5 | 7 | 5 |
| 32-1 | 6 | 7 | 10 | 8 | 3 |
| 5-1 | 10 | 27 | 23 | 6 | 6 |

ND = Not Determined

Example 67

Mouse Pharmacokinetics Studies

Compounds were formulated in 5% DMSO, 5% Solutol, and 9000 phosphate buffered saline at a concentration of 5 mg/mL, and typically appeared as a fine homogenous suspension. Male C57BL/6 mice (n=3/compound) were administered a 50 mg/kg dose of each compound by oral gavage under a non-fasted condition. Blood samples were collected via the saphenous vein onto $K_2$-EDTA at 0.25, 0.5, 1, 2, 4, 8 and 24 hours after dosing, and plasma was prepared and stored at ≤60° C. until analysis. Plasma sample preparation for analysis was done by protein precipitation using acetonitrile (including Celecoxib as an internal standard) followed by centrifugation. Compound concentrations were determined in extracted plasma using LC-MS/MS relative to an 8 point standard curve covering the 1 to 3000 ng/mL range. Non-compartmental analysis using Phoenix WinNonlin was used to estimate pharmacokinetic parameters including area under the curve, clearance, and half-life. The administered dose was confirmed by analysis of residual dosing material by UPLC-UV relative to a single point calibration sample. The results of these studies are presented in Table 67.

TABLE 67

| Cpd No. | Cmax (μM) | AUC (μM×hr) | T-1/2 (hr) |
|---|---|---|---|
| 1-18 | 113 | 376 | 4.2 |
| 1-115 | 306 | 1206 | 3.0 |
| 4-1 | 231 | 1503 | 5.9 |
| 1-29 | 196 | 615 | 4.6 |
| 1-55 | 230 | 2150 | 11.2 |
| 1-56 | 162 | 880 | 3.2 |
| 1-65 | 220 | 1037 | 4.8 |
| 1-78 | 57 | 219 | 4.0 |
| 1-85 | 239 | 1069 | 4.7 |
| 4-10 | 260 | 974 | 4.6 |
| 4-11 | 257 | 572 | 3.6 |
| 1-101 | 230 | 1200 | 4.8 |
| 42-3 | 460 | 4700 | 5.4 |

Example 68

Urobilin is a Potent MRGPRX4 Agonist and Pruritogen

Plasma urobilin is an oxidative product of the heme metabolite urobilinogen. Urobilinogen is a by-product of bilirubin reduction in the intestines. Some of urobilinogen remains in the large intestine, where it is converted to stercobilin. Some urobilinogen is reabsorbed into the bloodstream and delivered to the kidney, where it is oxidized to urobilin upon exposure to air.

Metabolites of heme (bilirubin, biliverdin, urobilin, urobilinogen, and stercobilin) were analyzed for in vitro activation of MRGPRX4. Cells were plated in a 384-well assay plate at 20,000 cells per well in 12 μL of Opti-MEM and kept in an incubator overnight. On the day of the assay, different agonists solubilized at 10 mM in 0.1% NaOH were added as a 10-point curve (10 mM final top concentration with 1:3 serial dilutions) using a Tecan D300E digital dispenser. Agonists were diluted in assay buffer (final concentrations of 5.7 mM Tris-HCl, 43 mM NaCl, 50 mM LiCl, pH=8) and 2 μL of the appropriate agonist are added to each well. Plates were incubated in the dark for 1 h at 37° C. and then for 30 minutes at room temperature. IP-1 standards and HTRF detection reagents were added according to the IP-One—Gq Kit purchased from Cisbio (part number 62IPAPEJ) and incubated in the dark for 1 h at room temperature. The plate was read on a Molecular Devices SpectraMax iD5 plate reader. The HTRF ratio was calculated from the raw data and graphed using GraphPad Prism to calculate an IC50 value for each compound.

The results of this study are shown in FIG. 1. Urobilin was shown to be at least 10-fold more efficacious at activating MRGPRX4 than bilirubin.

The ability of urobilin to induce itch in wild type mice was also tested. Typical mouse itch studies occurred as follows: C57B6J male mice were multiple-housed in a normal light cycle (6 am on; 6 μm off) under temperature and humidity-controlled conditions. The mice were handled and habituated to test chambers before testing, then placed in individual SCLABA test chambers. After 20 minutes, the mice were dosed PO with vehicle (saline, pH 7-8). After 30 minutes, the pruritogen of study (100 mL in saline) or saline is given subcutaneously (SC) on the neck on the midline behind the ears. Video was recorded from the first pruritogen injection for 30 minutes using the SCLABA system. Scratching bouts were scored from SCLABA thumbnails using 12/45/85/100 waveform criteria. Group sizes were typically 9-10 animals per group.

Figure 2A:
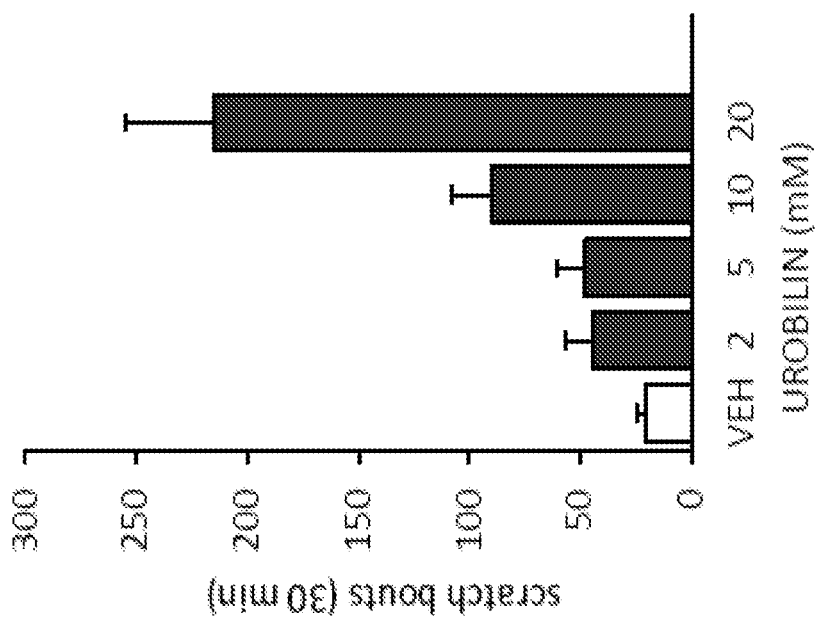
FIGS. 2A-2B show induction of itch in wild type mice by urobilin compared to vehicle (VEH) (FIG. 2A) and by urobilin, bilirubin, and deoxycholic acid (FIG. 2B).
Figure 2B:
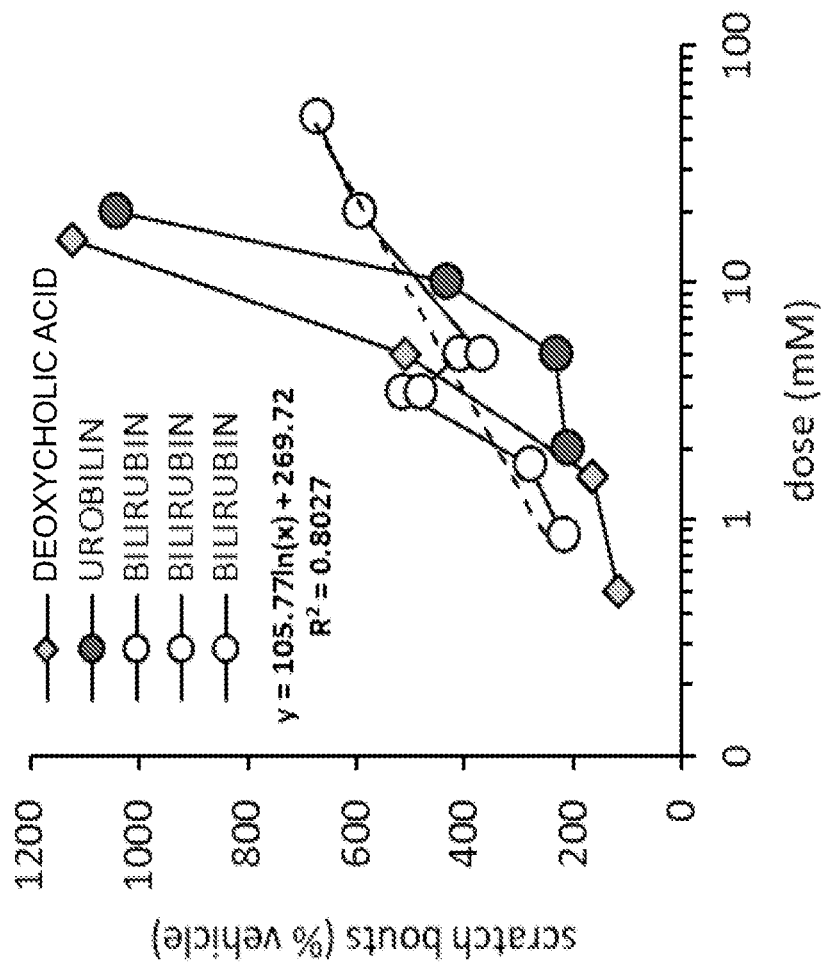

As shown in FIG. 2A, urobilin induced scratch response in mice in a dose dependent manner. Itch induction of urobilin was also compared to deoxycholic acid agonist and bilirubin agonist. As shown in FIG. 2B, urobilin is a potent inducer of scratch response in mice.

Example 69

Bilirubin and Urobilin can be Degraded by Light, Reducing Their Agonist Activity on MRGPRX4

Bilirubin and Urobilin are agonists of MRGPRX4 that have been demonstrated to be active pruitogens. Light therapy has been shown to reduce itch in cholestatic pruitis patients, which has been attributed to light-induced decomposition or chemical modification of bilirubin. To further explore the contribution of light degradation toward the reduction of MRGPRX4 agonism, bilirubin and urobilin were pre-treated with different lighting and their activities were measured.

Stock solutions of both bilirubin and urobilin were made at 210 μM in 0.1N NaOH (aq). Samples were stored either at room temperature in the dark, in a −20° C. freezer in the dark, room temperature on the countertop under normal, lab lighting conditions, or at room temperature under a 400 nM blue-light lamp (similar to medical lamps used for treating jaundice). Samples were evaluated after 24 hours and the percent remaining of urobilin and bilirubin, relative to a time zero standard, were determined by measurement of the degradation of the analyte contained in the samples as determined by tandem mass spectroscopy (LC MS/MS). The samples (at 24 h) were also evaluated for their ability to agonize MRGPRX4.

Figure 3A:
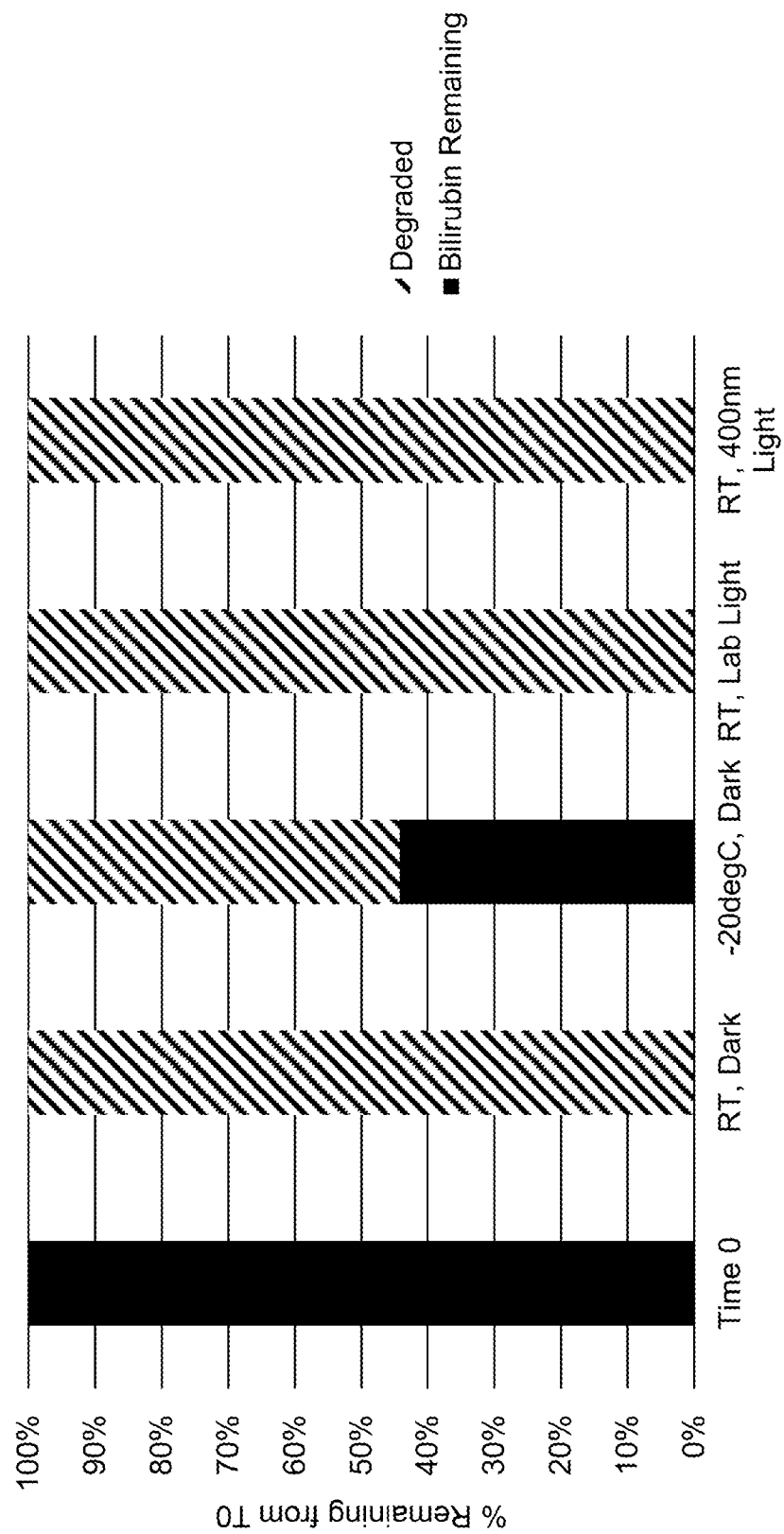
FIGS. 3A-3B show bilirubin stability (FIG. 3A) and bilirubin agonism of MRGPRX4 (FIG. 3B) after 24 hours storage under various temperature and light storage conditions (time zero (freshly prepared), room temperature dark, −20° C. dark, room temperature lab light, and room temperature 400 nm blue light).
Figure 3B:
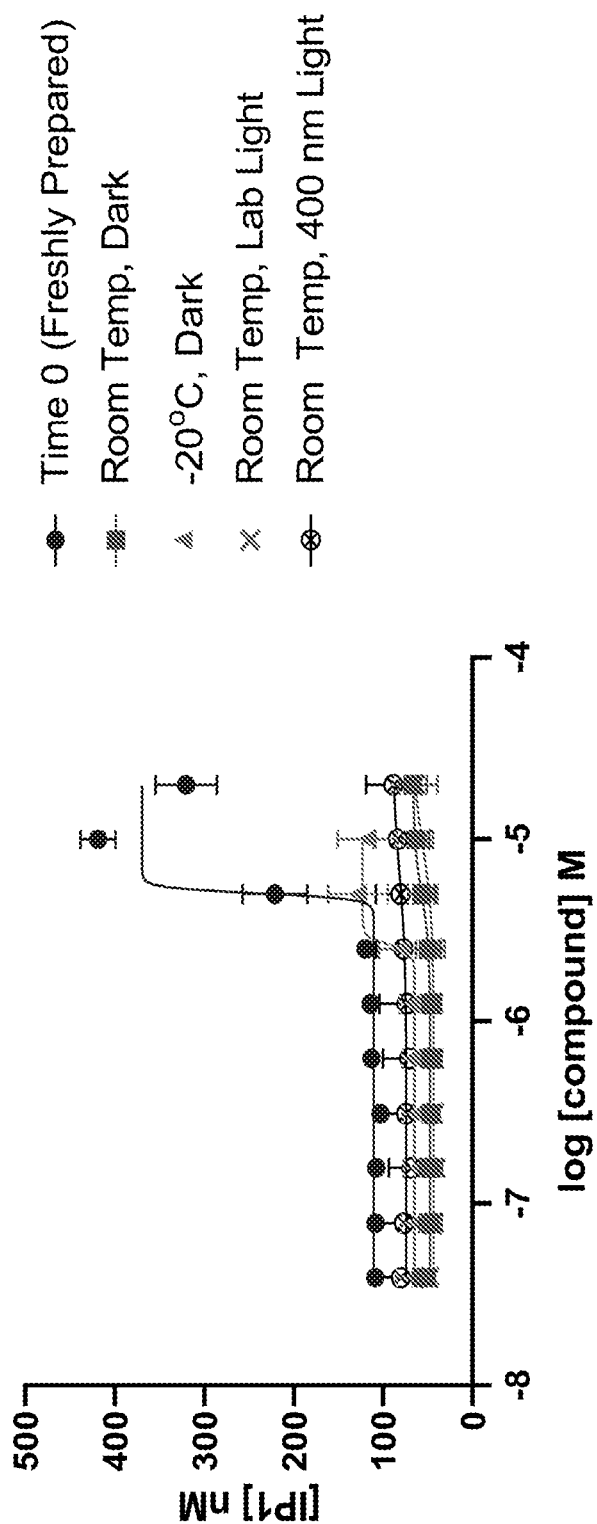

After 24 h, the freezer stock showed the highest amount of bilirubin remaining (44% of time zero), whereas all other conditions (room temperature dark, room temperature lab light, and room temperature blue light) did not have any detectable bilirubin remaining. (FIG. 3A). All samples that were stored at room temperature (dark, room light and blue light) showed significantly decreased agonist activity relative to the frozen sample. (FIG. 3B)

Figure 4A:
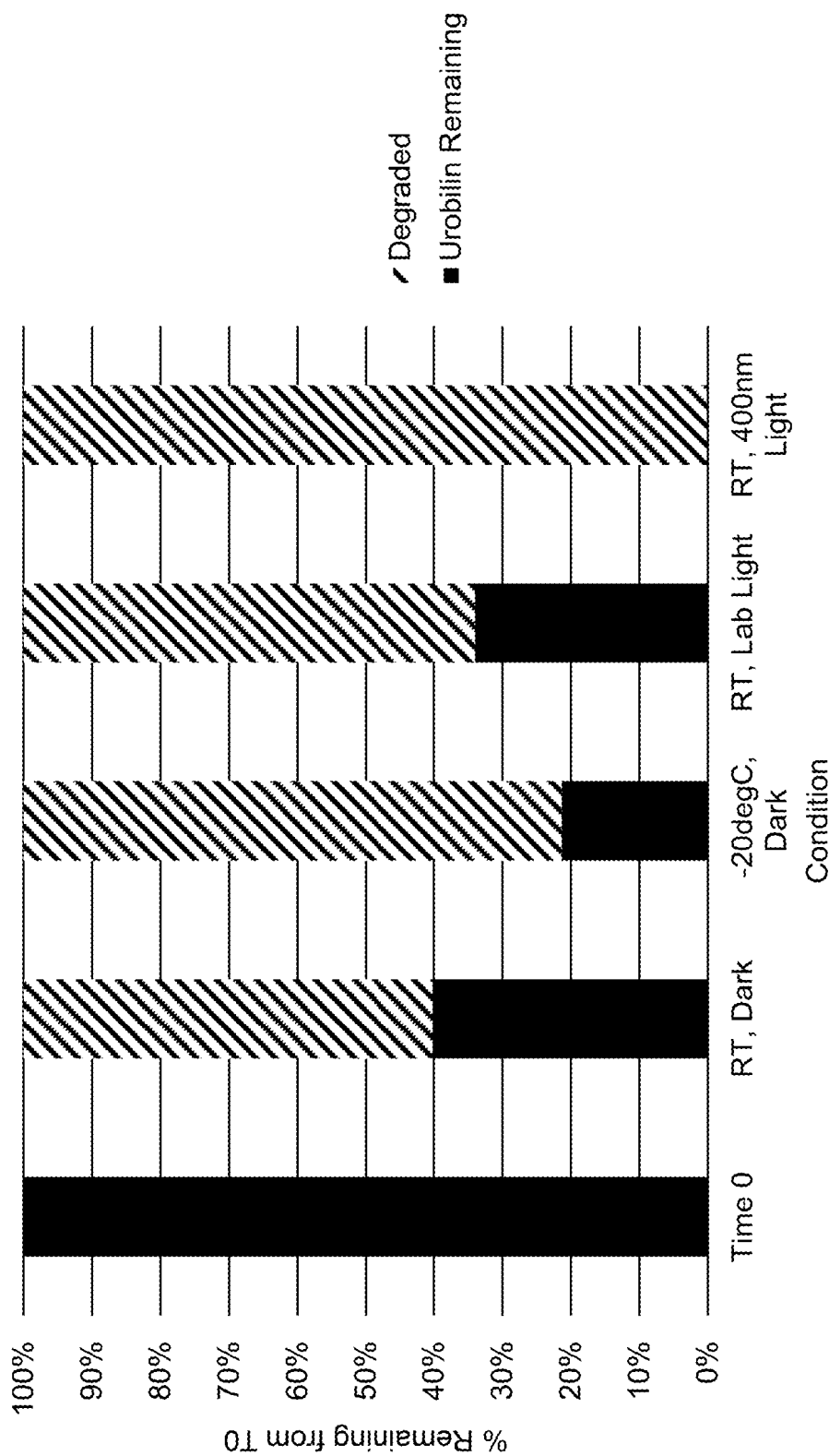
FIGS. 4A-4B show urobilin stability (FIG. 4A) and urobilin agonism of MRGPRX4 (FIG. 4B) after 24 hours storage under various temperature and light storage conditions (time zero (freshly prepared), room temperature dark, −20° C. dark, room temperature lab light, and room temperature blue light).
Figure 4B:
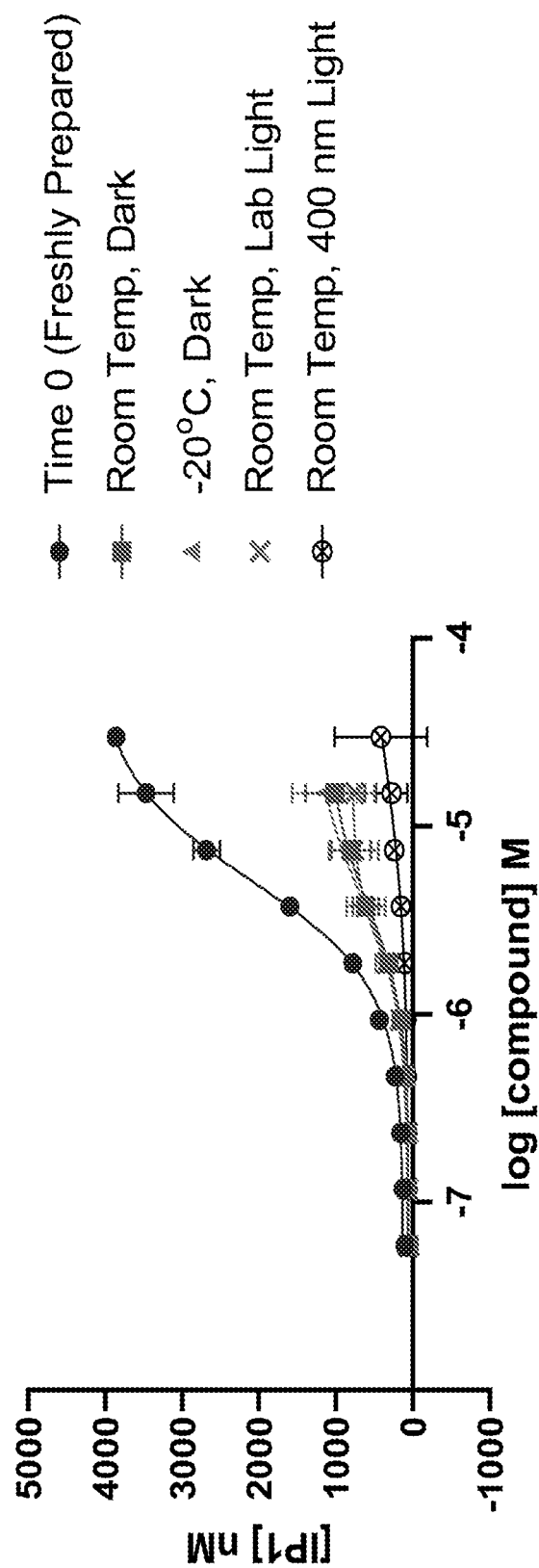

Urobilin exhibited more stability than bilirubin, but degradation was still observed for all conditions. After 24 h, the sample stored in the dark had the highest remaining amount of urobilin relative to the time zero measurement (40%), while the freezer sample in the dark only had 21% remaining. The room temperature sample under ambient lighting had 34% remaining, but the room temperature sample under blue light had no detectable urobilin remaining, indicating a higher vulnerability to that wavelength of light. (FIG. 4A) The blue-light sample demonstrated very little agonist activity relative to the other three groups that were examined (room temp dark, frozen dark, and room temp light), corresponding to the measured remaining urobilin in those samples. (FIG. 4B)

Example 70

Agonism of MRGPRX4 by an FXR Agonist can be Blocked by Representative MRGPRX4 Antagonists BAR502, a dual FXR and GPBAR1 agonist also has agonist activity (5700 nM) against MRGPRX4. Activity data for selected MRGPRX4 antagonists versus 10 μM BAR502 in Table 70 show a range of antagonism from 11 to 48 nM.

TABLE 70

| Cpd No. | $IC_{50}$ (10 μM BAR502) nM |
|---|---|
| 1-18 | 48 |
| 1-55 | 16 |
| 1-56 | 16 |
| 1-65 | 13 |
| 1-78 | 20 |
| 32-2 | 17 |
| 42-3 | 17 |
| 1-31 | 11 |

All of the U.S. patents, U.S. patent application publications, U.S. patent applications, foreign patents, foreign patent applications and non-patent publications referred to in this specification and/or listed in the Application Data Sheet are incorporated herein by reference, in their entirety. In addition, the terms used in the following claims should not be construed as limited to the specific embodiments disclosed in the specification but should be construed to include all possible embodiments along with the full scope of equivalents to which such claims are entitled.

The invention claimed is:

1. A method for modulating a Mas-Related G-Protein Receptor (MRGPR) X4 by contacting the MRGPRX4 with an effective amount of a compound having one of the following structures, or a pharmaceutically acceptable isomer, racemate, hydrate, solvate, isotope, or salt thereof:

| Cpd No. | Structure |
|---|---|
| 1-55 | ![structure] |

-continued
| Cpd No. | Structure |
|---|---|
| 1-78 | 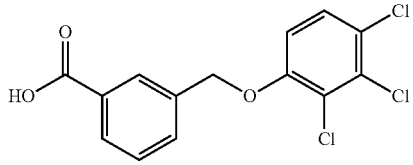 [SMILES: O=C(O)c1cccc(COc2ccc(Cl)c(Cl)c2Cl)c1] |
| 5-1 | 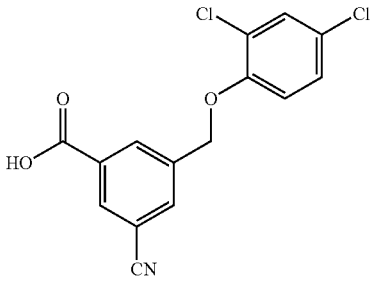 [SMILES: N#Cc1cc(COc2ccc(Cl)cc2Cl)cc(C(=O)O)c1] |
| 4-10 | 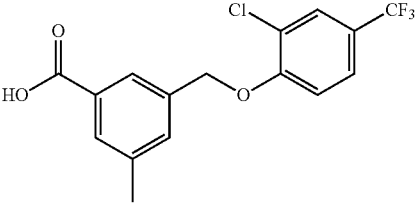 [SMILES: Cc1cc(COc2ccc(C(F)(F)F)cc2Cl)cc(C(=O)O)c1] |
| 1-65 | 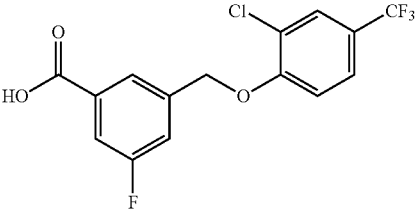 |
| 4-11 | 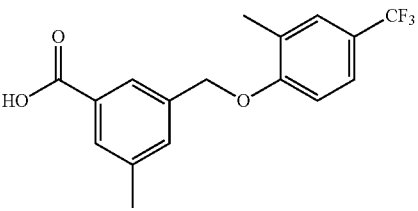 [SMILES: Cc1cc(COc2ccc(C(F)(F)F)cc2C)cc(C(=O)O)c1] |
| 1-58 | 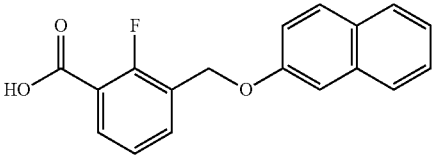 [SMILES: O=C(O)c1cccc(COc2ccc3ccccc3c2)c1F] |
| 1-56 | 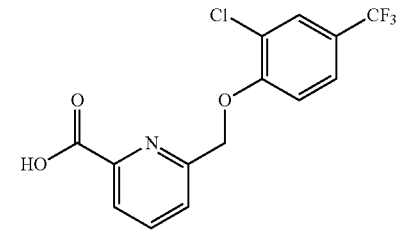 [SMILES: O=C(O)c1cccc(COc2ccc(C(F)(F)F)cc2Cl)n1] |
-continued
| Cpd No. | Structure |
|---|---|
| 9-1 | 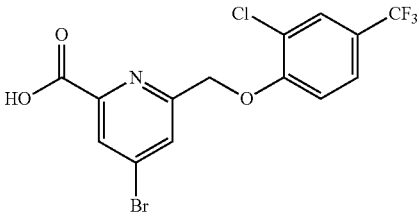 [SMILES: O=C(O)c1cc(Br)cc(COc2ccc(C(F)(F)F)cc2Cl)n1] |
| 1-82 | 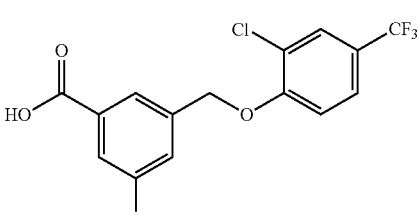 |
| 1-85 | 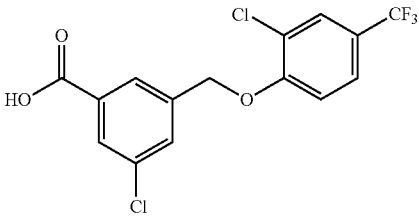 |
| 1-29 | 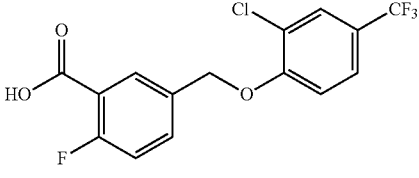 [SMILES: O=C(O)c1cc(COc2ccc(C(F)(F)F)cc2Cl)ccc1F] |
| 1-101 | 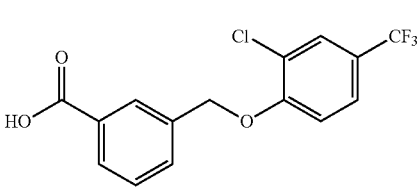 |
| 2-3 | 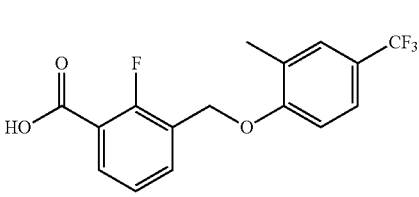 [SMILES: Cc1cc(C(F)(F)F)ccc1OCc1cccc(C(=O)O)c1F] |
| 1-103 | 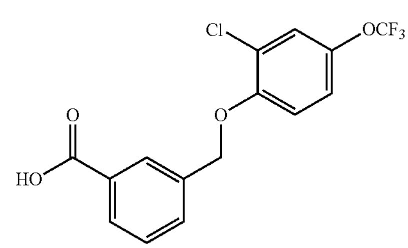 [SMILES: O=C(O)c1cccc(COc2ccc(OC(F)(F)F)cc2Cl)c1] |

| Cpd No. | Structure |
|---------|-----------|
| 1-112 | 3-[(3-fluoro-4-trifluoromethylphenoxy)methyl]benzoic acid |
| 4-7 | 3-[(2,4-dichlorophenoxy)methyl]-5-methylbenzoic acid |
| 11-1 | 3-[(2-chloro-4-trifluoromethylphenoxy)methyl]-5-cyclopropylbenzoic acid |

2. A method for treating an Mas-Related G-Protein Receptor (MRGPR) X4 dependent condition by administering to a subject in need thereof an effective amount of a compound having one of the following structures, or a pharmaceutically acceptable isomer, racemate, hydrate, solvate, isotope, or salt thereof:

| Cpd No. | Structure |
|---------|-----------|
| 1-55 | 3-[(2-chloro-4-trifluoromethylphenoxy)methyl]-2-fluorobenzoic acid |
| 1-78 | 3-[(2,3,4-trichlorophenoxy)methyl]benzoic acid |
| 5-1 | 3-[(2,4-dichlorophenoxy)methyl]-5-cyanobenzoic acid |
| 4-10 | 3-[(2-chloro-4-trifluoromethylphenoxy)methyl]-5-methylbenzoic acid |
| 1-65 | 3-[(2-chloro-4-trifluoromethylphenoxy)methyl]-5-fluorobenzoic acid |
| 4-11 | 3-[(2-methyl-4-trifluoromethylphenoxy)methyl]-5-methylbenzoic acid |
| 1-58 | 2-fluoro-3-[(naphthalen-2-yloxy)methyl]benzoic acid |
| 1-56 | 6-[(2-chloro-4-trifluoromethylphenoxy)methyl]picolinic acid |
| 9-1 | 4-bromo-6-[(2-chloro-4-trifluoromethylphenoxy)methyl]picolinic acid |

| Cpd No. | Structure |
|---|---|
| 1-82 | 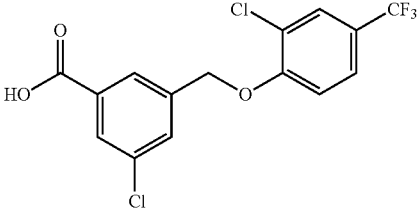 |
| 1-85 | 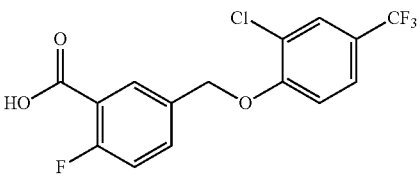 |
| 1-29 | 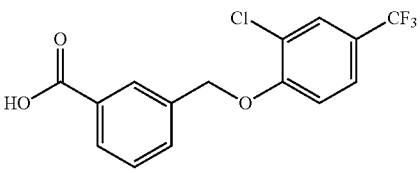 |
| 1-101 | 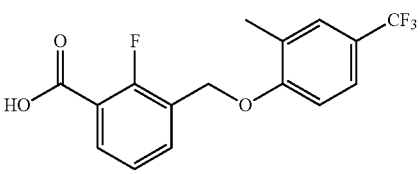 |
| 2-3 | 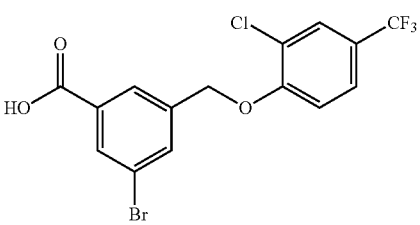 |
| 1-103 | 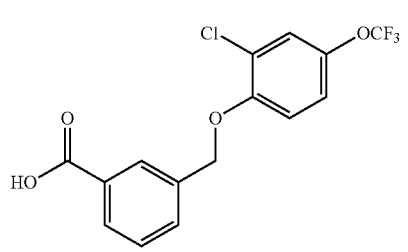 |
| 1-112 | 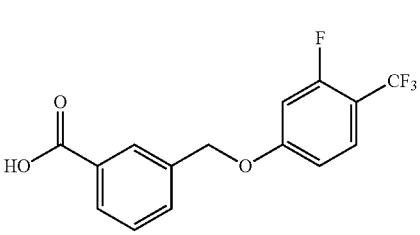 |
| 4-7 | 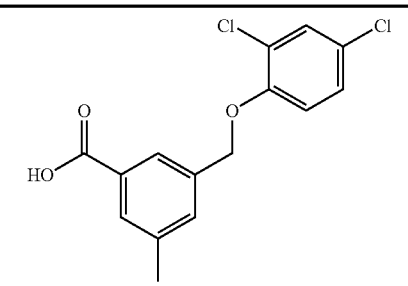 |
| 11-1 | 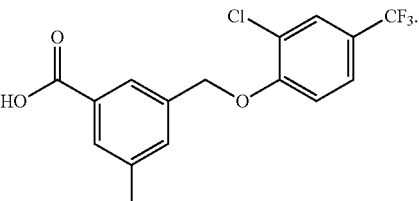 |

3. The method of claim 2, wherein the MRGPR X4 dependent condition is a condition that is caused by the activation of MRGPR X4 by a bile acid or analog thereof.

4. The method of claim 2 wherein the MRGPR X4 dependent condition is an itch associated condition, a pain associated condition, or an autoimmune disorder.

5. The method of claim 4 wherein the itch associated condition is chronic itch, cholestatic pruritus, contact dermatitis, allergic blepharitis, anemia, atopic dermatitis, bullous pemphigoid, candidiasis, chicken pox, cholestasis, end-stage renal failure, hemodialysis, contact dermatitis, dermatitis herpetiformis, diabetes, drug allergy, dry skin, dyshidrotic dermatitis, ectopic eczema, eczema, erythrasma, folliculitis, fungal skin infection, hemorrhoids, herpes, HIV infection, Hodgkin's disease, hyperthyroidism, iron deficiency anemia, kidney disease, leukemia, liver disease, lymphoma, malignancy, multiple myeloma, neurodermatitis, onchocerciasis, Paget's disease, pediculosis, polycythemia *rubra* vera, pruritus ani, pseudorabies, psoriasis, rectal prolapse, scabies, schistosomiasis, scleroderma, severe stress, stasia dermatitis, swimmer's itch, thyroid disease, tinea cruris, uremic pruritus, or urticaria.

6. The method of claim 5 wherein the itch associated condition is cholestatic pruritus, uremic pruritus, atopic dermatitis, dry skin, psoriasis, contact dermatitis, or eczema.

7. The method of claim 5, wherein the itch associated condition is a liver disease, wherein the liver disease is primary biliary cholangitis, primary sclerosing cholangitis, Alagille syndrome, Progressive familial intrahepatic cholestasis, Intrahepatic cholestasis of pregnancy, nonalcoholic steatohepatitis (NASH), nonalcoholic fatty liver disease (NAFLD), biliary atresia, chronic B hepatitis, drug-chronic viral hepatitis, induced liver injury (DILI), liver fibrosis, cholestatic liver disease, or alcoholic liver disease.

8. The method of claim 2, further comprises administering to the subject a pharmaceutically effective amount of a second therapeutic agent.

9. The method of claim 8, wherein the MRGPR X4 dependent condition is a liver disease and the second therapeutic agent is ursodeoxycholic acid (UDCA), norUrsodeoxycholic acid, cholestyramine, stanozolol, naltrexone, rifampicin, Alisol B 23-acetate (AB23A), curcumin, dihydroartemisinin, fenofibrate, bezafibrate, metronidazole, methotrexate, colchicine, metformin, betaine, glucagon, naltrexone, a farnesoid X-receptor (FXR) agonist, a peroxisome proliferator-activated receptor (PPAR) agonist, a thyroid hormone receptor beta (TRβ) agonist, or any combination thereof.

10. The method of claim 9, wherein the FXR agonist is obeticholic acid, Turofexorate isopropyl (WAY-362450), 3-(2,6-dichlorophenyl)-4-(3'-carboxy-2-chlorostilben-4-yl) oxymethyl-5-isopropylisoxazole (GW4064), PX20606 (PX-102), PX-101, INT-767, INT-787, TERN-101, altenusin, tropifexor (LJN452), nidufexor, turofexorate isopropyl, fexaramine, silymarin, silybin, hedragonic acid, cafestol, Cilofexor (GS-9674 or Px-104), EDP-305, BAR704, BAR502, EYP-001, RDX-023, AGN-242266, HPG-1860, MET-409, AGN-242256, EP-024297, 10T-022, M-480, INV-33, RDX023-02, or any combination thereof.

11. The method of claim 9, wherein the PPAR agonist is a PPAR-alpha agonist, a PPAR-gamma agonist, a PPAR-delta agonist, a PPAR-alpha/gamma dual agonist, a PPAR alpha/delta dual agonist, a PPAR gamma/delta dual agonist, or PPAR alpha/gamma/delta pan agonist, optionally wherein:
the PPAR alpha agonist is fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate, or SRI 0171;
the PPAR gamma agonist is rosiglitazone, pioglitazone, deuterium-stabilized R-pioglitazone, efatutazone, ATx08-001, OMS-405, CHS-131, THR-0921, SER-150-DN, KDT-501, GED-0507-34-Levo, CLC-3001, or ALL-4;
the PPAR delta agonist is GW501516 (endurabol or ({4-[({4-methyl-2-[4-(trifluoromethyl)phenyl]-1,3-thiazol-5-yl}methyl)sulfanyl]-2-methylphenoxy} acetic acid)), MBX8025 (seladelpar or {2-methyl-4-[5-methyl-2-(4-trifluoromethyl-phenyl)-2H-[1,2,3]triazol-4-ylmethylsylfanyl]-phenoxy}-acetic acid), GW0742 ([4-[[[2-[3-fluoro-4-(trifluoromethyl)phenyl]-4-methyl-5-thiazolyl]methyl]thio]-2-methyl phenoxy] acetic acid), L165041, HPP-593, or NCP-1046;
the PPAR alpha/gamma agonist is saroglitazar, aleglitazar, muraglitazar, tesaglitazar, or DSP-8658;
the PPAR alpha/delta agonist is elafibranor or T913659;
the PPAR gamma/delta agonist is a conjugated linoleic acid (CLA) or T3D-959; and
the PPAR alpha/gamma/delta agonist is IVA337 (lanifibranor), TTA (tetradecylthioacetic acid), bavachinin, GW4148, GW9135, bezafibrate, lobeglitazone, 2-(4-(5, 6-methylenedioxybenzo[d]thiazol-2-yl)-2-methylphenoxy)-2-methylpropanoic acid (MHY2013), or CS038.

12. The method of claim 9, wherein the TRβ agonist is sobetirome, eprotirome, GC-24, MGL-3196, MGL-3745, VK-2809, KB141 [3,5-dichloro-4-(4-hydroxy-3-isopropylphenoxy) phenylacetic acid], MB07811 (2R,4S)-4-(3-chlorophenyl)-2-[(3,5-dimethyl-4-(4'-hydroxy-3'-isopropylbenzyl)phenoxy)methyl]-2-oxido-[1,3,2]-dioxaphosphonane), or any combination thereof.

13. The method of claim 4 wherein the pain associated condition is acute pain, advanced prostate cancer, AIDS-related pain, ankylosing spondylitis, arachnoiditis, arthritis, arthrofibrosis, ataxic cerebral palsy, autoimmune atrophic gastritis, avascular necrosis, back pain, Behcet's disease (syndrome), burning mouth syndrome, bursitis, cancer pain, carpal tunnel, cauda *equina* syndrome, central pain syndrome, cerebral palsy, cervical stenosis, Charcot-Marie-Tooth (CMT) disease, chronic fatigue syndrome (CFS), chronic functional abdominal pain (CFAP), chronic pain, chronic pancreatitis, collapsed lung (pneumothorax), complex regional pain syndrome (RSD), corneal neuropathic pain, Crohn's disease, degenerative disc disease, Dercum's disease, dermatomyositis, diabetic peripheral neuropathy (DPN), dystonia, Ehlers-Danlos syndrome (EDS), endometriosis, eosinophilia-myalgia syndrome (EMS), erythromelalgia, fibromyalgia, gout, headaches, herniated disc, hydrocephalus, intercostal neuraligia, interstitial cystitis, irritable bowel syndrome (IBS), juvenile dermatositis, knee injury, leg pain, loin pain-haematuria syndrome, lupus, lyme disease, medullary sponge kidney (MSK), meralgia paresthetica, mesothelioma, migraine, musculoskeletal pain, myofascial pain, myositis, neck pain, neuropathic pain, occipital neuralgia, osteoarthritis, Paget's disease, Parsonage Turner syndrome, pelvic pain, peripheral neuropathy, phantom limb pain, pinched nerve, polycystic kidney disease, polymyalgia rhuematica, polymyositis, *porphyria*, post herniorraphy pain syndrome, post mastectomy pain syndrome, post stroke pain, post thorocotomy pain syndrome, postherpetic neuralgia (Shingles), post-polio syndrome, primary lateral sclerosis, psoriatic arthritis, pudendal neuralgia, radiculopathy, Raynaud's disease, rheumatoid arthritis (RA), sacroiliac joint dysfunction, sarcoidosi, Scheuemann's kyphosis disease, sciatica, Scoliosis, shingles (Herpes Zoster), Sjogren's syndrome, spasmodic torticollis, sphincter of oddi dysfunction, spinal cerebellum ataxia (SCA ataxia), spinal cord injury, spinal stenosis, syringomyelia, tarlov cysts, transverse myelitis, trigeminal neuralgia, neuropathic pain, ulcerative colitis, vascular pain or vulvodynia.

14. The method of claim 4 wherein the autoimmune disorder is chronic inflammation, multiple sclerosis, Steven Johnson's syndrome, appendicitis, bursitis, colitis, cystitis, dermatitis, phlebitis, reflex sympathetic dystrophy/complex regional pain syndrome (rsd/crps), rhinitis, tendonitis, tonsillitis, acne vulgaris, reactive airway disorder, asthma, airway infection, autoinflammatory disease, celiac disease, chronic prostatitis, diverticulitis, glomerulonephritis, hidradenitis suppurativa, hypersensitivities, intestinal disorder, epithelial intestinal disorder, inflammatory bowel disease, irritable bowel syndrome, colitis, interstitial cystitis, otitis, pelvic inflammatory disease, endometrial pain, reperfusion injury, rheumatic fever, rheumatoid arthritis, sarcoidosis, transplant rejection, or vasculitis.

15. The method of claim 6, wherein the compound is Cpd. No. 1-55 having the following structure, or a pharmaceutically acceptable hydrate, solvate, isotope, or salt thereof:

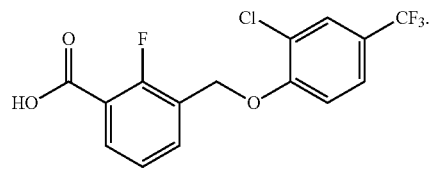

16. The method of claim 6, wherein the compound is Cpd. No. 1-78 having the following structure, or a pharmaceutically acceptable hydrate, solvate, isotope, or salt thereof

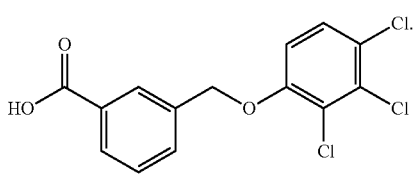

17. The method of claim 6, wherein the compound is Cpd. No. 5-1 having the following structure, or a pharmaceutically acceptable hydrate, solvate, isotope, or salt thereof

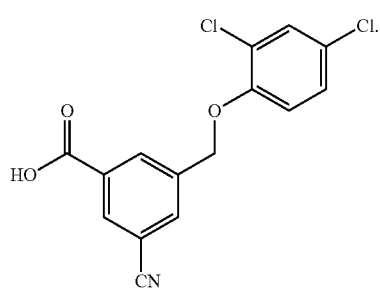 [SMILES: N#Cc1cc(COc2ccc(Cl)cc2Cl)cc(C(=O)O)c1]

18. The method of claim 6, wherein the compound is Cpd. No. 4-10 having the following structure, or a pharmaceutically acceptable hydrate, solvate, isotope, or salt thereof

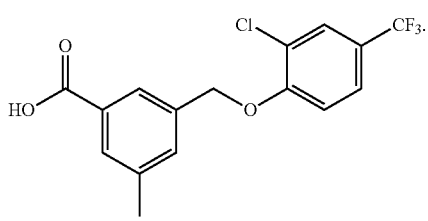

19. The method of claim 6, wherein the compound is Cpd. No. 1-65 having the following structure, or a pharmaceutically acceptable hydrate, solvate, isotope, or salt thereof

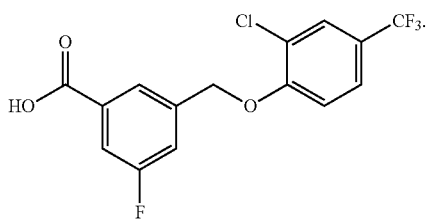 [SMILES: O=C(O)c1cc(F)cc(COc2ccc(C(F)(F)F)cc2Cl)c1]

20. The method of claim 6, wherein the compound is Cpd. No. 4-11 having the following structure, or a pharmaceutically acceptable hydrate, solvate, isotope, or salt thereof

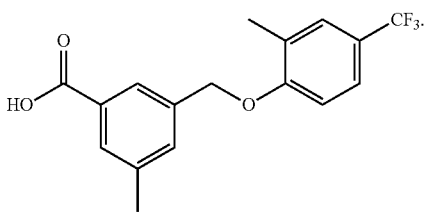 [SMILES: Cc1cc(COc2ccc(C(F)(F)F)cc2C)cc(C(=O)O)c1]

21. The method of claim 6, wherein the compound is Cpd. No. 1-58 having the following structure, or a pharmaceutically acceptable hydrate, solvate, isotope, or salt thereof

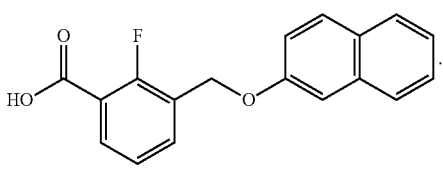 [SMILES: O=C(O)c1cccc(COc2ccc3ccccc3c2)c1F]

22. The method of claim 6, wherein the compound is Cpd. No. 1-56 having the following structure, or a pharmaceutically acceptable hydrate, solvate, isotope, or salt thereof

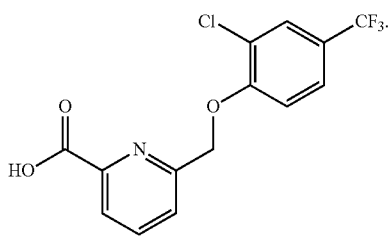 [SMILES: O=C(O)c1cccc(COc2ccc(C(F)(F)F)cc2Cl)n1]

23. The method of claim 6, wherein the compound is Cpd. No. 9-1 having the following structure, or a pharmaceutically acceptable hydrate, solvate, isotope, or salt thereof

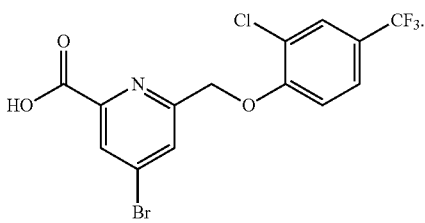 [SMILES: O=C(O)c1cc(Br)cc(COc2ccc(C(F)(F)F)cc2Cl)n1]

24. The method of claim 6, wherein the compound is Cpd. No. 1-82 having the following structure, or a pharmaceutically acceptable hydrate, solvate, isotope, or salt thereof

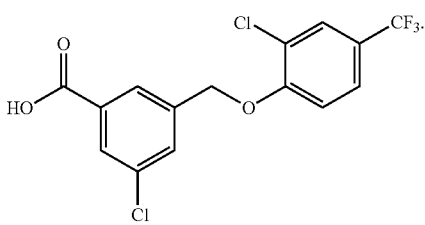

25. The method of claim 6, wherein the compound is Cpd. No. 1-85 having the following structure, or a pharmaceutically acceptable hydrate, solvate, isotope, or salt thereof

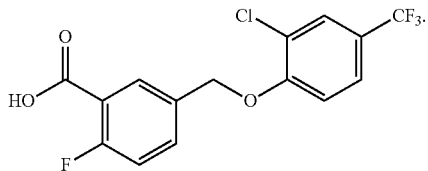 [SMILES: O=C(O)c1cc(COc2ccc(C(F)(F)F)cc2Cl)ccc1F]

26. The method of claim 6, wherein the compound is Cpd. No. 1-29 having the following structure, or a pharmaceutically acceptable hydrate, solvate, isotope, or salt thereof

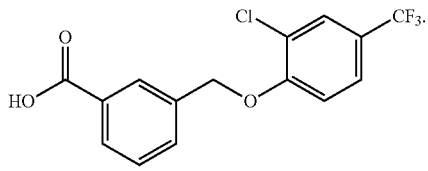 [SMILES: O=C(O)c1cccc(COc2ccc(C(F)(F)F)cc2Cl)c1]

27. The method of claim 6, wherein the compound is Cpd. No. 1-101 having the following structure, or a pharmaceutically acceptable hydrate, solvate, isotope, or salt thereof

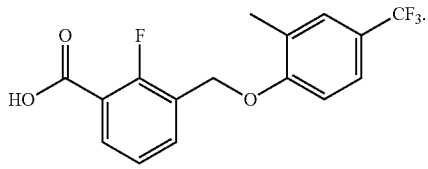

28. The method of claim 6, wherein the compound is Cpd. No. 2-3 having the following structure, or a pharmaceutically acceptable hydrate, solvate, isotope, or salt thereof

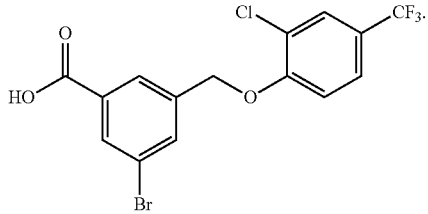

29. The method of claim 6, wherein the compound is Cpd. No. 1-103 having the following structure, or a pharmaceutically acceptable hydrate, solvate, isotope, or salt thereof

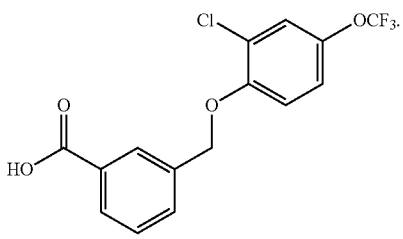

30. The method of claim 6, wherein the compound is Cpd. No. 1-112 having the following structure, or a pharmaceutically acceptable hydrate, solvate, isotope, or salt thereof

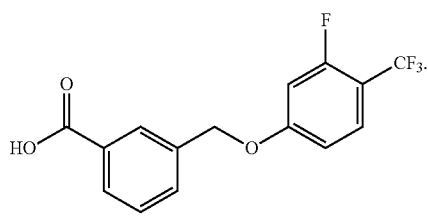 [SMILES: O=C(O)c1cccc(COc2ccc(C(F)(F)F)c(F)c2)c1]

31. The method of claim 6, wherein the compound is Cpd. No. 4-7 having the following structure, or a pharmaceutically acceptable hydrate, solvate, isotope, or salt thereof

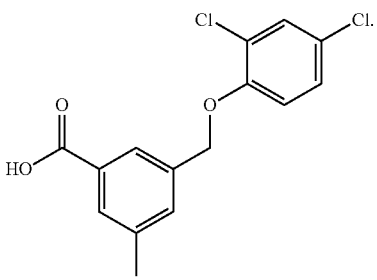 [SMILES: Cc1cc(COc2ccc(Cl)cc2Cl)cc(C(=O)O)c1]

32. The method of claim 6, wherein the compound is Cpd. No. 11-1 having the following structure, or a pharmaceutically acceptable hydrate, solvate, isotope, or salt thereof

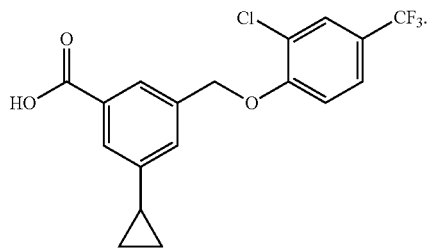 [SMILES: O=C(O)c1cc(COc2ccc(C(F)(F)F)cc2Cl)cc(C2CC2)c1]

* * * * *